US010058624B2

(12) United States Patent
Doering et al.

(10) Patent No.: US 10,058,624 B2
(45) Date of Patent: Aug. 28, 2018

(54) RECOMBINANT PROMOTERS AND VECTORS FOR PROTEIN EXPRESSION IN LIVER AND USE THEREOF

(71) Applicants: Emory University, Atlanta, GA (US); Children's Healthcare of Atlanta, Inc., Atlanta, GA (US)

(72) Inventors: Christopher B. Doering, Atlanta, GA (US); H. Trent Spencer, Atlanta, GA (US); Harrison C. Brown, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 4 days.

(21) Appl. No.: 15/128,912

(22) PCT Filed: Apr. 15, 2016

(86) PCT No.: PCT/US2016/027931

§ 371 (c)(1),
(2) Date: Sep. 23, 2016

(87) PCT Pub. No.: WO2016/168728

PCT Pub. Date: Oct. 20, 2016

(65) Prior Publication Data

US 2017/0326256 A1 Nov. 16, 2017

Related U.S. Application Data

(60) Provisional application No. 62/202,133, filed on Aug. 6, 2015, provisional application No. 62/212,634, filed on Sep. 1, 2015, provisional application No. 62/148,696, filed on Apr. 16, 2015.

(51) Int. Cl.

| | |
|---|---|
| ***C07K 14/745*** | (2006.01) |
| ***C07K 14/755*** | (2006.01) |
| ***C12N 15/85*** | (2006.01) |
| ***A61K 48/00*** | (2006.01) |
| ***C12N 7/00*** | (2006.01) |
| *A61K 38/00* | (2006.01) |

(52) U.S. Cl.

CPC ........ *A61K 48/0058* (2013.01); *C07K 14/755* (2013.01); *C12N 7/00* (2013.01); *C12N 15/85* (2013.01); *C12Y 304/21022* (2013.01); *A61K 38/00* (2013.01); *C12N 2750/14132* (2013.01); *C12N 2750/14143* (2013.01); *C12N 2830/008* (2013.01)

(58) Field of Classification Search

CPC .............. A61K 48/0058; C07K 14/745; C07K 14/755; C12N 15/85; C12N 2830/008; C12Y 304/21022

See application file for complete search history.

(56) References Cited

U.S. PATENT DOCUMENTS

| | | | | |
|---|---|---|---|---|
| 8,198,421 | B2 * | 6/2012 | Samulski | C12N 9/644 424/93.2 |
| 8,309,698 | B2 * | 11/2012 | Koh | C12N 15/63 435/320.1 |
| 8,865,881 | B2 | 10/2014 | Balazs et al. | |
| 9,447,168 | B2 * | 9/2016 | Nathwani | A01K 67/0275 |
| 2003/0027320 | A1 * | 2/2003 | Kim | C07K 14/005 435/235.1 |
| 2003/0077812 | A1 * | 4/2003 | McArthur | C07K 14/755 435/235.1 |
| 2008/0153156 | A1 * | 6/2008 | Gray | A61K 48/0066 435/320.1 |
| 2012/0094375 | A1 | 4/2012 | Rhoads et al. | |
| 2013/0024960 | A1 | 1/2013 | Nathwani et al. | |
| 2017/0095538 | A1 * | 4/2017 | Colosi | A61K 38/37 |
| 2017/0233456 | A1 * | 8/2017 | Sabatino | A61K 48/005 424/450 |
| 2017/0260516 | A1 * | 9/2017 | Tan | C12N 9/644 |

FOREIGN PATENT DOCUMENTS

| | | |
|---|---|---|
| WO | WO 1999/029848 | 6/1999 |
| WO | WO 2010/141924 | 12/2010 |
| WO | WO 2014/064277 | 5/2014 |

OTHER PUBLICATIONS

Brown, et al. "Bioengineered coagulation factor VIII enables long-term correction of murine hemophilia A following liver-directed adeno-associated viral vector delivery," *Molecular Therapy-Methods & Clinical Development* 1 (2014): 14036.
Chi et al., "Diabetes mutations delineate an atypical POU domain in HNF-1alpha," *Mol. Cell.* 10 (2002): 1129-1137.
Chuah et al., "Liver-specific transcriptional modules identified by genome-wide in silico analysis enable efficient gene therapy in mice and non-human primates." *Molecular Therapy* 22, No. 9 (2014): 1605-1613.
Faust et al., "CpG-depleted adeno-associated virus vectors evade immune detection." *The Journal of Clinical Investigation* 123, No. 7 (2013): 2994-3001.
Genbank Accession No. E00527, available at https://www.ncbi.nlm.nih.gov/nuccore/E00527, as accessed Mar. 14, 2017.
Genbank Accession No. J00136, available at https://www.ncbi.nlm.nih.gov/nuccore/J00136, as accessed Mar. 14, 2017.
Genbank Accession No. J00137, available at https://www.ncbi.nlm.nih.gov/nuccore/J00137, as accessed Mar. 14, 2017.
Genbank Accession No. K01740, available at https://www.ncbi.nlm.nih.gov/nuccore/K01740, as accessed Mar. 14, 2017.
Genbank Accession No. K02402, available at https://www.ncbi.nlm.nih.gov/nuccore/K02402, as accessed Mar. 14, 2017.
Genbank Accession No. M11309, available at https://www.ncbi.nlm.nih.gov/nuccore/M11309, as accessed Mar. 14, 2017.

(Continued)

*Primary Examiner* — Kevin K Hill
(74) *Attorney, Agent, or Firm* — Klarquist Sparkman, LLP

(57) ABSTRACT

Disclosed herein are recombinant viral vectors comprising a liver specific promotor in operable combination with a heterologous nucleic acid sequence encoding a protein, such as a clotting factor. Methods of treating a subject with a clotting disorder, such as hemophilia A or hemophilia B, are also provided.

28 Claims, 22 Drawing Sheets

Specification includes a Sequence Listing.

(56) References Cited

OTHER PUBLICATIONS

Genbank Accession No. M14113, available at https://www.ncbi.nlm.nih.gov/nuccore/M14113, as accessed Mar. 14, 2017.

Genbank Accession No. XM045316, available at https://www.ncbi.nlm.nih.gov/nuccore/XM_045316.1?report=genbank, as accessed Mar. 14, 2017.

Godbout, et al. "Multiple regulatory elements in the intergenic region between the alpha-fetoprotein and albumin genes." *Molecular and Cellular Biology* 6, No. 2 (1986): 477-487.

Graham et al. "The Malmö polymorphism of coagulation factor IX, an immunologic polymorphism due to dimorphism of residue 148 that is in linkage disequilibrium with two other F. IX polymorphisms." *American journal of human genetics* 42, No. 4 (1988): 573.

Gui et al., "Circulating and binding characteristics of wild-type factor IX and certain Gla domain mutants in vivo." *Blood* 100, No. 1 (2002): 153-158.

International Search Report and Written Opinion for PCT/US2016/027931, mailed by the European Patent Office acting as the International Searching Authority dated Oct. 20, 2016 (18 pages).

Juven-Gershon, et al. "Rational design of a super core promoter that enhances gene expression." *Nature Methods* 3, No. 11 (2006): 917-922.

Kurachi et al., "Isolation and characterization of a cDNA coding for human factor IX." *Proceedings of the National Academy of Sciences* 79, No. 21 (1982): 6461-6464.

Laganiere et al., "Location analysis of estrogen receptor alpha target promoters reveals that FOXA1 defines a domain of the estrogen response," *Proc. Natl. Acad. Sci. U.S.A.* 102:11651-11656, 2005.

Lupien et al., "FoxA1 translates epigenetic signatures into enhancer-driven lineage-specific transcription," *Cell* 132:958-970, 2008.

McIntosh et al., "Therapeutic levels of FVIII following a single peripheral vein administration of rAAV vector encoding a novel human factor VIII variant," Blood, 121(17):3335-44, 2013.

Nair, et al. "Computationally designed liver-specific transcriptional modules and hyperactive factor IX improve hepatic gene therapy." *Blood* 123, No. 20 (2014): 3195-3199.

Notley, et al. "The canine factor VIII 3'-untranslated region and a concatemeric hepatocyte nuclear factor 1 regulatory element enhance factor VIII transgene expression in vivo." *Human Gene Therapy* 13 , No. 13 (2002): 1583-1593.

Papadakis, et al. "Promoters and control elements: designing expression cassettes for gene therapy." *Current Gene Therapy* 4, No. 1 (2004): 89-113.

Rose, et al. "Structural basis of dimerization, coactivator recognition and MODY3 mutations in HNF-1α." *Nature Structural & Molecular Biology* 7, No. 9 (2000): 744-748.

Rouet, et al. "A potent enhancer made of clustered liver-specific elements in the transcription control sequences of human alpha 1-microglobulin/bikunin gene." *Journal of Biological Chemistry* 267, No. 29 (1992): 20765-20773.

Ryffel, et al. "Liver cell specific gene transcription in vitro: the promoter elements HP1 and TATA box are necessary and sufficient to generate a liver-specific promoter." *Nucleic Acids Research* 17, No. 3 (1989): 939-953.

Schlabach, et al. "Synthetic design of strong promoters." *Proceedings of the National Academy of Sciences* 107, No. 6 (2010): 2538-2543.

Schorpp, et al. "Hepatocyte-specific promoter element HP1 of the Xenopus albumin gene interacts with transcriptional factors of mammalian hepatocytes." *Journal of Molecular Biology* 202, No. 2 (1988): 307-320.

Simioni et al., "X-linked thrombophilia with a mutant factor IX (factor IX Padua)." *New England Journal of Medicine* 361, No. 17 (2009): 1671-1675.

Song et al., "Role of Foxa1 in regulation of bcl2 expression during oxidative-stress-induced apoptosis in A549 type II pneumocytes," *Cell Stress Chaperones,* 14:417-425, 2009.

Wang et al., "Hepatocyte nuclear factor-4α interacts with other hepatocyte nuclear factors in regulating transthyretin gene expression," *FEBS* J., 277(19):4066-75, 2010.

Williamson et al., "BRCA1 and FOXA1 proteins coregulate the expression of the cell cycle-dependent kinase inhibitor p27(Kip1)," *Oncogene* 25:1391-1399, 2006.

* cited by examiner

Liver-specific human codon optimization table

| AA | Codon | Total Frequency | Liver Frequency | Liver:Total |
|---|---|---|---|---|
| Ala | GCC | 0.4 | 0.44 | 1.10 |
| Ala | GCA | 0.23 | 0.19 | 0.83 |
| Ala | GCT | 0.26 | 0.27 | 1.04 |
| Ala | GCG | 0.11 | 0.1 | 0.91 |
| Arg | CGC | 0.19 | 0.24 | 1.26 |
| Arg | AGA | 0.2 | 0.18 | 0.90 |
| Arg | CGA | 0.11 | 0.1 | 0.91 |
| Arg | CGT | 0.08 | 0.07 | 0.88 |
| Arg | AGG | 0.2 | 0.2 | 1.00 |
| Arg | CGG | 0.21 | 0.21 | 1.00 |
| Asn | AAC | 0.54 | 0.59 | 1.09 |
| Asn | AAT | 0.46 | 0.41 | 0.89 |
| Asp | GAC | 0.54 | 0.61 | 1.13* |
| Asp | GAT | 0.46 | 0.39 | 0.85 |
| Cys | TGC | 0.55 | 0.6 | 1.09 |
| Cys | TGT | 0.45 | 0.4 | 0.89 |
| Gln | CAA | 0.25 | 0.25 | 1.00 |
| Gln | CAG | 0.75 | 0.75 | 1.00 |
| Glu | GAG | 0.58 | 0.65 | 1.12* |
| Glu | GAA | 0.42 | 0.35 | 0.83 |
| Gly | GGC | 0.34 | 0.37 | 1.09 |

| AA | Codon | Total Frequency | Liver Frequency | Liver:Total |
|---|---|---|---|---|
| Gly | GGT | 0.16 | 0.12 | 0.75 |
| Gly | GGG | 0.25 | 0.28 | 1.12 |
| Gly | GGA | 0.25 | 0.23 | 0.92 |
| His | CAC | 0.59 | 0.59 | 1.00 |
| His | CAT | 0.41 | 0.41 | 1.00 |
| Ile | ATC | 0.48 | 0.61 | 1.27* |
| Ile | ATT | 0.36 | 0.28 | 0.78 |
| Ile | ATA | 0.16 | 0.11 | 0.69 |
| Leu | CTG | 0.41 | 0.47 | 1.15 |
| Leu | CTC | 0.2 | 0.23 | 1.15* |
| Leu | CTT | 0.13 | 0.1 | 0.77 |
| Leu | TTA | 0.07 | 0.04 | 0.57 |
| Leu | TTG | 0.13 | 0.11 | 0.85 |
| Leu | CTA | 0.07 | 0.06 | 0.86 |
| Lys | AAG | 0.58 | 0.65 | 1.12* |
| Lys | AAA | 0.42 | 0.35 | 0.83 |
| Met | ATG | 1 | 1 | 1.00 |
| Phe | TTC | 0.55 | 0.65 | 1.18* |
| Phe | TTT | 0.45 | 0.35 | 0.78* |
| Pro | CCC | 0.33 | 0.38 | 1.15 |
| Pro | CCA | 0.27 | 0.24 | 0.89 |

| AA | Codon | Total Frequency | Liver Frequency | Liver:Total |
|---|---|---|---|---|
| Pro | CCG | 0.11 | 0.1 | 0.91 |
| Pro | CCT | 0.28 | 0.28 | 1.00 |
| Ser | TCC | 0.22 | 0.28 | 1.27 |
| Ser | AGT | 0.15 | 0.12 | 0.80 |
| Ser | TCA | 0.15 | 0.13 | 0.87 |
| Ser | AGC | 0.24 | 0.25 | 1.04 |
| Ser | TCT | 0.18 | 0.17 | 0.94 |
| Ser | TCG | 0.06 | 0.06 | 1.00 |
| Thr | ACC | 0.36 | 0.47 | 1.31 |
| Thr | ACA | 0.28 | 0.21 | 0.75 |
| Thr | ACT | 0.24 | 0.19 | 0.79 |
| Thr | ACG | 0.12 | 0.12 | 1.00 |
| Trp | TGG | 1 | 1 | 1.00 |
| Tyr | TAC | 0.57 | 0.63 | 1.11 |
| Tyr | TAT | 0.43 | 0.37 | 0.86 |
| Val | GTG | 0.47 | 0.52 | 1.11 |
| Val | GTT | 0.18 | 0.13 | 0.72 |
| Val | GTA | 0.11 | 0.08 | 0.73 |
| Val | GTC | 0.24 | 0.26 | 1.08 |

FIG. 2A

Standard human codon optimization table

| Codon | Frequency | Count | Codon | Frequency | Count | Codon | Frequency | Count | Codon | Frequency | Count |
|---|---|---|---|---|---|---|---|---|---|---|---|
| UUU | 0.464134 | 714298 | UCU | 0.187586 | 618711 | UAU | 0.443338 | 495699 | UGU | 0.456157 | 430311 |
| UUC | 0.535866 | 824692 | UCC | 0.21796 | 718892 | UAC | 0.556662 | 622407 | UGC | 0.543843 | 513028 |
| UUA | 0.076568 | 311881 | UCA | 0.150517 | 496448 | UAA | 0 | 0 | UGA | 1 | 10000 |
| UUG | 0.129058 | 525688 | UCG | 0.054398 | 179419 | UAG | 0 | 0 | UGG | 1 | 535595 |
| | | | | | | | | | | | |
| CUU | 0.131716 | 536515 | CCU | 0.286731 | 713233 | CAU | 0.418515 | 441711 | CGU | 0.080108 | 184609 |
| CUC | 0.195577 | 796638 | CCC | 0.32347 | 804620 | CAC | 0.581485 | 613713 | CGC | 0.183777 | 423516 |
| CUA | 0.07138 | 290751 | CCA | 0.276603 | 688038 | CAA | 0.265017 | 501911 | CGA | 0.108812 | 250760 |
| CUG | 0.395702 | 1611801 | CCG | 0.113196 | 281570 | CAG | 0.734983 | 1391973 | CGG | 0.201554 | 464485 |
| | | | | | | | | | | | |
| AUU | 0.361072 | 650473 | ACU | 0.246769 | 533609 | AAU | 0.470367 | 689701 | AGU | 0.149602 | 493429 |
| AUC | 0.469866 | 846466 | ACC | 0.355232 | 768147 | AAC | 0.529633 | 776603 | AGC | 0.239938 | 791383 |
| AUA | 0.169062 | 304565 | ACA | 0.284188 | 614523 | AAA | 0.434049 | 993621 | AGA | 0.214658 | 494682 |
| AUG | 1 | 896005 | ACG | 0.113812 | 246105 | AAG | 0.565951 | 1295568 | AGG | 0.211091 | 486463 |
| | | | | | | | | | | | |
| GUU | 0.18177 | 448607 | GCU | 0.265922 | 750096 | GAU | 0.464542 | 885429 | GGU | 0.163087 | 437126 |
| GUC | 0.238306 | 588138 | GCC | 0.399781 | 1127679 | GAC | 0.535458 | 1020595 | GGC | 0.337109 | 903565 |
| GUA | 0.116577 | 287712 | GCA | 0.228121 | 643471 | GAA | 0.422453 | 1177632 | GGA | 0.249922 | 669873 |
| GUG | 0.463346 | 1143534 | GCG | 0.106176 | 299495 | GAG | 0.577547 | 1609975 | GGG | 0.249882 | 669768 |

FIG. 2B

Monocyte/Myeloid Codon optimization tables

| Codon | Frequency | Count | Codon | Frequency | Count | Codon | Frequency | Count | Codon | Frequency | Count |
|---|---|---|---|---|---|---|---|---|---|---|---|
| UUU | 0.39 | 95 | UCU | 0.15 | 72 | UAU | 0.4 | 70 | UGU | 0.33 | 52 |
| UUC | 0.61 | 150 | UCC | 0.22 | 103 | UAC | 0.6 | 107 | UGC | 0.67 | 106 |
| UUA | 0.05 | 27 | UCA | 0.17 | 77 | UAA | 0 | 0 | UGA | 1 | 100 |
| UUG | 0.12 | 67 | UCG | 0.04 | 17 | UAG | 0 | 0 | UGG | 1 | 92 |
| | | | | | | | | | | | |
| CUU | 0.1 | 56 | CCU | 0.22 | 75 | CAU | 0.39 | 54 | CGU | 0.1 | 27 |
| CUC | 0.24 | 139 | CCC | 0.38 | 127 | CAC | 0.61 | 83 | CGC | 0.14 | 37 |
| CUA | 0.07 | 40 | CCA | 0.31 | 104 | CAA | 0.28 | 71 | CGA | 0.09 | 25 |
| CUG | 0.43 | 251 | CCG | 0.09 | 30 | CAG | 0.72 | 180 | CGG | 0.18 | 48 |
| | | | | | | | | | | | |
| AUU | 0.26 | 66 | ACU | 0.21 | 78 | AAU | 0.43 | 121 | AGU | 0.14 | 66 |
| AUC | 0.6 | 155 | ACC | 0.42 | 153 | AAC | 0.57 | 161 | AGC | 0.28 | 131 |
| AUA | 0.14 | 37 | ACA | 0.27 | 98 | AAA | 0.37 | 130 | AGA | 0.22 | 58 |
| AUG | 1 | 137 | ACG | 0.1 | 36 | AAG | 0.63 | 225 | AGG | 0.27 | 71 |
| | | | | | | | | | | | |
| GUU | 0.16 | 56 | GCU | 0.32 | 114 | GAU | 0.46 | 137 | GGU | 0.13 | 56 |
| GUC | 0.29 | 103 | GCC | 0.35 | 124 | GAC | 0.54 | 161 | GGC | 0.37 | 153 |
| GUA | 0.09 | 32 | GCA | 0.25 | 88 | GAA | 0.44 | 180 | GGA | 0.24 | 98 |
| GUG | 0.47 | 169 | GCG | 0.07 | 25 | GAG | 0.56 | 230 | GGG | 0.26 | 109 |

FIG. 2C

Benefits of tissue-specific codon optimization
(expression HepG2 cells by transient transfection)

Tissue-specific codon optimization expression in cells from different species (expression in baby hamster kidney cells by transient transfection)
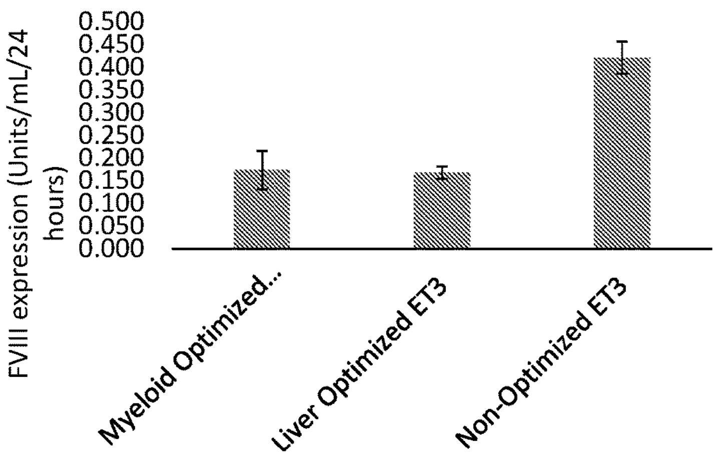
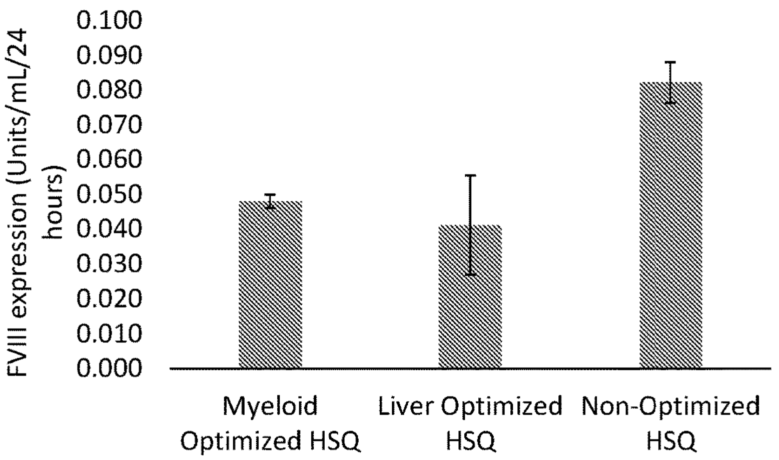
FIG. 6

(1) ABP (SEQ ID NO: 113)

(2) GTTAATTT TTAAAAAGCAGTCAAAAGTCCAA (3) GTGGCCCTTGC GAGCAT

TTACTCTCTC (4) TGTTTGC TC (5) TGGTTAATAATCTCA GGAGC (6) ACAAACA

(7) SynO (SEQ ID NO: 114)

GAG (8) GTTAATAATTTTC CAGATCTCTCTGAGCAATAG (9) TATAAAA

(10) God (SEQ ID NO: 115)

AGTCATATGTTTGCTCACTGAAGGTTACTAGTTAACAGGCATCCCTTAAACAGGA

ABP-SynO (SEQ ID NO: 131)

(1) GTTAATTTTTAAAAAGCAGTCAAAAGTCCAAGTGGCCCTTGCGAGCATTTACTCTCTCTGTTTG
CTCTGGTTAATAATCTCAGGAGCACAAACA (7) GAGGTTAATAATTTTCCAGATCTCTCTGAGCAATAGTATAAAA

ABP-Hp1-God (SEQ ID NO: 6)

(1) GTTAATTTTTAAAAAGCAGTCAAAAGTCCAAGTGGCCCTTGCGAGCATTTACTCTCTCTGTTTG
CTCTGGTTAATAATCTCAGGAGCACAAACA

GAG (7) GTTAATAATTTTC

(10) AGTCATATGTTTGCTCACTGAAGGTTACTAGTTAACAGGCATCCCTTAAACAGGA

TATAAAA (1) ABP element
(2) HNF1-1 TF binding site
(3) HNF4 TF binding site
(4) HNF3a TF binding site
(5) HNF1-2 TF binding site
(6) HNF3-2 TF binding site
(7) SynO element
(8) HP1 TF binding site
(9) TATA box
(10) God element

FIG. 8

(11) ABP-exact (SEQ ID NO: 116)

(12) (13)
GTTAATCATTAACTTAAAAAGCAGTCAAAAGTCCAAAGGTCAAAGGTCAGAGCATTTA
CTCTCTCCAATGTTGACTCTCGTTAATGATTAAGGAGCAATTGTTGACTT
(14) (15) (16)

(17) Short-ABP-exact (SEQ ID NO: 117)

(12) (13) (14) (15)
GTTAATCATTAACTTAGGTCAAAGGTCAGACAATGTTGACTCTCGTTAATGATTAACC
GCAATTGTTGACTT
(16)

(18) Transcription start site, TSS (nuc. 116-146 of SEQ ID NO: 4)

(19) (20)
GCCAGCAGCAGCCTGACCACATCTCATCCTC

(21) HNF1a TF binding site
GTTAATCATTAA

(22) Sp1 TF binding site
GTTAATCATTAA

(23) SV40 intron
CTCTAAGGTAAATATAAAATTTTTAAGTGTATAATGTGTTAAACTACTGATTCTAAT
TGTTTGTGTATTTTAGATTCCAACCTATGGAACTGA

(11) ABP-exact (consensus TF binding sites)
(12) HNF1-1 consensus TF binding site
(13) HNF4 consensus TF binding site
(14) HNF3a consensus TF binding site
(15) HNF1-2 consensus TF binding site
(16) HNF3-2 consensus TF binding site
(17) Short-ABP-exact
(18) Transcription Start Site (TSS)
(19) GC rich spacer
(20) Transcription start motif
(21) HNF1a TF binding site (liver-directed TF binding site)
(22) Sp1 TF binding site (liver-directed TF binding site)
(23) SV40 intron

FIG. 10

ABP Enhancer
GC rich spacer
tata box
Godbout Proximal Enhancer

ABP-exact-SynO (SEQ ID NO: 118)

(11) GTTAATCATTAACTTAAAAAGCAGTCAAAAGTCCAAAGGTCAAAGGTCAGAGCATTTACTCTCTCCA
ATGTTGACTCTCGTTAATGATTAAGGAGCAATTGTTGACTT
(7) GAGGTTAATAATTTTCCAGATCTCTCTGAGCAATAGTATAAAA

ShortABP-exact-SynO (SEQ ID NO: 119)

(17) GTTAATCATTAACTTAGGTCAAAGGTCAGACAATGTTGACTCTCGTTAATGATTAACCGGAATTGTT
GACTT
(7) GAGGTTAATAATTTTCCAGATCTCTCTGAGCAATAGTATAAAA

ABP-HP1-God-TSS (SEQ ID NO: 7)

(1) GTTAATTTTTAAAAAGCAGTCAAAAGTCCAAGTGGCCCTTGCGAGCATTTACTCTCTCTGTTTG
CTCTGGTTAATAATCTCAGGAGCACAAACA
GAG
(8) GTTAATAATTTTC
(10) AGTCATATGTTTGCTCACTGAAGGTTACTAGTTAACAGGCATCCCTTAAACAGGA
TATAAAAG
(18) GCCAGCAGCAGCCTGACCACATCTCATCCTC

FIG. 11A

HNF1a-ABP-SynO (SEQ ID NO: 120)

(21) GTTAATCATTAA
GTC
(1) GTTAATTTTTAAAAAGCAGTCAAAAGTCCAAGTGGCCCTTGCGAGCATTTACTCTCTCTGTTTG
CTCTGGTTAATAATCTCAGGAGCACAAACA
(7) GAGGTTAATAATTTTCCAGATCTCTCTGAGCAATAGTATAAAA

Sp1-ABP-SynO (SEQ ID NO: 121)

(22) TGGGCGGAGT
GTC
(1) GTTAATTTTTAAAAAGCAGTCAAAAGTCCAAGTGGCCCTTGCGAGCATTTACTCTCTCTGTTTG
CTCTGGTTAATAATCTCAGGAGCACAAACA
(7) GAGGTTAATAATTTTCCAGATCTCTCTGAGCAATAGTATAAAA

HNF1-ShortABPExact-SynO-TSS-Int (SEQ ID NO: 112)

(21) GTTAATCATTAA
GTC
(17) GTTAATCATTAACTTAGGTCAAAGGTCAGACAATGTTGACTCTCGTTAATGATTAACCGGAATTGT
TGACTT
(7) GAGGTTAATAATTTTCCAGATCTCTCTGAGCAATAGTATAA
AAG
(18) GCCAGCAGCAGCCTGACCACATCTCATCCTC
(23) CTCTAAGGTAAATATAAAATTTTTAAGTGTATAATGTGTTAAACTACTGATTCTAATTGTTTGTGT
ATTTTAGATTCCAACCTATGGAACTGA

FIG. 11B

(24) shortABP (SEQ ID NO: 34)

GTTAATTT TT GTGGCCCTTGC GA TGTTTGC TC TGGTTAATAATCTCA GG ACAAACA
(2) (3) (4) (5) (6)

(25) HNF1-shortABP-SynO-TSS (also called Hepatic Combinatorial Bundle, or HCB) (SEQ ID NO: 4)

(21) GTTAATCATTAA
GTC
(24) GTTAATTTTTGTGGCCCTTGCGATGTTTGCTCTGGTTAATAATCTCAGGACAAACA
(7) GAGGTTAATAATTTTCCAGATCTCTCTGAGCAATAGTATAAAA
G
(18) GCCAGCAGCAGCCTGACCACATCTCATCCTC

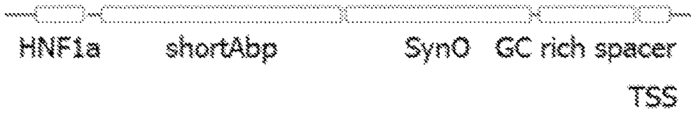

(27) shortABP-HP1-God-TSS (SEQ ID NO: 5)

(24) GTTAATTTTTGTGGCCCTTGCGATGTTTGCTCTGGTTAATAATCTCAGGACAAACA
TAC
(8a) ATTTTC
(10) AGTCATATGTTTGCTCACTGAAGGTTACTAGTTAACAGGCATCCCTTAAACAGGA
TATAAAAG
(18) GCCAGCAGCAGCCTGACCACATCTCATCCTC

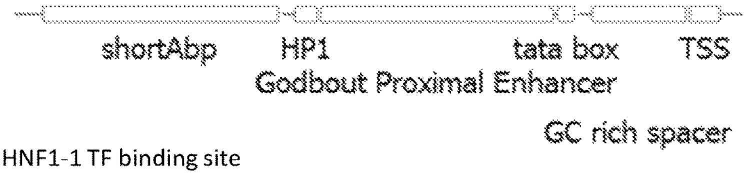

(2) HNF1-1 TF binding site
(3) HNF4 TF binding site
(4) HNF3a TF binding site
(5) HNF1-2 TF binding site
(6) HNF3-2 TF binding site
(7) SynO element
(8a) shortened HP1 TF binding site
(10) God element
(18) Transcription Start Site (TSS)
(21) HNF1a TF binding site
(24) shortABP
(25) HNF1-shortABP-SynO-TSS (Hepatic Combinatorial Bundle, or HCB)
(27) shortABP-HP1-God-TSS

FIG. 13

AAV-HCB-MVM-ET3-LCO-NCG Transduced mice

RECOMBINANT PROMOTERS AND VECTORS FOR PROTEIN EXPRESSION IN LIVER AND USE THEREOF

CROSS REFERENCE TO RELATED APPLICATIONS

This is the U.S. National Stage of International Application No. PCT/US2016/027931, filed Apr. 15, 2016, which was published in English under PCT Article 21(2), which in turn claims the benefit of U.S. Provisional Application No. 62/202,133, filed Aug. 6, 2015, U.S. Provisional Application No. 62/212,634, filed Sep. 1, 2015, and U.S. Provisional Application No. 62/148,696, filed Apr. 16, 2015. Each of the provisional patent applications is incorporated by reference in its entirety.

ACKNOWLEDGMENT OF GOVERNMENT SUPPORT

This invention was made with government support under Grant Nos. R01 HL092179 U54 HL112309 awarded by the National Institutes of Health. The government has certain rights in the invention.

FIELD OF THE DISCLOSURE

This relates to recombinant promoters and vectors transgene expression, as well as recombinant nucleic acid molecules encoding novel clotting factors.

BACKGROUND

Mutations in the clotting factor VIII (fVIII) gene result in a decreased or defective clotting factor (fVIII) protein that gives rise to hemophilia A, which is characterized by uncontrolled bleeding. Hemophilia B is similarly associated with clotting factor IX (fix). Treatment of hemophilia A typically entails lifelong, multi-weekly intravenous infusion of either human plasma-derived or recombinant fVIII product. Due to the high cost, less than 30% of the global hemophilia A population receives this form of treatment. Furthermore, about 25% of patients treated with fVIII replacement products develop neutralizing antibodies that render future treatment ineffective. Thus, there is a need to identify improved therapies.

Gene therapies are typically based on genetically engineering viruses designed to deliver functional transgenes to the patient so that their own cells can biosynthesize missing or defective proteins. Clinical advancements have been made using recombinant adeno-associated viral (rAAV) vectors for the expression of fIX in the liver; however, using rAAV for fVIII expression for patients with hemophilia A has been challenging due to inefficient biosynthesis of human fVIII (hfVIII). Recombinant adeno-associated viral (rAAV) vectors produce capsids that have a limited space for encapsulating nucleic acids. FVIII is a large glycoprotein, and the rAAV sequences needed for encoding and expressing fVIII typically exceed capsid packing capacity.

SUMMARY

Disclosed herein are embodiments of a novel recombinant nucleic acid molecule comprising a promoter that has been optimized to be of minimal length and to promote tissue-specific protein expression. In several embodiments, the promoter can be a liver-specific promoter that promotes substantially more protein expression in liver and liver cells than in other tissue types. In some embodiments, promoter can be included in a viral vector (such as an adeno-associated virus vector) in operable combination with a heterologous nucleic acid sequence encoding a protein of interest in order to promote expression of the protein of interest, for example in liver tissue and/or cells.

In some embodiments, the recombinant nucleic acid molecule can comprise a promoter comprising a first response element that comprises a set of transcription factor (TF) binding sites including: a HNF1a TF binding site, a HNF1-1 TF binding site, a HNF4 TF binding site, a HNF3a TF binding site, a HNF1-2 TF binding site, a HNF3-2 TF binding site, a HP1 TF binding site, a TATA box; and a Transcription Start Site. In some embodiments, the HNF1a TF binding site comprises or consists of nucleotides 1-12 of SEQ ID NO: 4; the HNF1-1 TF binding site comprises or consists of nucleotides 16-23 of SEQ ID NO: 4; the HNF4 TF binding site comprises or consists of nucleotides 26-36 of SEQ ID NO: 4; the HNF3a TF binding site comprises or consists of nucleotides 39-45 of SEQ ID NO: 4; the HNF1-2 TF binding site comprises or consists of nucleotides 48-62 of SEQ ID NO: 4; the HNF3-2 TF binding site comprises or consists of nucleotides 65-71 of SEQ ID NO: 4; the HP1 TF binding site comprises or consists of nucleotides 75-87 of SEQ ID NO: 4; the TATA box comprises or consists of nucleotides 108-114 of SEQ ID NO: 4; and/or the Transcription Start Site (TSS) comprises or consists of nucleotides 116-146 of SEQ ID NO: 4. In some embodiments, the first response element can be of no more than 160 nucleotides in length (such as no more than 150 nucleotides in length, such as 146 nucleotides in length).

In some embodiments, the first response element comprises, from 5' to 3', the HNF1a TF binding site, the HNF1-1 TF binding site, the HNF4 TF binding site, the HNF3a TF binding site, the HNF1-2 TF binding site, the HNF3-2 TF binding site, the HP1 TF binding site, the TATA box, and the Transcription Start Site (TSS).

In some embodiments, the recombinant nucleic acid molecule comprises a promoter comprising or consisting of the nucleic acid sequence set forth as SEQ ID NO: 4 (HCB), or a sequence at least 90% identical thereto.

In some embodiments, the recombinant nucleic acid molecule can comprise a promoter comprising the first response element as discussed above, and can further comprise a second response element. The second response element can comprise, for example, a HSh response element (for example, comprising or consisting of the nucleotide sequence set forth as SEQ ID NO: 111, or a sequence at least 90% identical thereto), a 5'HS response element (for example, comprising or consisting of the nucleotide sequence set forth as nucleotides 6-32 of SEQ ID NO: 111, or a sequence at least 90% identical thereto), or a 3'HS response element (for example, comprising or consisting of the nucleotide sequence set forth as nucleotides 44-68 of SEQ ID NO: 111, or a sequence at least 90% identical thereto).

In some embodiments, the recombinant nucleic acid molecule comprises a promoter comprising or consisting of the nucleic acid sequence set forth as one of SEQ ID NO: 102 (HSh-HCB), SEQ ID NO: 104 (5'HSh-HCB), or SEQ ID NO: 103 (3'HSh-HCB), or a sequence at least 90% identical to one of SEQ ID NO: 102 (HSh-HCB), SEQ ID NO: 104 (5'HSh-HCB), or SEQ ID NO: 103 (3'HSh-HCB). In additional embodiments, the recombinant nucleic acid molecule comprises a promoter comprising or consisting of the nucleic acid sequence set forth as one of SEQ ID NO: 5

(shortABP-HP1-God-TSS), SEQ ID NO: 7 (ABP-HP1-God-TSS), SEQ ID NO: 105 (HSh-SynO-TSS), SEQ ID NO: 106 (sHS-SynO-TSS), SEQ ID NO: 107 (Agro), SEQ ID NO: 108 (HS-SynO-TSS), or SEQ ID NO: 112 (HNF1-ShortABPExact-SynO-TSS-Int), or a sequence at least 90% identical to one of SEQ ID NO: 5 (shortABP-HP1-God-TSS), SEQ ID NO: 7 (ABP-HP1-God-TSS), SEQ ID NO: 105 (HSh-SynO-TSS), SEQ ID NO: 106 (sHS-SynO-TSS), SEQ ID NO: 107 (Agro), SEQ ID NO: 108 (HS-SynO-TSS), or SEQ ID NO: 112 (HNF1-ShortABPExact-SynO-TSS-Int).

In some embodiments, promoter can be included in a vector, such as a viral vector (for example, an adeno-associated virus vector). In some embodiments, the promoter is included on the vector in operable combination with a heterologous nucleic acid sequence encoding a protein of interest in order to promote expression of the protein of interest, for example in liver tissue and/or cells. In some embodiments, the protein of interest can be a clotting factor, such as fVIII or fIX or variant thereof, such as a fVIII variant comprising fVIII A1, A2, A3, C1, and C2 domains, with the A2 and A3 domains joined by a peptide linker, and deletion of the fVIII B domain. In some embodiments, the protein of interest can be a fVIII variant and the heterologous nucleic molecule can comprise or consist of the nucleic acid sequence set forth as SEQ ID NO: 2, SEQ ID NO: 11, SEQ ID NO: 12, SEQ ID NO: 125, or SEQ ID NO: 126, or a nucleic acid sequence at least 90% identical to SEQ ID NO: 2, SEQ ID NO: 11, SEQ ID NO: 12, SEQ ID NO: 125, or SEQ ID NO: 126. In some embodiments, the protein of interest can be a fIX and the heterologous nucleic molecule can comprise or consist of the nucleic acid sequence set forth as SEQ ID NO: 8, SEQ ID NO: 9, SEQ ID NO: 10, SEQ ID NO: 124, or SEQ ID NO: 127, or a nucleic acid sequence at least 90% identical SEQ ID NO: 8, SEQ ID NO: 9, SEQ ID NO: 10, SEQ ID NO: 124, or SEQ ID NO: 127.

In some embodiments, the vector can be a recombinant AAV vector comprising a genome comprising a nucleic acid molecule encoding any of the liver-specific promoters provided herein (such as the HCB promoter, SEQ ID NO: 4) operably linked to a heterologous nucleic molecule encoding a fVIII variant, wherein the heterologous nucleic acid molecule comprises or consists of the nucleic acid sequence set forth as SEQ ID NO: 2, SEQ ID NO: 11, SEQ ID NO: 12, SEQ ID NO: 125, or SEQ ID NO: 126, or a nucleic acid sequence at least 90% identical to SEQ ID NO: 2, SEQ ID NO: 11, SEQ ID NO: 12, SEQ ID NO: 125, or SEQ ID NO: 126. Is several such embodiments, the recombinant AAV genome (from 5' to 3' ITR) is no more than 5.1, 5.0, 4.9, 4.8, 4.7, 4.6, or 4.5 kb in length.

In some embodiments, the vector can be a recombinant AAV vector comprising a genome comprising a nucleic acid molecule encoding any of the liver-specific promoters provided herein (such as the HCB promoter, SEQ ID NO: 4) operably linked to a heterologous nucleic molecule encoding a fIX variant, wherein the heterologous nucleic acid molecule comprises or consists of the nucleic acid sequence set forth as SEQ ID NO: 8, SEQ ID NO: 9, SEQ ID NO: 10, SEQ ID NO: 124, or SEQ ID NO: 127, or a nucleic acid sequence at least 90% identical SEQ ID NO: 8, SEQ ID NO: 9, SEQ ID NO: 10, SEQ ID NO: 124, or SEQ ID NO: 127. In several such embodiments, the recombinant AAV genome (from 5' to 3' ITR) is no more than 5.1, 5.0, 4.9, 4.8, 4.7, 4.6, or 4.5 kb in length.

In some embodiments, a method of inducing blood clotting in a subject in need thereof is provided. The method comprises administering to the subject a therapeutically effective amount of a vector (such as an AAV vector) encoding a clotting factor as described herein. In some embodiments, the subject is a subject with a clotting disorder, such as hemophilia A or hemophilia B. In some embodiments, the clotting disorder is hemophilia A and the subject is administered a vector comprising a nucleic acid molecule encoding a protein with fVIII activity. In other embodiments, the clotting disorder is hemophilia B and the subject is administered a vector comprising a nucleic acid molecule encoding a protein with fIX activity.

The foregoing and other features and advantages of this disclosure will become more apparent from the following detailed description of several embodiments which proceeds with reference to the accompanying figures.

BRIEF DESCRIPTION OF THE FIGURES

(FIG. 1A) Sequence alignment of the A1 domain for human (upper sequence, SEQ ID NO: 13) and porcine (middle sequence, SEQ ID NO: 14) ET3 variant of fVIII. The lower sequence shows identical residues. Amino acid sequence alignments for the signal peptide (N-terminal bar), heavy chain acidic domain (C-terminal bar), human (top) and ET3 (bottom) fVIII are shown. Disulfide linkages are noted by the lines connecting cysteine residues. Places where either human, ET3 or both sequences encode an N-linked glycosylation attachment site (N-X-S/T) are outlined with a box. (FIG. 1B) Sequence alignment of the A3 domain for human (upper sequence, SEQ ID NO: 15) and porcine (middle sequence, SEQ ID NO: 16) ET3 variant of fVIII. The lower sequence shows identical residues. Amino acid sequence alignments for the activation peptide (bar), human (top) and ET3 (bottom) fVIII are shown. Disulfide linkages are noted by the lines connecting cysteine residues. Places where either human, ET3 or both sequences encode an N-linked glycosylation attachment site (N-X-S/T) are outlined with a box.

FIGS. 2A-2C show liver, total human, and myeloid specific codon bias tables.

FIG. 6 shows in vitro expression data in HepG2 cells indicating that liver specific codon optimization, but not myeloid specific codon optimization, improves expression of HSQ and ET3 variants of the fVIII protein in liver cells.

FIG. 8 illustrates promotors comprising an ABP enhancer or a shortened ABP enhancer.

(FIG. 9A) In vitro expression data in HepG2 cells. (FIG. 9B) In vivo expression of fVIII following hydrodynamic injection of an AAV-vector.

FIG. 10 illustrates response element sequences and components of the indicated response elements.

FIGS. 11A and 11B illustrate promotor sequences and components of the indicated promoters.

(FIG. 12A) In vitro expression data in HepG2 cells. (FIG. 12B) In vivo expression of fVIII following hydrodynamic injection of an AAV-vector.

FIG. 13 illustrates promotor sequences and components of the indicated promoters.

(FIG. 14A) In vitro expression data in HepG2 cells. (FIG. 14B) In vivo expression of fVIII following hydrodynamic injection of an AAV-vector.

SEQUENCE LISTING

Figure 1A:
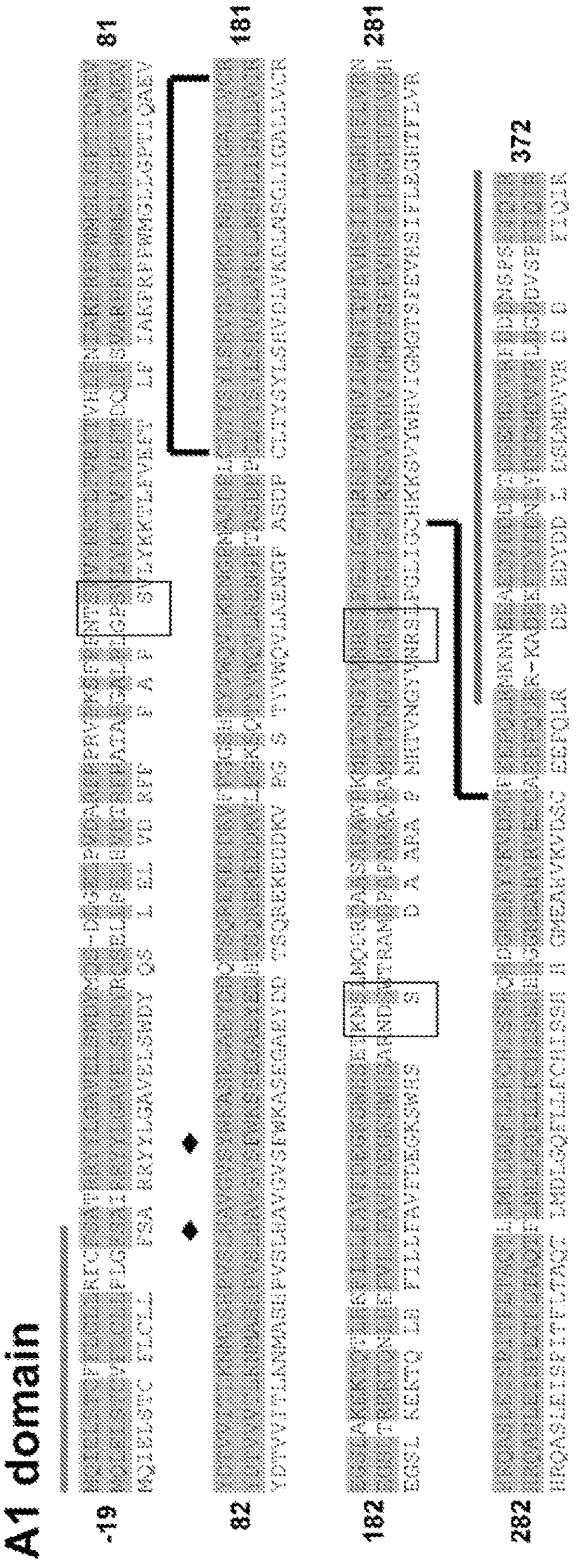
FIGS. 1A and 1B illustrate a sequence alignment of the A1 and A3 domains for human and porcine orthologues of the ET3 variant fVIII protein.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~148 kb), which was created on Apr. 19, 2016 which is incorporated by reference herein.

DETAILED DESCRIPTION

There is a need to develop a safe and efficient gene transfer strategy for the treatment of hemophilia, such as hemophilia A and B, and acquired hemophilia. In the context of gene therapies for the treatment of hemophilia A, several obstacles have hindered the development of using an adeno-associated viral vector as the gene delivery vehicle, such as the limited DNA packaging capacity of the adeno-associated virus for the large fVIII transgene, and inefficient biosynthesis of human fVIII. Reported herein is an AAV-based transgene delivery system that utilizes improvements for the expression of fVIII in the context of liver-directed AAV gene transfer. These include: 1) The use a nucleotide coding sequence that has an improved codon usage bias for the human liver cell compared to the naturally occurring nucleotide sequence of fVIII; 2) Optimization of the codon usage to remove 5'-CG-3' dinucleotides and other deleterious cis-acting DNA motifs, e.g., cryptic splice sites, TATA boxes, terminal signal, mRNA secondary structure, premature polyA signals, RNA instability motifs, internal ribosomal binding sites; and 3) Minimally sized, liver-directed promoters in order to reduce the size of the transgene so it may be used in the size-constrained environment of the adeno-associated viral vector system. The improvements may be generalized for the improved expression of any AAV transgene. In some embodiments, the AAV vector delivers efficacious expression of fVIII at viral doses not predicted to cause toxicity in humans.

In some embodiments, these improvements may be applied to fIX as well, especially for self-complimentary fIX vector designs. Self-complimentary designs have half the packaging capacity is single stranded designs, so vector size limitations (~2.4 kb) become a concern even for fIX.

Prior work suggested that treatment of fVIII-deficient (hemophilia A) mice with an AAV vector encoding a modified form of fVIII (B-domain deleted) termed ET3 at vector doses ranging from $5\times10^{11}$-$2\times10^{13}$ vp/kg could theoretically correct their fVIII deficiency and bleeding phenotype (see Brown et al., "Bioengineered Factor FVIII Enables Long-Term Correction of Murine Hemophilia A Following Liver-Directed Adeno-Associated Viral Vector Delivery," *Molecular Therapy—Methods and Clinical Development.* 1:14036, 2014). However, due the oversized genome of ET3, the vector suffered from low titer manufacture and substantial inter-particle heterogeneity. The large size of the codon optimized ET3-AAV genome remained incompatible with efficient viral vector packaging. For AAV vectors, an AAV genome size of no more than 4.7-5.0 kb is preferred for higher yield and consistency than genomes exceeding 5.0 kb. The B-domain deleted ET3 coding sequence is 4.4 kb. However, with the addition of necessary viral and regulatory control elements, fVIII ET3-AAV genomes substantially exceeded the packaging capacity.

Disclosed herein for the first time is an fVIII (ET3 or other B-domain deleted variant)-AAV genome of less than 5.0 kb in length that was developed to allow for both enhanced fVIII (or variant thereof) expression and efficient viral packaging. Multiple steps were taken to reduce the size of the AAV genome to acceptable levels. For example, a combinatorial transcription factor binding site assembly approach was used to create a panel of liver-specific promoters ranging in size. These promoters represent a 30-90% size reduction over currently utilized liver specific promoters such as HLP and HCR-hAAT, which range in size from 250 to over 700 bases. Some of these promoters drive comparable or better transgene expression levels and specificity to that observed with HLP and HCR-hAAT.

A significant barrier to the development of successful clinical gene transfer-based therapeutics is the availability of naturally occurring or synthetic genetic elements capable of functional, and often cell type-directed or restricted, expression in the context of a vector-delivered nucleic acid cassette (see, e.g., Papadakis et al., "Promoters and control elements: designing expression cassettes for gene therapy," Curr Gene Ther., 4(1):89-113, 2004). It is generally believed that naturally existing promoters have been honed by evolution to drive finely tuned expression through the combination of multiple cis-regulatory sequences. In most living organisms, and especially eukaryotes with large genome sizes, there does not appear to be a driving force to limit promoter size and thus most endogenous promotes are spread over hundreds, and more often thousands, of DNA basepairs (bp). Due to their size, these endogenous, native gene promoters typically are not amenable to inclusion into gene therapy products due to size constraints.

Endogenous viral promoters on the other hand have evolved to possess an efficiency of strength and size than make them attractive for use in gene transfer technologies. Prominent examples include the cytomegalovirus (CMV) immediate early (IE) promoter, the adenovirus (Ad) major late promoter, simian virus 40 (SV40) promoter and Moloney murine leukemia virus (MoMLV) long terminal repeat (LTR). Each of these promoters can drive high-level transcription of exogenous heterologous transgenes in a variety of eukaryotic cell types. However, not surprisingly, eukaryotic cells have developed cellular defense mechanisms to effectively detect and inactivate (i.e. silence) viral promoters and thus these promoters perform more effectively in cell culture model systems than in vivo gene therapy applications.

For these reasons, there has been significant interest in the development of synthetic promoters, either generic (see, e.g., Juven-Gershon et al., "Rational design of a super core promoter that enhances gene expression," Nat Methods, 3(11):917-22, 2006; Schlabach et al., "Synthetic design of strong promoters." *PNAS,* 2010; 107(6):2538-43, 2010), or tailored to specific gene therapy applications including hemophilia A and B (see, e.g., McIntosh et al., "Therapeutic levels of FVIII following a single peripheral vein administration of rAAV vector encoding a novel human factor VIII variant," Blood, 121(17):3335-44, 2013; Nair et al., "Computationally designed liver-specific transcriptional modules and hyperactive factor IX improve hepatic gene therapy," Blood, 123(20):3195-9, 2014).

Knowledge of promoters and enhances remains limited and currently it is not possible to computationally design an optimal promoter with any confidence. Studies such as those described by Juven-Gershon and Kadonaga have made progress defining optimized core promoter designs such as their Super Core Promoter 1 (SCP1) and are informative to the field. However, as we show in promoters described in the examples herein, which do not contain strong similarity to SCP1 in the core promoter domain, these sequences are not necessary for strong promoter function, at least in the context of liver-directed gene therapy applications (see also, Juven-Gershon et al., "Rational design of a super core promoter that enhances gene expression," Nat Methods, 3(11):917-22, 2006).

Most generic promoter development has focused on achieving an optimal balance of transcriptional potency with minimal size. In the field of liver-directed promoter design, the use of rational design approaches by McIntosh et al. and Nair et al. (supra) led to identification of promoters for use in AAV-fVIII and AAV-fIX gene therapy approaches. However despite extensive study, both groups describe promoter designs that are significantly larger (≥252 bp) and no more (or less) potent than those described herein such as SEQ ID NO: 4 (HCB). Indeed, given the prior attempts to optimize promoter design, it was particularly surprising to identify promoters such as those described herein that are smaller that prior art promoters (such as the HLP promoter), yet equivalent or enhanced potency for driving transcription, particularly in the context of in vivo gene therapy applications.

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

5' and/or 3': Nucleic acid molecules (such as, DNA and RNA) are said to have "5' ends" and "3' ends" because mononucleotides are reacted to make polynucleotides in a manner such that the 5' phosphate of one mononucleotide pentose ring is attached to the 3' oxygen of its neighbor in one direction via a phosphodiester linkage. Therefore, one end of a linear polynucleotide is referred to as the "5' end" when its 5' phosphate is not linked to the 3' oxygen of a mononucleotide pentose ring. The other end of a polynucleotide is referred to as the "3' end" when its 3' oxygen is not linked to a 5' phosphate of another mononucleotide pentose ring. Notwithstanding that a 5' phosphate of one mononucleotide pentose ring is attached to the 3' oxygen of its neighbor, an internal nucleic acid sequence also may be said to have 5' and 3' ends.

In either a linear or circular nucleic acid molecule, discrete internal elements are referred to as being "upstream" or 5' of the "downstream" or 3' elements. With regard to DNA, this terminology reflects that transcription proceeds in a 5' to 3' direction along a DNA strand. Promoter and enhancer elements, which direct transcription of a linked gene, are generally located 5' or upstream of the coding region. However, enhancer elements can exert their effect even when located 3' of the promoter element and the coding region. Transcription termination and polyadenylation signals are located 3' or downstream of the coding region.

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 11 recognized serotypes of AAV (AAV1-11).

Administration/Administer: To provide or give a subject an agent, such as a therapeutic agent (e.g. a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Bleeding Time Assay: An assay used to measure the amount of time it takes for a subject's blood to clot. A blood pressure cuff is placed on the upper arm and inflated. Two incisions are made on the lower arm. These are about 10 mm (less than ½ inch) long and 1 mm deep (just deep enough to cause minimal bleeding). The blood pressure cuff is immediately deflated. Blotting paper is touched to the cuts every 30 seconds until the bleeding stops. The length of time it takes for the cuts to stop bleeding is recorded. In normal, non-hemophiliacs, bleeding stops within about one to ten minutes and may vary from lab to lab, depending on how the assay is measured. In contrast, severe hemophiliacs having less than 1% of normal levels of the appropriate clotting factor have a whole blood clotting time of greater than 60 minutes. In mice, the bleeding time is assayed by transecting the tip of the tail and periodically touching a blotting paper until a clot is formed at the tip of the tail. Normal bleeding time is between 2-4 minutes. In contrast, hemophiliac mice having less than 1% of normal levels of the appropriate clotting factor have a bleeding time of greater than 15 minutes.

cDNA (complementary DNA): A piece of DNA lacking internal, non-coding segments (introns) and regulatory sequences that determine transcription. cDNA is synthesized in the laboratory by reverse transcription from messenger RNA extracted from cells. cDNA can also contain untranslated regions (UTRs) that are responsible for translational control in the corresponding RNA molecule.

Clotting disorder: A general term for a wide range of medical problems that lead to poor blood clotting and continuous bleeding. Doctors also refer to clotting disorders by terms such as, for example, coagulopathy, abnormal bleeding and bleeding disorders. Clotting disorders include any congenital, acquired or induced defect that results in abnormal (or pathological) bleeding. Examples include, but are not limited to, disorders of insufficient clotting or hemostasis, such as hemophilia A (a deficiency in fVIII), hemophilia B (a deficiency in fIX), hemophilia C (a deficiency in Factor XI), other clotting factor deficiencies (such as Factor VII or fXIII), abnormal levels of clotting factor inhibitors, platelet disorders, thrombocytopenia, vitamin K deficiency and von Willebrand's disease.

Some clotting disorders are present at birth and in some instances are inherited disorders. Specific examples include, but are not limited to: hemophilia A, hemophilia B, protein C deficiency, and Von Willebrand's disease. Some clotting disorders are developed during certain illnesses (such as vitamin K deficiency, severe liver disease), or treatments (such as use of anticoagulant drugs or prolonged use of antibiotics).

Clotting factor: Includes any protein which promotes proper hemostasis. In one embodiment, a clotting factor is fVIII or fIX, or a variant or fragment thereof which retains its hemostatic activity, for example as measured using an APTT assay or a bleeding time assay. In some embodiments, when administered in a therapeutically effective amount, the clotting factor increases hemostasis in a subject suffering from a clotting disorder, such as hemophilia.

Clotting Factor VIII (fVIII): fVIII is a protein required for the efficient clotting of blood, and functions in coagulation as a cofactor in the activation of factor X by fix. A concentration of about 100 ng/ml for fVIII in the blood is considered in the normal range. Deficiency of fVIII is associated with hemophilia A, and severe forms of the disease can result when a subject has less than about 1% of the normal amount of fVIII (i.e. less than about 1 ng of fVIII per ml of blood). fVIII is synthesized as a 2351 amino acid single chain precursor protein, which is proteolytically processed. The human factor VIII gene (186,000 base-pairs) consists of 26 exons ranging in size from 69 to 3,106 bp and introns as large as 32.4 kilobases (kb). Examples of fVIII nucleic acid and protein sequences are publicly available (for example, see Genbank Accession Nos: K01740, M14113, and E00527). fVIII variants are provided herein that retain fVIII activity for blood clotting but are reduced in size, such as fVIII variants that lack the fVIII B domain Exemplary fVIII variants include the HSQ and ET3 variants.

Clotting Factor IX (fIX): fIX is a vitamin K-dependent protein required for the efficient clotting of blood, and functions in coagulation as an activator of factor X. A concentration of about 1-5 μg/ml of fIX in the blood is considered in the normal range. Deficiency of fIX is associated with hemophilia B, and severe cases result when the concentration of fIX is less than about 1% of the normal concentration of fIX (i.e. less than about 0.01-0.05 μg fIX per ml of blood). fX nucleic acid and protein sequences are publicly available (for example see Kurachi et al., 1982. Proc. Natl. Acad. Sci. U.S.A. 79(21):6461-4; Genbank Accession Nos: J00136, XM045316, K02402, J00137, and M11309.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

The term "liver specific amino acids codons" refers to codons that are differentially utilized-represented in genes highly expressed within the human liver compared to the codon usage of the entire coding region of the human genome. A strategy using a maximum amount of liver specific amino acid codons seeks to avoid codons that are under-represented, e.g., because of low quantities of codon matching tRNA in liver cells resulting in slower protein translation.

Control: A reference standard. In some embodiments, the control is a negative control sample obtained from a healthy patient. In other embodiments, the control is a positive control sample obtained from a patient diagnosed with hemophilia. In still other embodiments, the control is a historical control or standard reference value or range of values (such as a previously tested control sample, such as a group of hemophilia A patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Enhancer: A nucleic acid sequence that increases the rate of transcription by increasing the activity of a promoter.

Flanking: Near or next to, also, including adjoining, for instance in a linear or circular polynucleotide, such as a DNA molecule.

Gene: A nucleic acid sequence, typically a DNA sequence, that comprises control and coding sequences necessary for the transcription of an RNA, whether an mRNA or otherwise. For instance, a gene may comprise a promoter, one or more enhancers or silencers, a nucleic acid sequence that encodes a RNA and/or a polypeptide, downstream regulatory sequences and, possibly, other nucleic acid sequences involved in regulation of the expression of an mRNA.

As is well known in the art, most eukaryotic genes contain both exons and introns. The term “exon” refers to a nucleic acid sequence found in genomic DNA that is bioinformatically predicted and/or experimentally confirmed to contribute a contiguous sequence to a mature mRNA transcript. The term “intron” refers to a nucleic acid sequence found in genomic DNA that is predicted and/or confirmed not to contribute to a mature mRNA transcript, but rather to be “spliced out” during processing of the transcript.

Gene therapy: The introduction of a heterologous nucleic acid molecule into one or more recipient cells, wherein expression of the heterologous nucleic acid in the recipient cell affects the cell’s function and results in a therapeutic effect in a subject. For example, the heterologous nucleic acid molecule may encode a protein, which affects a function of the recipient cell.

Hemophilia: A blood coagulation disorder caused by a deficient clotting factor activity, which decreases hemostasis. Severe forms result when the concentration of clotting factor is less than about 1% of the normal concentration of the clotting factor in a normal subject. In some subjects, hemophilia is due to a genetic mutation which results in impaired expression of a clotting factor. In others, hemophilia is an auto-immune disorder, referred to as acquired hemophilia, in which the antibodies which are generated against a clotting factor in a subject result in decreased hemostasis.

Hemophilia A results from a deficiency of functional clotting fVIII, while hemophilia B results from a deficiency of functional clotting fix. These conditions which are due to a genetic mutation are caused by an inherited sex-linked recessive trait with the defective gene located on the X chromosome, and this disease is therefore generally found only in males. The severity of symptoms can vary with this disease, and the severe forms become apparent early on. Bleeding is the hallmark of the disease and typically occurs when a male infant is circumcised. Additional bleeding manifestations make their appearance when the infant becomes mobile. Mild cases may go unnoticed until later in life when they occur in response to surgery or trauma. Internal bleeding may happen anywhere, and bleeding into joints is common.

Hemostasis: Arrest of bleeding blood by blood clot formation. Blood clotting time is the length of time it takes for peripheral blood to clot using an activated partial thromboplastin time assay (APTT) or by measuring bleeding time. In a particular embodiment, the blood clotting time decreases by at least 50%, for example at least 60%, at least 70%, at least 75%, at least 80%, at least 90%, at least 95%, at least 98%, at least 99% or even about 100% (i.e. the blood clotting time is similar to what is observed for a normal subject) when compared to the blood clotting time of the subject prior to administration of a therapeutic vector encoding the appropriate clotting factor as described herein. In yet another embodiment, the blood clotting time in the affected subject is corrected to about 50% of a normal subject, to about 75% of a normal subject, to about 90% of a normal subject, for example to about 95%, for example about 100%, after oral administration of a therapeutically effective amount of the appropriate clotting factor. As used herein, “about” refers to plus or minus 5% from a reference value. Thus, about 50% refers to 47.5% to 52.5%.

Intron: A stretch of DNA within a gene that does not contain coding information for a protein. Introns are removed before translation of a messenger RNA.

Inverted terminal repeat (ITR): Symmetrical nucleic acid sequences in the genome of adeno-associated viruses required for efficient replication. ITR sequences are located at each end of the AAV DNA genome. The ITRs serve as the origins of replication for viral DNA synthesis and are essential cis components for generating AAV integrating vectors.

Isolated: An “isolated” biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been “isolated” include those purified by standard purification methods. The term also embraces nucleic acid molecules and proteins prepared by recombinant expression in a host cell as well as chemically synthesized nucleic acid molecules and proteins.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term “nucleic acid molecule” as used herein is synonymous with “nucleic acid” and “polynucleotide.” A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. “cDNA” refers to a DNA that is complementary or identical to an mRNA, in either single stranded or double stranded form. “Encoding” refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Nucleotide: This term includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids. These sequences are usually translatable into a peptide.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed vectors.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as vector compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Preventing, treating or ameliorating a disease: "Preventing" a disease (such as hemophilia) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription. A tissue-specific promoter is a promoter that directs/initiated transcription primarily in a single type of tissue or cell. For example, a liver-specific promoter is a promoter that directs/initiates transcription in liver tissue to a substantially greater extent than other tissue types.

Protein: A biological molecule expressed by a gene or other encoding nucleic acid (e.g., a cDNA) and comprised of amino acids.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule. As used herein, "recombinant AAV" refers to an AAV particle in which a recombinant nucleic acid molecule (such as a recombinant nucleic acid molecule encoding a clotting factor) has been packaged.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Response element (RE): A DNA sequence included in a promoter to which one or more transcription factors can bind to and confer an aspect of control of gene expression.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci.*

*USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Subject: Living multi-cellular vertebrate organisms, a category that includes human and non-human mammals.

Synthetic: Produced by artificial means in a laboratory, for example a synthetic nucleic acid can be chemically synthesized in a laboratory.

TATA box: A DNA sequence found in the promoter region of a gene that can be bound by TATA binding protein and transcription factor II D during DNA unwinding and binding by RNA polymerase II. A TATA box sequence typically includes a TATAAA sequence and often includes additional 3' adenine nucleotides. An exemplary TATA box sequence is provided as nucleotides 108-114 of SEQ ID NO: 4.

Therapeutically effective amount: A quantity of a specified pharmaceutical or therapeutic agent (e.g. a recombinant AAV) sufficient to achieve a desired effect in a subject, or in a cell, being treated with the agent. The effective amount of the agent will be dependent on several factors, including, but not limited to the subject or cells being treated, and the manner of administration of the therapeutic composition.

Transcription factor (TF): A protein that binds to specific DNA sequences and thereby controls the transfer (or transcription) of genetic information from DNA to RNA. TFs perform this function alone or with other proteins in a complex, by promoting (as an activator), or blocking (as a repressor) the recruitment of RNA polymerase (the enzyme that performs the transcription of genetic information from DNA to RNA) to specific genes. The specific DNA sequences to which a TF binds is known as a response element (RE) or regulatory element. Other names include cis-element and cis-acting transcriptional regulatory element.

Transcription factors interact with their binding sites using a combination of electrostatic (of which hydrogen bonds are a special case) and Van der Waals forces. Due to the nature of these chemical interactions, most transcription factors bind DNA in a sequence specific manner. However, not all bases in the transcription factor-binding site may actually interact with the transcription factor. In addition, some of these interactions may be weaker than others. Thus, many transcription factors do not bind just one sequence but are capable of binding a subset of closely related sequences, each with a different strength of interaction.

For example, although the consensus binding site for the TATA-binding protein (TBP) is TATAAAA; however, the TBP transcription factor can also bind similar sequences such as TATATAT or TATATAA.

Transcription factors (TFs) are classified based on many aspects. For example, the secondary, tertiary and quaternary structures of the protein structures DNA-binding sequence and properties, the interaction with the double helix of the DNA, and the metal and other binding characteristics. The JASPAR database and TRANSFAC (TRANSFAC® 7.0 Public 2005) are two web-based transcription factor databases, their experimentally-proven binding sites, and regulated genes.

HNF1a: Also called HNF1 Homeobox A or HNF1, the HNF1a protein is a transcription factor required for the expression of several liver specific genes. HNF1a forms a homodimer that binds to particular promoter sequences. Exemplary HNF1a TF binding sites include the "HNF1a" TF binding site provided as nucleotides 1-12 of SEQ ID NO: 4, the "HNF1-1" TF binding site provided as nucleotides 16-23 of SEQ ID NO: 4, and the "HNF1-2" TF binding site provided as nucleotides 48-62 of SEQ ID NO: 4. (See, e.g., PubMed Gene ID NO. 6927; Chi et al., "Diabetes mutations delineate an atypical POU domain in HNF-1alpha," Mol. Cell., 10:1129-1137, 2002; and Rose et al., "Structural basis of dimerization, coactivator recognition and MODY3 mutations in HNF-1alpha," Nat. Struct. Biol. 7:744-748, 2000).

HNF3a: A transcription factor required for the expression of several liver specific genes. HNF3a binds to particular promoter sequences. An exemplary HNF3a TF binding site is provided as nucleotides 39-45 of SEQ ID NO: 4. An exemplary HNF3-2 TF binding site is provided as nucleotides 65-71 of SEQ ID NO: 4. (see, e.g., Laganiere et al., "Location analysis of estrogen receptor alpha target promoters reveals that FOXA1 defines a domain of the estrogen response," Proc. Natl. Acad. Sci. U.S.A. 102:11651-11656, 2005; Williamson et al., "BRCA1 and FOXA1 proteins coregulate the expression of the cell cycle-dependent kinase inhibitor p27(Kip1)," Oncogene 25:1391-1399, 2006; Lupien et al., "FoxA1 translates epigenetic signatures into enhancer-driven lineage-specific transcription," Cell 132:958-970, 2008; Song et al., "Role of Foxa1 in regulation of bcl2 expression during oxidative-stress-induced apoptosis in A549 type II pneumocytes," Cell Stress Chaperones, 14:417-425, 2009); and Malik et al., "Histone deacetylase 7 and FoxA1 in estrogen-mediated repression of RPRM," Mol. Cell. Biol. 30:399-412, 2010).

HNF4: A transcription factor required for the expression of several liver specific genes. HNF4 binds to particular promoter sequences. An exemplary HNF4 TF binding site is provided as nucleotides 26-36 of SEQ ID NO: 4. (See, e.g., Wang et al., "Hepatocyte nuclear factor-4α interacts with other hepatocyte nuclear factors in regulating transthyretin gene expression," FEBS J., 277 (19):4066-75, 2010).

HP1: A transcription factor required for the expression of several liver specific genes. HP1 binds to particular promoter sequences. An exemplary HP1 TF binding site is provided as nucleotides 75-87 of SEQ ID NO: 4. (See, e.g., Schorpp et al., "Hepatocyte-specific promoter element HP1 of the *Xenopus* albumin gene interacts with transcriptional factors of mammalian hepatocytes," J Mol Biol., 202(2):307-20, 1988)

Transcription Start Site: The location where transcription starts at the 5' end of a gene sequence. An exemplary Transcription Start Site is provided as nucleotides 116-146 of SEQ ID NO: 4.

Therapeutically effective amount: The amount of agent, such as a disclosed recombinant AAV vector encoding a clotting factor, that is sufficient to prevent, treat (including prophylaxis), reduce and/or ameliorate the symptoms and/or underlying causes of a disorder or disease, for example to prevent, inhibit, and/or treat hemophilia. For instance, this can be the amount necessary to inhibit or prevent viral replication or to measurably alter outward symptoms of the disease or condition.

In one example, a desired response is to reduce clotting time in a subject (such as a subject with hemophilia), for example as measured using a bleeding time assay. The clotting time does not need to be completely restored to that of normal healthy subjects without hemophilia for the method to be effective. For example, administration of a therapeutically effective amount of a vector (such as a fVIII encoding vector) as disclosed herein can decrease the clotting time (or other symptom of the hemophilia) by a desired amount, for example by at least 20%, at least 30%, at least 40%, at least 50%, at least 60%, at least 70%, at least 80%, at least 90%, at least 95%, at least 98%, at least 100% or more, as compared to a suitable control.

It is understood that to obtain a therapeutic response to the disease or condition can require multiple administrations of the agent. Thus, a therapeutically effective amount encompasses a fractional dose that contributes in combination with previous or subsequent administrations to attaining a therapeutic outcome in the patient. For example, a therapeutically effective amount of an agent can be administered in a single dose, or in several doses, for example daily, during a course of treatment. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an adeno-associated virus (AAV) vector. In some embodiments, the vector is a gamma-retroviral vector, a lentiviral vector, or an adenoviral vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

II. Optimized Promotors for Liver-Directed Transcription

Novel promoters are provided herein for promoting transcription in liver tissue and/or cells. As discussed in Example 2, the new promoters were designed using an iterative approach that ultimately identified several promoter sequences that provide unexpectedly high transcription levels (as assayed by measuring expressed protein activity), and are substantially shorter than prior promoter sequences, such as the HLP promoter sequence.

In some embodiments, a recombinant nucleic acid molecule is provided that comprises a promoter comprising a first response element comprises a set of transcription factor (TF) binding sites, including: a HNF1a TF binding site, a HNF1-1 TF binding site, a HNF4 TF binding site, a HNF3a TF binding site, a HNF1-2 TF binding site, a HNF3-2 TF binding site, a HP1 TF binding site, a TATA box; and a Transcription Start Site. These are the transcription factor binding sites included on the HCB promoter.

In some embodiments, the first response element can comprise a nucleotide sequence that is no more than 160 nucleotides in length (such as no more than 150 nucleotides in length, such as 146 nucleotides in length).

In some embodiments, the HNF1a TF binding site comprises or consists of nucleotides 1-12 of SEQ ID NO: 4; the HNF1-1 TF binding site comprises or consists of nucleotides 16-23 of SEQ ID NO: 4; the HNF4 TF binding site comprises or consists of nucleotides 26-36 of SEQ ID NO: 4; the HNF3a TF binding site comprises or consists of nucleotides 39-45 of SEQ ID NO: 4; the HNF1-2 TF binding site comprises or consists of nucleotides 48-62 of SEQ ID NO: 4; the HNF3-2 TF binding site comprises or consists of nucleotides 65-71 of SEQ ID NO: 4; the HP1 TF binding site comprises or consists of nucleotides 75-87 of SEQ ID NO: 4; the TATA box comprises or consists of nucleotides 108-114 of SEQ ID NO: 4; and/or the Transcription Start Site (TSS) comprises or consists of nucleotides 116-146 of SEQ ID NO: 4.

In some embodiments, the first response element comprises, from 5' to 3', the HNF1a TF binding site, the HNF1-1 TF binding site, the HNF-4 TF binding site, the HNF3a TF binding site, the HNF1-2 TF binding site, the HNF3-2 TF binding site, the HP1 TF binding site, the TATA box, and the Transcription Start Site (TSS).

In some embodiments, the recombinant nucleic acid molecule comprises a promoter comprising or consisting of the nucleic acid sequence set forth as SEQ ID NO: 4 (HCB), or a sequence at least 90% (such as at least 91%, at least 92%, at least 93%, at least 94%, at least 95%, at least 98%, or at least 99%) identical thereto.

In some embodiments, the recombinant nucleic acid molecule can comprise a promoter comprising the first response element as discussed above, and further comprising a second response element.

In some embodiments, the second response element can comprise an HSh response element. For example, a HSh response element comprising or consisting of the nucleotide sequence set forth as SEQ ID NO: 111, or a sequence at least 90% (such as at least 91%, at least 92%, at least 93%, at least 94%, at least 95%, at least 98%, or at least 99%) identical thereto.

In some embodiments, the second response element can comprise a 5'HS response element. For example, a 5'HS response element comprising or consisting of the nucleotide sequence set forth as nucleotides 6-32 of SEQ ID NO: 111, or a sequence at least 90% (such as at least 91%, at least 92%, at least 93%, at least 94%, at least 95%, at least 98%, or at least 99%) identical thereto.

In some embodiments, the second response element can comprise a 3'HS response element. For example, a 3'HS response element comprising or consisting of the nucleotide sequence set forth as nucleotides 44-68 of SEQ ID NO: 111, or a sequence at least 90% (such as at least 91%, at least 92%, at least 93%, at least 94%, at least 95%, at least 98%, or at least 99%) identical thereto.

In some embodiments, the recombinant nucleic acid molecule comprises a promoter comprising or consisting of the nucleic acid sequence set forth as SEQ ID NO: 102 (HSh-HCB), or a sequence at least 90% (such as at least 91%, at least 92%, at least 93%, at least 94%, at least 95%, at least 98%, or at least 99%) identical thereto.

In some embodiments, the recombinant nucleic acid molecule comprises a promoter comprising or consisting of the nucleic acid sequence set forth as SEQ ID NO: 104 (5'HSh-HCB), or a sequence at least 90% (such as at least 91%, at least 92%, at least 93%, at least 94%, at least 95%, at least 98%, or at least 99%) identical thereto.

In some embodiments, the recombinant nucleic acid molecule comprises a promoter comprising or consisting of the nucleic acid sequence set forth as SEQ ID NO: 103 (3'HSh-HCB), In some embodiments, the recombinant nucleic acid molecule comprises a promoter comprising or consisting of the nucleic acid sequence set forth as SEQ ID NO: 7 (ABP-HP1-God-TSS), or a sequence at least 90% (such as at least 91%, at least 92%, at least 93%, at least 94%, at least 95%, at least 98%, or at least 99%) identical thereto.

In some embodiments, the recombinant nucleic acid molecule comprises a promoter comprising or consisting of the nucleic acid sequence set forth as SEQ ID NO: 105 (HSh-SynO-TSS), or a sequence at least 90% (such as at least 91%, at least 92%, at least 93%, at least 94%, at least 95%, at least 98%, or at least 99%) identical thereto.

In some embodiments, the recombinant nucleic acid molecule comprises a promoter comprising or consisting of the nucleic acid sequence set forth as SEQ ID NO: 106 (sHS-SynO-TSS), or a sequence at least 90% (such as at least 91%, at least 92%, at least 93%, at least 94%, at least 95%, at least 98%, or at least 99%) identical thereto.

In some embodiments, the recombinant nucleic acid molecule comprises a promoter comprising or consisting of the nucleic acid sequence set forth as SEQ ID NO: 107 (Agro), or a sequence at least 90% (such as at least 91%, at least 92%, at least 93%, at least 94%, at least 95%, at least 98%, or at least 99%) identical thereto.

In some embodiments, the recombinant nucleic acid molecule comprises a promoter comprising or consisting of the nucleic acid sequence set forth as SEQ ID NO: 108 (HS-SynO-TSS), or a sequence at least 90% (such as at least 91%, at least 92%, at least 93%, at least 94%, at least 95%, at least 98%, or at least 99%) identical thereto.

In some embodiments, the recombinant nucleic acid molecule comprises a promoter comprising or consisting of the nucleic acid sequence set forth as SEQ ID NO: 112 (HNF1-ShortABPExact-SynO-TSS-Int), or a sequence at least 90% (such as at least 91%, at least 92%, at least 93%, at least 94%, at least 95%, at least 98%, or at least 99%) identical thereto.

In some embodiments, the recombinant nucleic acid molecule comprises a promoter comprising or consisting of the nucleic acid sequence set forth as SEQ ID NO: 5 (shortABP-HP1-God-TSS), or a sequence at least 90% (such as at least 91%, at least 92%, at least 93%, at least 94%, at least 95%, at least 98%, or at least 99%) identical thereto.

In some embodiments, the recombinant nucleic acid molecule comprises a promoter comprising or consisting of the nucleic acid sequence set forth as SEQ ID NO: 7 (ABP-HP1-God-TSS), or a sequence at least 90% (such as at least 91%, at least 92%, at least 93%, at least 94%, at least 95%, at least 98%, or at least 99%) identical thereto.

The disclosed promoters can be utilized in any situation where liver-specific transcription is desired. In several embodiments, any one of the disclosed promoters can be included on a vector (such as an AAV vector) for gene therapy methods where liver-specific expression of a transgene is desired, such as liver specific expression of a clotting factor as disclosed herein.

III. Recombinant Nucleic Acid Molecules Encoding Clotting Factors

The blood clotting system is a proteolytic cascade. Blood clotting factors are present in the plasma as a zymogen, in other words in an inactive form, which on activation undergoes proteolytic cleavage to release the active factor form the precursor molecule. The ultimate goal is to produce thrombin. Thrombin converts fibrinogen into fibrin, which forms a clot.

Factor X is the first molecule of the common pathway and is activated by a complex of molecules containing activated fix, fVIII, calcium, and phospholipids which are on the platelet surface. FVIII is activated by thrombin, and it facilitates the activation of factor X by fIXa. FVIII, contains multiple domains (A1-A2-B-ap-A3-C1-C2) and circulates in blood in an inactivated form bound to von Willebrand factor (VWF). The C2 domain is involved with fVIII binding to VWF. Thrombin cleaves fVIII causing dissociation with VWF ultimately leading to fibrin formation through fIX. Congenital hemophilia A is associated with genetic mutations in the fVIII gene and results in impaired clotting due to lower than normal levels of circulating fVIII. Hemophilia B is similarly associated with genetic mutations in the fIX gene.

FVIII domain boundaries refer to the human fVIII amino acid sequence numbering as follows; residues 1-19 (Signal Sequence), 20-391 (A1), 392-759 (A2), 760-1667 (B), 1668-1708 (ap), 1709-2038 (A3), 2039-2191 (C1) and 2192-2351 (C2) (see Gitschier et al., Nature, 1984, 312, 326-330) of SEQ ID NO: 1:

```
MQIELSTCFFLCLLRFCFSATRRYYLGAVELSWDYMQSDLGELPVDARFP
PRVPKSFPFNTSVVYKKTLFVEFTDHLFNIAKPRPPWMGLLGPTIQAEVY
DTVVITLKNMASHPVSLHAVGVSYWKASEGAEYDDQTSQREKEDDKVFPG
GSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKM
HTVNGYVNRSLPGLIGCHRKSVYWHVIGMGTTPEVHSIFLEGHTFLVRNH
RQASLEISPITFLTAQTLLMDLGQFLLFCHISSHQHDGMEAYVKVDSCPE
EPQLRMKNNEEAEDYDDDLTDSEMDVVRFDDDNSPSFIQIRSVAKKHPKT
WVHYIAAEEEDWDYAPLVLAPDDRSYKSQYLNNGPQRIGRKYKKVRFMAY
TDETFKTREAIQHESGILGPLLYGEVGDTLLIIFKNQASRPYNIYPHGIT
DVRPLYSRRLPKGVKHLKDFPILPGEIFKYKWTVTVEDGPTKSDPRCLTR
YYSSFVNMERDLASGLIGPLLICYKESVDQRGNQIMSDKRNVILFSVFDE
```

-continued

```
NRSWYLTENIQRFLPNPAGVQLEDPEFQASNIMHSINGYVFDSLQLSVCL

HEVAYWYILSIGAQTDFLSVFFSGYTFKHKMVYEDTLTLFPFSGETVFMS

MENPGLWILGCHNSDFRNRGMTALLKVSSCDKNTGDYYEDSYEDISAYLL

SKNNAIEPRSFSQNSRHPSTRQKQFNATTIPENDIEKTDPWFAHRTPMPK

IQNVSSSDLLMLLRQSPTPHGLSLSDLQEAKYETFSDDPSPGAIDSNNSL

SEMTHFRPQLHHSGDMVFTPESGLQLRLNEKLGTTAATELKKLDFKVSST

SNNLISTIPSDNLAAGTDNTSSLGPPSMPVHYDSQLDTTLFGKKSSPLTE

SGGPLSLSEENNDSKLLESGLMNSQESSWGKNVSSTESGRLFKGKRAHGP

ALLTKDNALFKVSISLLKTNKTSNNSATNRKTHIDGPSLLIENSPSVWQN

ILESDTEFKKVTPLIHDRMLMDKNATALRLNHMSNKTTSSKNMEMVQQKK

EGPIPPDAQNPDMSFFKMLFLPESARWIQRTHGKNSLNSGQGPSPKQLVS

LGPEKSVEGQNFLSEKNKVVVGKGEFTKDVGLKEMVFPSSRNLFLTNLDN

LHENNTHNQEKKIQEEIEKKETLIQENVVLPQIHTVTGTKNFMKNLFLLS

TRQNVEGSYDGAYAPVLQDFRSLNDSTNRTKKHTAHFSKKGEEENLEGLG

NQTKQIVEKYACTTRISPNTSQQNFVTQRSKRALKQFRLPLEETELEKRI

IVDDTSTQWSKNMKHLTPSTLTQIDYNEKEKGAITQSPLSDCLTRSHSIP

QANRSPLPIAKVSSFPSIRPIYLTRVLFQDNSSHLPAASYRKKDSGVQES

SHFLQGAKKNNLSLAILTLEMTGDQREVGSLGTSATNSVTYKKVENTVLP

KPDLPKTSGKVELLPKVHIYQKDLFPTETSNGSPGHLDLVEGSLLQGTEG

AIKWNEANRPGKVPFLRVATESSAKTPSKLLDPLAWDNHYGTQIPKEEWK

SQEKSPEKTAFKKKDTILSLNACESNHAIAAINEGQNKPEIEVTWAKQGR

TERLCSQNPPVLKRHQREITRTTLQSDQEEIDYDDTISVEMKKEDFDIYD

EDENQSPRSFQKKTRHYFIAAVERLWDYGMSSSPHVLRNRAQSGSVPQFK

KVVFQEFTDGSFTQPLYRGELNEHLGLLGPYIRAEVEDNIMVTFRNQASR

PYSFYSSLISYEEDQRQGAEPRKNFVKPNETKTYFWKVQHHMAPTKDEFD

CKAWAYFSDVDLEKDVHSGLIGPLLVCHTNTLNPAHGRQVTVQEFALFFT

IFDETKSWYFTENMERNCRAPCNIQMEDPTFKENYRFHAINGYIMDTLPG

LVMAQDQRIRWYLLSMGSNENIHSIHFSGHVFTVRKKEEYKMALYNLYPG

VFETVEMLPSKAGIWRVECLIGEHLHAGMSTLFLVYSNKCQTPLGMASGH

IRDFQITASGQYGQWAPKLARLHYSGSINAWSTKEPFSWIKVDLLAPMII

HGIKTQGARQKFSSLYISQFIIMYSLDGKKWQTYRGNSTGTLMVFFGNVD

SSGIKHNIFNPPIIARYIRLHPTHYSIRSTLRMELMGCDLNSCSMPLGME

SKAISDAQITASSYFTNMFATWSPSKARLHLQGRSNAWRPQVNNPKEWLQ

VDFQKTMKVTGVTTQGVKSLLTSMYVKEFLISSSQDGHQWTLFFQNGKVK

VFQGNQDSFTPVVNSLDPPLLTRYLRIHPQSWVHQIALRMEVLGCEAQDL

Y
```

As discussed in Example 1, the cDNA nucleotide sequences coding for fVIII variants ET3 and HSQ were improved by implementing a codon usage bias specific for the human liver cell as compared to naturally occurring nucleotide sequence coding for the corresponding non-codon optimized sequence for a human. Additional changes were also made to improve translation efficacy, such as optimization of GC content, mRNA secondary structure, premature PolyA sites, RNA instability motif, stable free energy of mRNA, internal chi sites, ribosomal binding sites, cryptic splicing sites, negative CpG islands, SD sequence, TATA boxes, and cyptic terminal signals.

In addition, CpG DNA motifs were removed because they may lead to gene methylation and silencing. See Bird, DNA methylation and the frequency of CpG in animal DNA, 1980, Nucleic Acids Res, 8: 1499-1504. Codons were substituted with the most highly used human/liver alternative that did not result in the formation of a 5'-CG-3' dinucleotide in the sequence. CpG removal can also reduce any immune response to a vector including the modified transgene, enhancing the safety and efficacy of the vector. See J Clin Invest. 2013, 123(7):2994-3001, entitled "CpG-depleted adeno-associated virus vectors evade immune detection."

Figure 1B:
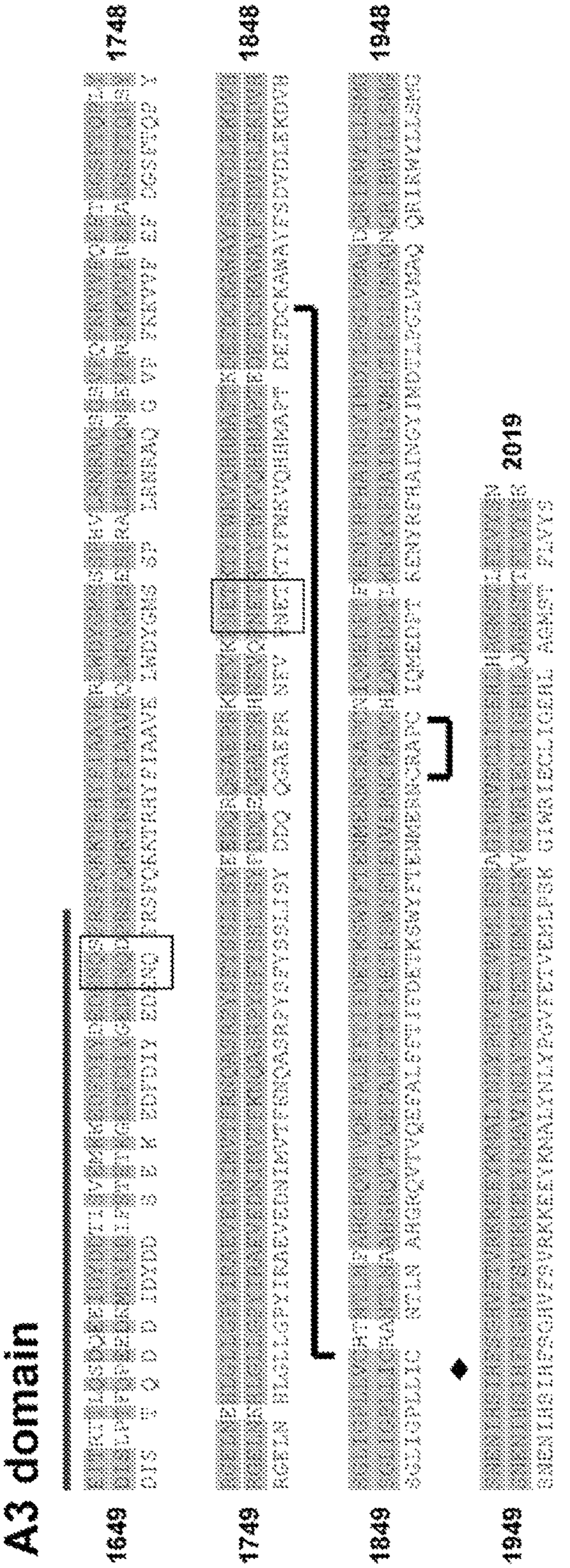

ET3 is a B domain deleted (BDD) fVIII hybrid that contains human and porcine domains, i.e., sequence (A1 and A3 porcine, see FIGS. 1A and 1B) with a linker in the deleted B domain ET3 utilizes a 24 amino acid porcine sequence-derived OL linker sequence, i.e., porcine-derived sequence SFAQNSRPPSASAPKPPVLRRHQR (SEQ ID NO: 23). HSQ is a human fVIII variant wherein the BDD human fVIII protein is substituted with a 14 amino acid human-derived SQ linker SFSQNPPVLKRHQR (SEQ ID NO: 22). HSQ amino acid sequence is provided as SEQ ID NO: 3. Both HSQ and ET3 contain the RHQR (SEQ ID NO: 24) recognition sequence for PACE/furin processing sequence for the B-domain.

As discussed in Example 1, the nucleotide sequence encoding ET3 was codon-optimized for expression in human liver. An exemplary liver codon optimized ET3 sequence is provided as SEQ ID NO: 12. In some embodiments, a recombinant nucleic acid molecule is provided comprising the nucleotide sequence set forth as SEQ ID NO: 12, or a sequence at least 90% (such as at least 95%) identical thereto. Further, CpG motifs within the codon-optimized ET3 sequence were removed, to provide the CpG deleted, liver codon optimized ET3 sequence set forth as SEQ ID NO: 11. In some embodiments, a recombinant nucleic acid molecule is provided comprising the nucleotide sequence set forth as SEQ ID NO: 11, or a sequence at least 90% (such as at least 95%) identical thereto.

As discussed in Example 1, the nucleotide sequence encoding HSQ was codon-optimized for expression in human liver. Further, CpG motifs within the codon-optimized HSQ sequence were removed, to provide the CpG deleted, liver codon optimized HSQ sequence set forth as SEQ ID NO: 2. In some embodiments, a recombinant nucleic acid molecule is provided comprising the nucleotide sequence set forth as SEQ ID NO: 2, or a sequence at least 90% (such as at least 95%) identical thereto.

Additionally, the nucleotide sequences encoding ET3 and HSQ were optimized for expression in myeloid cells. An exemplary CpG deleted, myeloid codon-optimized ET3 sequence is provided as SEQ ID NO: 125. In some embodiments, a recombinant nucleic acid molecule is provided comprising the nucleotide sequence set forth as SEQ ID NO: 125, or a sequence at least 90% (such as at least 95%) identical thereto. An exemplary CpG deleted, myeloid codon-optimized HSQ sequence is provided as SEQ ID NO: 126. In some embodiments, a recombinant nucleic acid molecule is provided comprising the nucleotide sequence set forth as SEQ ID NO: 126, or a sequence at least 90% (such as at least 95%) identical thereto.

In additional embodiments, fIX coding sequence variants are provided that are designed for high levels of expression when the transgene is expressed from the liver, which is the target tissue of many fIX-targeted gene therapy strategies. To create this coding sequence, one utilizes a liver-directed codon optimization strategy.

As discussed in Example 1, the nucleotide sequence coding for fIX was optimized by implementing a codon usage bias specific for the human liver cell as compared to naturally occurring nucleotide sequence coding for the corresponding non-codon optimized sequence for a human Additional changes were also made to improve Translation efficacy, such as optimization of GC content, mRNA secondary structure, premature PolyA sites, RNA instability motif, stable free energy of mRNA, internal chi sites, ribosomal binding sites, cryptic splicing sites, negative CpG islands, SD sequence, TATA boxes, and cyptic terminal signals.

In addition to adjusting the codon usage bias, the resulting sequences are further modified to remove CpG motifs which may inhibit efficient expression of the transgene. Further, in some embodiments, the recombinant fIX nucleic acid molecule can encode fIX with the K5A mutation (Darrel Stafford collagen binding mutation, Gui et al. Blood. 2002, 100(1):153-8). In certain embodiments, the recombinant fIX nucleic acid molecule can encode fIX with the R338L mutation (Padua mutation), which is a naturally occurring gain of function mutation that has been shown to improve the specific activity of fIX by 8-fold. Sequence variants were additionally created to reflect two major polymorphisms of fIX at residue 148, including alanine or threonine. In some embodiments, these fIX sequences may be grafted into liver-directed AAV as either single-stranded or self-complimentary double stranded transgene designs.

Exemplary recombinant nucleic acid sequences encoding fVIII or fIX proteins, or variants thereof, that are modified for tissue-specific expression are discussed in Example 1.

SEQ ID NO: 12 provides an exemplary liver codon optimized ET3 sequence. In some embodiments, a recombinant nucleic acid molecule is provided that comprises or consists of the nucleic acid sequence set forth as SEQ ID NO: 12, or a sequence at least 90% (such as at least 95%) identical thereto.

SEQ ID NO: 11 provides an exemplary CpG deleted, liver codon optimized ET3 sequence. In some embodiments, a recombinant nucleic acid molecule is provided that comprises or consists of the nucleic acid sequence set forth as SEQ ID NO: 11, or a sequence at least 90% (such as at least 95%) identical thereto.

SEQ ID NO: 2 provides an exemplary CpG deleted, liver codon optimized HSQ sequence. In some embodiments, a recombinant nucleic acid molecule is provided that comprises or consists of the nucleic acid sequence set forth as SEQ ID NO: 2, or a sequence at least 90% (such as at least 95%) identical thereto.

SEQ ID NO: 125 provides an exemplary CpG deleted, myeloid codon optimized ET3 sequence. In some embodiments, a recombinant nucleic acid molecule is provided that comprises or consists of the nucleic acid sequence set forth as SEQ ID NO: 125, or a sequence at least 90% (such as at least 95%) identical thereto.

SEQ ID NO: 126 provides an exemplary CpG deleted, myeloid codon optimized HSQ sequence. In some embodiments, a recombinant nucleic acid molecule is provided that comprises or consists of the nucleic acid sequence set forth as SEQ ID NO: 125, or a sequence at least 90% (such as at least 95%) identical thereto.

Exemplary recombinant nucleic acid sequences encoding fIX proteins, or variants thereof, that are modified for tissue-specific expression are discussed in Example 1.

SEQ ID NO: 124 provides an exemplary liver codon optimized fIX sequence with Padua/Malmo mutations and no CpG. In some embodiments, a recombinant nucleic acid molecule is provided that comprises or consists of the nucleic acid sequence set forth as SEQ ID NO: 124, or a sequence at least 90% (such as at least 95%) identical thereto.

SEQ ID NO: 8 provides an exemplary liver-codon optimized fIX sequence with no CpG and encoding A582 modifications. In some embodiments, a recombinant nucleic acid molecule is provided that comprises or consists of the nucleic acid sequence set forth as SEQ ID NO: 8, or a sequence at least 90% (such as at least 95%) identical thereto.

SEQ ID NO: 9 provides an exemplary liver codon optimized fIX sequence with no CpG and including Padua and A582 modifications. In some embodiments, a recombinant nucleic acid molecule is provided that comprises or consists of the nucleic acid sequence set forth as SEQ ID NO: 9, or a sequence at least 90% (such as at least 95%) identical thereto.

SEQ ID NO: 10 provides an exemplary liver codon optimized fIX sequence with Padua/Malmo mutations and no CpG. In some embodiments, a recombinant nucleic acid molecule is provided that comprises or consists of the nucleic acid sequence set forth as SEQ ID NO:10, or a sequence at least 90% (such as at least 95%) identical thereto.

SEQ ID NO: 127 provides an exemplary human codon optimized fIX sequence with Padua/Malmo mutations and no CpG. In some embodiments, a recombinant nucleic acid molecule is provided that comprises or consists of the nucleic acid sequence set forth as SEQ ID NO:127, or a sequence at least 90% (such as at least 95%) identical thereto.

Any of the above discussed recombinant nucleic acid molecules encoding a fVIII or fIX protein, or variant thereof, can be included in an vector (such as a AAV vector) as described herein for embodiments where expression of a fVIII or FIX protein or variant thereof is of interest.

In some embodiments, an isolated protein is provided comprising an amino acid sequence encoded by one of SEQ ID NOs: 8, 9, or 10, such as the amino acid sequences set forth as SEQ ID NOs: 17-18 below. In some embodiments, an isolated protein is provided comprising an amino acid sequence set forth as SEQ ID NO: 17, or an amino acid sequence at least 90% (such as at least 95%) identical thereto having fIX activity. In some embodiments, an isolated protein is provided comprising an amino acid sequence set forth as SEQ ID NO: 18, or an amino acid sequence at least 90% (such as at least 95%) identical thereto having fIX activity. In some embodiments, an isolated protein is provided comprising an amino acid sequence set forth as SEQ ID NO: 19, or an amino acid sequence at least 90% (such as at least 95%) identical thereto having fIX activity.

```
SEQ ID NO: 8 encodes the amino acid sequence set
forth as SEQ ID NO: 17:
MQRVNMIMAESPGLITICLLGYLLSAECTVFLDHENANKILNRPKRYNSG

KLEEFVQGNLERECMEEKCSFEEAREVFENTERTTEFWKQYVDGDQCESN

PCLNGGSCKDDINSYECWCPFGFEGKNCELDVTCNIKNGRCEQFCKNSAD

NKVVCSCTEGYRLAENQKSCEPAVPFPCGRVSVSQTSKLTRAEAVFPDVD

YVNSTEAETILDNITQSTQSFNDFTRVVGGEDAKPGQFPWQVVLNGKVDA
```

-continued

FCGGSIVNEKWIVTAAHCVETGVKITVVAGEHNIEETEHTEQKRNVIRII

PHHNYNAAINKYNHDIALLELDEPLVLNSYVTPICIADKEYTNIFLKFGS

GYVSGWGRVFHKGRSALVLQYLRVPLVDRATCLRSTKFTIYNNMFCAGFH

EGGRDSCQGDSGGPHVTEVEGTSFLTGIISWGEECAMKGKYGIYTKVSRY

VNWIKEKTKLT

SEQ ID NO: 9 encodes the amino acid sequence set forth as SEQ ID NO: 18:
MQRVNMIMAESPGLITICLLGYLLSAECTVFLDHENANKILNRPKRYNSG

KLEEFVQGNLERECMEEKCSFEEAREVFENTERTTEFWKQYVDGDQCESN

PCLNGGSCKDDINSYECWCPFGFEGKNCELDVTCNIKNGRCEQFCKNSAD

NKVVCSCTEGYRLAENQKSCEPAVPFPCGRVSVSQTSKLTRAEAVFPDVD

YVNSTEAETILDNITQSTQSFNDFTRVVGGEDAKPGQFPWQVVLNGKVDA

FCGGSIVNEKWIVTAAHCVETGVKITVVAGEHNIEETEHTEQKRNVIRII

PHHNYNAAINKYNHDIALLELDEPLVLNSYVTPICIADKEYTNIFLKFGS

GYVSGWGRVFHKGRSALVLQYLRVPLVDRATCLLSTKFTIYNNMFCAGFH

EGGRDSCQGDSGGPHVTEVEGTSFLTGIISWGEECAMKGKYGIYTKVSRY

VNWIKEKTKLT

SEQ ID NO: 10 encodes the amino acid sequence set forth as SEQ ID NO: 19:
MQRVNMIMAESPGLITICLLGYLLSAECTVFLDHENANKILNRPKRYNSG

KLEEFVQGNLERECMEEKCSFEEAREVFENTERTTEFWKQYVDGDQCESN

PCLNGGSCKDDINSYECWCPFGFEGKNCELDVTCNIKNGRCEQFCKNSAD

NKVVCSCTEGYRLAENQKSCEPAVPFPCGRVSVSQTSKLTRAETVFPDVD

YVNSTEAETILDNITQSTQSFNDFTRVVGGEDAKPGQFPWQVVLNGKVDA

FCGGSIVNEKWIVTAAHCVETGVKITVVAGEHNIEETEHTEQKRNVIRII

PHHNYNAAINKYNHDIALLELDEPLVLNSYVTPICIADKEYTNIFLKFGS

GYVSGWGRVFHKGRSALVLQYLRVPLVDRATCLLSTKFTIYNNMFCAGFH

EGGRDSCQGDSGGPHVTEVEGTSFLTGIISWGEECAMKGKYGIYTKVSRY

VNWIKEKTKLT

Exemplary nucleic acids can be prepared by cloning techniques, or can be generated synthetically. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

IV. Recombinant Vectors and Gene Therapy Applications

The nucleic acid and promotor sequences disclosed herein are useful in production of vectors (such as rAAV vectors), and are also useful as antisense delivery vectors, gene therapy vectors, or vaccine vectors. In certain embodiments, the disclosure provides for gene delivery vectors, and host cells which contain the nucleic acid sequences disclosed herein. In some embodiments, the selected vector may be delivered to a subject by any suitable method, including intravenous injection, ex-vivo transduction, transfection, electroporation, liposome delivery, membrane fusion techniques, high velocity DNA-coated pellets, viral infection, or protoplast fusion, to introduce a transgene into the subject.

In certain embodiments, the disclosure relates to virus particle, e.g., capsids, containing the nucleic acid sequences encoding promotors and proteins disclosed herein. The virus particles, capsids, and recombinant vectors are useful in delivery of a heterologous gene or other nucleic acid sequences to a target cell. The nucleic acids may be readily utilized in a variety of vector systems, capsids, and host cells. In certain embodiments, the nucleic acids are in vectors contained within a capsid comprising cap proteins, including AAV capsid proteins vp1, vp2, vp3 and hypervariable regions.

In certain embodiments, the nucleic acids disclosed herein may be a part of any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon.

In certain embodiments, a vector may be a lentivirus based (containing lentiviral genes or sequences) vector, e.g., having nucleic acid sequences derived from VSVG or GP64 pseudotypes or both. In certain embodiments, the nucleic acid sequences derived from VSVG or GP64 pseudotypes may be at least one or two or more genes or gene fragments of more than 1000, 500, 400, 300, 200, 100, 50, or 25 continuous nucleotides or nucleotides sequences with greater than 50, 60, 70, 80, 90, 95 or 99% identity to the gene or fragment.

In some embodiments, a method of inducing blood clotting in a subject in need thereof is provided. The method comprises administering to the subject a therapeutically effective amount of a vector (such as an AAV vector) encoding a clotting factor as described herein. In some embodiments, the subject is a subject with a clotting disorder, such as hemophilia A or hemophilia B. In some embodiments, the clotting disorder is hemophilia A and the subject is administered a vector comprising a nucleic acid molecule encoding a protein with fVIII activity. In other embodiments, the clotting disorder is hemophilia B and the subject is administered a vector comprising a nucleic acid molecule encoding a protein with fIX activity.

In some embodiments, the nucleic acid and promotor sequences disclosed herein are useful in production of AAV vectors. AAV belongs to the family Parvoviridae and the genus Dependovirus. AAV is a small, non-enveloped virus that packages a linear, single-stranded DNA genome. Both sense and antisense strands of AAV DNA are packaged into AAV capsids with equal frequency.

The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, *Clin Microbiol Rev* 21(4):583-593, 2008).

The left ORF of AAV contains the Rep gene, which encodes four proteins—Rep78, Rep 68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21(4):583-593, 2008).

AAV vectors typically contain a transgene expression cassette between the ITRs that replaces the rep and cap genes. Vector particles are produced by the co-transfection of cells with a plasmid containing the vector genome and a packaging/helper construct that expresses the rep and cap proteins in trans. During infection, AAV vector genomes enter the cell nucleus and can persist in multiple molecular states. One common outcome is the conversion of the AAV genome to a double-stranded circular episome by second-strand synthesis or complementary strand pairing.

In the context of AAV vectors, the disclosed vectors typically have a recombinant genome comprising the following structure:

(5'AAV ITR)-(promoter)-(transgene)-(3'AAV ITR)

As discussed above, these recombinant AAV vectors contain a transgene expression cassette between the ITRs that replaces the rep and cap genes. Vector particles are produced, for example, by the co-transfection of cells with a plasmid containing the recombinant vector genome and a packaging/helper construct that expresses the rep and cap proteins in trans. For example, in some embodiments, the recombinant AAV vector can have a genome with a structure set forth as one of:

(5'AAV ITR)-(HCB)-(transgene)-(3'AAV ITR)
(5'AAV ITR)-(HCB)-(fVIII)-(3'AAV ITR)
(5'AAV ITR)-(HCB)-(fVIII-B-domain deleted)-(3'AAV ITR)
(5'AAV ITR)-(HCB)-(ET3)-(3'AAV ITR)
(5'AAV ITR)-(HCB)-(ET3, Seq_12)-(3'AAV ITR)
(5'AAV ITR)-(HCB)-(ET3, Seq_11)-(3'AAV ITR)
(5'AAV ITR)-(HCB)-(HSQ)-(3'AAV ITR)
(5'AAV ITR)-(HCB)-(HSQ, Seq_2)-(3'AAV ITR)
(5'AAV ITR)-(HCB)-(fIX)-(3'AAV ITR)
(5'AAV ITR)-(HCB)-(fIX, Seq_124)-(3'AAV ITR)
(5'AAV ITR)-(HCB)-(fIX, Seq_8)-(3'AAV ITR)
(5'AAV ITR)-(HCB)-(fIX, Seq_9)-(3'AAV ITR)
(5'AAV ITR)-(HCB)-(fIX, Seq_10)-(3'AAV ITR)
(5'AAV ITR)-(HSh-HCB)-(transgene)-(3'AAV ITR)
(5'AAV ITR)-(HSh-HCB)-(fVIII)-(3'AAV ITR)
(5'AAV ITR)-(HSh-HCB)-(fVIII-B-domain deleted)-(3'AAV ITR)
(5'AAV ITR)-(HSh-HCB)-(ET3)-(3'AAV ITR)
(5'AAV ITR)-(HSh-HCB)-(ET3, Seq_12)-(3'AAV ITR)
(5'AAV ITR)-(HSh-HCB)-(ET3, Seq_11)-(3'AAV ITR)
(5'AAV ITR)-(HSh-HCB)-(HSQ)-(3'AAV ITR)
(5'AAV ITR)-(HSh-HCB)-(HSQ, Seq_2)-(3'AAV ITR)
(5'AAV ITR)-(HSh-HCB)-(fIX)-(3'AAV ITR)
(5'AAV ITR)-(HSh-HCB)-(fIX, Seq_124)-(3'AAV ITR)
(5'AAV ITR)-(HSh-HCB)-(fIX, Seq_8)-(3'AAV ITR)
(5'AAV ITR)-(HSh-HCB)-(fIX, Seq_9)-(3'AAV ITR)
(5'AAV ITR)-(HSh-HCB)-(fIX, Seq_10)-(3'AAV ITR)
(5'AAV ITR)-(5'HSh-HCB)-(transgene)-(3'AAV ITR)
(5'AAV ITR)-(5'HSh-HCB)-(fVIII-B-domain deleted)-(3'AAV ITR)
(5'AAV ITR)-(5'HSh-HCB)-(ET3)-(3'AAV ITR)
(5'AAV ITR)-(5'HSh-HCB)-(ET3, Seq_12)-(3'AAV ITR)
(5'AAV ITR)-(5'HSh-HCB)-(ET3, Seq_11)-(3'AAV ITR)
(5'AAV ITR)-(5'HSh-HCB)-(HSQ)-(3'AAV ITR)
(5'AAV ITR)-(5'HSh-HCB)-(HSQ, Seq_2)-(3'AAV ITR)
(5'AAV ITR)-(5'HSh-HCB)-(fIX)-(3'AAV ITR)
(5'AAV ITR)-(5'HSh-HCB)-(fIX, Seq_124)-(3'AAV ITR)
(5'AAV ITR)-(5'HSh-HCB)-(fIX, Seq_8)-(3'AAV ITR)
(5'AAV ITR)-(5'HSh-HCB)-(fIX, Seq_9)-(3'AAV ITR)
(5'AAV ITR)-(5'HSh-HCB)-(fIX, Seq_10)-(3'AAV ITR)
(5'AAV ITR)-(3'HSh-HCB)-(transgene)-(3'AAV ITR)
(5'AAV ITR)-(3'HSh-HCB)-(fVIII)-(3'AAV ITR)
(5'AAV ITR)-(3'HSh-HCB)-(fVIII-B-domain deleted)-(3'AAV ITR)
(5'AAV ITR)-(3'HSh-HCB)-(ET3)-(3'AAV ITR)
(5'AAV ITR)-(3'HSh-HCB)-(ET3, Seq_12)-(3'AAV ITR)
(5'AAV ITR)-(3'HSh-HCB)-(ET3, Seq_11)-(3'AAV ITR)
(5'AAV ITR)-(3'HSh-HCB)-(HSQ)-(3'AAV ITR)
(5'AAV ITR)-(3'HSh-HCB)-(HSQ, Seq_2)-(3'AAV ITR)
(5'AAV ITR)-(3'HSh-HCB)-(fIX)-(3'AAV ITR)
(5'AAV ITR)-(3'HSh-HCB)-(fIX, Seq_124)-(3'AAV ITR)
(5'AAV ITR)-(3'HSh-HCB)-(fIX, Seq_8)-(3'AAV ITR)
(5'AAV ITR)-(3'HSh-HCB)-(fIX, Seq_9)-(3'AAV ITR)
(5'AAV ITR)-(3'HSh-HCB)-(fIX, Seq_10)-(3'AAV ITR)
(5'AAV ITR)-(ABP-HP1-God-TSS)-(transgene)-(3'AAV ITR)
(5'AAV ITR)-(ABP-HP1-God-TSS)-(fVIII)-(3'AAV ITR)
(5'AAV ITR)-(ABP-HP1-God-TSS)-(fVIII-B-domain deleted)-(3'AAV ITR)
(5'AAV ITR)-(ABP-HP1-God-TSS)-(ET3)-(3'AAV ITR)
(5'AAV ITR)-(ABP-HP1-God-TSS)-(ET3, Seq_12)-(3'AAV ITR)
(5'AAV ITR)-(ABP-HP1-God-TSS)-(ET3, Seq_11)-(3'AAV ITR)
(5'AAV ITR)-(ABP-HP1-God-TSS)-(HSQ)-(3'AAV ITR)
(5'AAV ITR)-(ABP-HP1-God-TSS)-(HSQ, Seq_2)-(3'AAV ITR)
(5'AAV ITR)-(ABP-HP1-God-TSS)-(fIX)-(3'AAV ITR)
(5'AAV ITR)-(ABP-HP1-God-TSS)-(fIX, Seq_124)-(3'AAV ITR)
(5'AAV ITR)-(ABP-HP1-God-TSS)-(fIX, Seq_8)-(3'AAV ITR)
(5'AAV ITR)-(ABP-HP1-God-TSS)-(fIX, Seq_9)-(3'AAV ITR)
(5'AAV ITR)-(ABP-HP1-God-TSS)-(fIX, Seq_10)-(3'AAV ITR)
(5'AAV ITR)-(HSh-SynO-TSS)-(transgene)-(3'AAV ITR)
(5'AAV ITR)-(HSh-SynO-TSS)-(fVIII)-(3'AAV ITR)

(5'AAV ITR)-(HSh-SynO-TSS)-(fVIII-B-domain deleted)-(3'AAV ITR)
(5'AAV ITR)-(HSh-SynO-TSS)-(ET3)-(3'AAV ITR)
(5'AAV ITR)-(HSh-SynO-TSS)-(ET3, Seq_12)-(3'AAV ITR)
(5'AAV ITR)-(HSh-SynO-TSS)-(ET3, Seq_11)-(3'AAV ITR)
(5'AAV ITR)-(HSh-SynO-TSS)-(HSQ)-(3'AAV ITR)
(5'AAV ITR)-(HSh-SynO-TSS)-(HSQ, Seq_2)-(3'AAV ITR)
(5'AAV ITR)-(HSh-SynO-TSS)-(fIX)-(3'AAV ITR)
(5'AAV ITR)-(HSh-SynO-TSS)-(fIX, Seq_124)-(3'AAV ITR)
(5'AAV ITR)-(HSh-SynO-TSS)-(fIX, Seq_8)-(3'AAV ITR)
(5'AAV ITR)-(HSh-SynO-TSS)-(fIX, Seq_9)-(3'AAV ITR)
(5'AAV ITR)-(HSh-SynO-TSS)-(fIX, Seq_10)-(3'AAV ITR)
(5'AAV ITR)-(sHS-SynO-TSS)-(transgene)-(3'AAV ITR)
(5'AAV ITR)-(sHS-SynO-TSS)-(fVIII)-(3'AAV ITR)
(5'AAV ITR)-(sHS-SynO-TSS)-(fVIII-B-domain deleted)-(3'AAV ITR)
(5'AAV ITR)-(sHS-SynO-TSS)-(ET3)-(3'AAV ITR)
(5'AAV ITR)-(sHS-SynO-TSS)-(ET3, Seq_12)-(3'AAV ITR)
(5'AAV ITR)-(sHS-SynO-TSS)-(ET3, Seq_11)-(3'AAV ITR)
(5'AAV ITR)-(sHS-SynO-TSS)-(HSQ)-(3'AAV ITR)
(5'AAV ITR)-(sHS-SynO-TSS)-(HSQ, Seq_2)-(3'AAV ITR)
(5'AAV ITR)-(sHS-SynO-TSS)-(fIX)-(3'AAV ITR)
(5'AAV ITR)-(sHS-SynO-TSS)-(fIX, Seq_124)-(3'AAV ITR)
(5'AAV ITR)-(sHS-SynO-TSS)-(fIX, Seq_8)-(3'AAV ITR)
(5'AAV ITR)-(sHS-SynO-TSS)-(fIX, Seq_9)-(3'AAV ITR)
(5'AAV ITR)-(sHS-SynO-TSS)-(fIX, Seq_10)-(3'AAV ITR)

The transgene can be flanked by regulatory sequences such as a 5' Kozak sequence and/or a 3' polyadenylation signal. For example, in some embodiments, the recombinant AAV vector can have a genome with a structure set forth as one of:

(5'AAV ITR)-(HCB)-(Kozak)-(transgene)-(polyA signal)-(polyA signal)-(3'AAV ITR)
(5'AAV ITR)-(HCB)-(Kozak)-(fVIII)-(polyA signal)-(3'AAV ITR)
(5'AAV ITR)-(HCB)-(Kozak)-(fVIII-B-domain deleted)-(polyA signal)-(3'AAV ITR)
(5'AAV ITR)-(HCB)-(Kozak)-(ET3)-(polyA signal)-(3'AAV ITR)
(5'AAV ITR)-(HCB)-(Kozak)-(ET3, Seq_12)-(polyA signal)-(3'AAV ITR)
(5'AAV ITR)-(HCB)-(Kozak)-(ET3, Seq_11)-(polyA signal)-(3'AAV ITR)
(5'AAV ITR)-(HCB)-(Kozak)-(HSQ)-(polyA signal)-(3'AAV ITR)
(5'AAV ITR)-(HCB)-(Kozak)-(HSQ, Seq_2)-(polyA signal)-(3'AAV ITR)
(5'AAV ITR)-(HCB)-(Kozak)-(fIX)-(polyA signal)-(3'AAV ITR)
(5'AAV ITR)-(HCB)-(Kozak)-(fIX, Seq_124)-(polyA signal)-(3'AAV ITR)
(5'AAV ITR)-(HCB)-(Kozak)-(fIX, Seq_8)-(polyA signal)-(3'AAV ITR)
(5'AAV ITR)-(HCB)-(Kozak)-(fIX, Seq_9)-(polyA signal)-(3'AAV ITR)
(5'AAV ITR)-(HCB)-(Kozak)-(fIX, Seq_10)-(polyA signal)-(3'AAV ITR)
(5'AAV ITR)-(HSh-HCB)-(Kozak)-(transgene)-(polyA signal)-(3'AAV ITR)

(5'AAV ITR)-(HSh-HCB)-(Kozak)-(fVIII)-(polyA signal)-(3'AAV ITR)
(5'AAV ITR)-(HSh-HCB)-(Kozak)-(fVIII-B-domain deleted)-(polyA signal)-(3'AAV ITR)
(5'AAV ITR)-(HSh-HCB)-(Kozak)-(ET3)-(polyA signal)-(3'AAV ITR)
(5'AAV ITR)-(HSh-HCB)-(Kozak)-(ET3, Seq_12)-(polyA signal)-(3'AAV ITR)
(5'AAV ITR)-(HSh-HCB)-(Kozak)-(ET3, Seq_11)-(polyA signal)-(3'AAV ITR)
(5'AAV ITR)-(HSh-HCB)-(Kozak)-(HSQ)-(polyA signal)-(3'AAV ITR)
(5'AAV ITR)-(HSh-HCB)-(Kozak)-(HSQ, Seq_2)-(polyA signal)-(3'AAV ITR)
(5'AAV ITR)-(HSh-HCB)-(Kozak)-(fIX)-(polyA signal)-(3'AAV ITR)
(5'AAV ITR)-(HSh-HCB)-(Kozak)-(fix, Seq_124)-(polyA signal)-(3'AAV ITR)
(5'AAV ITR)-(HSh-HCB)-(Kozak)-(fix, Seq_8)-(polyA signal)-(3'AAV ITR)
(5'AAV ITR)-(HSh-HCB)-(Kozak)-(fIX, Seq_9)-(polyA signal)-(3'AAV ITR)
(5'AAV ITR)-(HSh-HCB)-(Kozak)-(fIX, Seq_10)-(polyA signal)-(3'AAV ITR)
(5'AAV ITR)-(5'HSh-HCB)-(Kozak)-(transgene)-(polyA signal)-(3'AAV ITR)
(5'AAV ITR)-(5'HSh-HCB)-(Kozak)-(fVIII)-(polyA signal)-(3'AAV ITR)
(5'AAV ITR)-(5'HSh-HCB)-(Kozak)-(fVIII-B-domain deleted)-(polyA signal)-(3'AAV ITR)
(5'AAV ITR)-(5'HSh-HCB)-(Kozak)-(ET3)-(polyA signal)-(3'AAV ITR)
(5'AAV ITR)-(5'HSh-HCB)-(Kozak)-(ET3, Seq_12)-(polyA signal)-(3'AAV ITR)
(5'AAV ITR)-(5'HSh-HCB)-(Kozak)-(ET3, Seq_11)-(polyA signal)-(3'AAV ITR)
(5'AAV ITR)-(5'HSh-HCB)-(Kozak)-(HSQ)-(polyA signal)-(3'AAV ITR)
(5'AAV ITR)-(5'HSh-HCB)-(Kozak)-(HSQ, Seq_2)-(polyA signal)-(3'AAV ITR)
(5'AAV ITR)-(5'HSh-HCB)-(Kozak)-(fIX)-(polyA signal)-(3'AAV ITR)
(5'AAV ITR)-(5'HSh-HCB)-(Kozak)-(fix, Seq_124)-(polyA signal)-(3'AAV ITR)
(5'AAV ITR)-(5'HSh-HCB)-(Kozak)-(fix, Seq_8)-(polyA signal)-(3'AAV ITR)
(5'AAV ITR)-(5'HSh-HCB)-(Kozak)-(fix, Seq_9)-(polyA signal)-(3'AAV ITR)
(5'AAV ITR)-(5'HSh-HCB)-(Kozak)-(fix, Seq_10)-(polyA signal)-(3'AAV ITR)
(5'AAV ITR)-(3'HSh-HCB)-(Kozak)-(transgene)-(polyA signal)-(3'AAV ITR)
(5'AAV ITR)-(3'HSh-HCB)-(Kozak)-(fVIII)-(polyA signal)-(3'AAV ITR)
(5'AAV ITR)-(3'HSh-HCB)-(Kozak)-(fVIII-B-domain deleted)-(polyA signal)-(3'AAV ITR)
(5'AAV ITR)-(3'HSh-HCB)-(Kozak)-(ET3)-(polyA signal)-(3'AAV ITR)
(5'AAV ITR)-(3'HSh-HCB)-(Kozak)-(ET3, Seq_12)-(polyA signal)-(3'AAV ITR)
(5'AAV ITR)-(3'HSh-HCB)-(Kozak)-(ET3, Seq_11)-(polyA signal)-(3'AAV ITR)
(5'AAV ITR)-(3'HSh-HCB)-(Kozak)-(HSQ)-(polyA signal)-(3'AAV ITR)
(5'AAV ITR)-(3'HSh-HCB)-(Kozak)-(HSQ, Seq_2)-(polyA signal)-(3'AAV ITR)

(5'AAV ITR)-(3'HSh-HCB)-(Kozak)-(fIX)-(polyA signal)-(3'AAV ITR)

(5'AAV ITR)-(3'HSh-HCB)-(Kozak)-(fix, Seq_124)-(polyA signal)-(3'AAV ITR)

(5'AAV ITR)-(3'HSh-HCB)-(Kozak)-(fIX, Seq_8)-(polyA signal)-(3'AAV ITR)

(5'AAV ITR)-(3'HSh-HCB)-(Kozak)-(fIX, Seq_9)-(polyA signal)-(3'AAV ITR)

(5'AAV ITR)-(3'HSh-HCB)-(Kozak)-(fIX, Seq_10)-(polyA signal)-(3'AAV ITR)

(5'AAV ITR)-(ABP-HP1-God-TSS)-(Kozak)-(transgene)-(polyA signal)-(3'AAV ITR)

(5'AAV ITR)-(ABP-HP1-God-TSS)-(Kozak)-(fVIII)-(polyA signal)-(3'AAV ITR)

(5'AAV ITR)-(ABP-HP1-God-TSS)-(Kozak)-(fVIII-B-domain deleted)-(polyA signal)-(3'AAV ITR)

(5'AAV ITR)-(ABP-HP1-God-TSS)-(Kozak)-(ET3)-(polyA signal)-(3'AAV ITR)

(5'AAV ITR)-(ABP-HP1-God-TSS)-(Kozak)-(ET3, Seq_12)-(polyA signal)-(3'AAV ITR)

(5'AAV ITR)-(ABP-HP1-God-TSS)-(Kozak)-(ET3, Seq_11)-(polyA signal)-(3'AAV ITR)

(5'AAV ITR)-(ABP-HP1-God-TSS)-(Kozak)-(HSQ)-(polyA signal)-(3'AAV ITR)

(5'AAV ITR)-(ABP-HP1-God-TSS)-(Kozak)-(HSQ, Seq_2)-(polyA signal)-(3'AAV ITR)

(5'AAV ITR)-(ABP-HP1-God-TSS)-(Kozak)-(fIX)-(polyA signal)-(3'AAV ITR)

(5'AAV ITR)-(ABP-HP1-God-TSS)-(Kozak)-(fIX, Seq_124)-(polyA signal)-(3'AAV ITR)

(5'AAV ITR)-(ABP-HP1-God-TSS)-(Kozak)-(fIX, Seq_8)-(polyA signal)-(3'AAV ITR)

(5'AAV ITR)-(ABP-HP1-God-TSS)-(Kozak)-(fIX, Seq_9)-(polyA signal)-(3'AAV ITR)

(5'AAV ITR)-(ABP-HP1-God-TSS)-(Kozak)-(fIX, Seq_10)-(polyA signal)-(3'AAV ITR)

(5'AAV ITR)-(HSh-SynO-TSS)-(Kozak)-(transgene)-(polyA signal)-(3'AAV ITR)

(5'AAV ITR)-(HSh-SynO-TSS)-(Kozak)-(fVIII)-(polyA signal)-(3'AAV ITR)

(5'AAV ITR)-(HSh-SynO-TSS)-(Kozak)-(fVIII-B-domain deleted)-(polyA signal)-(3'AAV ITR)

(5'AAV ITR)-(HSh-SynO-TSS)-(Kozak)-(ET3)-(polyA signal)-(3'AAV ITR)

(5'AAV ITR)-(HSh-SynO-TSS)-(Kozak)-(ET3, Seq_12)-(polyA signal)-(3'AAV ITR)

(5'AAV ITR)-(HSh-SynO-TSS)-(Kozak)-(ET3, Seq_11)-(polyA signal)-(3'AAV ITR)

(5'AAV ITR)-(HSh-SynO-TSS)-(Kozak)-(HSQ)-(polyA signal)-(3'AAV ITR)

(5'AAV ITR)-(HSh-SynO-TSS)-(Kozak)-(HSQ, Seq_2)-(polyA signal)-(3'AAV ITR)

(5'AAV ITR)-(HSh-SynO-TSS)-(Kozak)-(fIX)-(polyA signal)-(3'AAV ITR)

(5'AAV ITR)-(HSh-SynO-TSS)-(Kozak)-(fIX, Seq_124)-(polyA signal)-(3'AAV ITR)

(5'AAV ITR)-(HSh-SynO-TSS)-(Kozak)-(fIX, Seq_8)-(polyA signal)-(3'AAV ITR)

(5'AAV ITR)-(HSh-SynO-TSS)-(Kozak)-(fIX, Seq_9)-(polyA signal)-(3'AAV ITR)

(5'AAV ITR)-(HSh-SynO-TSS)-(Kozak)-(fIX, Seq_10)-(polyA signal)-(3'AAV ITR)

(5'AAV ITR)-(sHS-SynO-TSS)-(Kozak)-(transgene)-(polyA signal)-(3'AAV ITR)

(5'AAV ITR)-(sHS-SynO-TSS)-(Kozak)-(fVIII)-(polyA signal)-(3'AAV ITR)

(5'AAV ITR)-(sHS-SynO-TSS)-(Kozak)-(fVIII-B-domain deleted)-(polyA signal)-(3'AAV ITR)

(5'AAV ITR)-(sHS-SynO-TSS)-(Kozak)-(ET3)-(polyA signal)-(3'AAV ITR)

(5'AAV ITR)-(sHS-SynO-TSS)-(Kozak)-(ET3, Seq_12)-(polyA signal)-(3'AAV ITR)

(5'AAV ITR)-(sHS-SynO-TSS)-(Kozak)-(ET3, Seq_11)-(polyA signal)-(3'AAV ITR)

(5'AAV ITR)-(sHS-SynO-TSS)-(Kozak)-(HSQ)-(polyA signal)-(3'AAV ITR)

(5'AAV ITR)-(sHS-SynO-TSS)-(Kozak)-(HSQ, Seq_2)-(polyA signal)-(3'AAV ITR)

(5'AAV ITR)-(sHS-SynO-TSS)-(Kozak)-(fIX)-(polyA signal)-(3'AAV ITR)

(5'AAV ITR)-(sHS-SynO-TSS)-(Kozak)-(fIX, Seq_124)-(polyA signal)-(3'AAV ITR)

(5'AAV ITR)-(sHS-SynO-TSS)-(Kozak)-(fIX, Seq_8)-(polyA signal)-(3'AAV ITR)

(5'AAV ITR)-(sHS-SynO-TSS)-(Kozak)-(fIX, Seq_9)-(polyA signal)-(3'AAV ITR)

(5'AAV ITR)-(sHS-SynO-TSS)-(Kozak)-(fIX, Seq_10)-(polyA signal)-(3'AAV ITR)

The AAV ITRs, and other selected AAV components described herein, may be readily selected from among any AAV serotype, including, without limitation, AAV1, AAV2, AAV3, AAV4, AAV5, AAV6, AAV7, AAV8, AAV9 and function variants thereof. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

In some embodiments, the vector can be a recombinant AAV vector comprising a genome comprising a nucleic acid molecule encoding any of the liver-specific promoters provided herein (such as the HCB promoter, SEQ ID NO: 4) operably linked to a heterologous nucleic molecule encoding a fVIII variant, wherein the heterologous nucleic acid molecule comprises or consists of the nucleic acid sequence set forth as SEQ ID NO: 2, SEQ ID NO: 11, SEQ ID NO: 12, SEQ ID NO: 125, or SEQ ID NO: 126, or a nucleic acid sequence at least 90% identical to SEQ ID NO: 2, SEQ ID NO: 11, SEQ ID NO: 12, SEQ ID NO: 125, or SEQ ID NO: 126. Is several such embodiments, the recombinant AAV genome (from 5' to 3' ITR) is no more than 5.1, 5.0, 4.9, 4.8, 4.7, 4.6, or 4.5 kb in length.

In some embodiments, the vector can be a recombinant AAV vector comprising a genome comprising a nucleic acid molecule encoding any of the liver-specific promoters provided herein (such as the HCB promoter, SEQ ID NO: 4) operably linked to a heterologous nucleic molecule encoding a fIX variant, wherein the heterologous nucleic acid molecule comprises or consists of the nucleic acid sequence set forth as SEQ ID NO: 8, SEQ ID NO: 9, SEQ ID NO: 10, SEQ ID NO: 124, or SEQ ID NO: 127, or a nucleic acid sequence at least 90% identical SEQ ID NO: 8, SEQ ID NO: 9, SEQ ID NO: 10, SEQ ID NO: 124, or SEQ ID NO: 127. Is several such embodiments, the recombinant AAV genome (from 5' to 3' ITR) is no more than 5.1, 5.0, 4.9, 4.8, 4.7, 4.6, or 4.5 kb in length.

AAV is currently one of the most frequently used viruses for gene therapy. Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. Because of the advantageous features of AAV, the present disclosure contemplates the use of AAV for the recombinant nucleic acid molecules and methods disclosed herein.

AAV possesses several desirable features for a gene therapy vector, including the ability to bind and enter target cells, enter the nucleus, the ability to be expressed in the nucleus for a prolonged period of time, and low toxicity. However, the small size of the AAV genome limits the size of heterologous DNA that can be incorporated. To minimize this problem, AAV vectors have been constructed that do not encode Rep and the integration efficiency element (IEE). The ITRs are retained as they are cis signals required for packaging (Daya and Berns, *Clin Microbiol Rev* 21(4):583-593, 2008).

Methods for producing rAAV suitable for gene therapy are known (see, for example, U.S. Patent Application Nos. 2012/0100606; 2012/0135515; 2011/0229971; and 2013/0072548; and Ghosh et al., *Gene Ther* 13(4):321-329, 2006), and can be utilized with the recombinant nucleic acid molecules and methods disclosed herein.

In some embodiments, the nucleic acids disclosed herein are part of an expression cassette or transgene. See e.g., US Pat. App. Pub. 20150139953. The expression cassette is composed of a transgene and regulatory sequences, e.g., promotor and 5' and 3' AAV inverted terminal repeats (ITRs). In one desirable embodiment, the ITRs of AAV serotype 2 or 8 are used. However, ITRs from other suitable serotypes may be selected. An expression cassette is typically packaged into a capsid protein and delivered to a selected host cell.

In some embodiments, the disclosure provides for a method of generating a recombinant adeno-associated virus (AAV) having an AAV serotype capsid, or a portion thereof. Such a method involves culturing a host cell which contains a nucleic acid sequence encoding an adeno-associated virus (AAV) serotype capsid protein; a functional rep gene; an expression cassette composed of AAV inverted terminal repeats (ITRs) and a transgene; and sufficient helper functions to permit packaging of the expression cassette into the AAV capsid protein. See e.g., US Pat. App. Pub. 20150139953.

The components for culturing in the host cell to package an AAV expression cassette in an AAV capsid may be provided to the host cell in trans. Alternatively, any one or more of the components (e.g., expression cassette, rep sequences, cap sequences, and/or helper functions) may be provided by a stable host cell which has been engineered to contain one or more of the required components using methods known to those of skill in the art. Most suitably, such a stable host cell will contain the component(s) under the control of an inducible promoter. However, the required component(s) may be under the control of a constitutive promoter. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

In some embodiments, the disclosure relates to recombinant vectors comprising a liver specific promotor nucleic acid sequence in operable combination with transgene. The transgene is a nucleic acid sequence, heterologous to the vector sequences flanking the transgene, which encodes a protein, or other product, of interest. The nucleic acid coding sequence is operatively linked to regulatory components in a manner which permits transgene transcription, translation, and/or expression in a host cell.

A typical transgene is a sequence encoding a product which is useful in biology and medicine, such as proteins, peptides, RNA, enzymes, dominant negative mutants, or catalytic RNAs. Desirable RNA molecules include mRNA, tRNA, dsRNA, ribosomal RNA, catalytic RNAs, siRNA, microRNA, small hairpin RNA, trans-splicing RNA, and antisense RNAs. One example of a useful RNA sequence is a sequence which inhibits or extinguishes expression of a targeted nucleic acid sequence in the treated animal. Typically, suitable target sequences in include oncologic targets and viral diseases.

The transgene may be used to correct or ameliorate gene deficiencies, which may include deficiencies in which normal genes are expressed at less than normal levels or deficiencies in which the functional gene product is not expressed. A preferred type of transgene sequence encodes a therapeutic protein or polypeptide which is expressed in a host cell. The disclosure further contemplates using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits and cis-regulatory control regions such as a promoter, intron, polyA signal is small, e.g., the total size of the DNA encoding the subunits and the IRES and cis-regulatory control regions is less than five kilobases. As an alternative to an IRES, the DNA may be separated by sequences encoding a 2A peptide, which self-cleaves in a post-translational event. See, e.g., M. L. Donnelly, et al., J. Gen. Virol., 78(Pt 1):13-21 (January 1997); Furler, S., et al, Gene Ther., 8(11):864-873 (June 2001); Klump H., et al., Gene Ther., 8(10):811-817 (May 2001). In certain embodiments, rAAV carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study.

The expression cassette can be carried on any suitable vector, e.g., a plasmid, which is delivered to a host cell. The plasmids useful in this disclosure may be engineered such that they are suitable for replication and, optionally, integration in prokaryotic cells, mammalian cells, or both. These plasmids (or other vectors carrying the 5' AAV ITR-heterologous molecule-3' ITR) contain sequences permitting replication of the expression cassette in eukaryotes and/or prokaryotes and selection markers for these systems. Preferably, the molecule carrying the expression cassette is transfected into the cell, where it may exist transiently. Alternatively, the expression cassette (carrying the 5' AAV ITR-heterologous molecule-3' ITR) may be stably integrated into the genome of the host cell, either chromosomally or as an episome. In certain embodiments, the expression cassette may be present in multiple copies, optionally in head-to-head, head-to-tail, or tail-to-tail concatamers. Suitable transfection techniques are known and may readily be utilized to deliver the expression cassette to the host cell.

Generally, when delivering the vector comprising the expression cassette by transfection, the vector and the relative amounts of vector DNA to host cells may be adjusted, taking into consideration such factors as the selected vector, the delivery method and the host cells selected. In addition to the expression cassette, the host cell contains the sequences which drive expression of the AAV capsid protein in the host cell and rep sequences of the same serotype as the serotype of the AAV ITRs found in the expression cassette, or a cross-complementing serotype. Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell.

The packaging host cell also typically contains helper functions in order to package the rAAV of the disclosure. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). The desired helper functions, can be provided using any means that allows their expression in a cell.

Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

Introduction of the molecules (as plasmids or viruses) into the host cell may be accomplished using techniques known to the skilled artisan. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

One of skill in the art will readily understand that the AAV techniques can be adapted for use in these and other viral vector systems for in vitro, ex vivo or in vivo gene delivery. The in certain embodiments the disclosure contemplates the use of nucleic acids and vectors disclosed herein in a variety of rAAV and non-rAAV vector systems. Such vectors systems may include, e.g., lentiviruses, retroviruses, poxviruses, vaccinia viruses, and adenoviral systems, among others.

In some embodiments, it is contemplated that viral particles, nucleic acids and vectors disclosed herein are useful for a variety of purposes, including for delivery of therapeutic molecules for gene expression of therapeutic proteins.

Therapeutic proteins encoded by the nucleic acids (e.g., operably in combination with promoters) reported herein include those used for treatment of hemophilia, including hemophilia B (including fIX) and hemophilia A (including fVIII and its variants, such as the light chain and heavy chain of the heterodimer and the B-deleted domain; U.S. Pat. No. 6,200,560 and U.S. Pat. No. 6,221,349). The Factor VIII gene codes for 2351 amino acids and the protein has six domains, designated from the amino to the terminal carboxy terminus as A1-A2-B-A3-C1-C2 [Wood et al, Nature, 312: 330 (1984); Vehar et al., Nature 312:337 (1984); and Toole et al, Nature, 342:337 (1984)]. Human fVIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, which releases the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

A treatment option for a patient diagnosed with hemophilia A is the exogenous administration of recombinant fVIII sometimes referred to as fVIII replacement therapy. In some patients, this therapy can lead to the development of antibodies that bind to the administered fVIII protein. Subsequently, the fVIII-antibody bound conjugates, typically referred to as inhibitors, interfere with or retard the ability of fVIII to cause blood clotting. Inhibitory autoantibodies also sometimes occur spontaneously in a subject that is not genetically at risk of having hemophilia, termed acquired hemophilia. Inhibitory antibodies assays are typically performed prior to exogenous fVIII treatment in order to determine whether the anti-coagulant therapy will be effective.

A "Bethesda assay" has historically been used to quantitate the inhibitory strength the concentration of fVIII binding antibodies. In the assay, serial dilutions of plasma from a patient, e.g., prior to having surgery, are prepared and each dilution is mixed with an equal volume of normal plasma as a source of fVIII. After incubating for a couple hours, the activities of fVIII in each of the diluted mixtures are measured. Having antibody inhibitor concentrations that prevent fVIII clotting activity after multiple repeated dilutions indicates a heightened risk of uncontrolled bleeding. Patients with inhibitor titers after about ten dilutions are felt to be unlikely to respond to exogenous fVIII infusions to stop bleeding. A Bethesda titer is defined as the reciprocal of the dilution that results in 50% inhibition of FVIII activity present in normal human plasma. A Bethesda titer greater than 10 is considered the threshold of response to FVIII replacement therapy.

In certain embodiments, the disclosure relates to methods of inducing blood clotting comprising administering an effective amount of a viral particle or capsid comprising a vector comprising a nucleic acid encoding a blood clotting factor as disclosed herein to a subject in need thereof.

In certain embodiments, the subject is diagnosed with hemophilia A or B or acquired hemophilia or unlikely to respond to exogenous fVIII infusions.

In some embodiments, this disclosure relates to methods gene transfer for the treatment of hemophilia B using an adeno-associated viral (AAV) vector encoding human fIX as the gene delivery vehicle. While several such AAV-based gene therapies for hemophilia B have entered into human clinical trials, they have been hampered by low expression of the therapeutic protein, clotting fIX, after administration of the virus resulting on only partial correction of the disease. AAV vector toxicity limits the dose of the virus that may be safely administered. To successfully transition to a clinically viable therapy, a vector should provide efficacious expression of fIX at viral doses below the threshold of toxicity.

Treating patients with inhibitors to fVIII has also been accomplished by methods of immune tolerance induction (ITI) which typically involves the daily infusion of fVIII until circulating inhibitor/antibody levels decline. However, 20-30% of patients fail to become tolerant after an immune tolerance induction (ITI) therapy. Persistence of fVIII inhibitors is associated with increased risks of morbidity and mortality. In certain embodiments, the disclosure relates to methods of immune tolerance induction comprising administering an effective amount of a vector or a capsid as disclosed herein to a subject in need thereof.

In some embodiments, the therapeutic proteins encoded by the nucleic acids (e.g., operably in combination with promoters) reported herein comprises first 57 base pairs of the fVIII heavy chain which encodes the 10 amino acid signal sequence, as well as the human beta globin polyadenylation sequence or growth hormone (hGH) polyadenylation sequence. In alternative embodiments, the A1 and A2 domains, as well as 5 amino acids from the N-terminus of the B domain, and/or 85 amino acids of the C-terminus of the B domain, as well as the A3, C1 and C2 domains. In yet other embodiments, the nucleic acids encoding fVIII heavy chain and light chain are provided in a single nucleic acid separated by 42 nucleic acids coding for 14 amino acids of the B domain. See U.S. Pat. No. 6,200,560.

As used herein, a therapeutically effective amount is an amount of AAV vector that produces sufficient amounts of fVIII to decrease the time it takes for the blood of a subject to clot. Generally, severe hemophiliacs having less than 1% of normal levels of fVIII have a whole blood clotting time of greater than 60 minutes as compared to approximately 10 minutes for non-hemophiliacs.

The present disclosure is not limited to any specific fVIII or fIX or other protein sequence reported herein. Many natural and recombinant forms of fVIII have been isolated and generated. Examples of naturally occurring and recombinant forms of fVII can be found in the patent and scientific literature including, U.S. Pat. Nos. 5,563,045, 5,451,521, 5,422,260, 5,004,803, 4,757,006, 5,661,008, 5,789,203, 5,681,746, 5,595,886, 5,045,455, 5,668,108, 5,633,150, 5,693,499, 5,587,310, 5,171,844, 5,149,637, 5,112,950, 4,886,876, WO 94/11503, WO 87/07144, WO 92/16557, WO 91/09122, WO 97/03195, WO 96/21035, WO 91/07490, EP 0 672138, EP 0 270 618, EP 0 182 448, EP 0 162 067, EP 0 786 474, EP 0 533 862, EP 0 506 757, EP 0 874 057, EP 0 795 021, EP 0 670 332, EP 0 500 734, EP 0 232 112, EP 0 160 457, Sanberg et al., Int. Congress of the World Fed. Of Hemophilia (1992), and Lind et al., Eur. J. Biochem., 232:19 (1995).

Furthermore, the disclosure is not limited to human fVIII. Indeed, it is intended that the present disclosure encompass fVIII from animals other than humans, including but not limited to companion animals (e.g., canine, felines, and equines), livestock (e.g., bovines, caprines and ovines), laboratory animals, marine mammals, large cats, etc.

The AAV vectors may contain a nucleic acid coding for fragments of fVIII which is itself not biologically active, yet when administered into the subject improves or restores the blood clotting time. For example, the fVIII protein comprises two polypeptide chains: a heavy chain and a light chain separated by a B-domain which is cleaved during processing. Co-transducing recipient cells with the FVIII heavy and light chains leads to the expression of biologically active fVIII. Administration of only the chain defective is contemplated in patients because most hemophiliacs contain a mutation or deletion in only one of the chains (e.g., heavy or light chain).

Thus, in certain embodiments, the disclosure relates to vectors disclosed herein having nucleic acids encoding a light chain containing the A3, C1 and C2 domains or a heavy chain consisting of the A1 and A2 domains.

Additional Description of Recombinant Vectors and Therapeutic Modalities

The recombinant vectors disclosed herein (for example, a recombinant AAV vector) can be used in several different therapeutic applications, depending on the protein of interest encoded by the recombinant vector.

In certain embodiments, the uses are for the treatment of hereditary hemochromatosis (HH), a major disorder of iron overload, Wilson's disease, a genetic disorder of copper overload, and alpha1-antitrypsin (α1-AT) deficiency. In certain embodiments, the protein is human Alpha1-antitrypsin (α1-AT, Accession: P01009.3), HFE protein (Accession NP_000401.1 or Q30201), or hepatic protein ATP7B (Accession P35670.4) or variants with greater than 50, 60, 70, 80, 90, 95, or 95 sequence identity or similarity.

In certain embodiments, the use is for the treatment of hypercholesterolaemia using a promotor herein in operable combination with a nucleic acid that encodes for human phenylalanine hydroxylase (Accession: P00439.1) or variants with greater than 50, 60, 70, 80, 90, 95, or 95 sequence identity or similarity.

In certain embodiments, the use is for the treatment of Type 1 tyrosinemia using a promotor herein in operable combination with a nucleic acid that encodes for human fumarylacetoacetate hydrolase (Accession: P16930.2) or variants with greater than 50, 60, 70, 80, 90, 95, or 95 sequence identity or similarity.

In certain embodiments, the use is for the treatment of Type 2 tyrosinemia using a promotor herein in operable combination with a nucleic acid that encodes for human tyrosine aminotransferase (Accession: P17735.1) or variants with greater than 50, 60, 70, 80, 90, 95, or 95 sequence identity or similarity.

In certain embodiments, the use is for the treatment of homocystinuria and hyperhomocysteinemia using a promotor herein in operable combination with a nucleic acid that encodes for human methylenetetrahydrofolate reductase (Accession: P42898.3) or variants with greater than 50, 60, 70, 80, 90, 95, or 95 sequence identity or similarity.

In certain embodiments, the use is for the treatment of hyperlipidemia and hypercholesterolemia using a promotor herein in operable combination with a nucleic acid that encodes for human medium chain acyl-CoA dehydrogenase (Accession: P11310.1) or variants with greater than 50, 60, 70, 80, 90, 95, or 95 sequence identity or similarity.

In certain embodiments, the use is for the treatment of Galactosemia using a promotor herein in operable combination with a nucleic acid that encodes for human galactose-1-phosphate uridyl transferase (Accession: P07902.3) or variants with greater than 50, 60, 70, 80, 90, 95, or 95 sequence identity or similarity.

In certain embodiments, the use is for the treatment of Lesch-Nyhan syndrome using a promotor herein in operable combination with a nucleic acid that encodes for human hypoxanthine phosphoribosyl-transferase (Accession: P00492.2) or variants with greater than 50, 60, 70, 80, 90, 95, or 95 sequence identity or similarity.

In certain embodiments, the use is for the treatment of Gaucher disease using a promotor herein in operable combination with a nucleic acid that encodes for human cerebrosidase (Accession: P07602.2, Accession: P04062.3) or variants with greater than 50, 60, 70, 80, 90, 95, or 95 sequence identity or similarity.

In certain embodiments, the use is for the treatment of Tay-Sachs disease using a promotor herein in operable combination with a nucleic acid that encodes for human beta-hexosaminidase A (Accession: P06865.2) or variants with greater than 50, 60, 70, 80, 90, 95, or 95 sequence identity or similarity.

In certain embodiments, the use is for the treatment of Fabry disease using a promotor in operable combination with a nucleic acid that encodes for human α-galactosidase (Accession: P06280.1) or variants with greater than 50, 60, 70, 80, 90, 95, or 95 sequence identity or similarity.

In certain embodiments, the use is for the treatment of Hunter syndrome using a promotor in operable combination with a nucleic acid that encodes for human iduronate sulphatase (Accession: P22304.1) or variants with greater than 50, 60, 70, 80, 90, 95, or 95 sequence identity or similarity.

In certain embodiments, the use is for the treatment of glycogen storage disease type Ia using a promotor in operable combination with a nucleic acid that encodes for human glucose-6-phosphatase (Accession: P35575.2) or variants with greater than 50, 60, 70, 80, 90, 95, or 95 sequence identity or similarity.

In certain embodiments, the use is for the treatment of ammonia metabolism using a promotor in operable combination with a nucleic acid that encodes for human ornithine transcarbamylase (Accession: P00480.3) or variants with greater than 50, 60, 70, 80, 90, 95, or 95 sequence identity or similarity.

In certain embodiments, the use is for the treatment of phenylketonuria using a promotor in operable combination with a nucleic acid that encodes for human low-density lipoprotein receptor (Accession: P01130.1) or variants with greater than 50, 60, 70, 80, 90, 95, or 95 sequence identity or similarity.

In certain embodiments, the use is for the treatment of propionic acidemia using a promotor in operable combination with a nucleic acid that encodes for human propionyl-coenzyme A carboxylase, either PCCA and/or PCCB (Accession: P05166.3 beta, NP_000273.2 alpha, NP_001121164.1 alpha) or variants with greater than 50, 60, 70, 80, 90, 95, or 95 sequence identity or similarity.

Also contemplated are uses in vaccine regimens, e.g., for co-delivery of a cytokine, or for delivery of an immunogen or antigen.

Recombinant virus particles, capsids, or vectors comprising nucleic acids disclosed herein can be delivered to liver via the hepatic artery, the portal vein, or intravenously to yield therapeutic levels of therapeutic proteins or clotting factors in the blood. The capsid or vector is preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, sesame oil, and water.

Optionally, the compositions of the disclosure may contain other pharmaceutically acceptable excipients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The recombinant virus particles, capsids, or vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined, if desired.

Dosages of the recombinant virus particles, capsids, or vectors will depend primarily on factors such as the condition being treated, the age, weight and health of the patient, and may thus vary among patients. For example, a therapeutically effective human dosage of the viral vector is generally in the range of from about 0.1 ml to about 100 ml of solution containing concentrations of from about $1\times10^9$ to $1\times10^{16}$ genomes virus vector.

Other useful therapeutic proteins encoded by the nucleic acids (e.g., operably in combination with promoters) reported herein include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor alpha superfamily, including TGFalpha, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other therapeutic proteins encoded by the nucleic acids (e.g., operably in combination with promoters) reported herein include those that regulate the immune system including, without limitation, cytokines and lymphokines such as thrombopoietin (TPO), interleukins (IL) IL-1 through IL-25 (including IL-2, IL-4, IL-12 and IL-18), monocyte chemoattractant protein, leukemia inhibitory factor, granulocyte-macrophage colony stimulating factor, Fas ligand, tumor necrosis factors alpha and beta, interferons alpha, beta, and gamma, stem cell factor, flk-2/flt3 ligand. Proteins produced by the immune system are also useful. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful proteins also include complement regulatory proteins such as complement regulatory proteins, membrane cofactor protein (MCP), decay accelerating factor (DAF), CR1, CF2 and CD59.

Other therapeutic proteins encoded by the nucleic acids (e.g., operably in combination with promoters) reported herein are receptors for the hormones, growth factors, cytokines, lymphokines, regulatory proteins and immune system proteins. The disclosure encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The disclosure also encompasses proteins such as members of the steroid hormone receptor superfamily including glucocorticoid receptors and estrogen receptors, Vitamin D receptors and other nuclear receptors. In addition, useful proteins include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZFS, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful proteins include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful proteins include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding beta-glucuronidase (GUSB)).

Other useful proteins include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a protein is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

Vectors reported herein may be formulated in a manner which permits the expression of a protein carried by the vectors to induce an immune response to a selected antigen. For example, in order to promote an immune response, the antigen may be expressed from a promoter disclosed herein, the vector can be adjuvanted as described herein, and/or the vector can be put into degenerating tissue.

Examples of suitable immunogenic antigens include those selected from a variety of viral families Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Other viral families include the astroviruses and the calcivirus family. The calcivirus family encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, Ross-River virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis, and which include the putative cause of sudden acute respiratory syndrome (SARS). Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the arterivirus family and the rhabdovirus family. The rhabdovirus family includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. Another source of antigens is the bornavirus family. The reovirus family includes the genera reovirus, rotavirus (which causes acute gastroenteritis in children), orbiviruses, and cultivirus (Colorado Tick fever, Lebombo (humans), equine encephalosis, blue tongue). The retrovirus family includes the sub-family oncorivirinal which encompasses such human and veterinary diseases as feline leukemia virus, HTLVI and HTLVII, lentivirinal (which includes HIV, simian immunodeficiency virus, feline immunodeficiency virus, equine infectious anemia virus, and spumavirinal). The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gamma herpesvirinae, which includes the genera lymphocryptovirus, EBV (Burkitts lymphoma), human herpesviruses 6A, 6B and 7, Kaposi's sarcoma-associated herpesvirus and cercopithecine herpesvirus (B virus), infectious rhinotracheitis, Marek's disease virus, and rhadinovirus. The poxvirus family includes the sub-family chordopoxvirinae, which encompasses the genera orthopoxvirus (Variola major (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus, Hepatitis E virus, and prions. Another virus which is a source of antigens is Nipan Virus. Still other viral sources may include avian infectious bursal disease virus and porcine respiratory and reproductive syndrome virus. The alphavirus family includes equine arteritis virus and various Encephalitis viruses.

The present disclosure may also encompass protein based immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci (and the toxins produced thereby, e.g., enterotoxin B); and streptococci. Pathogenic gram-negative cocci include meningococcus; gonococcus. Pathogenic enteric gram-negative bacilli include enterobacteriaceae; *pseudomonas*, acinetobacteria and eikenella; melioidosis; *salmonella; shigella; haemophilus; moraxella; H. ducreyi* (which causes chancroid); *brucella* species (brucellosis); *Francisella tularensis* (which causes tularemia); *Yersinia pestis* (plague) and other *Yersinia* (*pasteurella*); *streptobacillus moniliformis* and spirillum; Gram-positive bacilli include *listeria monocytogenes; erysipelothrix rhusiopathiae; Corynebacterium diphtheria* (diphtheria); cholera; *B. anthracia* (anthrax); donovanosis (granuloma inguinale); and bartonellosis. Diseases caused by pathogenic anaerobic bacteria include tetanus; botulism (*Clostridum botulinum* and its toxin); *Clostridium perfringens* and its epsilon toxin; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include glanders (*Burkholderia mallei*); actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever (*Coxiella burnetti*), and Rickettsialpox. Examples of *mycoplasma* and chlamydial infections include: *mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii*; Trichans; *Toxoplasma gondii*; babesiosis; giardiasis; trichinosis; filariasis; schistosomiasis; nematodes; trematodes or flukes; and cestode (tapeworm) infections.

Many of these organisms and/or the toxins produced thereby have been identified by the Centers for Disease Control [(CDC), Department of Health and Human Services, USA], as agents which have potential for use in biological attacks. For example, some of these biological agents, include, *Bacillus anthracia* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella*

*burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

In certain embodiments, a protein for expression in a vector of the disclosure are a segment of a variable region of T cells eliciting an immune response, i.e., to eliminate cytotoxic T cells. In rheumatoid arthritis (RA), several specific variable regions of TCRs which are involved in the disease have been characterized. These TCRs include V-3, V-14, V-17 and V-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and V-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and V-16, V-3C, V-7, V-14, V-15, V-16, V-28 and V-12. Thus, delivery of a nucleic acid molecule that encodes at least one of these polypeptides will elicit an immune response that will target T cells involved in scleroderma.

Recombinant viral vectors of the disclosure provides an efficient gene transfer vehicle which can deliver a selected proteins to a selected host cell in vivo or ex vivo even where the organism has neutralizing antibodies to the protein. In one embodiment, the vectors disclosed herein and the cells are mixed ex vivo; the infected cells are cultured using conventional methodologies; and the transduced cells are re-infused into the patient.

Additional Embodiments

In certain embodiments, the disclosure relates to recombinant viral vectors comprising a liver specific promotor nucleic acid sequence in operable combination with a heterologous nucleic acid sequence encoding a protein. Typically, the nucleic acid sequence encoding the protein comprises a higher percentage of liver cell specific amino acid codons compared to overall human codon usage. In certain embodiments, the disclosure relates to methods of treating a subject diagnosed with a genetic trait that results in expression of a mutated or truncated non-functional protein by administering an effective amount of a vector disclosed herein configured to express a functional protein from the liver.

In certain embodiments, the vector comprises a viral nucleic acid sequence of greater than 10, 20, 30, 40, 50, 100, or 200 nucleotides. In certain embodiments, the viral nucleic acid sequence is a segment of human adeno-associated virus (hAAV) of serotypes 1, 2, 3B, 4, 5, 6, 7, 8, 9 or combinations or variants thereof, typically comprising an AAV inverted terminal repeat.

In certain embodiments, the disclosure relates to a viral particle, e.g., capsid comprising a vector disclosed herein, e.g., the vector packaged in a capsid. The capsid may be a recombinant or chimeric particle or capsid, e.g., capsid having amino acid sequences that are a combination of AAV pseudotypes for VP 1, 2, or 3. An AAV capsid VP may be derived from a human gene or animal AAV gene, or combinations with genetically engineered alterations, i.e., AAV isolated from infected human cells or a non-human primate Animal AAV include those derived from avian, bovine, porcine, mice, etc. In certain embodiments, the capsid may have amino acid sequences that are bioengineered or synthetic capsids identified through methods such as directed evolution or rational design.

In certain embodiments, vectors disclosed herein are a single or double stranded nucleic acid or self-complementary nucleic acid of less than 5.1, 5.0, 4.9, 4.8, 4.7, 4.6, or 4.5 kb of nucleotides in total. In certain embodiments, the vector is replication-incompetent inside a human host, e.g., vector does not encode a viral polymerase.

In certain embodiments, the liver specific promotor sequence comprises a sequence having at least 50, 60, 70, 80, 85, 90, 95, 96, 97, 98, 99, or 100% sequence identity to GTTAATTTTTGTGGCCCTTGCGATGTTTGCTCTGGTTA (SEQ ID NO: 21) ATAATCTCAGGACAAACA (SEQ ID NO: 43) and/or TATAAAAGGCCAGCAGCAGCCTGACCACATCTCATCCTC (SEQ ID NO: 20).

In certain embodiments, SEQ ID NO 20 is 3' or after SEQ ID NO: 21 between a nucleotide linker, e.g., connected with a linker as illustrated: 5'-SEQ ID NO: 21 followed by a linker followed by SEQ ID NO: 20-3'. The linker may be between 0 to 200 nucleotides, 10 to 100 nucleotides, 20 to 70 nucleotides, 30 to 60 nucleotides, 30 to 40 nucleotides, 32 to 36 nucleotides. In certain embodiments, the liver specific promotor sequence comprises a sequence having at least 50, 60, 70, 80, 85, 90, 95, 96, 97, 98, 99, or 100% sequence identity to SEQ ID NO: 4, 5, 6, or 7.

As used herein, the liver specific promotor refers to the sequences in the 5' direction of the transcriptional start site of the protein to be produced. Promotor sequences disclosed herein may contain combinations of other known promotors, enhancers, other sequences, and fragments thereof. For example, SEQ ID NO: 21 is the sequence of the shortened ABP enhancer. By itself it does not function as a promoter, it serves to enhance the expression conferred by the core promoter, SEQ ID NO: 20, SynO, which by itself does not confer efficient gene expression. Additional enhancer sequences which may replace or augment the short ABP enhancer are contemplated.

In certain embodiments, the liver specific promotor sequence comprises a sequence having at least 50, 60, 70, 80, 85, 90, 95, 96, 97, 98, 99, or 100% sequence identity to CGGAGGAGCAAACAGGG (SEQ ID NO: 97) and/or TATAAAAGGCCAGCAGCAGCCTGACCACATCTCATCCTC (SEQ ID NO: 20).

In certain embodiments, SEQ ID NO 20 is 3' or after SEQ ID NO: 97 between a nucleotide linker, e.g., connected with a linker as illustrated: 5'-SEQ ID NO: 97 followed by a linker followed by SEQ ID NO: 20-3'. The linker may be between 0 to 200 nucleotides, 10 to 100 nucleotides, 20 to 70 nucleotides, 30 to 60 nucleotides, 30 to 40 nucleotides, 32 to 36 nucleotides.

In certain embodiments, the liver specific promotor sequence comprises a sequence having at least 50, 60, 70, 80, 85, 90, 95, 96, 97, 98, 99, or 100% sequence identity to CGGAGGAGCAAACAGGGGCTAAGTCCAC (SEQ ID NO: 98) and/or TATAAAAGGCCAGCAGCAGCCTGACCACATCTCATCCTC (SEQ ID NO: 20).

In certain embodiments, SEQ ID NO 20 is 3' or after SEQ ID NO: 98 between a nucleotide linker, e.g., connected with a linker as illustrated: 5'-SEQ ID NO: 98 followed by a linker followed by SEQ ID NO: 20-3'. The linker may be between 0 to 200 nucleotides, 10 to 100 nucleotides, 20 to 70 nucleotides, 30 to 60 nucleotides, 30 to 40 nucleotides, 32 to 36 nucleotides.

In certain embodiments, the liver specific promotor sequence comprises a sequence having at least 50, 60, 70, 80, 85, 90, 95, 96, 97, 98, 99, or 100% sequence identity to GGCTGCTGGTGAATATTAACCAAGGTC (SEQ ID NO: 99) and/or TATAAAAGGCCAGCAGCAGCCTGACCACATCTCATCCTC (SEQ ID NO: 20).

In certain embodiments, SEQ ID NO 20 is 3' or after SEQ ID NO: 99 between a nucleotide linker, e.g., connected with a linker as illustrated: 5'-SEQ ID NO: 99 followed by a linker followed by SEQ ID NO: 20-3'. The linker may be between 0 to 200 nucleotides, 10 to 100 nucleotides, 20 to 70 nucleotides, 30 to 60 nucleotides, 30 to 40 nucleotides, 32 to 36 nucleotides.

In certain embodiments, the liver specific promotor sequence comprises a sequence having at least 50, 60, 70, 80, 85, 90, 95, 96, 97, 98, 99, or 100% sequence identity to GGGGAGGCTGCTGGTGAATATTAACCAAGGTCACCCCAGTTATCGGAGGAGCAAACAGGGG CTAAGTCCAC (SEQ ID NO: 100) and/or TATAAAAGGCCAGCAGCAGCCTGACCACATCTCATCCTC (SEQ ID NO: 20).

In certain embodiments, SEQ ID NO 20 is 3' or after SEQ ID NO: 100 between a nucleotide linker, e.g., connected with a linker as illustrated: 5'-SEQ ID NO: 100 followed by a linker followed by SEQ ID NO: 20-3'. The linker may be between 0 to 200 nucleotides, 10 to 100 nucleotides, 20 to 70 nucleotides, 30 to 60 nucleotides, 30 to 40 nucleotides, 32 to 36 nucleotides.

In certain embodiments, the liver specific promotor sequence comprises a sequence having at least 50, 60, 70, 80, 85, 90, 95, 96, 97, 98, 99, or 100% sequence identity to GGGGAGGCTGCTGGTGAATATTAACCAAGGTCACCCCAGTTATCGGAGGAGCAAACAGGGA CTAAGTCCAC (SEQ ID NO: 101) and/or TATAAAAGGCCAGCAGCAGCCTGACCACATCTCATCCTC (SEQ ID NO: 20).

In certain embodiments, SEQ ID NO 20 is 3' or after SEQ ID NO: 101 between a nucleotide linker, e.g., connected with a linker as illustrated: 5'-SEQ ID NO: 101 followed by a linker followed by SEQ ID NO: 20-3'. The linker may be between 0 to 200 nucleotides, 10 to 100 nucleotides, 20 to 70 nucleotides, 30 to 60 nucleotides, 30 to 40 nucleotides, 32 to 36 nucleotides.

In certain embodiments, the liver specific promotor sequence comprises a sequence having at least 50, 60, 70, 80, 85, 90, 95, 96, 97, 98, 99, or 100% sequence identity to SEQ ID NO: 4, 5, 6, 7, 102, 103, 104, 105, 106, 107, or 108.

In certain embodiments, liver specific promotor nucleic acid sequence is of less than 205 or 250 nucleotides. The terms "less than 205 or 250 nucleotides" refers to the length of a single strand or the length of double stranded base pairs. The functional promoter is double stranded after intracellular conversion following viral infection. It would not function if it were single stranded.

In certain embodiments, the disclosure contemplates the first nucleotide of the promotor sequence is the 5' "G" in the HFN1a TF binding site, GTTAAT (SEQ ID NO: 25), e.g., promotor is 5'-SEQ ID NO: 21 which is followed by a linker and further followed by a transcriptional start site (TSS), e.g. TCATCCTC (SEQ ID NO: 109), wherein the last nucleotide in the transcriptional start site is the end of the promotor sequence. In certain embodiments the linker comprises a TATAA (SEQ ID NO: 26) box and a GC rich spacer. In certain embodiments, the disclosure contemplates the first nucleotide of the promotor sequence is a 5' "G" in GTTAA (SEQ ID NO: 27), GTTA (SEQ ID NO: 28), GTT (SEQ ID NO: 29). In certain embodiments, the first nucleotide of the promotor sequence is a 5' "T" in TTAAT (SEQ ID NO: 30), TTAA (SEQ ID NO: 31), TTA (SEQ ID NO: 32). In certain embodiments, the first nucleotide of the promotor sequence is a 5' "A" in AAT (SEQ ID NO: 33).

In certain embodiments, the disclosure contemplates a promotor comprising 5'-SEQ ID NO: 21 or 97 or 98 or 99 or 100 or 101 optionally followed by a linker, followed by a TATAA box, followed by a GC rich spacer followed by and a transcriptional start site. In certain embodiments, the GC rich spacer is a sequence wherein greater than 60, 70, 80, or 90% of the nucleotides are G or C, e.g., over a window of 5 to 35 nucleotide, 10 to 30 nucleotides, or 15 to 40 nucleotide, or 5 to 50 or 60 nucleotides. In certain embodiments, the CG rich spacer is GGCCAGCAGCAGCCTGACCACATC (SEQ ID NO: 110). In certain embodiments, the liver specific promotor sequence comprises a sequence having at least 50, 60, 70, 80, 85, 90, 95, 96, 97, 98, 99, or 100% sequence identity to SEQ ID NO: 110.

In certain embodiments, the liver specific promotor sequence comprises a sequence having at least 50, 60, 70, 80, 85, 90, 95, 96, 97, 98, 99, or 100% sequence identity to one of:

```
SEQ ID NO: 34: GTTAATTTTTGTGGCCCTTGCGATGTTTGCTCTGGTTAATAATCTCAGGACAAACA;

SEQ ID NO: 35: TTAATTTTTGTGGCCCTTGCGATGTTTGCTCTGGTTAATAATCTCAGGACAAACA;

SEQ ID NO: 36: TAATTTTTGTGGCCCTTGCGATGTTTGCTCTGGTTAATAATCTCAGGACAAACA;

SEQ ID NO: 37: AATTTTTGTGGCCCTTGCGATGTTTGCTCTGGTTAATAATCTCAGGACAAACA;

SEQ ID NO: 38: ATTTTTGTGGCCCTTGCGATGTTTGCTCTGGTTAATAATCTCAGGACAAACA;

SEQ ID NO: 39: TTTTTGTGGCCCTTGCGATGTTTGCTCTGGTTAATAATCTCAGGACAAACA;

SEQ ID NO: 40: TTTTGTGGCCCTTGCGATGTTTGCTCTGGTTAATAATCTCAGGACAAACA;

SEQ ID NO: 41: TTTGTGGCCCTTGCGATGTTTGCTCTGGTTAATAATCTCAGGACAAACA;

SEQ ID NO: 42: TTGTGGCCCTTGCGATGTTTGCTCTGGTTAATAATCTCAGGACAAACA;

SEQ ID NO: 44: TGTGGCCCTTGCGATGTTTGCTCTGGTTAATAATCTCAGGACAAACA;
```

-continued

SEQ ID NO: 45: GTGGCCCTTGCGATGTTTGCTCTGGTTAATAATCTCAGGACAAACA;

SEQ ID NO: 46: TGGCCCTTGCGATGTTTGCTCTGGTTAATAATCTCAGGACAAACA;

SEQ ID NO: 47: GCCCTTGCGATGTTTGCTCTGGTTAATAATCTCAGGACAAACA;

SEQ ID NO: 48: CCCTTGCGATGTTTGCTCTGGTTAATAATCTCAGGACAAACA;

SEQ ID NO: 49: CCTTGCGATGTTTGCTCTGGTTAATAATCTCAGGACAAACA;

SEQ ID NO: 50: CTTGCGATGTTTGCTCTGGTTAATAATCTCAGGACAAACA;

SEQ ID NO: 51: GTTAATTTTTGTGGCCCTTGCGATGTTTGCTCTGGTTAATAATCTCAGGACAAAC;

SEQ ID NO: 52: GTTAATTTTTGTGGCCCTTGCGATGTTTGCTCTGGTTAATAATCTCAGGACAAA;

SEQ ID NO: 53: GTTAATTTTTGTGGCCCTTGCGATGTTTGCTCTGGTTAATAATCTCAGGACAA;

SEQ ID NO: 54: GTTAATTTTTGTGGCCCTTGCGATGTTTGCTCTGGTTAATAATCTCAGGACAA;

SEQ ID NO: 55: GTTAATTTTTGTGGCCCTTGCGATGTTTGCTCTGGTTAATAATCTCAGGACA;

SEQ ID NO: 56: GTTAATTTTTGTGGCCCTTGCGATGTTTGCTCTGGTTAATAATCTCAGGAC;

SEQ ID NO: 57: GTTAATTTTTGTGGCCCTTGCGATGTTTGCTCTGGTTAATAATCTCAGGA;

SEQ ID NO: 58: GTTAATTTTTGTGGCCCTTGCGATGTTTGCTCTGGTTAATAATCTCAGG;

SEQ ID NO: 59: GTTAATTTTTGTGGCCCTTGCGATGTTTGCTCTGGTTAATAATCTCAG;

SEQ ID NO: 60: GTTAATTTTTGTGGCCCTTGCGATGTTTGCTCTGGTTAATAATCTCA;

SEQ ID NO: 61: GTTAATTTTTGTGGCCCTTGCGATGTTTGCTCTGGTTAATAATCTC;

SEQ ID NO: 62: GTTAATTTTTGTGGCCCTTGCGATGTTTGCTCTGGTTAATAATCT;

SEQ ID NO: 63: GTTAATTTTTGTGGCCCTTGCGATGTTTGCTCTGGTTAATAATC;

SEQ ID NO: 64: GTTAATTTTTGTGGCCCTTGCGATGTTTGCTCTGGTTAATAAT;

SEQ ID NO: 65: GTTAATTTTTGTGGCCCTTGCGATGTTTGCTCTGGTTAATAA;

SEQ ID NO: 66: GTTAATTTTTGTGGCCCTTGCGATGTTTGCTCTGGTTAATAATCTCAGGACAAAC;

SEQ ID NO: 67: TTAATTTTTGTGGCCCTTGCGATGTTTGCTCTGGTTAATAATCTCAGGACAAA;

SEQ ID NO: 68: TAATTTTTGTGGCCCTTGCGATGTTTGCTCTGGTTAATAATCTCAGGACAA;

SEQ ID NO: 69: AATTTTTGTGGCCCTTGCGATGTTTGCTCTGGTTAATAATCTCAGGACA;

SEQ ID NO: 70: ATTTTTGTGGCCCTTGCGATGTTTGCTCTGGTTAATAATCTCAGGAC;

SEQ ID NO: 71: TTTTTGTGGCCCTTGCGATGTTTGCTCTGGTTAATAATCTCAGGA;

SEQ ID NO: 72: TTTTGTGGCCCTTGCGATGTTTGCTCTGGTTAATAATCTCAGG;

SEQ ID NO: 73: TTTGTGGCCCTTGCGATGTTTGCTCTGGTTAATAATCTCAG;

SEQ ID NO: 74: TTGTGGCCCTTGCGATGTTTGCTCTGGTTAATAATCTCA;

SEQ ID NO: 75: TGTGGCCCTTGCGATGTTTGCTCTGGTTAATAATCTC;

SEQ ID NO: 76: GTGGCCCTTGCGATGTTTGCTCTGGTTAATAATCT;

SEQ ID NO: 77: TGGCCCTTGCGATGTTTGCTCTGGTTAATAATC;

SEQ ID NO: 78: GCCCTTGCGATGTTTGCTCTGGTTAATAAT;

SEQ ID NO: 79: CCCTTGCGATGTTTGCTCTGGTTAATAA;

SEQ ID NO: 80: CCTTGCGATGTTTGCTCTGGTTAATA;

SEQ ID NO: 81: CTTGCGATGTTTGCTCTGGTTAAT;

SEQ ID NO: 82: TTAATTTTTGTGGCCCTTGCGATGTTTGCTCTGGTTAATAATCTCAGGACAAAC;

SEQ ID NO: 83: TAATTTTTGTGGCCCTTGCGATGTTTGCTCTGGTTAATAATCTCAGGACAAA;

SEQ ID NO: 84: AATTTTTGTGGCCCTTGCGATGTTTGCTCTGGTTAATAATCTCAGGACAA;

-continued

SEQ ID NO: 85: ATTTTTGTGGCCCTTGCGATGTTTGCTCTGGTTAATAATCTCAGGACAA;

SEQ ID NO: 86: TTTTTGTGGCCCTTGCGATGTTTGCTCTGGTTAATAATCTCAGGACA;

SEQ ID NO: 87: TTTTGTGGCCCTTGCGATGTTTGCTCTGGTTAATAATCTCAGGAC;

SEQ ID NO: 88: TTTGTGGCCCTTGCGATGTTTGCTCTGGTTAATAATCTCAGGA;

SEQ ID NO: 89: TTGTGGCCCTTGCGATGTTTGCTCTGGTTAATAATCTCAGG;

SEQ ID NO: 90: TGTGGCCCTTGCGATGTTTGCTCTGGTTAATAATCTCAG;

SEQ ID NO: 91: TGGCCCTTGCGATGTTTGCTCTGGTTAATAATCTCA;

SEQ ID NO: 92: GGCCCTTGCGATGTTTGCTCTGGTTAATAATCTC;

SEQ ID NO: 93: GCCCTTGCGATGTTTGCTCTGGTTAATAATCT;

SEQ ID NO: 94: CCCTTGCGATGTTTGCTCTGGTTAATAATC;

SEQ ID NO: 95: CCTTGCGATGTTTGCTCTGGTTAATAAT;
or

SEQ ID NO: 96: CTTGCGATGTTTGCTCTGGTTAATAA.

In certain embodiments, the promotor may start with the first 5' nucleotide of SEQ ID NO: 34-96, and end with the last nucleotide of the TSS.

In certain embodiments, the protein is a fVIII or fIX or variant thereof. In certain embodiments, the promoter and codon optimization schemes disclosed herein could be used for any liver-directed AAV gene therapies. Other metabolic diseases caused by deficiencies of liver enzymes and expression of those functional proteins are contemplated.

In certain embodiments, fVIII variant comprises an A1 domain, an A2 domain, a RHQR sequence (SEQ ID NO: 24), an A3 domain, a C1 domain, and a C2 domain. In certain embodiments, the fVIII variant comprises a deleted B domain.

In certain embodiments, the fVIII variant comprises a linker of between two and fifty, or two and twenty five, or two and fifteen amino acids between the A2 domain and the A3 domain.

In certain embodiments, fVIII variant comprises an A1 domain, an A2 domain, an activation peptide (ap) domain, an A3 domain, a C1 domain, and a C2 domain. In certain embodiments, the fVIII variant comprises a deleted B domain.

In certain embodiments, the fVIII variant comprises a linker of between two and fifty, or two and twenty five, or two and fifteen amino acids between the A2 domain and the an activation peptide (ap) domain.

In certain embodiments, the fVIII variant comprises a sequence having at least 50, 60, 70, 80, 85, 90, 95, 96, 97, 98, 99, or 100% sequence identity to SEQ ID NO: 3.

In certain embodiments, the fVIII variant comprises a sequence having at least 50, 60, 70, 80, 85, 90, 95, 96, 97, 98, 99, or 100% sequence identity to SEQ ID NO: 13, 14, 15, or 16.

In certain embodiments, the disclosure relates to methods wherein codon usage of a gene is adjusted according to the tissue it will be expressed, e.g., liver tissue. In certain embodiments, the nucleic acid sequence encoding a protein comprises codons that are differentially utilized or represented in genes highly expressed within the liver or other specific tissue compared to the codon usage of the entire coding region of the human genome and avoids codons that are under-represented in the liver or other specific tissue.

In certain embodiments, the nucleic acid sequence encoding the protein comprises codons for greater than 50, 60, 70, 80, 90, or 95% or 100% of the amino acids that are preferred as provided in FIG. 2.

In certain embodiments, the nucleic acid sequence encoding a protein comprises a higher percentage of liver cell specific amino acid codons compared to overall human codon usage is a sequence having at least 50, 60, 70, 80, 85, 90, 95, 96, 97, 98, 99, or 100% sequence identity to SEQ ID NO: 1.

In certain embodiments, fIX variant comprises a sequence having at least 50, 60, 70, 80, 85, 90, 95, 96, 97, 98, 99, or 100% sequence identity to SEQ ID NO: 17, 18, or 19.

In certain embodiments, the nucleic acid sequence encoding a protein comprising a higher percentage of liver cell specific amino acid codons compared to overall human codon usage is a sequence having at least 50, 60, 70, 80, 85, 90, 95, 96, 97, 98, 99, or 100% sequence identity to SEQ ID NO: 8, 9, or 10.

In certain embodiments, the nucleic acid sequence encoding the protein comprises at least one of a) to g) wherein, a) a ATC codon is in greater than 50% or 52% for Ile;

b) a ACC codon is in greater than 38% or 40% for Thr;

c) a TTC codon is in greater than 57% or 59% for Phe;

d) a GAG codon is in greater than 60% or 62% for Glu;

e) a CTG codon is in greater than 43% or 45% for Leu;

f) a AAG codon is in greater than 60% or 62% for Lys; and/or g) a GAC codon is in greater than 56% or 58% for Asp.

In certain embodiments, the nucleic acid sequence encoding the protein comprises at least two or more, or three or more, or four or more, five or more, six or more, or all of a), b), c), d), e), f) and g).

In certain embodiments, the nucleic acid sequence encoding the protein comprises less than 100, 50, 30, 25, 20, 15, 10, 9, 8, 7, 6, 5, 4, 3, 2 or no 5'-CG-3' dinucleotides.

In certain embodiments, the disclosure relates to pharmaceutical compositions comprising a vector or a capsid as disclosed herein and a pharmaceutically acceptable excipient.

In certain embodiments, the disclosure relates to methods of inducing blood clotting comprising administering an effective amount of a virus particle, capsid, or vector as disclosed herein to a subject in need thereof.

In certain embodiments, the subject is diagnosed with hemophilia A or B or acquired hemophilia or unlikely to respond to exogenous fVIII infusions.

In certain embodiments, the vector, virus particle, or capsid is administered in combination with an immunosuppressive agent, e.g., ciclosporin, tacrolimus, sirolimus, cyclophosphamide, methotrexate, azathioprine, mercaptopurine, fluorouracil, mycophenolic acid, dactinomycin, fingolimod, T-cell receptor antibody or binding protein, muromonab-CD3, IL-2 receptor antibody or binding protein, basiliximab, daclizumab, recombinant IFN-beta, TNF-alpha antibody or binding protein, infliximab, etanercept, adalimumab, or combinations thereof.

In certain embodiments, the disclosure relates to expression systems comprising nucleic acids or vectors comprising nucleic acids disclosed herein.

In certain embodiments, the disclosure relates to expression systems comprising nucleic acids or vectors comprising nucleic acids disclosed herein.

Additional Embodiments are Illustrated by the Following Clauses:

Clause 1. A vector comprising a liver specific promotor nucleic acid sequence of less than 250 nucleotides in operable combination with a heterologous nucleic acid sequence encoding a protein.

Clause 2. The vector of clause 1, wherein the liver specific promotor sequence comprises a sequence having greater than 50, 60, 70, 80, 85, 90, 95, 96, 97, 98, or 99% sequence identity to GGCCAGCAGCAGCCTGACCACATC (SEQ ID NO: 110).

Clause 3. The vector of clause 1, wherein the liver specific promotor sequence comprises a sequence having greater than 50, 60, 70, 80, 85, 90, 95, 96, 97, 98, or 99% sequence identity to SEQ ID NO: 4, 5, 6, 7, 102, 103, 104, 105, 106, 107, or 108.

Clause 4. The vector of clause 1, wherein the protein is a fVIII or fIX or variant thereof.

Clause 5. The vector of clause 4, wherein fVIII variant comprises an A1 domain, an A2 domain, an ap domain, an A3 domain, a C1 domain, and a C2 domain Clause 6. The vector of clause 4, wherein the fVIII variant comprising a deleted B domain.

Clause 7. The vector of clause 4, wherein the fVIII variant comprises a linker of between two and fifty, or two and twenty five, or two and fifteen amino acids between the A2 domain and the an activation peptide (ap) domain.

Clause 8. The vector of clause 4, wherein the fVIII variant comprises a sequence having greater than 50, 60, 70, 80, 85, 90, 91, 92, 93, 94, 95, 96, 97, 98, or 99% sequence identity to SEQ ID NO: 3.

Clause 9. The vector of clause 4, wherein the fVIII variant comprises a sequence having greater than 50, 60, 70, 80, 85, 90, 91, 92, 93, 94, 95, 96, 97, 98, or 99% sequence identity to SEQ ID NO: 13, 14, 15, or 16.

Clause 10. The method of clause 1 wherein the heterologous nucleic acids sequence comprises a higher percentage of liver cell specific amino acid codons compared to overall human codon usage.

Clause 11. The vector of clause 1, wherein the nucleic acid sequence encoding a protein comprising a higher percentage of liver cell specific amino acid codons compared to overall human codon usage is a sequence having greater than 70, 80, 85, 90, 95, 96, 97, 98, or 99% sequence identity to SEQ ID NO: 2 or 11.

Clause 12. The vector of clause 3, wherein fIX variant comprises a sequence having greater than 50, 60, 70, 80, 85, 90, 91, 92, 93, 94, 95, 96, 97, 98, or 99% sequence identity to SEQ ID NO: 17, 18, or 19.

Clause 13. The vector of clause 1, wherein the nucleic acid sequence encoding a protein comprising a higher percentage of liver cell specific amino acid codons compared to overall human codon usage is a sequence having greater than 70, 80, 85, 90, 95, 96, 97, 98, or 99% sequence identity to SEQ ID NO: 8, 9, or 10.

Clause 14. A pharmaceutical composition comprising a vector of clause 1 and a pharmaceutically acceptable excipient.

Clause 15. A method of inducing blood clotting comprising administering an effective amount of a vector of clause 1 to a subject in need thereof.

Clause 16. The method of clause 15, wherein the subject is diagnosed with hemophilia A or B or acquired hemophilia.

Clause 17. The method of clause 15, wherein the vector is administered in combination with an immunosuppressive agent.

Clause 18. The method of clause 17, wherein the immunosuppressive agent is ciclosporin, tacrolimus, sirolimus, cyclophosphamide, methotrexate, azathioprine, mercaptopurine, fluorouracil, mycophenolic acid, dactinomycin, fingolimod, T-cell receptor antibody or binding protein, muromonab-CD3, IL-2 receptor antibody or binding protein, basiliximab, daclizumab, recombinant IFN-beta, TNF-alpha antibody or binding protein, infliximab, etanercept, or adalimumab.

The following examples are provided to illustrate certain particular features and/or embodiments. These examples should not be construed to limit the disclosure to the particular features or embodiments described.

EXAMPLES

Example 1

Optimization of Clotting Factors and their Encoding DNA

This example illustrates the optimization of the coding sequences for fVIII and fIX proteins to improve their utility for in vivo expression and gene therapy.

The cDNA nucleotide sequence coding for fVIII and fIX was initially optimized by implementing a codon usage bias specific for the human liver cell as compared to naturally occurring nucleotide sequence coding for the corresponding non-codon optimized sequence for a human.

The adaptiveness of a nucleotide sequence encoding fVIII to the codon usage of human liver cells may be expressed as liver codon adaptation index (LCAI). A codon adaptation index is defined as a measurement of the relative adaptiveness of the codon usage of a gene towards the codon usage of genes highly expressed in the human liver. The relative adaptiveness of each codon is the ratio of the usage of each codon, to that of the most abundant codon for the same amino acid. The CAI is defined as the geometric mean of these relative adaptiveness values. Non-synonymous codons and termination codons (dependent on genetic code) are excluded. CAI values range from 0 to 1, with higher values indicating a higher proportion of the most abundant codons. Using the sequences of 43 highly expressed genes in the human liver, a custom codon-usage bias table specific for the human liver was constructed (see FIG. 2A) that differs substantially from the most prevalent codons used in total human coding sequences (FIG. 2B). Optimized coding sequence of the ET3 and HSQ variants of fVIII was developed with the most statistically prevalent codons identified by the liver-usage bias analysis.

ET3 is a B domain deleted (BDD) fVIII hybrid that contains human and porcine domains, i.e., sequence (A1 and A3 porcine, see FIGS. 1A and 1B) with a linker in the deleted B domain. ET3 utilizes a 24 amino acid porcine sequence-derived OL linker sequence, i.e., porcine-derived sequence SFAQNSRPPSASAPKPPVLRRHQR (SEQ ID NO: 23). The ET3 amino acid sequence is SEQ ID NO: 123:

```
MQLELSTCVFLCLLPLGFSAIRRYYLGAVELSWDYRQSELLRELHVDTRF
PATAPGALPLGPSVLYKKTVFVEFTDQLFSVARPRPPWMGLLGPTIQAEV
YDTVVVTLKNMASHPVSLHAVGVSFWKSSEGAEYEDHTSQREKEDDKVLP
GKSQTYVWQVLKENGPTASDPPCLTYSYLSHVDLVKDLNSGLIGALLVCR
EGSLTRERTQNLHEFVLLFAVFDEGKSWHSARNDSWTRAMDPAPARAQPA
MHTVNGYVNRSLPGLIGCHKKSVYWHVIGMGTSPEVHSIFLEGHTFLVRH
HRQASLEISPLTFLTAQTFLMDLGQFLLFCHISSHHHGGMEAHVRVESCA
EEPQLRRKADEEEDYDDNLYDSDMDVVRLDGDDVSPFIQIRSVAKKHPKT
WVHYIAAEEEDWDYAPLVLAPDDRSYKSQYLNNGPQRIGRKYKKVRFMAY
TDETFKTREAIQHESGILGPLLYGEVGDTLLIIFKNQASRPYNIYPHGIT
DVRPLYSRRLPKGVKHLKDFPILPGEIFKYKWTVTVEDGPTKSDPRCLTR
YYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCL
HEVAYWYILSIGAQTDFLSVFFSGYTFKHKMVYEDTLTLFPFSGETVFMS
MENPGLWILGCHNSDFRNRGMTALLKVSSCDKNTGDYYEDSYEDISAYLL
SKNNAIEPRSFAQNSRPPSASAPKPPVLRRHQRDISLPTFQPEEDKMDYD
DIFSTETKGEDFDIYGEDENQDPRSFQKRTRHYFIAAVEQLWDYGMSESP
RALRNRAQNGEVPRFKKVVFREFADGSFTQPSYRGELNKHLGLLGPYIRA
EVEDNIMVTFKNQASRPYSFYSSLISYPDDQEQGAEPRHNFVQPNETRTY
FWKVQHHMAPTEDEFDCKAWAYFSDVDLEKDVHSGLIGPLLICRANTLNA
AHGRQVTVQEFALFFTIFDETKSWYFTENVERNCRAPCHLQMEDPTLKEN
YRFHAINGYVMDTLPGLVMAQNQRIRWYLLSMGSNENIHSIHFSGHVFSV
RKKEEYKMAVYNLYPGVFETVEMLPSKVGIWRIECLIGEHLQAGMSTTFL
VYSKKCQTPLGMASGHIRDFQITASGQYGQWAPKLARLHYSGSINAWSTK
EPFSWIKVDLLAPMIIHGIKTQGARQKFSSLYISQFIIMYSLDGKKWQTY
RGNSTGTLMVFFGNVDSSGIKHNIFNPPIIARYIRLHPTHYSIRSTLRME
LMGCDLNSCSMPLGMESKAISDAQITASSYFTNMFATWSPSKARLHLQGR
SNAWRPQVNNPKEWLQVDFQKTMKVTGVTTQGVKSLLTSMYVKEFLISSS
QDGHQWTLFFQNGKVKVFQGNQDSFTPVVNSLDPPLLTRYLRIHPQSWVH
QIALRMEVLGCEAQDLY
```

HSQ is a human fVIII variant wherein the BDD human fVIII protein is substituted with a 14 amino acid human-derived SQ linker SFSQNPPVLKRHQR (SEQ ID NO: 22). The HSQ amino acid sequence is SEQ ID NO: 3:

```
MQIELSTCFFLCLLRFCFSATRRYYLGAVELSWDYMQSDLGELPVDARFP
PRVPKSFPFNTSVVYKKTLFVEFTVHLFNIAKPRPPWMGLLGPTIQAEVY
DTVVITLKNMASHPVSLHAVGVSYWKASEGAEYDDQTSQREKEDDKVFPG
GSHTYVWQVLKENGPMASDPLCLTYSYLSHVDLVKDLNSGLIGALLVCRE
```

-continued

```
GSLAKEKTQTLHKFILLFAVFDEGKSWHSETKNSLMQDRDAASARAWPKM
HTVNGYVNRSLPGLIGCHRKSVYWHVIGMGTTPEVHSIFLEGHTFLVRNH
RQASLEISPITFLTAQTLLMDLGQFLLFCHISSHQHDGMEAYVKVDSCPE
EPQLRMKNNEEAEDYDDDLTDSEMDVVRFDDDNSPSFIQIRSVAKKHPKT
WVHYIAAEEEDWDYAPLVLAPDDRSYKSQYLNNGPQRIGRKYKKVRFMAY
TDETFKTREAIQHESGILGPLLYGEVGDTLLIIFKNQASRPYNIYPHGIT
DVRPLYSRRLPKGVKHLKDFPILPGEIFKYKWTVTVEDGPTKSDPRCLTR
YYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCL
HEVAYWYILSIGAQTDFLSVFFSGYTFKHKMVYEDTLTLFPFSGETVFMS
MENPGLWILGCHNSDFRNRGMTALLKVSSCDKNTGDYYEDSYEDISAYLL
SKNNAIEPRSFSQNPPVLKRHQREITRTTLQSDQEEIDYDDTISVEMKKE
DFDIYDEDENQSPRSFQKKTRHYFIAAVERLWDYGMSSSPHVLRNRAQSG
SVPQFKKVVFQEFTDGSFTQPLYRGELNEHLGLLGPYIRAEVEDNIMVTF
RNQASRPYSFYSSLISYEEDQRQGAEPRKNFVKPNETKTYFWKVQHHMAP
TKDEFDCKAWAYFSDVDLEKDVHSGLIGPLLVCHTNTLNPAHGRQVTVQE
FALFFTIFDETKSWYFTENMERNCRAPCNIQMEDPTFKENYRFHAINGYI
MDTLPGLVMAQDQRIRWYLLSMGSNENIHSIHFSGHVFTVRKKEEYKMAL
YNLYPGVFETVEMLPSKAGIWRVECLIGEHLHAGMSTLFLVYSNKCQTPL
GMASGHIRDFQITASGQYGQWAPKLARLHYSGSINAWSTKEPFSWIKVDL
LAPMIIHGIKTQGARQKFSSLYISQFIIMYSLDGKKWQTYRGNSTGTLMV
FFGNVDSSGIKHNIFNPPIIARYIRLHPTHYSIRSTLRMELMGCDLNSCS
MPLGMESKAISDAQITASSYFTNMFATWSPSKARLHLQGRSNAWRPQVNN
PKEWLQVDFQKTMKVTGVTTQGVKSLLTSMYVKEFLISSSQDGHQWTLFF
QNGKVKVFQGNQDSFTPVVNSLDPPLLTRYLRIHPQSWVHQIALRMEVLG
CEAQDLY
```

Both HSQ and ET3 contain the RHQR (SEQ ID NO: 24) recognition sequence for PACE/furin processing sequence for the B-domain.

```
The liver codon optimized ET3 sequence is
                                                (SEQ ID NO: 12)
ATGCAGCTGGAACTGTCTACCTGTGTGTTTCTGTGTCTGCTGCCTCTGGG
GTTTTCTGCTATCCGCCGCTACTATCTGGGAGCCGTGGAGCTGTCCTGGG
ACTACAGGCAGAGCGAGCTGCTGAGAGAACTGCACGTGGATACCAGATTC
CCAGCTACCGCTCCAGGAGCTCTGCCTCTGGGCCCATCCGTGCTGTACAA
GAAAACCGTCTTCGTGGAGTTTACCGACCAGCTGTTCAGCGTGGCCAGGC
CAAGACCACCTTGGATGGGACTGCTGGGACCAACCATCCAGGCTGAGGTG
TACGATACCGTGGTCGTGACCCTGAAAAACATGGCCTCCCATCCCGTGAG
CCTGCACGCTGTCGGGGTGTCCTTCTGGAAGTCCAGCGAGGGAGCCGAGT
ACGAAGACCATACCTCCCAGCGCGAGAAAGAAGACGATAAGGTGCTGCCT
GGCAAAAGCCAGACCTATGTCTGGCAGGTGCTGAAGGAGAACGGACCAAC
CGCTAGCGACCCACCATGCCTGACCTACTCTTATCTGTCCCACGTCGATC
```

-continued

TGGTGAAGGACCTGAATTCCGGACTGATCGGAGCTCTGCTGGTGTGTAGA

GAGGGAAGCCTGACCAGAGAAAGAACCCAGAACCTGCATGAGTTCGTCCT

GCTGTTCGCCGTGTTTGACGAAGGGAAGAGCTGGCACTCTGCCCGCAATG

ACTCCTGGACCAGAGCTATGGATCCAGCTCCTGCTAGAGCTCAGCCTGCT

ATGCACACCGTCAACGGCTACGTGAATCGGTCTCTGCCAGGACTGATCGG

CTGCCATAAGAAAAGCGTCTATTGGCACGTGATCGGAATGGGCACCAGCC

CCGAGGTGCATTCTATCTTCCTGGAAGGCCACACCTTTCTGGTCAGGCAC

CATAGACAGGCCTCTCTGGAGATCTCCCCTCTGACCTTCCTGACCGCTCA

GACCTTTCTGATGGACCTGGGGCAGTTCCTGCTGTTTTGCCATATCTCTT

CCCACCATCACGGAGGAATGGAGGCTCACGTCAGGGTGGAATCCTGTGCT

GAGGAACCACAGCTGAGAAGAAAGGCTGATGAGGAAGAGGACTACGACGA

TAACCTGTATGACAGCGATATGGACGTCGTGCGCCTGGACGGCGACGATG

TCAGCCCTTTCATCCAGATCCGGTCTGTGGCCAAGAAACATCCAAAGACC

TGGGTCCACTACATCGCCGCTGAAGAGGAAGATTGGGACTATGCCCCCCT

GGTGCTGGCTCCTGACGATAGATCCTACAAAAGCCAGTATCTGAACAATG

GGCCCCAGCGCATCGGACGGAAGTACAAGAAAGTGAGGTTCATGGCCTAT

ACCGACGAGACCTTTAAGACCAGAGAGGCTATCCAGCACGAATCCGGGAT

CCTGGGACCTCTGCTGTACGGCGAAGTGGGGGATACCCTGCTGATCATCT

TCAAGAACCAGGCCTCCAGGCCATACAATATCTATCCCCATGGCATCACC

GACGTGAGACCACTGTACAGCAGGAGACTGCCCAAGGGGGTCAAACACCT

GAAGGATTTCCCCATCCTGCCTGGAGAGATCTTTAAGTATAAATGGACCG

TCACCGTGGAAGACGGGCCTACCAAGTCCGATCCACGCTGCCTGACCCGG

TACTATAGCTCTTTCGTGAACATGGAGAGAGACCTGGCTAGCGGACTGAT

CGGACCCCTGCTGATCTGTTACAAAGAGAGCGTGGACCAGAGGGGCAACC

AGATCATGTCTGATAAGAGAAATGTCATCCTGTTCTCCGTGTTTGACGAG

AACCGCAGCTGGTACCTGACCGAGAACATCCAGCGGTTCCTGCCAAATCC

AGCTGGAGTGCAGCTGGAGGACCCAGAATTTCAGGCTTCCAACATCATGC

ATAGCATCAATGGCTACGTGTTCGATAGCCTGCAGCTGTCTGTCTGCCTG

CACGAGGTGGCCTACTGGTATATCCTGTCCATCGGCGCTCAGACCGACTT

CCTGTCCGTGTTCTTTAGCGGGTACACCTTTAAGCATAAAATGGTGTATG

AGGATACCCTGACCCTGTTCCCCTTTTCTGGCGAGACCGTGTTCATGTCC

ATGGAAAACCCTGGCCTGTGGATCCTGGGGTGCCACAACAGCGACTTCAG

GAATAGAGGAATGACCGCCCTGCTGAAAGTGTCCAGCTGTGATAAGAATA

CCGGCGATTACTATGAGGACTCTTACGAAGATATCTCCGCTTATCTGCTG

AGCAAGAACAATGCCATCGAGCCCAGGTCTTTCGCTCAGAACTCCAGACC

TCCAAGCGCTTCTGCTCCTAAGCCACCTGTGCTGAGAAGACATCAGAGGG

ACATCTCCCTGCCTACCTTCCAGCCAGAGGAAGATAAAATGGACTACGAC

GATATCTTCAGCACCGAGACCAAGGGGGAAGATTTTGACATCTATGGAGA

GGACGAAAACCAGGATCCAAGATCCTTCCAGAAGAGAACCAGACACTACT

TTATCGCCGCTGTGGAGCAGCTGTGGGACTATGGGATGTCCGAAAGCCCA

-continued

CGGGCCCTGAGGAACAGAGCTCAGAATGGAGAGGTGCCCCGCTTCAAGAA

AGTCGTGTTCCGGGAGTTTGCCGACGGCAGCTTTACCCAGCCATCTTACA

GGGGGGAGCTGAACAAGCATCTGGGGCTGCTGGGACCCTATATCAGAGCC

GAGGTCGAAGATAACATCATGGTGACCTTCAAGAATCAGGCTTCTCGCCC

CTACTCCTTTTATTCTTCCCTGATCTCCTACCCTGACGATCAGGAGCAGG

GCGCCGAACCTAGGCACAACTTCGTGCAGCCAAATGAGACCAGAACCTAC

TTTTGGAAGGTGCAGCATCACATGGCTCCCACCGAGGATGAATTCGACTG

CAAAGCTTGGGCCTATTTTTCCGATGTCGACCTGGAGAAGGACGTGCATA

GCGGCCTGATCGGGCCTCTGCTGATCTGTCGCGCCAACACCCTGAATGCT

GCTCACGGAAGACAGGTCACCGTGCAGGAGTTCGCTCTGTTCTTTACCAT

CTTTGACGAAACCAAGAGCTGGTACTTCACCGAGAACGTGGAAAGGAATT

GCAGAGCCCCCTGTCATCTGCAGATGGAGGACCCTACCCTGAAGGAAAAC

TACAGGTTCCACGCCATCAATGGATATGTCATGGATACCCTGCCCGGCCT

GGTCATGGCTCAGAACCAGCGCATCCGGTGGTACCTGCTGTCTATGGGAT

CCAACGAGAATATCCATAGCATCCACTTCTCTGGCCATGTCTTTTCCGTG

AGGAAGAAAGAGGAATACAAAATGGCCGTGTACAATCTGTATCCTGGGGT

CTTCGAGACCGTGGAAATGCTGCCAAGCAAAGTGGGAATCTGGAGAATCG

AGTGCCTGATCGGCGAACACCTGCAGGCCGGGATGAGCACCACCTTCCTG

GTGTACTCTAAGAAATGTCAGACCCCACTGGGGATGGCCTCCGGACATAT

CCGCGACTTCCAGATCACCGCTAGCGGACAGTACGGACAGTGGGCTCCAA

AGCTGGCTAGACTGCACTATTCTGGCTCCATCAACGCCTGGTCTACCAAA

GAGCCATTCTCCTGGATCAAGGTGGACCTGCTGGCCCCCATGATCATCCA

CGGAATCAAAACCCAGGGCGCTAGGCAGAAGTTCAGCTCTCTGTACATCT

CCCAGTTTATCATCATGTATAGCCTGGACGGGAAGAAATGGCAGACCTAC

AGAGGCAATTCCACCGGGACCCTGATGGTCTTCTTTGGAAACGTGGATTC

CAGCGGCATCAAGCACAACATCTTCAATCCACCCATCATCGCCCGCTACA

TCCGGCTGCATCCTACCCACTATAGCATCAGGTCTACCCTGAGAATGGAG

CTGATGGGATGCGACCTGAACAGCTGTTCTATGCCACTGGGCATGGAGTC

CAAGGCTATCAGCGATGCCCAGATCACCGCTTCTTCCTACTTCACCAATA

TGTTTGCTACCTGGTCCCCAAGCAAGGCTAGACTGCACCTGCAGGGAAGA

TCCAACGCTTGGAGACCCCAGGTGAACAATCCTAAGGAGTGGCTGCAGGT

CGACTTCCAGAAAACCATGAAGGTCACCGGGGTGACCACCCAGGGAGTGA

AATCTCTGCTGACCTCCATGTACGTCAAGGAGTTCCTGATCAGCTCTTCC

CAGGACGGCCACCAGTGGACCCTGTTCTTTCAGAACGGCAAGGTCAAAGT

GTTCCAGGGGAATCAGGACTCTTTTACCCCCGTCGTGAACTCCCTGGATC

CTCCACTGCTGACCAGGTACCTGAGAATCCATCCTCAGAGCTGGGTGCAC

CAGATCGCTCTGAGAATGGAGGTCCTGGGATGCGAAGCTCAGGACCTGTA

TTGA

In addition, CpG DNA motifs in the liver-codon optimized coding sequence for ET3 and HSQ were removed because they may lead to gene methylation and silencing. See Bird, DNA methylation and the frequency of CpG in animal DNA, 1980, Nucleic Acids Res, 8: 1499-1504.

Codons were substituted with the most highly used human/liver alternative (based on the liver-usage bias analysis discussed above) that did not result in the formation of a 5'-CG-3' dinucleotide in the sequence. These modifications removed 174 and 175 CpGs from the liver-codon optimized ET3 and HSQ sequences, respectively. CpG removal also helps the vector evade immune detection, enhancing the safety and efficacy of the vector. See J Clin Invest. 2013, 123(7):2994-3001, entitled "CpG-depleted adeno-associated virus vectors evade immune detection."

The CpG deleted, liver codon optimized ET3 sequence is SEQ ID NO: 11:

```
ATGCAGCTGGAACTGTCTACCTGTGTGTTTCTGTGTCTGCTGCCTCTGGG
GTTTTCTGCTATCAGGAGATACTATCTGGGAGCTGTGGAGCTGTCCTGGG
ACTACAGGCAGTCTGAGCTGCTGAGAGAACTGCATGTGGATACCAGATTC
CCAGCTACAGCTCCAGGAGCTCTGCCTCTGGGCCCATCTGTGCTGTACAA
GAAAACAGTCTTTGTGGAGTTTACAGACCAGCTGTTCTCTGTGGCCAGGC
CAAGACCACCTTGGATGGGACTGCTGGGACCAACCATCCAGGCTGAGGTG
TATGATACAGTGGTGGTGACCCTGAAAAACATGGCCTCCCATCCTGTGAG
CCTGCATGCTGTGGGGGTGTCCTTCTGGAAGTCCTCTGAGGGAGCTGAGT
ATGAAGACCATACCTCCCAGAGGGAGAAAGAAGATGATAAGGTGCTGCCT
GGCAAAAGCCAGACCTATGTCTGGCAGGTGCTGAAGGAGAATGGACCAAC
TGCTTCTGACCCACCATGCCTGACCTACTCTTATCTGTCCCATGTGGATC
TGGTGAAGGACCTGAATTCTGGACTGATTGGAGCTCTGCTGGTGTGTAGA
GAGGGAAGCCTGACCAGAGAAAGAACCCAGAACCTGCATGAGTTTGTCCT
GCTGTTTGCTGTGTTTGATGAAGGGAAGAGCTGGCACTCTGCCAGGAATG
ACTCCTGGACCAGAGCTATGGATCCAGCTCCTGCTAGAGCTCAGCCTGCT
ATGCACACAGTCAATGGCTATGTGAATAGGTCTCTGCCAGGACTGATTGG
CTGCCATAAGAAATCTGTCTATTGGCATGTGATTGGAATGGGCACCAGCC
CTGAGGTGCATTCTATCTTCCTGGAAGGCCACACCTTTCTGGTCAGGCAC
CATAGACAGGCCTCTCTGGAGATCTCCCCTCTGACCTTCCTGACAGCTCA
GACCTTTCTGATGGACCTGGGGCAGTTCCTGCTGTTTTGCCATATCTCTT
CCCACCATCATGGAGGAATGGAGGCTCATGTCAGGGTGGAATCCTGTGCT
GAGGAACCACAGCTGAGAAGAAAGGCTGATGAGGAAGAGGACTATGATGA
TAACCTGTATGACTCTGATATGGATGTGGTGAGGCTGGATGGGGATGATG
TCAGCCCTTTCATCCAGATCAGGTCTGTGGCCAAGAAACATCCAAAGACC
TGGGTCCACTACATTGCTGCTGAAGAGGAAGATTGGGACTATGCCCCCCT
GGTGCTGGCTCCTGATGATAGATCCTACAAAAGCCAGTATCTGAACAATG
GGCCCCAGAGGATTGGAAGGAAGTACAAGAAAGTGAGGTTCATGGCCTAT
ACAGATGAGACCTTTAAGACCAGAGAGGCTATCCAGCATGAATCTGGGAT
CCTGGGACCTCTGCTGTATGGAGAAGTGGGGGATACCCTGCTGATCATCT
TCAAGAACCAGGCCTCCAGGCCATACAATATCTATCCCCATGGCATCACA
GATGTGAGACCACTGTACAGCAGGAGACTGCCCAAGGGGGTCAAACACCT
GAAGGATTTCCCCATCCTGCCTGGAGAGATCTTTAAGTATAAATGGACAG
TCACAGTGGAAGATGGGCCTACCAAGTCTGATCCAAGGTGCCTGACCAGA
```

-continued

```
TACTATAGCTCTTTTGTGAACATGGAGAGAGACCTGGCTTCTGGACTGAT
TGGACCCCTGCTGATCTGTTACAAAGAGTCTGTGGACCAGAGGGGCAACC
AGATCATGTCTGATAAGAGAAATGTCATCCTGTTCTCTGTGTTTGATGAG
AACAGGAGCTGGTACCTGACAGAGAACATCCAGAGGTTCCTGCCAAATCC
AGCTGGAGTGCAGCTGGAGGACCCAGAATTTCAGGCTTCCAACATCATGC
ATAGCATCAATGGCTATGTGTTTGATAGCCTGCAGCTGTCTGTCTGCCTG
CATGAGGTGGCCTACTGGTATATCCTGTCCATTGGAGCTCAGACAGACTT
CCTGTCTGTGTTCTTTAGTGGGTACACCTTTAAGCATAAAATGGTGTATG
AGGATACCCTGACCCTGTTCCCCTTTTCTGGGGAGACAGTGTTCATGTCC
ATGGAAAACCCTGGCCTGTGGATCCTGGGGTGCCACAACTCTGACTTCAG
GAATAGAGGAATGACAGCCCTGCTGAAAGTGTCCAGCTGTGATAAGAATA
CAGGGGATTACTATGAGGACTCTTATGAAGATATCTCTGCTTATCTGCTG
AGCAAGAACAATGCCATTGAGCCCAGGTCTTTTGCTCAGAACTCCAGACC
TCCATCTGCTTCTGCTCCTAAGCCACCTGTGCTGAGAAGACATCAGAGGG
ACATCTCCCTGCCTACCTTCCAGCCAGAGGAAGATAAAATGGACTATGAT
GATATCTTCAGCACAGAGACCAAGGGGGAAGATTTTGACATCTATGGAGA
GGATGAAAACCAGGATCCAAGATCCTTCCAGAAGAGAACCAGACACTACT
TTATTGCTGCTGTGGAGCAGCTGTGGGACTATGGGATGTCTGAAAGCCCA
AGGGCCCTGAGGAACAGAGCTCAGAATGGAGAGGTGCCCAGATTCAAGAA
AGTGGTGTTCAGAGAGTTTGCTGATGGCAGCTTTACCCAGCCATCTTACA
GGGGGGAGCTGAACAAGCATCTGGGGCTGCTGGGACCCTATATCAGAGCT
GAGGTGGAAGATAACATCATGGTGACCTTCAAGAATCAGGCTTCTAGGCC
CTACTCCTTTTATTCTTCCCTGATCTCCTACCCTGATGATCAGGAGCAGG
GAGCTGAACCTAGGCACAACTTTGTGCAGCCAAATGAGACCAGAACCTAC
TTTTGGAAGGTGCAGCATCACATGGCTCCCACAGAGGATGAATTTGACTG
CAAAGCTTGGGCCTATTTTTCTGATGTGGACCTGGAGAAGGATGTGCATT
CTGGCCTGATTGGGCCTCTGCTGATCTGTAGGGCCAACACCCTGAATGCT
GCTCATGGAAGACAGGTCACAGTGCAGGAGTTTGCTCTGTTCTTTACCAT
CTTTGATGAAACCAAGAGCTGGTACTTCACAGAGAATGTGGAAAGGAATT
GCAGAGCCCCCTGTCATCTGCAGATGGAGGACCCTACCCTGAAGGAAAAC
TACAGGTTCCATGCCATCAATGGATATGTCATGGATACCCTGCCTGGCCT
GGTCATGGCTCAGAACCAGAGGATCAGATGGTACCTGCTGTCTATGGGAT
CCAATGAGAATATCCATAGCATCCACTTCTCTGGCCATGTCTTTTCTGTG
AGGAAGAAAGAGGAATACAAAATGGCTGTGTACAATCTGTATCCTGGGGT
CTTTGAGACAGTGGAAATGCTGCCAAGCAAAGTGGGAATCTGGAGAATTG
AGTGCCTGATTGGGGAACACCTGCAGGCTGGGATGAGCACCACCTTCCTG
GTGTACTCTAAGAAATGTCAGACCCCACTGGGGATGGCCTCTGGACATAT
CAGGGACTTCCAGATCACAGCTTCTGGACAGTATGGACAGTGGGCTCCAA
AGCTGGCTAGACTGCACTATTCTGGCTCCATCAATGCCTGGTCTACCAAA
GAGCCATTCTCCTGGATCAAGGTGGACCTGCTGGCCCCCATGATCATCCA
```

-continued

TGGAATCAAAACCCAGGGAGCTAGGCAGAAGTTCAGCTCTCTGTACATCT
CCCAGTTTATCATCATGTATAGCCTGGATGGGAAGAAATGGCAGACCTAC
AGAGGCAATTCCACTGGGACCCTGATGGTCTTCTTTGGAAATGTGGATTC
CTCTGGCATCAAGCACAACATCTTCAATCCACCCATCATTGCCAGGTACA
TCAGGCTGCATCCTACCCACTATAGCATCAGGTCTACCCTGAGAATGGAG
CTGATGGGATGTGACCTGAACAGCTGTTCTATGCCACTGGGCATGGAGTC
CAAGGCTATCTCTGATGCCCAGATCACAGCTTCTTCCTACTTCACCAATA
TGTTTGCTACCTGGTCCCCAAGCAAGGCTAGACTGCACCTGCAGGGAAGA
TCCAATGCTTGGAGACCCCAGGTGAACAATCCTAAGGAGTGGCTGCAGGT
GGACTTCCAGAAAACCATGAAGGTCACAGGGGTGACCACCCAGGGAGTGA
AATCTCTGCTGACCTCCATGTATGTCAAGGAGTTCCTGATCAGCTCTTCC
CAGGATGGCCACCAGTGGACCCTGTTCTTTCAGAATGGCAAGGTCAAAGT
GTTCCAGGGGAATCAGGACTCTTTTACCCCAGTGGTGAACTCCCTGGATC
CTCCACTGCTGACCAGGTACCTGAGAATCCATCCTCAGAGCTGGGTGCAC
CAGATTGCTCTGAGAATGGAGGTCCTGGGATGTGAAGCTCAGGACCTGTA
TTGA.

The CpG deleted, liver codon optimized HSQ sequence is SEQ ID NO: 2:

ATGCAGATTGAACTGTCTACCTGTTTCTTTCTGTGCCTGCTGAGGTTTTG
TTTTTCTGCTACCAGAAGATACTACCTGGGAGCTGTGGAACTGAGCTGGG
ATTACATGCAGTCTGACCTGGGAGAGCTGCCTGTGGATGCTAGATTCCCA
CCTAGAGTCCCTAAGTCCTTCCCCTTCAACACCTCTGTGGTCTACAAGAA
AACCCTGTTTGTGGAGTTTACAGACCACCTGTTCAACATTGCTAAGCCTA
GACCACCATGGATGGGACTGCTGGGACCAACCATCCAGGCAGAGGTGTAT
GACACAGTGGTCATCACCCTGAAAAACATGGCTTCTCACCCTGTGTCCCT
GCATGCTGTGGGAGTCTCCTACTGGAAGGCCTCTGAAGGGGCTGAGTATG
ATGATCAGACCAGCCAGAGGGAAAAAGAGGATGATAAGGTGTTCCCTGGA
GGGTCCCATACCTATGTGTGGCAGGTCCTGAAGGAGAATGGACCAATGGC
TTCTGACCCTCTGTGCCTGACCTACTCTTATCTGTCCCATGTGGACCTGG
TCAAGGATCTGAACTCTGGCCTGATTGGGGCTCTGCTGGTGTGTAGGGAA
GGGTCCCTGGCCAAGGAGAAAACCCAGACCCTGCATAAGTTCATCCTGCT
GTTTGCTGTGTTTGATGAAGGAAAAAGCTGGCACTCTGAGACCAAGAACT
CTCTGATGCAGGACAGGGATGCTGCTTCTGCCAGAGCTTGGCCCAAGATG
CACACAGTGAATGGCTATGTCAATAGGAGCCTGCCTGGACTGATTGGCTG
CCACAGAAAGTCTGTGTATTGGCATGTCATTGGAATGGGCACCACCCCTG
AAGTGCACAGCATCTTCCTGGAGGGGCATACCTTTCTGGTCAGGAACCAC
AGGCAGGCTAGCCTGGAGATCTCTCCAATCACCTTCCTGACAGCCCAGAC
CCTGCTGATGGACCTGGGACAGTTCCTGCTGTTTTGCCACATCTCCAGCC
ACCAGCATGATGGCATGGAGGCTTATGTGAAAGTGGACTCCTGTCCTGAG
GAACCTCAGCTGAGGATGAAGAACAATGAGGAAGCTGAAGACTATGATGA
TGACCTGACAGACTCTGAGATGGATGTGGTCAGGTTTGATGATGATAACT
CTCCCTCCTTTATCCAGATCAGGTCTGTGGCCAAGAAACACCCTAAGACC

-continued

TGGGTCCATTACATTGCTGCTGAGGAAGAGGACTGGGATTATGCTCCACT
GGTGCTGGCCCCTGATGATAGATCCTACAAAAGCCAGTATCTGAACAATG
GACCCCAGAGGATTGGCAGAAAGTACAAGAAAGTGAGGTTCATGGCTTAT
ACAGATGAGACCTTTAAGACCAGAGAAGCCATCCAGCATGAGTCTGGGAT
CCTGGGACCTCTGCTGTATGGGGAAGTGGGGGACACCCTGCTGATCATCT
TCAAGAACCAGGCCAGCAGGCCTTACAATATCTATCCACATGGCATCACA
GATGTGAGACCTCTGTACTCCAGGAGGCTGCCAAAGGGGGTGAAACACCT
GAAGGACTTCCCAATCCTGCCTGGGGAAATCTTTAAGTATAAATGGACAG
TCACAGTGGAGGATGGGCCCACCAAGTCTGACCCTAGGTGCCTGACCAGA
TACTATTCTTCCTTTGTGAATATGGAGAGAGACCTGGCTTCTGGACTGAT
TGGACCCCTGCTGATCTGTTACAAAGAGTCTGTGGATCAGAGGGGCAACC
AGATCATGTCTGACAAGAGGAATGTGATCCTGTTCTCTGTCTTTGATGAA
AACAGGTCTTGGTACCTGACAGAGAACATCCAGAGGTTCCTGCCTAATCC
AGCTGGAGTGCAGCTGGAAGATCCTGAGTTCCAGGCCTCTAACATCATGC
ATTCCATCAATGGCTATGTGTTTGACTCCCTGCAGCTGTCTGTGTGCCTG
CATGAGGTGGCTTACTGGTATATCCTGAGCATTGGAGCCCAGACAGATTT
CCTGTCTGTGTTCTTTTCTGGCTACACCTTTAAGCATAAAATGGTGTATG
AGGACACCCTGACCCTGTTCCCATTTTCTGGAGAAACTGTGTTCATGAGC
ATGGAGAATCCTGGGCTGTGGATCCTGGGATGCCACAACTCTGATTTCAG
GAATAGAGGGATGACAGCCCTGCTGAAAGTGAGCTCTTGTGACAAGAACA
CAGGAGACTACTATGAAGATAGCTATGAGGACATCTCTGCTTATCTGCTG
TCCAAAAACAATGCCATTGAGCCCAGGAGCTTCTCTCAGAACCCTCCAGT
GCTGAAGAGGCACCAGAGGGAGATCACCAGAACCACCCTGCAGTCTGATC
AGGAAGAGATTGACTATGATGATACCATCTCTGTGGAAATGAAGAAAGAG
GACTTTGATATCTATGATGAAGATGAGAACCAGTCTCCCAGGTCCTTCCA
GAAGAAAACCAGACATTACTTTATTGCTGCTGTGGAGAGGCTGTGGGACT
ATGGCATGTCCAGCTCTCCTCATGTGCTGAGAAATAGAGCTCAGTCTGGA
TCTGTCCCACAGTTCAAGAAAGTGGTCTTCCAGGAGTTTACAGATGGAAG
CTTTACCCAGCCACTGTACAGGGGAGAACTGAATGAGCACCTGGGGCTGC
TGGGACCCTATATCAGGGCTGAAGTGGAGGATAACATCATGGTCACCTTC
AGGAATCAGGCCAGCAGACCCTACTCTTTTTATTCCAGCCTGATCTCCTA
TGAAGAGGACCAGAGACAGGGAGCTGAACCAAGAAAAAACTTTGTGAAGC
CTAATGAGACCAAAACCTACTTTTGGAAGGTGCAGCACCATATGGCCCCT
ACCAAAGATGAGTTTGATTGCAAGGCCTGGGCTTATTTTTCTGATGTGGA
TCTGGAGAAGGATGTCCACTCTGGCCTGATTGGGCCACTGCTGGTGTGTC
ATACCAACACCCTGAATCCAGCTCATGGAAGGCAGGTGACAGTCCAGGAA
TTTGCCCTGTTCTTTACCATCTTTGATGAGACCAAGAGCTGGTACTTCAC
AGAAAACATGGAGAGGAATTGCAGAGCCCCATGTAACATCCAGATGGAAG
ACCCCACCTTCAAGGAGAACTACAGATTTCATGCTATCAATGGGTATATC
ATGGATACCCTGCCAGGACTGGTCATGGCTCAGGACCAGAGGATCAGATG

-continued

GTACCTGCTGAGCATGGGGTCTAATGAGAATATCCACTCCATCCATTTCT
CTGGACATGTGTTTACAGTAAGGAAGAAAGAAGAGTACAAGATGGCCCTG
TACAACCTGTATCCTGGGGTGTTTGAAACAGTGGAGATGCTGCCTTCCAA
GGCTGGGATCTGGAGGGTGGAATGCCTGATTGGGGAGCACCTGCATGCTG
GAATGTCTACCCTGTTCCTGGTGTACTCCAATAAGTGTCAGACCCCCCTG
GGGATGGCTTCTGGACATATCAGGGACTTCCAGATCACAGCTTCTGGACA
GTATGGACAGTGGGCTCCTAAGCTGGCTAGACTGCACTATTCTGGCTCCA
TCAATGCTTGGTCTACCAAAGAGCCTTTCTCCTGGATCAAGGTGGACCTG
CTGGCTCCAATGATCATCCATGGCATCAAAACCCAGGGGGCCAGGCAGAA
GTTCTCTTCCCTGTACATCAGCCAGTTTATCATCATGTATTCTCTGGATG
GGAAGAAATGGCAGACCTACAGAGGCAATTCCACAGGGACCCTGATGGTG
TTCTTTGGCAATGTGGACAGCTCTGGGATCAAGCACAACATCTTCAATCC
CCCTATCATTGCCAGGTACATCAGACTGCACCCAACCCATTATTCCATCA
GGAGCACCCTGAGAATGGAGCTGATGGGGTGTGATCTGAACAGCTGTTCT
ATGCCCCTGGGAATGGAGTCTAAGGCCATCTCTGATGCTCAGATCACAGC
CTCCAGCTACTTCACCAATATGTTTGCTACCTGGTCCCCAAGCAAGGCTA
GACTGCATCTGCAGGGAAGAAGCAATGCTTGGAGACCACAGGTGAACAAT
CCCAAGGAGTGGCTGCAGGTGGACTTCCAGAAAACCATGAAGGTGACAGG
AGTCACCACCCAGGGAGTGAAAAGCCTGCTGACCTCTATGTATGTCAAGG
AGTTCCTGATCTCTTCCAGCCAGGATGGGCACCAGTGGACCCTGTTCTTT
CAGAATGGAAAGGTGAAAGTCTTCCAGGGCAATCAGGATTCCTTTACCCC
TGTGGTCAACAGCCTGGACCCACCCCTGCTGACCAGGTACCTGAGAATCC
ACCCACAGTCCTGGGTGCATCAGATTGCTCTGAGGATGGAAGTCCTGGGC
TGTGAGGCCCAGGACCTGTATTGA

Figure 3A:
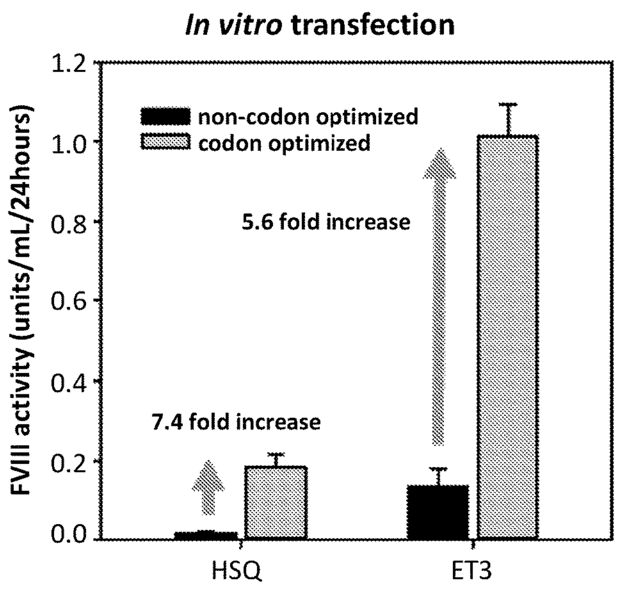
FIG. 3A shows in vitro expression data in HepG2 cells indicating that liver specific codon optimization improves expression for the HSQ and ET3 variants of the fVIII protein.
Figure 3B:
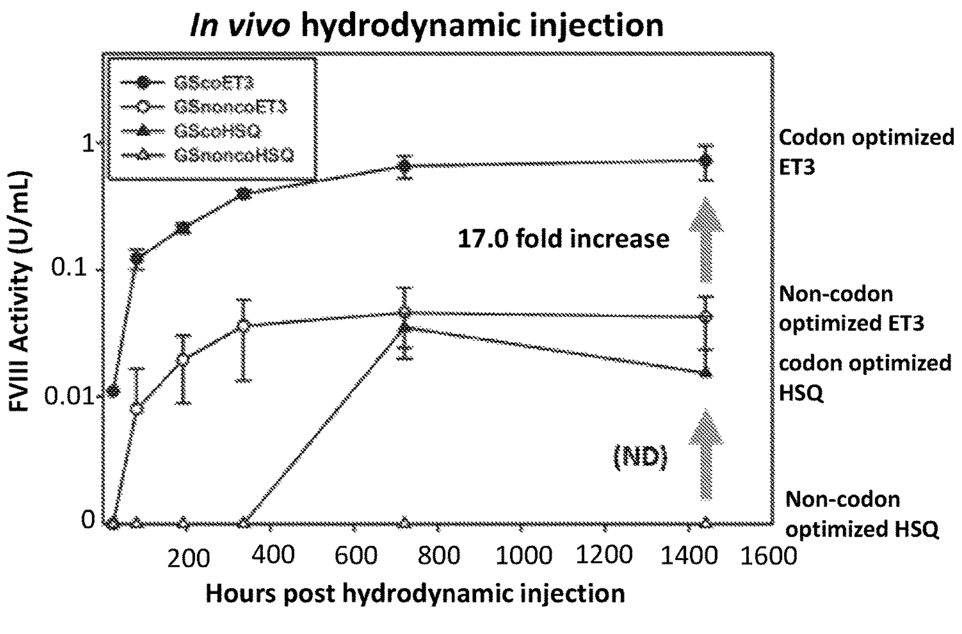
FIG. 3B shows in vivo data for codon optimized HSQ and ET3 indicating increased expression of fVIII following hydrodynamic injection of an AAV-vector encoding liver codon optimized variants of the HSQ and ET3 fVIII protein into mice.

This approach increased the LCAI from 0.62 to 0.86 for B domain deleted human fVIII (HSQ). In vitro expression of the optimized fVIII sequences was assessed in HepG2 cells transiently transfected with corresponding fVIII expression plasmids. The codon-optimization in the nucleic acid sequence coding for HSQ increased expression of HSQ 7.4 fold, and expressed as efficiently as non-codon optimized ET3 (FIG. 3A). The codon-optimization in the nucleic acid sequence coding for HSQ increased expression of ET3 5.6 fold. When tested in vivo by hydrodynamic injection of plasmid carrying the codon optimized fVIII variants into mice, HSQ activity rose to levels that could be detected by the assay which were nearly equivalent to the fVIII levels seen in the non-codon optimized ET3 (FIG. 3B). Further, a 17 fold increase in activity was observed for the codon optimized ET3 (FIG. 3B).

Figure 4:
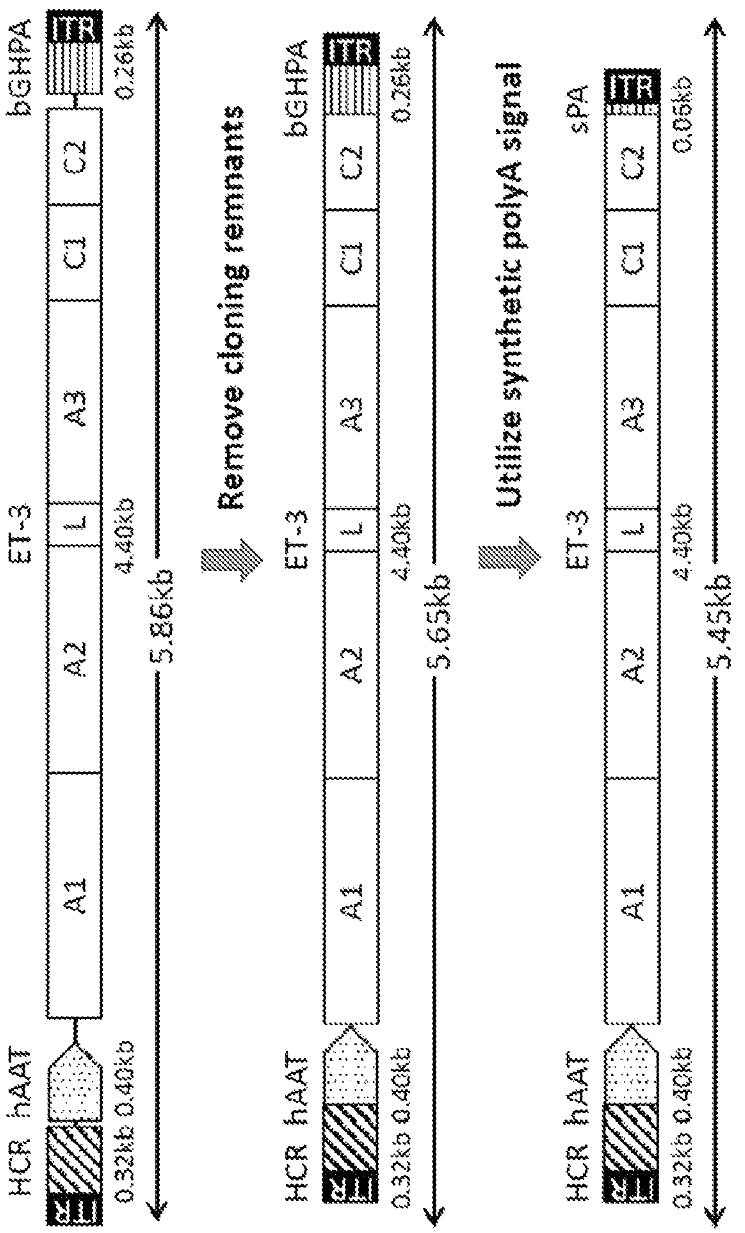
FIG. 4 illustrates AAV vectors encoding fVIII variants.

Translation efficacy can sometimes also be improved through optimization of GC content, mRNA secondary structure, premature PolyA sites, RNA instability motif, stable free energy of mRNA, internal chi sites, ribosomal binding sites, cryptic splicing sites, negative CpG islands, SD sequence, TATA boxes, and cyptic terminal signals, etc. FIG. 4 illustrates changes that were made to an AAV cassette encoding the ET3 codon-optimized CpG deleted sequence to increase its production. Several cis-acting elements within the HSQ sequence were additional modified to increase fVIII expression, as summarized in the following table.

| CIS-Acting Elements | Optimized | Original |
|---|---|---|
| Splice(GGTAAG) | 0 | 2 |
| Splice(GGTGAT) | 0 | 1 |
| PolyA(AATAAA) (4789-AATAAA) | 1 | 1 |
| PolyA(ATTAAA) | 0 | 0 |
| Destabilizing(ATTTA) | 0 | 6 |
| PolyT(TTTTTT) (4827-TTTTTT) | 1 | 2 |
| PolyA(AAAAAAA) | 0 | 1 |

In addition to the liver-optimized codon sequences provided above, the encoding sequence for the ET3 and HSQ fVIII proteins were codon-optimized for expression in myeloid cells. Using the sequences of highly expressed genes in the human myeloid cells, a custom codon-usage bias table specific for the human liver was constructed (see FIG. 2C) that differs substantially from the most prevalent codons used in total human coding sequences (FIG. 2B). Optimized coding sequence of the ET3 and HSQ variants of fVIII was developed with the most statistically prevalent codons identified by the liver-usage bias analysis. In addition, CpG DNA motifs in the myeloid-codon optimized coding sequence for ET3 and HSQ were removed because they may lead to gene methylation and silencing.

The CpG deleted, myeloid codon optimized ET3 sequence is SEQ ID NO: 125:

ATGCAGCTGGAGCTCTCAACCTGTGTGTTCCTCTGCCTGCTCCCCCTGGG
ATTTTCAGCTATCAGGAGATACTATCTGGGAGCAGTGGAACTGTCCTGGG
ACTACAGGCAGTCAGAGCTGCTCAGAGAACTGCATGTGGATACTAGGTTC
CCTGCAACAGCTCCTGGAGCACTGCCACTGGGACCTTCAGTGCTGTACAA
GAAAACTGTCTTTGTGGAGTTTACAGACCAGCTGTTCAGTGTGGCCAGGC
CCAGGCCCCCCTGGATGGGGCTGCTGGGACCCACCATCCAGGCTGAAGTG
TATGATACTGTGGTGGTGACCCTGAAAAACATGGCCTCTCATCCAGTCAG
CCTGCATGCTGTGGGAGTGAGCTTCTGGAAGAGCAGTGAGGGAGCTGAGT
ATGAAGACCATACCTCACAGAGGGAGAAAGAAGATGATAAGGTGCTGCCA
GGAAAAAGCCAGACCTATGTGTGGCAGGTGCTGAAGGAGAATGGCCCTAC
AGCTTCAGATCCTCCCTGCCTCACATACTCTTATCTGAGCCATGTGGATC
TGGTGAAGGACCTCAATAGTGGCCTGATTGGGGCACTGCTGGTGTGCAGA
GAGGGGTCCCTCACAAGGGAAAGAACTCAGAACCTGCATGAGTTTGTCCT
GCTCTTTGCTGTGTTTGATGAGGGAAAGTCCTGGCACTCAGCAAGGAATG
ACAGCTGGACCAGGGCTATGGACCCAGCACCAGCCAGAGCTCAGCCAGCT
ATGCACACTGTCAATGGCTATGTGAATAGGTCCCTGCCTGGACTCATTGG
CTGCCATAAGAAATCAGTCTATTGGCATGTGATTGGAATGGGCACCAGCC
CAGAGGTGCATTCCATCTTCCTGGAAGGCCACACATTTCTGGTCAGGCAC
CATAGACAGGCCAGCCTGGAGATCAGCCCACTGACTTTCCTCACAGCACA
GACATTTCTGATGGACCTGGGGCAGTTCCTGCTCTTTTGCCATATCTCAA
GTCACCATCATGGAGGGATGGAGGCTCATGTCAGGGTGGAAAGCTGTGCA
GAGGAACCTCAGCTGAGGAGGAAGGCAGATGAGGAAGAGGACTATGATGA
TAACCTGTATGACTCAGATATGGATGTGGTGAGGCTGGATGGAGATGATG
TCAGCCCATTCATCCAGATCAGGTCAGTGGCTAAGAAACACCCTAAGACC

-continued

TGGGTCCACTACATTGCAGCTGAAGAGGAAGATTGGGACTATGCACCCCT

GGTGCTGGCCCCAGATGATAGAAGTTACAAATCTCAGTATCTGAACAATG

GGCCCCAGAGGATTGGAAGGAAGTACAAGAAAGTGAGGTTCATGGCTTAT

ACTGATGAGACCTTTAAGACAAGAGAGGCAATCCAGCATGAAAGTGGCAT

CCTGGGACCACTGCTCTATGGAGAAGTGGGGGATACCCTGCTCATCATCT

TCAAGAACCAGGCCTCAAGGCCTTACAATATCTATCCCCATGGCATCACA

GATGTGAGGCCTCTCTACAGCAGGAGACTGCCCAAGGGAGTCAAACACCT

CAAGGATTTCCCCATCCTGCCAGGGGAAATCTTCAAGTATAAATGGACAG

TCACTGTGGAAGATGGGCCAACTAAGTCAGATCCTAGGTGCCTGACCAGG

TACTATTCTAGCTTTGTGAACATGGAGAGGGACCTGGCTTCAGGACTGAT

TGGACCTCTGCTCATCTGCTACAAAGAATCAGTGGACCAGAGGGGCAACC

AGATCATGAGTGATAAGAGAAATGTCATCCTGTTCTCAGTGTTTGATGAG

AATAGGAGTTGGTATCTGACAGAAAACATCCAGAGGTTCCTGCCTAATCC

TGCAGGAGTGCAGCTGGAGGACCCAGAATTTCAGGCTTCAAACATCATGC

ATAGTATCAATGGCTATGTGTTTGATAGTCTGCAGCTCTCTGTCTGCCTG

CATGAGGTGGCCTACTGGTATATCCTCAGCATTGGAGCTCAGACTGACTT

CCTGAGTGTGTTCTTTTCAGGCTACACATTCAAGCATAAGATGGTCTATG

AAGATACCCTGACACTCTTCCCCTTTTCTGGGGAGACTGTGTTTATGAGC

ATGGAAAACCCAGGCCTGTGGATTCTGGGGTGCCACAACAGTGACTTCAG

GAATAGAGGGATGACTGCTCTGCTCAAAGTGTCCTCATGTGATAAGAATA

CTGGAGATTACTATGAGGACTCTTATGAAGATATCAGTGCATATCTGCTC

TCCAAAAACAATGCCATTGAGCCCAGGTCATTTGCTCAGAACAGTAGACC

ACCTTCTGCAAGTGCACCAAAGCCTCCAGTGCTGAGGAGACACCAGAGGG

ACATCAGCCTGCCAACCTTCCAGCCTGAGGAAGATAAAATGGACTATGAT

GATATCTTCTCCACTGAGACCAAGGGGGAAGATTTTGACATCTATGGAGA

GGATGAAAACCAGGACCCCAGGTCCTTCCAGAAGAGGACCAGACACTACT

TTATTGCAGCTGTGGAGCAGCTGTGGGACTATGGCATGTCTGAATCACCT

AGAGCTCTGAGGAACAGAGCACAGAATGGGGAGGTGCCCAGGTTCAAGAA

AGTGGTGTTCAGAGAATTTGCAGATGGCTCTTTTACCCAGCCTAGCTACA

GGGGGGAGCTCAACAAGCATCTGGGGCTGCTGGGACCCTATATCAGAGCA

GAGGTGGAAGATAACATCATGGTGACATTCAAGAATCAGGCCTCAAGACC

CTACAGTTTTTATAGTTCTCTGATCAGCTACCCAGATGATCAGGAGCAGG

GGGCTGAACCAAGGCACAACTTTGTGCAGCCTAATGAGACAAGAACTTAC

TTTTGGAAGGTCCAGCATCACATGGCTCCCACAGAGGATGAGTTTGACTG

CAAGGCCTGGGCATATTTTTCTGATGTGGACCTGGAGAAGGATGTGCATA

GTGGCCTCATTGGGCCACTGCTCATCTGCAGGGCAAACACACTGAATGCT

GCACATGGCAGGCAGGTCACTGTGCAGGAGTTTGCCCTGTTCTTTACAAT

CTTTGATGAAACTAAGTCCTGGTACTTCACAGAGAATGTGGAAAGGAATT

GCAGAGCCCCCTGCCATCTCCAGATGGAGGACCCAACTCTGAAGGAAAAC

TACAGGTTCCATGCTATCAATGGATATGTCATGGATACACTGCCAGGCCT

GGTGATGGCACAGAACCAGAGGATCAGGTGGTATCTGCTCAGCATGGGGT

-continued

CCAATGAGAATATCCATTCTATCCACTTCTCAGGACATGTCTTTTCAGTG

AGGAAGAAAGAGGAATATAAAATGGCTGTGTACAATCTGTATCCAGGGGT

CTTTGAGACAGTGGAAATGCTGCCTAGCAAAGTGGGGATCTGGAGAATTG

AGTGCCTCATTGGAGAACACCTGCAGGCAGGGATGTCCACCACATTTCTG

GTGTACTCAAAGAAATGCCAGACTCCCCTGGGGATGGCAAGTGGACATAT

CAGGGACTTCCAGATCACTGCATCAGGACAGTATGGACAGTGGGCACCAA

AGCTGGCTAGGCTCCACTATAGTGGCTCTATCAATGCTTGGAGTACCAAA

GAGCCTTTCTCTTGGATCAAGGTGGATCTGCTGGCCCCCATGATCATCCA

TGGAATCAAAACACAGGGAGCTAGACAGAAGTTCAGCTCCCTGTACATCA

GTCAGTTTATCATCATGTATTCTCTGGATGGGAAGAAATGGCAGACCTAC

AGGGGCAATAGCACTGGGACACTGATGGTCTTCTTTGGAAATGTGGATTC

AAGTGGCATCAAGCACAACATCTTCAATCCTCCCATCATTGCCAGGTACA

TCAGACTGCATCCCACACACTATTCAATCAGGAGTACTCTCAGAATGGAG

CTGATGGGGTGTGACCTCAACAGCTGCTCCATGCCACTGGGAATGGAATC

CAAGGCAATCTCAGATGCCCAGATCACTGCTTCTAGCTACTTCACCAATA

TGTTTGCAACATGGTCACCCAGTAAAGCAAGGCTGCACCTCCAGGGAAGG

TCCAATGCTTGGAGACCCCAGGTGAACAATCCAAAGGAGTGGCTGCAGGT

GGACTTTCAGAAAACCATGAAGGTCACAGGGGTGACTACCCAGGGAGTGA

AAAGTCTGCTCACCTCTATGTATGTCAAGGAGTTCCTGATCTCCTCAAGT

CAGGATGGCCACCAGTGGACACTGTTCTTTCAGAATGGCAAGGTCAAAGT

GTTCCAGGGGAATCAGGACAGCTTTACACCAGTGGTGAACAGCCTGGACC

CCCCTCTGCTCACTAGATATCTGAGAATCCATCCACAGAGCTGGGTGCAC

CAGATTGCACTCAGAATGGAGGTCCTGGGCTGTGAAGCCCAGGACCTGTA

TTGA

The CpG deleted, myeloid codon optimized HSQ sequence is SEQ ID NO: 126:

ATGCAGATTGAGCTCAGCACCTGCTTCTTTCTGTGCCTGCTCAGGTTCTG

CTTTTCAGCCACAAGGAGATACTATCTGGGAGCTGTGGAACTGTCATGGG

ATTACATGCAGAGTGACCTGGGAGAGCTCCCTGTGGATGCTAGGTTCCCC

CCAAGGGTCCCAAAGTCTTTCCCTTTTAATACCAGTGTGGTCTATAAGAA

AACACTCTTTGTGGAATTTACTGATCACCTGTTCAACATTGCAAAGCCAA

GGCCTCCCTGGATGGGACTGCTGGGACCTACCATCCAGGCTGAGGTGTAT

GACACTGTGGTCATCACACTGAAAAACATGGCATCTCACCCTGTCAGCCT

GCATGCAGTGGGAGTCAGCTACTGGAAGGCTTCAGAAGGGGCAGAGTATG

ATGATCAGACAAGCCAGAGAGAAAAAGAGGATGATAAGGTGTTCCCAGGA

GGGAGCCATACTTATGTGTGGCAGGTCCTGAAGGAGAATGGCCCAATGGC

CAGTGACCCACTGTGCCTCACCTACTCATATCTGAGTCATGTGGACCTGG

TCAAGGATCTCAACTCAGGCCTGATTGGGGCACTGCTGGTGTGCAGGGAA

GGCTCACTGGCCAAGGAGAAAACCCAGACACTGCATAAGTTCATCCTGCT

CTTTGCTGTGTTTGATGAAGGGAAATCTTGGCACAGTGAGACCAAGAACA

GTCTGATGCAGGACAGGGATGCTGCTTCTGCCAGAGCTTGGCCCAAGATG

-continued

CACACAGTGAATGGATATGTCAATAGGTCCCTGCCAGGACTCATTGGCTG
CCACAGAAAGTCAGTGTATTGGCATGTCATTGGAATGGGCACCACACCAG
AAGTGCACAGCATCTTCCTGGAGGGGCATACCTTTCTGGTCAGGAACCAC
AGGCAGGCCAGCCTGGAGATCAGCCCAATCACCTTCCTGACAGCCCAGAC
TCTGCTCATGGATCTGGGGCAGTTCCTGCTCTTTTGCCACATCAGCTCCC
ACCAGCATGATGGAATGGAGGCATATGTGAAAGTGGACTCCTGCCCAGAG
GAACCACAGCTGAGGATGAAGAACAATGAGGAAGCTGAAGACTATGATGA
TGACCTGACAGACTCAGAGATGGATGTGGTCAGGTTTGATGATGATAACA
GCCCCTCCTTTATCCAGATCAGAAGTGTGGCCAAGAAACACCCAAAGACA
TGGGTCCATTACATTGCAGCTGAGGAAGAGGACTGGGATTATGCACCTCT
GGTGCTGGCCCCAGATGATAGATCCTACAAATCACAGTATCTGAACAATG
GACCCCAGAGGATTGGCAGAAAGTACAAGAAAGTGAGGTTCATGGCCTAT
ACTGATGAAACATTTAAGACTAGAGAAGCTATCCAGCATGAGTCAGGCAT
CCTGGGACCACTGCTCTATGGAGAAGTGGGGGACACCCTGCTCATCATCT
TCAAGAACCAGGCTTCCAGGCCATACAATATCTATCCTCATGGCATCACA
GATGTGAGACCACTCTACTCAAGGAGACTGCCTAAGGGAGTCAAACACCT
CAAGGACTTCCCTATCCTGCCAGGGGAAATCTTTAAGTATAAATGGACTG
TGACAGTGGAGGATGGGCCCACTAAGAGTGACCCAAGGTGCCTGACCAGA
TACTATTCAAGTTTTGTGAATATGGAAAGGGATCTGGCATCAGGACTGAT
TGGACCTCTGCTCATCTGCTACAAAGAGAGTGTGGATCAGAGGGGCAACC
AGATCATGTCAGACAAGAGGAATGTGATCCTGTTCAGTGTCTTTGATGAA
AACAGGTCTTGGTATCTGACAGAGAACATCCAGAGATTCCTGCCAAATCC
TGCAGGGGTGCAGCTGGAAGATCCAGAGTTTCAGGCCTCAAACATCATGC
ATAGTATCAATGGATATGTGTTTGACAGTCTGCAGCTCTCTGTGTGCCTG
CATGAAGTGGCCTACTGGTATATCCTGTCCATTGGAGCTCAGACAGATTT
CCTGAGTGTGTTCTTTTCAGGCTACACTTTTAAGCATAAAATGGTCTATG
AGGACACACTGACTCTCTTCCCTTTTAGTGGGGAAACAGTGTTTATGAGC
ATGGAGAATCCAGGGCTGTGGATTCTGGGATGCCACAACAGTGATTTCAG
GAATAGAGGCATGACTGCTCTGCTCAAAGTGTCTAGCTGTGACAAGAACA
CAGGGGACTACTATGAAGATTCTTATGAGGACATCAGTGCTTATCTGCTC
TCCAAAAACAATGCAATTGAACCCAGATCATTCAGTCAGAATCCACCTGT
GCTGAAGAGGCACCAGAGAGAGATCACTAGGACTACCCTGCAGTCAGATC
AGGAAGAGATTGACTATGATGATACCATCTCAGTGGAAATGAAGAAAGAG
GACTTTGATATCTATGATGAAGATGAGAACCAGAGTCCAAGGTCTTTCCA
GAAGAAAACCAGACATTACTTTATTGCTGCAGTGGAGAGGCTGTGGGATT
ATGGAATGTCCTCAAGTCCACATGTGCTGAGGAATAGGGCACAGTCTGGC
AGTGTCCCTCAGTTCAAGAAAGTGGTCTTCCAGGAGTTTACAGATGGCAG
CTTCACTCAGCCTCTGTACAGGGGAGAACTCAATGAGCACCTGGGGCTGC
TGGGACCCTATATCAGAGCTGAAGTGGAGGATAACATCATGGTCACCTTC
AGGAATCAGGCTTCAAGACCCTACAGTTTTTATTCTAGCCTGATCAGCTA
TGAAGAGGACCAGAGGCAGGGAGCTGAACCTAGGAAAAACTTTGTGAAGC

-continued

CAAATGAGACCAAAACATACTTTTGGAAGGTCCAGCACCACATGGCACCA
ACCAAAGATGAGTTTGATTGCAAGGCATGGGCCTATTTTTCAGATGTGGA
TCTGGAGAAGGATGTCCACAGTGGCCTCATTGGGCCTCTGCTGGTGTGCC
ATACTAACACCCTGAATCCAGCTCATGGCAGGCAGGTGACAGTCCAGGAG
TTTGCACTGTTCTTTACCATCTTTGATGAGACAAAGTCCTGGTACTTCAC
TGAAAACATGGAGAGGAATTGCAGAGCTCCTTGCAACATCCAGATGGAAG
ACCCCACCTTCAAGGAGAACTACAGATTTCATGCAATCAATGGGTATATC
ATGGATACACTGCCAGGACTGGTGATGGCCCAGGACCAGAGGATCAGATG
GTATCTGCTCAGCATGGGGTCCAATGAGAATATCCACTCTATCCATTTCA
GTGGACATGTGTTTACAGTCAGAAAGAAAGAAGAGTATAAAATGGCCCTG
TACAACCTCTATCCAGGAGTGTTTGAAACAGTGGAGATGCTGCCAAGCAA
GGCTGGGATCTGGAGGGTGGAATGCCTCATTGGGGAGCACCTGCATGCAG
GAATGTCAACCCTGTTTCTGGTCTACAGTAATAAGTGCCAGACACCTCTG
GGAATGGCAAGTGGACATATCAGGGATTTCCAGATCACTGCTAGTGGACA
GTATGGACAGTGGGCACCAAAGCTGGCTAGACTCCACTATTCAGGCTCAA
TCAATGCTTGGTCCACCAAAGAGCCATTCTCATGGATCAAGGTGGACCTG
CTGGCTCCTATGATCATCCATGGCATCAAAACACAGGGGGCAAGGCAGAA
GTTCTCCTCACTGTACATCTCTCAGTTTATCATCATGTATAGCCTGGATG
GCAAGAAATGGCAGACCTACAGGGGCAATAGCACAGGGACTCTGATGGTG
TTCTTTGGCAATGTGGACAGCAGTGGGATCAAGCACAACATCTTCAATCC
CCCAATCATTGCAAGGTACATCAGACTGCACCCCACCCATTATTCAATCA
GGAGTACACTCAGGATGGAACTGATGGGGTGTGATCTCAACAGTTGCTCT
ATGCCACTGGGAATGGAGTCCAAGGCAATCTCAGATGCCCAGATCACTGC
TAGCTCCTACTTCACTAATATGTTTGCTACCTGGAGCCCCTCCAAAGCAA
GGCTGCACCTCCAGGGAAGGAGCAATGCATGGAGGCCTCAGGTGAACAAT
CCCAAGGAATGGCTGCAGGTGGATTTCCAGAAAACTATGAAGGTGACTGG
AGTCACAACTCAGGGAGTGAAAAGTCTGCTCACTTCTATGTATGTCAAGG
AGTTCCTGATCTCAAGTTCTCAGGATGGCCACCAGTGGACCCTGTTCTTT
CAGAATGGAAAGGTGAAAGTCTTCCAGGGCAATCAGGATTCCTTTACACC
AGTGGTCAACTCACTGGACCCTCCCCTGCTCACTAGATATCTGAGAATCC
ACCCTCAGAGCTGGGTGCATCAGATTGCTCTCAGAATGGAAGTCCTGGGC
TGTGAGGCACAGGACCTGTATTGA

Figure 5:
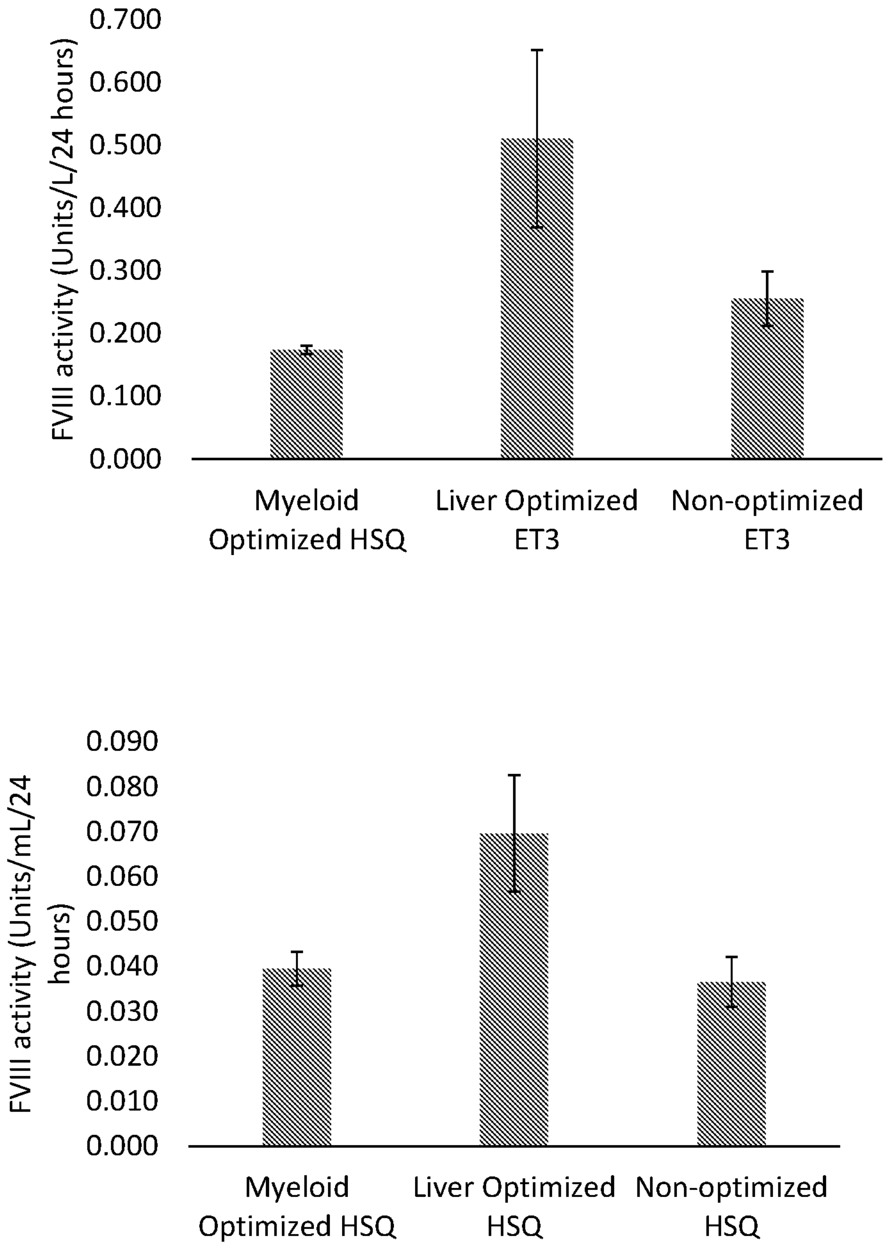
FIG. 5 shows in vitro expression data in HepG2 cells indicating that liver specific codon optimization, but not myeloid specific codon optimization, improves expression of HSQ and ET3 variants of the fVIII protein in liver cells.

In vitro expression of the non-optimized, liver-optimized, and myeloid optimized fVIII sequences was assessed in HepG2 cells transiently transfected with corresponding fVIII expression plasmids (FIG. 5). The tissue specific optimization lead to increased FVIII activity in the HepG2 (hepatic) cells expressing the liver-optimized fVIII compared to either non-optimized or myeloid optimized forms of ET3 or HSQ. These results show that liver optimization specifically benefits expression in hepatocyte derived cells and that expression of myeloid-optimized FVIII does not benefit expression in HepG2 cells.

Further, when these experiments were repeated using non-human cells (baby hamster kidney cells), it was found that the human-specific sequence optimization led to decreased expression in the non-human cells (FIG. 6).

Factor IX

Similar to the codon-optimization for clotting fVIII discussed above, fIX sequences were also codon optimized for expression in hepatocytes using the same codon optimization tables used for clotting factor fVIII. The fIX sequences selected for optimization include fIX with the pro-thrombogenic "Padua" mutation R338L ("fIX Padua," see Paolo et al, "X-Linked Thrombophilia with a Mutant Factor IX" N Engl J Med; 361:1671-1675, 2009) and fIX with the thrombophelic "Malmo" variant 148T (fIX Malmo," see Graham et al, "The Malmo Polymorphism of Coagulation Factor IX, An Immunologic Polymorphism Due to Dimorphism of Residue 148 That Is in Linkage Disequilibrium with Two Other FIX Polymorphisms," Am. J. Hum. Genet. 42:573-580, 1988)

Liver and myeloid optimized fIX cDNAs were designed and optimized according to the liver and myeloid tables shown in FIG. 2. All instances of "cg" in their sequence removed through synonymous codon substitution. Both cDNAs incorporate the Padua and Malmo substitutions.

```
Liver codon optimized fIX with Padua/Malmo
mutations and no CpG (Version 1)
                                        (SEQ ID NO: 124)
ATGCAGAGGGTCAATATGATCATGGCTGAATCTCCTGGGCTGATCACCAT

TTGCCTGCTGGGATACCTGCTGTCTGCTGAGTGTACAGTGTTCCTGGACC

ATGAGAATGCCAATAAGATCCTGAACAGGCCCAAAAGATACAATTCTGGA

AAGCTGGAGGAATTTGTGCAGGGCAACCTGGAGAGGGAATGCATGGAGGA

AAAGTGTAGCTTTGAGGAAGCTAGGGAGGTGTTTGAAAACACAGAGAGGA

CCACAGAATTCTGGAAGCAGTATGTGGATGGAGATCAGTGTGAGTCCAAC

CCCTGTCTGAATGGAGGGTCTTGCAAAGATGATATCAACTCCTATGAGTG

CTGGTGTCCTTTTGGATTTGAAGGCAAAAATTGTGAGCTGGATGTGACCT

GTAACATCAAGAATGGCAGGTGTGAGCAGTTCTGTAAAAACTCTGCTGAT

AATAAGGTGGTCTGCAGCTGTACAGAAGGCTATAGGCTGGCTGAGAACCA

GAAGAGCTGTGAACCAGCTGTGCCCTTCCCTTGTGGGAGGGTGTCTGTCA

GCCAGACCTCTAAGCTGACCAGAGCTGAGACTGTGTTCCCAGATGTGGAT

TATGTCAACTCCACAGAGGCTGAAACCATCCTGGACAACATCACCCAGTC

TACCCAGTCCTTCAATGACTTTACCAGAGTGGTGGGAGGAGAGGATGCCA

AACCAGGCCAGTTCCCCTGGCAGGTGGTCCTGAATGGGAAGGTGGATGCT

TTTTGTGGGGGATCCATTGTGAATGAGAAATGGATTGTCACAGCTGCTCA

CTGTGTGGAGACAGGGGTCAAGATCACTGTGGTGGCTGGAGAGCACAACA

TTGAGGAAACAGAACATACTGAGCAGAAGAGGAATGTGATCAGAATCATC

CCTCACCATAACTACAATGCTGCTATCAACAAATATAATCATGACATTGC

CCTGCTGGAACTGGATGAGCCTCTGGTGCTGAACAGCTATGTCACCCCAA

TCTGCATTGCTGACAAAGAGTATACCAATATCTTCCTGAAGTTTGGATCT

GGATATGTGTCTGGATGGGGAAGGGTCTTCCACAAGGGCAGGTCTGCCCT

GGTGCTGCAGTATCTGAGGGTGCCTCTGGTGGACAGAGCTACCTGCCTGC

TGTCTACCAAGTTCACCATCTACAACAATATGTTCTGTGCTGGATTTCAT

GAGGGAGGCAGGGACTCCTGTCAGGGGGATTCTGGAGGCCCACATGTGAC
```

-continued

```
AGAGGTGGAAGGCACCAGCTTCCTGACTGGCATCATCTCTTGGGGGGAGG

AATGTGCTATGAAGGGGAAATATGGAATCTACACCAAAGTGAGCAGGTAT

GTGAACTGGATCAAAGAGAAGACCAAACTGACCTGA

Liver-Codon Optimized fIX with no CpG encoding
A582 modifications
                                          (SEQ ID NO: 8)
ATGCAGAGGGTGAACATGATCATGGCTGAGTCTCCTGGACTGATCACCAT

CTGCCTGCTGGGCTATCTGCTGTCTGCTGAGTGTACAGTGTTCCTGGACC

ATGAAAATGCTAATAAAATCCTGAACAGGCCAAAGAGGTACAATTCTGGG

AAACTGGAGGAATTTGTGCAGGGAAACCTGGAGAGGGAATGCATGGAGGA

AAAGTGTAGCTTTGAGGAAGCCAGGGAGGTGTTTGAAAATACAGAGAGGA

CCACAGAGTTCTGGAAACAGTATGTGGATGGGGATCAGTGTGAGTCCAAC

CCCTGTCTGAATGGAGGGTCTTGCAAGGATGATATCAACTCCTATGAGTG

CTGGTGTCCTTTTGGATTTGAAGGCAAGAATTGTGAGCTGGATGTGACCT

GTAACATCAAAAATGGGAGGTGTGAGCAGTTCTGTAAGAACTCTGCTGAT

AATAAAGTGGTCTGCAGCTGTACAGAAGGCTACAGGCTGGCTGAGAACCA

GAAGAGCTGTGAACCAGCTGTGCCCTTCCCTTGTGGGAGGGTGTCTGTCA

GCCAGACCAGCAAGCTGACCAGAGCTGAGGCTGTGTTTCCTGATGTGGAT

TATGTCAACTCTACAGAGGCTGAAACCATCCTGGACAACATCACCCAGTC

TACCCAGTCCTTCAATGACTTTACCAGGGTGGTGGGAGGGGAGGATGCTA

AGCCAGGACAGTTCCCCTGGCAGGTGGTCCTGAATGGCAAAGTGGATGCT

TTTTGTGGGGGCTCCATTGTGAATGAGAAGTGGATTGTCACAGCTGCTCA

CTGTGTGGAAACTGGGGTCAAGATCACAGTGGTGGCTGGAGAGCACAACA

TTGAGGAAACTGAACATACAGAGCAGAAAAGGAATGTGATCAGAATCATC

CCCCACCATAACTACAATGCTGCTATCAACAAGTATAATCATGACATTGC

CCTGCTGGAACTGGATGAGCCTCTGGTGCTGAACAGCTATGTCACCCCAA

TCTGCATTGCTGACAAGGAGTATACCAATATCTTCCTGAAATTTGGGTCT

GGATATGTGTCTGGGTGGGGAAGGGTCTTCCACAAGGGAAGGTCTGCTCT

GGTGCTGCAGTATCTGAGGGTGCCCCTGGTGGACAGAGCTACCTGCCTGA

GGAGCACCAAGTTCACCATCTACAACAATATGTTCTGTGCTGGATTTCAT

GAGGGAGGGAGGGACTCCTGTCAGGGAGATTCTGGAGGCCCTCATGTGAC

AGAGGTGGAAGGCACCAGCTTCCTGACTGGCATCATCTCTTGGGGGGAGG

AATGTGCTATGAAGGGGAAATATGGAATCTATACCAAGGTGTCCAGATAT

GTCAACTGGATCAAGGAGAAAACCAAGCTGACCTGA

Liver codon optimized fIX with no CpG including
Padua and A582 modifications
                                          (SEQ ID NO: 9)
ATGCAGAGGGTGAACATGATCATGGCTGAGTCTCCTGGACTGATCACCAT

CTGCCTGCTGGGCTATCTGCTGTCTGCTGAGTGTACAGTGTTCCTGGACC

ATGAAAATGCTAATAAAATCCTGAACAGGCCAAAGAGGTACAATTCTGGG

AAACTGGAGGAATTTGTGCAGGGAAACCTGGAGAGGGAATGCATGGAGGA

AAAGTGTAGCTTTGAGGAAGCCAGGGAGGTGTTTGAAAATACAGAGAGGA

CCACAGAGTTCTGGAAACAGTATGTGGATGGGGATCAGTGTGAGTCCAAC
```

-continued

CCCTGTCTGAATGGAGGGTCTTGCAAGGATGATATCAACTCCTATGAGTG

CTGGTGTCCTTTTGGATTTGAAGGCAAGAATTGTGAGCTGGATGTGACCT

GTAACATCAAAAATGGGAGGTGTGAGCAGTTCTGTAAGAACTCTGCTGAT

AATAAAGTGGTCTGCAGCTGTACAGAAGGCTACAGGCTGGCTGAGAACCA

GAAGAGCTGTGAACCAGCTGTGCCCTTCCCTTGTGGGAGGGTGTCTGTCA

GCCAGACCAGCAAGCTGACCAGAGCTGAGGCTGTGTTTCCTGATGTGGAT

TATGTCAACTCTACAGAGGCTGAAACCATCCTGGACAACATCACCCAGTC

TACCCAGTCCTTCAATGACTTTACCAGGGTGGTGGGAGGGGAGGATGCTA

AGCCAGGACAGTTCCCCTGGCAGGTGGTCCTGAATGGCAAAGTGGATGCT

TTTTGTGGGGGCTCCATTGTGAATGAGAAGTGGATTGTCACAGCTGCTCA

CTGTGTGGAAACTGGGGTCAAGATCACAGTGGTGGCTGGAGAGCACAACA

TTGAGGAAACTGAACATACAGAGCAGAAAAGGAATGTGATCAGAATCATC

CCCCACCATAACTACAATGCTGCTATCAACAAGTATAATCATGACATTGC

CCTGCTGGAACTGGATGAGCCTCTGGTGCTGAACAGCTATGTCACCCCAA

TCTGCATTGCTGACAAGGAGTATACCAATATCTTCCTGAAATTTGGGTCT

GGATATGTGTCTGGGTGGGGAAGGGTCTTCCACAAGGGAAGGTCTGCTCT

GGTGCTGCAGTATCTGAGGGTGCCCCTGGTGGACAGAGCTACCTGCCTGC

TGAGCACCAAGTTCACCATCTACAACAATATGTTCTGTGCTGGATTTCAT

GAGGGAGGGAGGGACTCCTGTCAGGGAGATTCTGGAGGCCCTCATGTGAC

AGAGGTGGAAGGCACCAGCTTCCTGACTGGCATCATCTCTTGGGGGGAGG

AATGTGCTATGAAGGGGAAATATGGAATCTATACCAAGGTGTCCAGATAT

GTCAACTGGATCAAGGAGAAAACCAAGCTGACCTGA

In addition, two other variants were constructed. The first is a liver optimized, Padua, 148T variant that is very similar to the above liver optimized sequence, except it was synthesized using an alternate version of the codon optimization algorithm.

Liver codon optimized fIX with Padua/Malmo mutations and no CpG (version 2)

(SEQ ID NO: 10)

ATGCAGAGGGTGAACATGATCATGGCTGAGTCTCCTGGACTGATCACCAT

CTGCCTGCTGGGCTATCTGCTGTCTGCTGAGTGTACAGTGTTCCTGGACC

ATGAAAATGCTAATAAAATCCTGAACAGGCCAAAGAGGTACAATTCTGGG

AAACTGGAGGAATTTGTGCAGGGAAACCTGGAGAGGGAATGCATGGAGGA

AAAGTGTAGCTTTGAGGAAGCCAGGGAGGTGTTTGAAAATACAGAGAGGA

CCACAGAGTTCTGGAAACAGTATGTGGATGGGGATCAGTGTGAGTCCAAC

CCCTGTCTGAATGGAGGGTCTTGCAAGGATGATATCAACTCCTATGAGTG

CTGGTGTCCTTTTGGATTTGAAGGCAAGAATTGTGAGCTGGATGTGACCT

GTAACATCAAAAATGGGAGGTGTGAGCAGTTCTGTAAGAACTCTGCTGAT

AATAAAGTGGTCTGCAGCTGTACAGAAGGCTACAGGCTGGCTGAGAACCA

GAAGAGCTGTGAACCAGCTGTGCCCTTCCCTTGTGGGAGGGTGTCTGTCA

GCCAGACCAGCAAGCTGACCAGAGCTGAGACAGTGTTTCCTGATGTGGAT

TATGTCAACTCTACAGAGGCTGAAACCATCCTGGACAACATCACCCAGTC

-continued

TACCCAGTCCTTCAATGACTTTACCAGGGTGGTGGGAGGGGAGGATGCTA

AGCCAGGACAGTTCCCCTGGCAGGTGGTCCTGAATGGCAAAGTGGATGCT

TTTTGTGGGGGCTCCATTGTGAATGAGAAGTGGATTGTCACAGCTGCTCA

CTGTGTGGAAACTGGGGTCAAGATCACAGTGGTGGCTGGAGAGCACAACA

TTGAGGAAACTGAACATACAGAGCAGAAAAGGAATGTGATCAGAATCATC

CCCCACCATAACTACAATGCTGCTATCAACAAGTATAATCATGACATTGC

CCTGCTGGAACTGGATGAGCCTCTGGTGCTGAACAGCTATGTCACCCCAA

TCTGCATTGCTGACAAGGAGTATACCAATATCTTCCTGAAATTTGGGTCT

GGATATGTGTCTGGGTGGGGAAGGGTCTTCCACAAGGGAAGGTCTGCTCT

GGTGCTGCAGTATCTGAGGGTGCCCCTGGTGGACAGAGCTACCTGCCTGC

TGAGCACCAAGTTCACCATCTACAACAATATGTTCTGTGCTGGATTTCAT

GAGGGAGGGAGGGACTCCTGTCAGGGAGATTCTGGAGGCCCTCATGTGAC

AGAGGTGGAAGGCACCAGCTTCCTGACTGGCATCATCTCTTGGGGGGAGG

AATGTGCTATGAAGGGGAAATATGGAATCTATACCAAGGTGTCCAGATAT

GTCAACTGGATCAAGGAGAAAACCAAGCTGACCTGA

In addition, a fIX sequence with Padua/Malmo mutations and no CpG was optimized according to the standard human codon optimization table (see FIG. 2B).

Human codon optimized fIX with Padua/Malmo mutations and no CpG (SEQ ID NO: 127)

ATGCAGAGGGTGAATATGATTATGGCTGAGTCCCCTGGGCTGATTACCAT

TTGCCTGCTGGGATACCTGCTGTCTGCTGAGTGTACAGTGTTCCTGGACC

ATGAGAATGCAAATAAGATCCTGAACAGGCCCAAAAGATATAATAGTGGA

AAGCTGGAGGAATTTGTGCAGGGCAACCTGGAGAGAGAATGCATGGAGGA

AAAGTGTAGCTTTGAGGAAGCCAGGGAGGTGTTTGAAAATACAGAGAGAA

CCACAGAATTCTGGAAGCAGTATGTGGATGGAGATCAGTGTGAGAGCAAC

CCCTGTCTGAATGGAGGGAGTTGCAAAGATGATATCAACTCATATGAATG

CTGGTGTCCTTTTGGATTTGAAGGCAAAAATTGTGAGCTGGATGTGACCT

GTAACATTAAGAATGGGAGGTGTGAGCAGTTTTGTAAAAACTCTGCTGAT

AATAAGGTGGTCTGCAGTTGTACAGAAGGGTATAGACTGGCTGAGAACCA

GAAGTCCTGTGAACCAGCTGTGCCCTTCCCTTGTGGAAGGGTGTCTGTCT

CCCAGACTTCAAAACTGACCAGAGCTGAGACTGTGTTTCCTGATGTGGAT

TATGTCAACAGCACAGAGGCTGAAACTATCCTGGACAACATTACTCAGTC

TACCCAGAGTTTCAATGACTTTACCAGAGTGGTGGGAGGAGAGGATGCTA

AACCAGGCCAGTTCCCCTGGCAGGTGGTCCTGAATGGGAAGGTGGATGCA

TTTTGTGGGGGATCTATTGTGAATGAGAAATGGATTGTCACAGCTGCTCA

CTGTGTGGAAACTGGGGTCAAGATCACAGTGGTGGCTGGAGAGCACAACA

TTGAGGAAACAGAACATACTGAGCAGAAGAGGAATGTGATCAGAATCATT

CCTCACCATAACTACAATGCAGCCATCAACAAATATAATCATGACATTGC

CCTGCTGGAACTGGATGAGCCTCTGGTGCTGAACAGCTATGTCACACCAA

TCTGCATTGCTGACAAGGAGTACACTAACATCTTCCTGAAGTTTGGGTCA

-continued

GGATATGTGTCTGGATGGGGAAGAGTCTTCCACAAGGGCAGGTCTGCACT

GGTGCTGCAGTATCTGAGAGTGCCTCTGGTGGATAGGGCCACTTGTCTGC

TGTCTACCAAGTTCACCATCTACAACAATATGTTCTGTGCTGGATTTCAT

GAGGGAGGGAGAGACTCCTGTCAGGGAGATTCTGGAGGCCCACATGTGAC

AGAGGTGGAAGGCACCAGCTTCCTGACAGGCATCATTTCCTGGGGGGAGG

AATGTGCAATGAAGGGGAAATATGGAATCTACACCAAAGTGAGCAGGTAT

GTGAACTGGATCAAGGAAAAGACCAAACTGACATGA

Figure 7:
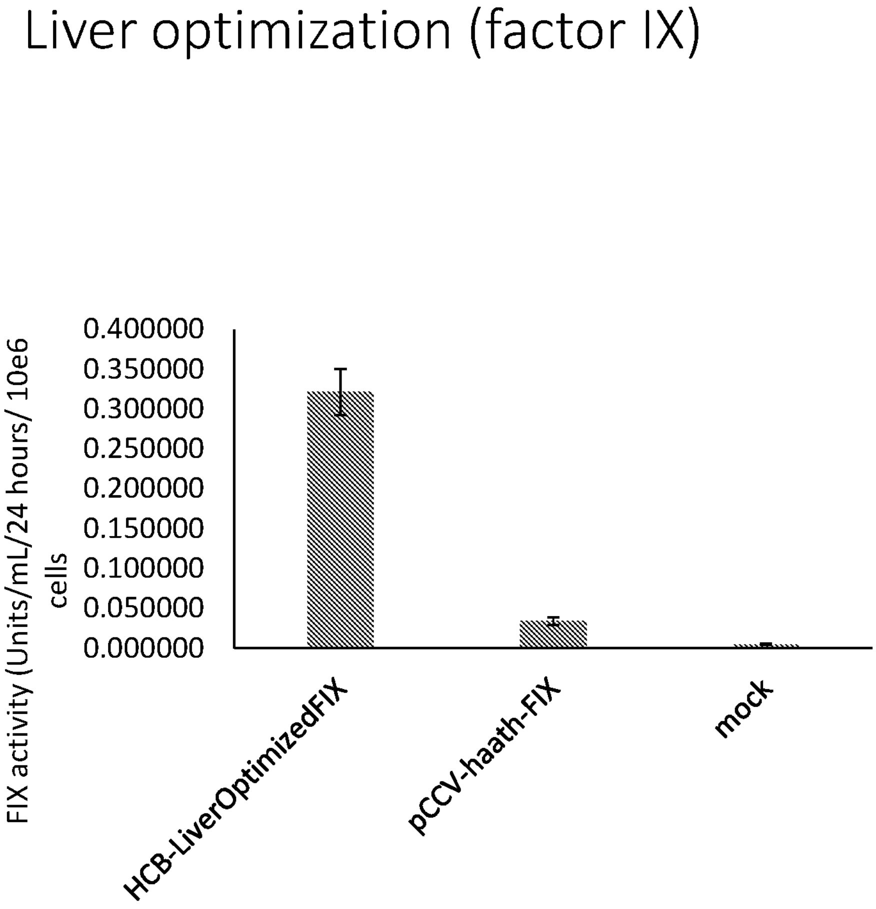
FIG. 7 shows in vitro expression data in HepG2 cells indicating that liver specific codon optimization, but not human specific codon optimization, improves expression of fIX protein in liver cells.

In vitro expression of the liver-optimized fIX sequence (SEQ ID NO: 10) and human-optimized fIX sequence (SEQ ID NO: 127) was assessed in HepG2 cells transiently transfected with corresponding fVIII expression plasmids (FIG. 7). The tissue specific optimization lead to increased fIX activity in the HepG2 (hepatic) cells expressing the liver-optimized fIX compared to human-optimized fIX. These results show that liver optimization specifically benefits expression in hepatocyte derived cells.

Example 2

Promoter Development

This example described the iterative development of optimized promoter sequences for expression of protein in liver tissue and cells.

The promoters were synthesized de novo and cloned into an expression plasmid driving the expression of clotting fVIII. FVIII activity was measured 48 hours after transfection by one-stage clot assay. As a comparator, the hybrid liver promoter (HLP) was used. HLP represents one of the shortest yet most powerful liver-directed promoters described to date. The HLP promoter and its use are described in McIntosh et al., "Therapeutic levels of FVIII following a single peripheral vein administration of rAAV vector encoding a novel human fVIII variant," Blood, 25; 121(17):3335-44, 2013. The HLP sequence is provided as SEQ ID NO: 128:

TGTTTGCTGCTTGCAATGTTTGCCCATTTTAGGGTGGACACAGGACGCTG

TGGTTTCTGAGCCAGGGGGCGACTCAGATCCCAGCCAGTGGACTTAGCCC

CTGTTTGCTCCTCCGATAACTGGGGTGACCTTGGTTAATATTCACCAGCA

GCCTCCCCCGTTGCCCCTCTGGATCCACTGCTTAAATACGGACGAGGACA

GGGCCCTGTCTCCTCAGCTTCAGGCACCACCACTGACCTGGGACAGTGAA

TC

Initial Promoter Design (1$^{st}$ Generation Promoters)

To begin construction of synthetic liver-directed promoters, two minimal liver directed promoters were selected that were designed platforms for further modification. These two promoters are designated as "ABP-SynO" (SEQ ID NO: 131) and "ABP-HP1-God". These promoters are novel fusions of previously described regulatory control elements. "ABP" is clustered region of transcription factor binding sites, "HP1" is a specific transcription factor binding site, "God" is an enhancer-like region that functions in direct proximity to the transcription start site, and "SynO" is a minimal promoter that contains the HP1 transcription factor binding site and a TATA box. For all constructs, where not provided within the native context, a TATA sequence (TATAAA) was added or completed immediately 3' to the promoter region.

Initial promoter designed were based on the "ABP" element, which is described, for example, in Rouet et al., "A potent enhancer made of clustered liver-specific elements in the transcription control sequences of human alpha 1-microglobulin/bikunin gene," J Biol Chem., 267(29):20765-73, 1992. ABP comprises the nucleotide sequence set forth as ABP element (SEQ ID NO: 113):
GTTAATTTTTAAAAAGCAGTCAAAAGTCCAAGTGGCCCTTGCGAGCATTT

ACTCTCTCTGTTTGCTCTGGTTAATAATCTCAGGAGCACAAACA

As illustrated in FIG. 8, ABP comprises the following TF binding sites: HNF-1-1 (nucleotides 16-23 of SEQ ID NO: 4), HNF-4 (nucleotides 26-36 of SEQ ID NO: 4), HNF-3a (nucleotides 39-45 of SEQ ID NO: 4), HNF1-2 (nucleotides 48-62 of SEQ ID NO: 4), and HNF-3-2 TF (nucleotides 65-71 of SEQ ID NO: 4).

Several of the disclosed promoters include an HP1 TF binding site (GTTAATAATTTTC, nucleotides 75-87 of SEQ ID NO: 4). The HP1 element is described, for example, in Schorpp et al., "Hepatocyte-specific promoter element HP1 of the *Xenopus* albumin gene interacts with transcriptional factors of mammalian hepatocytes," J Mol Biol., 202(2):307-20, 1988. The HP1 TF binding site is included in the SynO element (included in several of the disclosed promoters), which also includes a TATA box. The sequence of the SynO element is provided as SynO element (SEQ ID NO: 114)
GAGGTTAATAATTTTCCAGATCTCTCTGAGCAATAGTATAAAA The SynO element is described, for example, in Ryffel et al., "Liver cell specific gene transcription in vitro: the promoter elements HP1 and TATA box are necessary and sufficient to generate a liver-specific promoter." Nucleic Acids Res., 17(3): 939-953, 1989.

Several of the disclosed promoters include a "God" which comprises the sequence set forth as:

God element (SEQ ID NO: 115)
AGTCATATGTTTGCTCACTGAAGGTTACTAGTTAACAGGCATCCCTTAAA

CAGGA

The God element is described, for example, in Godbout et al., "Multiple regulatory elements in the intergenic region between the alpha-fetoprotein and albumin genes," Mol Cell Biol., 6(2):477-87, 1986.

The ABP, SynO, and God elements were combined to form two novel promoters, "ABP-SynO" and "ABP-HP1-God" as follows (see FIG. 8):

ABP-SynO promoter (SEQ ID NO: 131)
GTTAATTTTTAAAAAGCAGTCAAAAGTCCAAGTGGCCCTTGCGAGCATTT

ACTCTCTCTGTTTGCTCTGGTTAATAATCTCAGGAGCACAAACAGAGGTT

AATAATTTTCCAGATCTCTCTGAGCAATAGTATAAAA

-continued

Figure 9A:
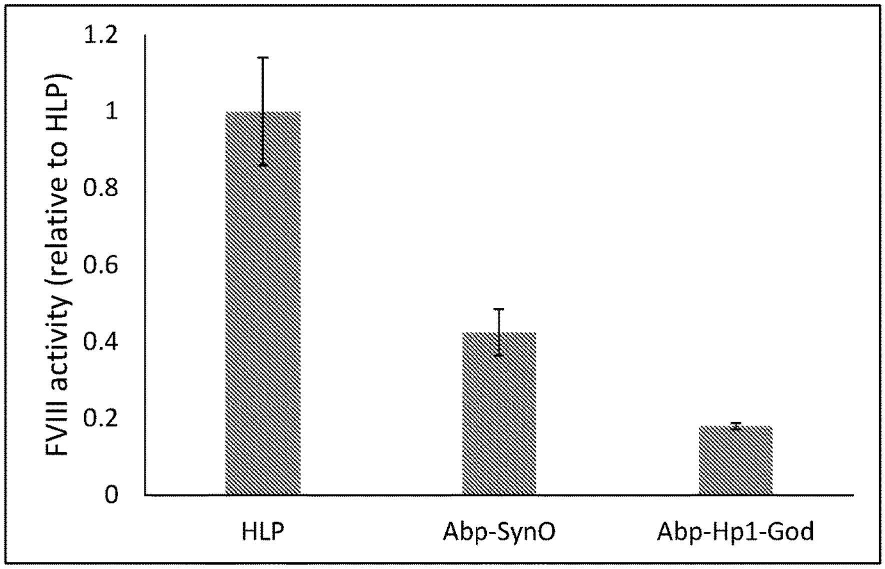
FIGS. 9A and 9B show data concerning use of AAV vectors containing the indicated promoters for expression of fVIII.
Figure 9B:
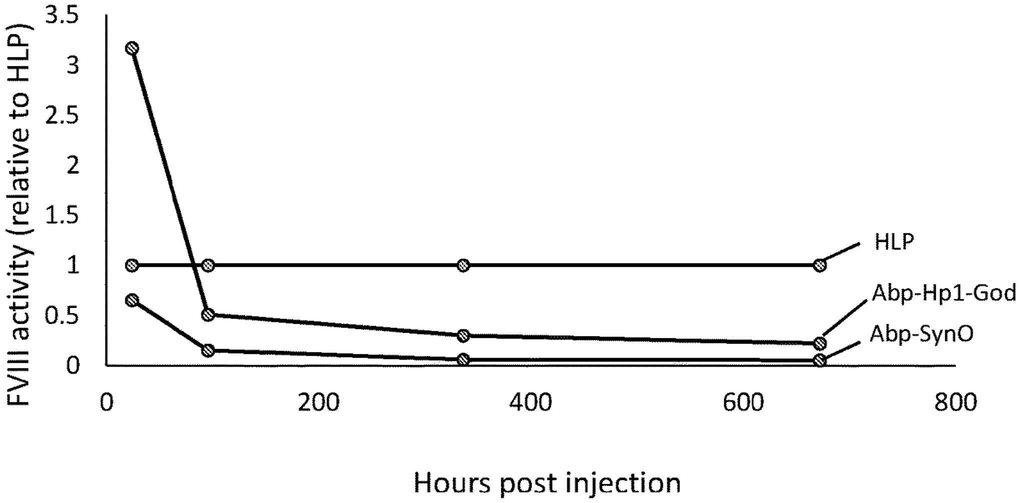

ABP-Hp1-God promoter
(SEQ ID NO: 6)
GTTAATTTTTAAAAAGCAGTCAAAAGTCCAAGTGGCCCTTGCGAGCATTT
ACTCTCTCTGTTTGCTCTGGTTAATAATCTCAGGAGCACAAACAGAGGTT
AATAATTTTCAGTCATATGTTTGCTCACTGAAGGTTACTAGTTAACAGGC
ATCCCTTAAACAGGATATAAAA In vitro expression of FVIII was assayed in HepG2 cells transiently transfected with FVIII expression plasmids driven by the ABP-SynO or ABP-Hp1-God promoter (FIG. 9A). Additionally, In vivo fVIII activity in mice was assayed by hydrodynamically delivered naked plasmid expressing FVIII driven by the ABP-SynO or ABP-Hp1-God promoter (FIG. 9B). From the results, it is shown that both the ABP-Syno and ABP-Hp1-God promoters drive fVIII expression in vitro and in vivo. However, these initial designs do not drive fVIII expression as strongly as the HLP promoter in vitro, and that the expression in vivo declines rapidly relative to HLP.

Initial Optimization ($2^{nd}$ Generation Promoters)

In order to increase the transcriptional strength of the ABP-SynO and ABP-Hp1-God promoters, multiple strategies for optimization were pursued. This includes altering the transcription factor binding sites to reflect the consensus binding sequence, removing intervening space between transcription factor binding sites, adding additional transcription factor binding sites, adding a transcription start site motif, and including the SV40 intron.

An ABP variant was generated that contains consensus TF binding sites, as follows:

ABP-exact (consensus transcription factor binding sites)
(SEQ ID NO: 116)
GTTAATCATTAACTTAAAAAGCAGTCAAAAGTCCAAAGGTCAAAGGTCAG
AGCATTTACTCTCTCCAATGTTGACTCTCGTTAATGATTAAGGAGCAATT
GTTGACTT As illustrated in FIG. 8, ABP-exact comprises the following consensus TF binding sites: consensus HNF-1-1, consensus HNF-4, consensus HNF-3a, consensus HNF1-2, and consensus HNF-3-2. A condensed version of Apb-exact was generated that includes the same consensus TF binding sites, but a shorter overall sequence, termed Short-ABP-exact, the sequence of which is set forth as:

Short-ABP-exact
(SEQ ID NO: 117)
GTTAATCATTAACTTAGGTCAAAGGTCAGACAATGTTGACTCTCGTTAAT
GATTAACCGGAATTGTTGACTT The following features were further included in certain of the disclosed promoters:

A transcription start site (TSS), which contains a 23 contains a GC rich spacer and was placed immediately after a TATA box in the promoter for optimal spacing with the transcription start motif immediately after the spacer (see FIG. 10). The TSS sequence assayed includes the sequence set forth as:

(nucleotides 116-146 of SEQ ID NO: 4)
GCCAGCAGCAGCCTGACCACATCTCATCCTC

A HNF1a transcription factor binding site. HNF1a is a liver-directed transcription factor:

(nucleotides 1-12 of SEQ ID NO: 4)
GTTAATCATTAA

A Sp1 transcription factor binding site. Sp1 is a liver-directed transcription factor: TGGGCGGAGT (nucleotides 1-10 of SEQ ID NO: 121)

A SV40 intron sequence set forth as:
(nucleotides 163-225 of SEQ ID NO: 112)
CTCTAAGGTAAATATAAAATTTTTAAGTGTATAATGTGTTAAACTACTGA
TTCTAATTGTTTGTGTATTTTAGATTCCAACCTATGGAACTGA These elements were combined to form several novel promoters, as follows (see FIG. 11):

ABP-exact-SynO
(SEQ ID NO: 118)
GTTAATCATTAACTTAAAAAGCAGTCAAAAGTCCAAAGGTCAAAGGTCAG
AGCATTTACTCTCTCCAATGTTGACTCTCGTTAATGATTAAGGAGCAATT
GTTGACTTGAGGTTAATAATTTTCCAGATCTCTCTGAGCAATAGTATAAA
A ShortABP-exact-SynO
(SEQ ID NO: 119)
GTTAATCATTAACTTAGGTCAAAGGTCAGACAATGTTGACTCTCGTTAAT
GATTAACCGGAATTGTTGACTTGAGGTTAATAATTTTCCAGATCTCTCTG
AGCAATAGTATAAAA ABP-HP1-God-TSS
(SEQ ID NO: 7)
GTTAATTTTTAAAAAGCAGTCAAAAGTCCAAGTGGCCCTTGCGAGCATTT
ACTCTCTCTGTTTGCTCTGGTTAATAATCTCAGGAGCACAAACAGAGGTT
AATAATTTTCAGTCATATGTTTGCTCACTGAAGGTTACTAGTTAACAGGC
ATCCCTTAAACAGGATATAAAAGGCCAGCAGCAGCCTGACCACATCTCAT
CCTC HNF1a-ABP-SynO
(SEQ ID NO: 120)
GTTAATCATTAAGTCGTTAATTTTTAAAAAGCAGTCAAAAGTCCAAGTGG
CCCTTGCGAGCATTTACTCTCTCTGTTTGCTCTGGTTAATAATCTCAGGA
GCACAAACAGAGGTTAATAATTTTCCAGATCTCTCTGAGCAATAGTATAA
AA Sp1-ABP-SynO
(SEQ ID NO: 121)
TGGGCGGAGTGTCGTTAATTTTTAAAAAGCAGTCAAAAGTCCAAGTGGCC
CTTGCGAGCATTTACTCTCTCTGTTTGCTCTGGTTAATAATCTCAGGAGC
ACAAACAGAGGTTAATAATTTTCCAGATCTCTCTGAGCAATAGTATAAAA HNF1-ShortABPExact-SynO-TSS-Int
(SEQ ID NO: 112)
GTTAATCATTAAGTCGTTAATCATTAACTTAGGTCAAAGGTCAGACAATG
TTGACTCTCGTTAATGATTAACCGGAATTGTTGACTTGAGGTTAATAATT
TTCCAGATCTCTCTGAGCAATAGTATAAAAGGCCAGCAGCAGCCTGACCA -continued

```
CATCTCATCCTCCTCTAAGGTAAATATAAAATTTTTAAGTGTATAATGTG

TTAAACTACTGATTCTAATTGTTTGTGTATTTTAGATTCCAACCTATGGA

ACTGA
```

The promoters were synthesized de novo and cloned into an expression plasmid driving the expression of clotting fVIII. FVIII activity was measured 48 hours after transfection by one-stage clot assay. As a comparator, the hybrid liver promoter (HLP) is used in this and other experiments.

Figure 12A:
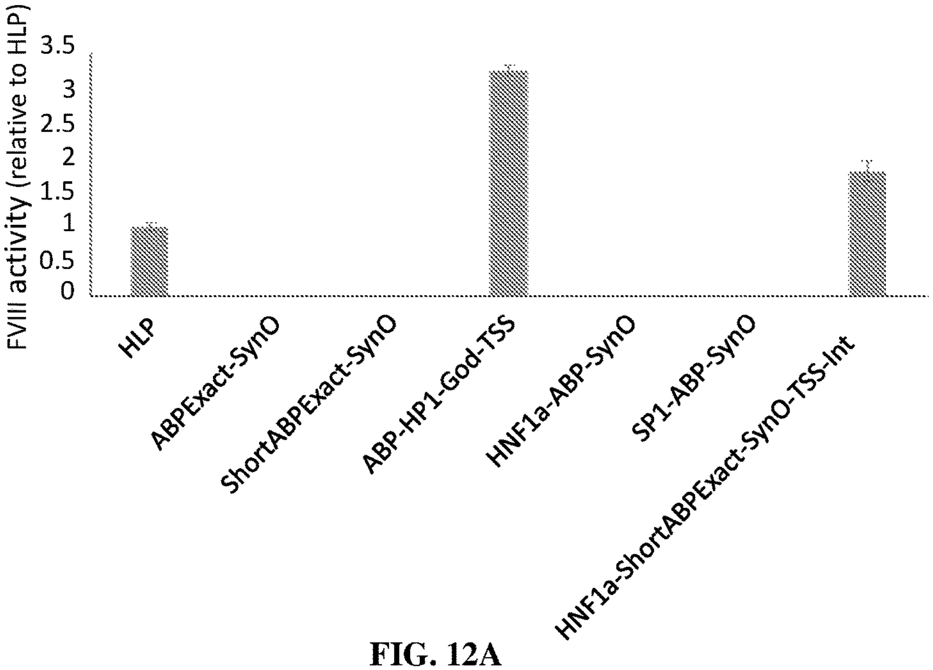
FIGS. 12A and 12B show data concerning use of AAV vectors containing the indicated promoters for expression of fVIII.
Figure 12B:
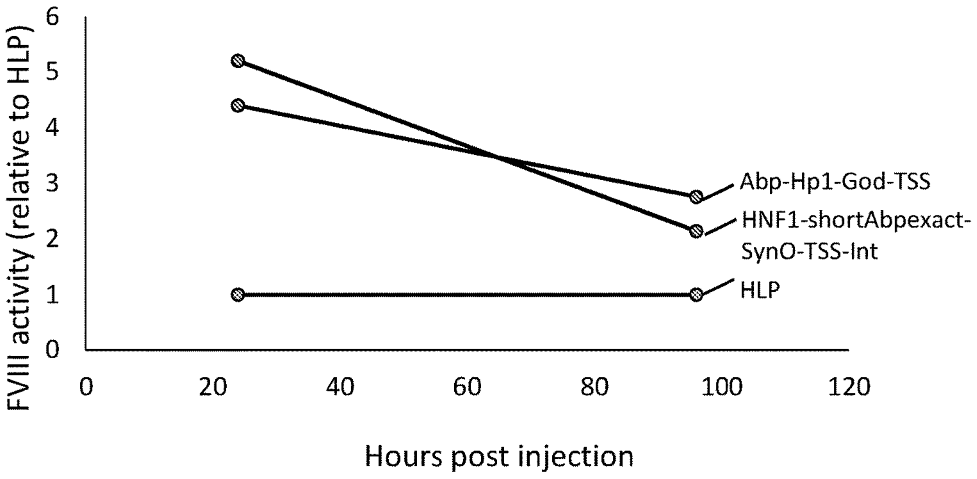

In vitro expression of FVIII was assayed in HepG2 cells transiently transfected with FVIII expression plasmids driven by the respective promoter (FIG. 12A). Additionally, In vivo fVIII activity in mice was assayed by hydrodynamically delivered naked plasmid expressing FVIII driven by the respective promoter (FIG. 12B). From these data, it is shown that the addition of the synthetic, novel, transcription start site motif substantially improves expression. Further, the addition of transcription factor binding sites outside of their native genomic context had unexpected and unpredicted impacts on expression. When added directly proximal to the ABP enhancer element, the HNF1 and Sp1 transcription factor binding sites completely abrogated expression. When the HNF1 transcription factor binding site was added directly proximal to the shortABPExact enhancer, expression was robust. This finding illustrates that the complex spatiotemporal interactions of transcription factors, in either their native or non-native genomic context, is difficult to model or predict. In addition, altering the transcription factor binding sites to the consensus binding sequences abrogated gene expression. However, the addition of the HNF1 transcription factor binding site, transcription start site, and SV40 intron was sufficient to rescue expression from HNF1 supplemented shortABPExact-SynO promoter design. As illustrated in FIG. 12B, the ABP-Hp1-God-TSS and the HNF1-shortABPExact-SynO-TSS-Int both maintained higher expression than the HLP promoter over the course of the experiment, showing that the addition of the transcription start site, HNF1 transcription factor binding site, adjustment of the ABP sequence to the consensus sequence and removal of intervening DNA between transcription factor binding sites, and/or the addition of the SV40 intron could improve the durability and strength of expression in vivo.

Further Optimization (3rd Generation Promoters)

While the ABP-Hp1-God-TSS promoter design tested far exceeded the strength of the HLP promoter, its size (204 bae pairs) remained incompatible with some complete packaging of AAV-vectors, such as those containing full-length containing fVIII transgenes. Further reduction in the size of the promoter was targeted by selection of the most promising elements tested and described above, as well as a novel element, shortABP, which is the ABP enhancer where the native genomic transcription factor binding site sequences are retained, but the intervening sequences between them have been truncated.

```
shortABP (nucleotides 16-71 of SEQ ID NO: 4):
GTTAATTTTTGTGGCCCTTGCGATGTTTGCTCTGGTTAATAATCTCAGGA

CAAACA
```

As illustrated in FIG. 13, shortABP contains the following TF binding sites: HNF-1-1 (nucleotides 16-23 of SEQ ID NO: 4), HNF-4 (nucleotides 26-36 of SEQ ID NO: 4), HNF-3a (nucleotides 39-45 of SEQ ID NO: 4), HNF1-2 (nucleotides 48-62 of SEQ ID NO: 4), and HNF-3-2 TF (nucleotides 65-71 of SEQ ID NO: 4).

As illustrated in FIG. 13, the HNF1 TF binding site, the SynO element (containing a HP1 TF binding site and a TATA box), and a transcription start site were linked to the shortABP to form the HNF1-shortABP-SynO-TSS (designated the Hepatic Combinatorial Bundle, or HCB), as follows:

```
HNF1-shortABP-SynO-TSS (also called Hepatic
Combinatorial Bundle, or HCB)
                                        (SEQ ID NO: 4)
GTTAATCATTAAGTCGTTAATTTTTGTGGCCCTTGCGATGTTTGCTCTGG

TTAATAATCTCAGGACAAACAGAGGTTAATAATTTTCCAGATCTCTCTGA

GCAATAGTATAAAAGGCCAGCAGCAGCCTGACCACATCTCATCCTC
```

As illustrated in FIG. 13, the HNF1 TF binding site, the God element, a TATA box, and a transcription start site were linked to the shortABP to form the shortABP-HP1-God-TSS, as follows:

```
shortABP-HP1-God-TSS
                                        (SEQ ID NO: 5)
GTTAATTTTTGTGGCCCTTGCGATGTTTGCTCTGGTTAATAATCTCAGGA

CAAACATACATTTTCAGTCATATGTTTGCTCACTGAAGGTTACTAGTTAA

CAGGCATCCCTTAAACAGGATATAAAAGGCCAGCAGCAGCCTGACCACAT

CTCATCCTC
```

Figure 14A:
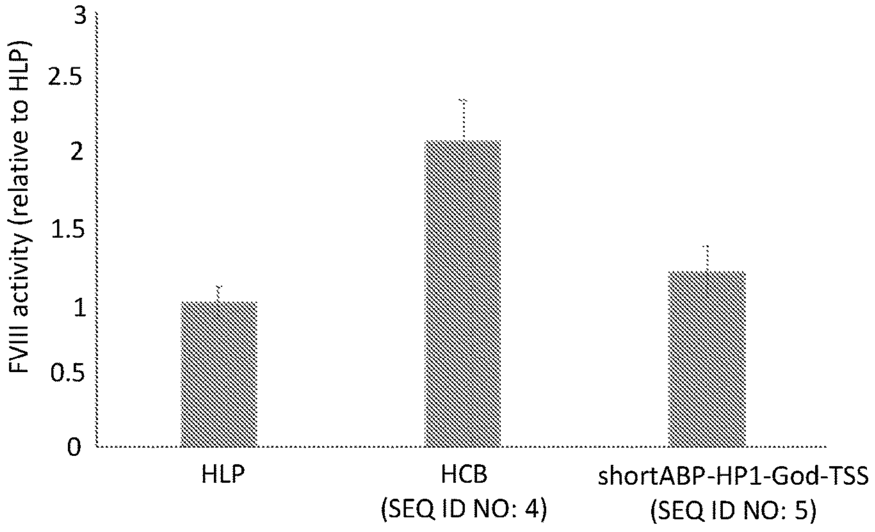
FIGS. 14A and 14B show data concerning use of AAV vectors containing the indicated promoters for expression of fVIII.
Figure 14B:
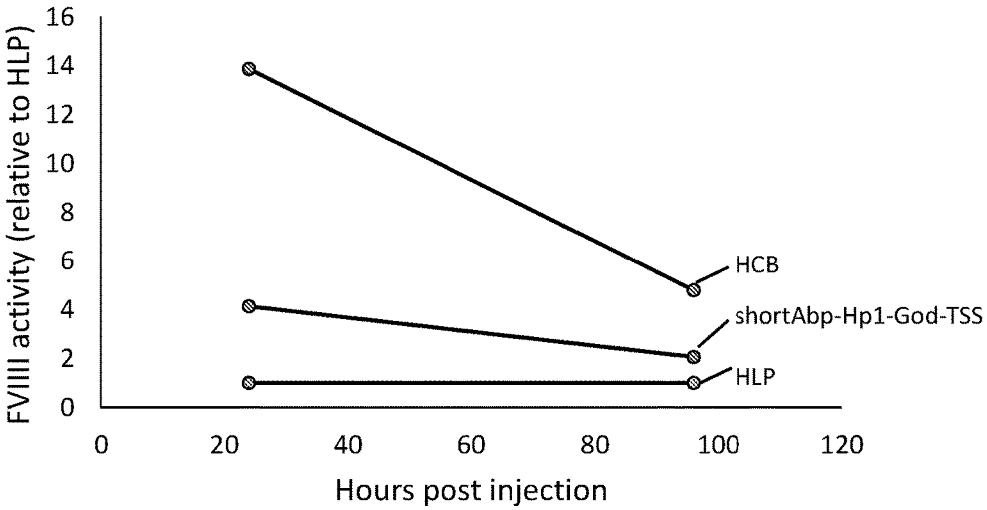

The promoters were synthesized de novo and cloned into an expression plasmid driving the expression of clotting fVIII. FVIII activity was measured 48 hours after transfection by one-stage clot assay. In vitro expression of FVIII was assayed in HepG2 cells transiently transfected with FVIII expression plasmids driven by the respective promoter is shown in FIG. 14A. Additionally, In vivo fVIII activity in mice was assayed by hydrodynamically delivered naked plasmid expressing FVIII driven by the respective promoter (FIG. 14). From these data, it is shown that the HNF1-shortABP-SynO-TSS promoter (HCB) promotes increased expression of fVIII compared to that of HLP both in vivo and in vitro, while maintaining durable expression 4-14 fold greater than that of HLP in vivo, despite the HNF1-shortABP-SynO-TSS being 42% smaller than HLP.

Supplemental Optimization (4th Generation Promoters)

A powerful, liver-directed enhancer, designated the hepatocyte specific computational regulatory module (HSCRM8 or "HS") was recently constructed by combining the sequences from several species into a computationally constructed novel enhancer (see, e.g., Nair et al., "Computationally designed liver-specific transcriptional modules and hyperactive fIX improve hepatic gene therapy," Blood, 23(20): 3195-3199, 2014). The sequence of the HS enhancer and corresponding transcription factor binding sites are provided as follows:

```
HS (HSCRM8 non-human enhancer sequence)
                                        (SEQ ID NO: 101)
GGGGAGGCTGCTGGTGAATATTAACCAAGGTCACCCCAGTTATCGGAGGA

GCAAACAGGGACTAAGTCCAC
```

The HS response element includes the following TF binding sites:

| | |
|---|---|
| MYOD | GGCTGCTGGTGAATATT, nucleotides 5-22 of SEQ ID NO: 101 |
| CEBP | GCTGCTGGTGAA, nucleotides 7-18 of SEQ ID NO: 101 |
| Nhf1 | GCTGGTGAATATTAACCA, nucleotides 10-27 of SEQ ID NO: 101 |
| Lef1/TCF1 | TTAACCAAGGT, nucleotides 21-31 of SEQ ID NO: 101 |
| CEBP | CGGAGGAGCAAA, nucleotides 44-55 of SEQ ID NO: 101 |
| Forkhead | GGAGCAAACAGGG, nucleotides 48-60 of SEQ ID NO: 101 |
| Lef1/TCF1 | AGGGACTAAG, nucleotides 57-66 of SEQ ID NO: 101 |

Figure 15:
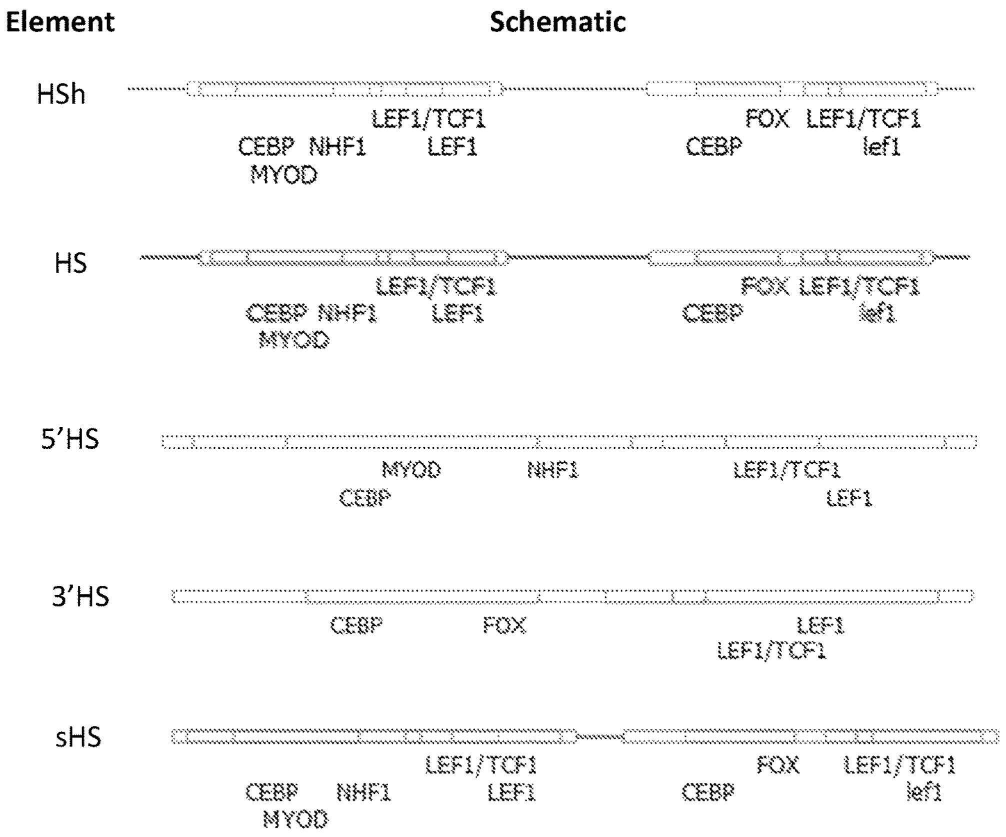
FIGS. 15 and 16 show schematic diagrams illustrating the structure of liver-specific enhancers (FIG. 15) and promoters including the liver specific enhancers (FIG. 16).

The human genome was examined to determine human sequences corresponding to those of the HS element and the HS element was modified to contain only human sequences to generate a fully human enhancer sequence termed "HSh." The sequence of the HSh enhancer and corresponding transcription factor binding sites are provided as follows (see also, FIG. 15):

```
HSh (human genomic sequence)
                                    (SEQ ID NO: 111)
GGGGAGGCTGCTGGTGAATATTAACCAAGGTCACCCCAGTTATCGGAGGA

GCAAACAGGGGCTAAGTCCAC
```

The HSh response element includes the following TF binding sites:

| | |
|---|---|
| MYOD | GGCTGCTGGTGAATATT, nucleotides 5-22 of SEQ ID NO: 101 |
| CEBP | GCTGCTGGTGAA, nucleotides 7-18 of SEQ ID NO: 101 |
| Nhf1 | GCTGGTGAATATTAACCA, nucleotides 10-27 of SEQ ID NO: 101 |
| Lef1/TCF1 | TTAACCAAGGT, nucleotides 21-31 of SEQ ID NO: 101 |
| CEBP | CGGAGGAGCAAA, nucleotides 44-55 of SEQ ID NO: 101 |
| Forkhead | GGAGCAAACAGGG, nucleotides 48-60 of SEQ ID NO: 101 |
| Lef1/TCF1 | AGGGGCTAAG, nucleotides 57-66 of SEQ ID NO: 111 |

Portions of the HSh enhancer were also utilized, as follows:

```
5'HSh (5' portion of HSCRM8h)
              (nucleotides 6-32 of SEQ ID NO: 111)
GGCTGCTGGTGAATATTAACCAAGGTC
```

The 5'HSh response element includes the following TF binding sites:

| | |
|---|---|
| MYOD | GGCTGCTGGTGAATATT, nucleotides 5-22 of SEQ ID NO: 101 |
| CEBP | GCTGCTGGTGAA, nucleotides 7-18 of SEQ ID NO: 101 |
| Nhf1 | GCTGGTGAATATTAACCA, nucleotides 10-27 of SEQ ID NO: 101 |
| Lef1/TCF1 | TTAACCAAGGT, nucleotides 21-31 of SEQ ID NO: 101 |

```
3'HSh (3' portion of HSCRM8h)
             (nucleotides 44-68 of SEQ ID NO: 111)
CGGAGGAGCAAACAGGGGCTAAGTC
```

The 3'HSh response element includes the following TF binding sites:

| | |
|---|---|
| CEBP | CGGAGGAGCAAA, nucleotides 44-55 of SEQ ID NO: 101 |
| Forkhead | GGAGCAAACAGGG, nucleotides 48-60 of SEQ ID NO: 101 |
| Lef1/TCF1 | AGGGGCTAAG nucleotides 57-66 of SEQ ID NO: 111 |

```
sHS (short HS, the intervening space between the
5' and 3' clusters of transcription factor
binding sites has been removed)
                  (nucleotides 1-54 of SEQ ID NO: 106)
GGCTGCTGGTGAATATTAACCAAGGTCATCGGAGGAGCAAACAGGGACTA

AGTC
```

The sHS response element includes the following TF binding sites:

| | |
|---|---|
| MYOD | GGCTGCTGGTGAATATT, nucleotides 5-22 of SEQ ID NO: 101 |
| CEBP | GCTGCTGGTGAA, nucleotides 7-18 of SEQ ID NO: 101 |
| Nhf1 | GCTGGTGAATATTAACCA, nucleotides 10-27 of SEQ ID NO: 101 |
| Lef1/TCF1 | TTAACCAAGGT, nucleotides 21-31 of SEQ ID NO: 101 |
| CEBP | CGGAGGAGCAAA, nucleotides 44-55 of SEQ ID NO: 101 |
| Forkhead | GGAGCAAACAGGG, nucleotides 48-60 of SEQ ID NO: 101 |
| Lef1/TCF1 | AGGGACTAAG, nucleotides 57-66 of SEQ ID NO: 111 |

Additionally, a modified form of the short ABP promoter, termed "supershortABP" was constructed by further deleting nucleotides and rearranging TF binding sites. The sequence of the supershort ABP response element and corresponding transcription factor binding sites are provided as follows:

```
Super short ABP (further shortened ABP-based
element)
                                    (SEQ ID NO: 122)
CCCTTGCTGGTTAATAATCTCAGTTAATTTGTTTGCACAAACA
```

The supershort ABP response element include the following TF binding sites:

| | |
|---|---|
| HNF4 | CCCTTGC, nucleotides 1-7 of SEQ ID NO: 122 |
| HNF1b | TGGTTAATAATCTCA, nucleotides 8-22 of SEQ ID NO: 122 |
| HNF1 | GTTAATT, nucleotides 23-29 of SEQ ID NO: 122 |
| HNF3 | TGTTTGC, nucleotides 30-36 of SEQ ID NO: 122 |
| HNF3b | ACAAACA, nucleotides 37-43 of SEQ ID NO: 122 |

Figure 16:
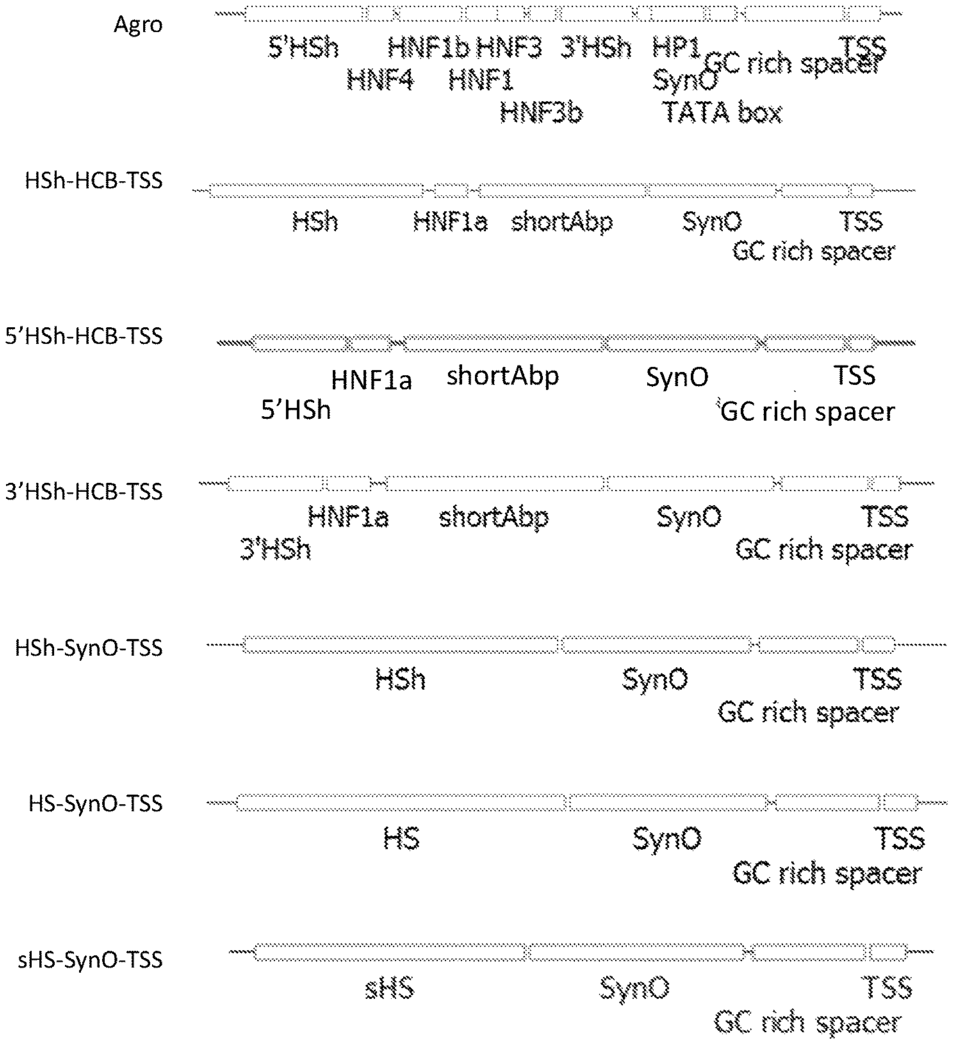

As illustrated in FIG. 16, the above elements were combined to form several novel promoters, as follows (see FIG. 11):

```
Agro
                                    (SEQ ID NO: 107)
GGCTGCTGGTGAATATTAACCAAGGTCCCCTTGCTGGTTAATAATCTCAG

TTAATTTGTTTGCACAAACACGGAGGAGCAAACAGGGGAGGTTAATAATT

TTCTATAAAAGGCCAGCAGCAGCCTGACCACATCTCATCCTC
```

The Agro sequence includes 5'HS (nucleotides 1-27 of SEQ ID NO: 107), Super short ABP (nucleotides 28-70 of SEQ ID NO: 107), 3'HSh (nucleotides 71-87 of SEQ ID NO: 107), SynO (nucleotides 88-110 of SEQ ID NO: 107), and TSS (nucleotides 111-142 of SEQ ID NO: 107)

```
HSh-HCB
                                        (SEQ ID NO: 102)
GGGGAGGCTGCTGGTGAATATTAACCAAGGTCACCCCAGTTATCGGAGGA

GCAAACAGGGGCTAAGTCCACTAGGTTAATCATTAAGTCGTTAATTTTTG

TGGCCCTTGCGATGTTTGCTCTGGTTAATAATCTCAGGACAAACAGAGGT

TAATAATTTTCCAGATCTCTCTGAGCAATAGTATAAAAGGCCAGCAGCAG

CCTGACCACATCTCATCCTC

5'HSh-HCB
                                        (SEQ ID NO: 104)
GGCTGCTGGTGAATATTAACCAAGGTCGTTAATCATTAAGTCGTTAATTT

TTGTGGCCCTTGCGATGTTTGCTCTGGTTAATAATCTCAGGACAAACAGA

GGTTAATAATTTTCCAGATCTCTCTGAGCAATAGTATAAAAGGCCAGCAG

CAGCCTGACCACATCTCATCCTC

3'HSh-HCB
                                        (SEQ ID NO: 103)
CGGAGGAGCAAACAGGGGCTAAGTCGTTAATCATTAAGTCGTTAATTTTT

GTGGCCCTTGCGATGTTTGCTCTGGTTAATAATCTCAGGACAAACAGAGG

TTAATAATTTTCCAGATCTCTCTGAGCAATAGTATAAAAGGCCAGCAGCA

GCCTGACCACATCTCATCCTC

HSh-SynO-TSS
                                        (SEQ ID NO: 105)
GGGGAGGCTGCTGGTGAATATTAACCAAGGTCACCCCAGTTATCGGAGGA

GCAAACAGGGGCTAAGTCCACGAGGTTAATAATTTTCCAGATCTCTCTGA

GCAATAGTATAAAAGGCCAGCAGCAGCCTGACCACATCTCATCCTC

HS-SynO-TSS
                                        (SEQ ID NO: 108)
GGGGAGGCTGCTGGTGAATATTAACCAAGGTCACCCCAGTTATCGGAGGA

GCAAACAGGGACTAAGTCCACGAGGTTAATAATTTTCCAGATCTCTCTGA

GCAATAGTATAAAAGGCCAGCAGCAGCCTGACCACATCTCATCCTC

sHS-SynO-TSS
                                        (SEQ ID NO: 106)
GGCTGCTGGTGAATATTAACCAAGGTCATCGGAGGAGCAAACAGGGACTA

AGTCGAGGTTAATAATTTTCCAGATCTCTCTGAGCAATAGTATAAAAGGC

CAGCAGCAGCCTGACCACATCTCATCCTC
```

Figure 17:
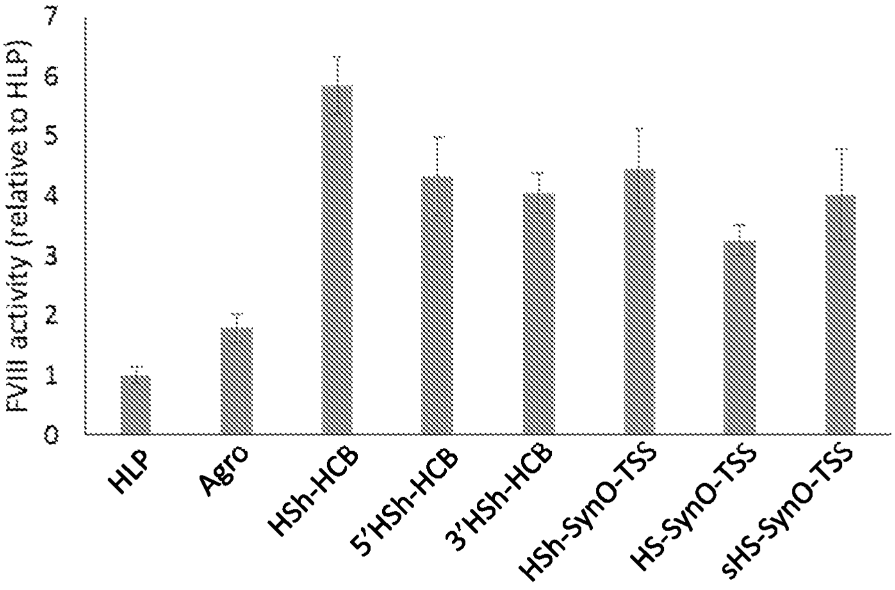
FIG. 17 shows data from in vitro assays concerning use of AAV vectors containing the indicated promoters for expression of fVIII in HepG2 cells.

The promoters were synthesized de novo and cloned into an expression plasmid driving the expression of clotting fVIII. FVIII activity was measured 48 hours after transfection by one-stage clot assay. In vitro expression of FVIII was assayed in HepG2 cells transiently transfected with FVIII expression plasmids driven by the respective promoter is shown in FIG. 17. These results demonstrate that the in vivo strength of the HCB promoter can be augmented by the addition of a supplemental enhancer sequences. The greatest benefit was seen when the complete, human, HSh enhancer was added to the 5' end of the HCB promoter. Supplementing only the 5' or 3' portions of the HSh attenuated the improved expression slightly compared to the complete HSh module. Additionally, when the shortABP enhancer was removed from the HCB design and instead replaced with either HSh or HS enhancers, fVIII expression declined slightly from the levels seen in the HSh-HCB promoter, which contains the shortABP-enhancer. However, when the sHS-SynO plasmid was administered hydrodynamically to mice, no expression was observed, showing that the short-ABP enhancer module may be a more suitable enhancer for durable in vivo expression.

Example 3

Recombinant AAV Vector for fVIII Expression

This example illustrates exemplary recombinant AAV vectors encoding a fVIII variant that comprise a genome sized for optimal AAV vector-based protein expression (that is, a genome of 5 kb or fewer bp).

FIG. 4 depicts AAV-based vectors for expression of fVIII variants that lack the B-domain. However, the constructs shown in FIG. 4 are above the 5.0 kb limit for optimal protein expression from an AAV vector. Removing nonessential viral genomic DNA and cloning remnants, and substituting shorter promoter sequences (such as the HCB promoter (SEQ ID NO: 4, 146 bp), enabled the development of a high expression fVIII-AAV genome of approximately 4.9 kb in length.

Figure 18:
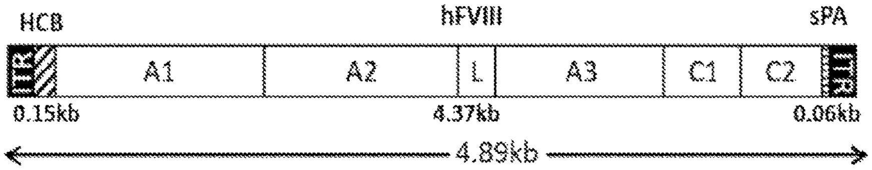
FIG. 18 illustrates an AAV vectors encoding an fVIII variant.

An exemplary AAV vector with such a genome is depicted in FIG. 18. This figure illustrates an AAV vector including 5' and 3' ITRs, the HCB (SEQ ID NO: 4) promoter, a nucleic acid molecule encoding a variant fVIII protein that lacks the B-domain (such as any one of the ET3 or HSQ CpG-depleted and liver codon optimized sequences provided herein), and a synthetic poly A sequence.

An exemplary sequence of an AAV cassette as shown in FIG. 18 is provided as SEQ ID NO: 129, which has the following structure:

(5'AAV2 ITR)-RE-(HCB Promoter)-Kozak-(HSQ coding region)-RE-(poly adenylation signal)-RE-(3'AAV2 ITR)

The elements of the AAV cassette of SEQ ID NO: 129 are as follows:

| Element | Start (bp) | End (bp) |
|---|---|---|
| 5' AAV2 ITR | 1 | 141 |
| AgeI (restriction site) | 142 | 147 |
| HCB promoter | 148 | 293 |
| Destroyed XhoI site | 294 | 299 |
| Kozak consensus sequence | 300 | 304 |
| Liver optimized HSQ with CpGs | 305 | 4678 |
| NotI (restriction site) | 4679 | 4686 |
| Rabbit beta globin polyA signal | 4687 | 4735 |
| MunI (restriction site) | 4736 | 4741 |
| 3' AAV2 ITR | 4742 | 4882 |

The restriction sites can optionally be removed from the cassette to provide a shortened recombinant AAV genome. Additionally, the transgene can be substituted as needed. Removing the restriction sites elements would generate a vector of 4885 base pairs (ET3) or 4855 (HSQ).

```
SEQ ID NO: 129:
CCTGCAGGCAGCTGCGCGCTCGCTCGCTCACTGAGGCCGCCCGGGCAAAG

CCCGGGCGTCGGGCGACCTTTGGTCGCCCGGCCTCAGTGAGCGAGCGAGC

GCGCAGAGAGGGAGTGGCCAACTCCATCACTAGGGGTTCCTACCGGTGTT

AATCATTAAGTCGTTAATTTTTGTGGCCCTTGCGATGTTTGCTCTGGTTA

ATAATCTCAGGACAAACAGAGGTTAATAATTTTCCAGATCTCTCTGAGCA
```

-continued

ATAGTATAAAAGGCCAGCAGCAGCCTGACCACATCTCATCCTCGTCGAGC
CACCATGCAGATCGAACTGTCTACCTGTTTCTTTCTGTGCCTGCTGCGGT
TTTGTTTTTCCGCTACCAGAAGATACTACCTGGGAGCCGTCGAACTGAGC
TGGGATTACATGCAGTCTGACCTGGGAGAGCTGCCCGTGGACGCTAGATT
CCCACCTAGAGTCCCTAAGTCCTTCCCCTTCAACACCAGCGTGGTCTACA
AGAAAACCCTGTTCGTGGAGTTTACCGACCACCTGTTCAACATCGCTAAG
CCTAGACCACCATGGATGGGACTGCTGGGACCAACCATCCAGGCCGAGGT
GTACGACACCGTGGTCATCACCCTGAAAAACATGGCTTCTCACCCCGTGT
CCCTGCATGCTGTGGGCGTCTCCTACTGGAAGGCCAGCGAAGGGGCTGAG
TATGACGATCAGACCAGCCAGCGGGAAAAAGAGGACGATAAGGTGTTCCC
TGGCGGGTCCCATACCTACGTGTGGCAGGTCCTGAAGGAGAATGGACCAA
TGGCTTCCGACCCTCTGTGCCTGACCTACTCTTATCTGTCCCACGTGGAC
CTGGTCAAGGATCTGAACAGCGGCCTGATCGGGGCTCTGCTGGTGTGTCG
CGAAGGGTCCCTGGCCAAGGAGAAAACCCAGACCCTGCATAAGTTCATCC
TGCTGTTCGCCGTGTTTGACGAAGGAAAAAGCTGGCACTCTGAGACCAAG
AACTCTCTGATGCAGGACAGGGATGCCGCTTCCGCCAGAGCTTGGCCCAA
GATGCACACCGTGAACGGCTACGTCAATAGGAGCCTGCCTGGACTGATCG
GCTGCCACAGAAAGTCCGTGTATTGGCATGTCATCGGAATGGGCACCACC
CCTGAAGTGCACAGCATCTTCCTGGAGGGGCATACCTTTCTGGTCCGCAA
CCACCGGCAGGCTAGCCTGGAGATCTCTCCAATCACCTTCCTGACCGCCC
AGACCCTGCTGATGGACCTGGGACAGTTCCTGCTGTTTTGCCACATCTCC
AGCCACCAGCATGATGGCATGGAGGCTTACGTGAAAGTCGACTCCTGTCC
CGAGGAACCTCAGCTGAGGATGAAGAACAATGAGGAAGCCGAAGACTATG
ACGATGACCTGACCGACAGCGAGATGGATGTGGTCCGCTTCGATGACGAT
AACTCTCCCTCCTTTATCCAGATCCGGTCCGTGGCCAAGAAACACCCTAA
GACCTGGGTCCATTACATCGCCGCTGAGGAAGAGGACTGGGATTATGCTC
CACTGGTGCTGGCCCCCGACGATAGATCCTACAAAAGCCAGTATCTGAAC
AATGGACCCCAGAGGATCGGCAGAAAGTACAAGAAAGTGAGGTTCATGGC
TTATACCGATGAGACCTTTAAGACCAGAGAAGCCATCCAGCACGAGTCCG
GGATCCTGGGACCTCTGCTGTACGGCGAAGTGGGGGACACCCTGCTGATC
ATCTTCAAGAACCAGGCCAGCAGGCCTTACAATATCTATCCACATGGCAT
CACCGATGTGAGACCTCTGTACTCCCGCCGGCTGCCAAAGGGCGTGAAAC
ACCTGAAGGACTTCCCAATCCTGCCCGGGGAAATCTTTAAGTATAAATGG
ACCGTCACCGTCGAGGATGGGCCCACCAAGAGCGACCCTAGGTGCCTGAC
CAGATACTATTCTTCCTTCGTGAATATGGAGAGAGACCTGGCTTCCGGAC
TGATCGGACCCCTGCTGATCTGTTACAAAGAGAGCGTGGATCAGCGCGGC
AACCAGATCATGTCTGACAAGCGGAATGTGATCCTGTTCAGCGTCTTTGA
CGAAAACCGCTCTTGGTACCTGACCGAGAACATCCAGCGGTTCCTGCCTA
ATCCAGCTGGAGTGCAGCTGGAAGATCCCGAGTTCCAGGCCTCTAACATC
ATGCATTCCATCAATGGCTACGTGTTCGACTCCCTGCAGCTGAGCGTGTG
CCTGCACGAGGTCGCTTACTGGTATATCCTGAGCATCGGAGCCCAGACCG

-continued

ATTTCCTGTCTGTGTTCTTTTCCGGCTACACCTTTAAGCATAAAATGGTG
TATGAGGACACCCTGACCCTGTTCCCATTTTCCGGCGAAACCGTGTTCAT
GAGCATGGAGAATCCCGGGCTGTGGATCCTGGGATGCCACAACTCCGATT
TCAGGAATAGAGGGATGACCGCCCTGCTGAAAGTGAGCTCTTGTGACAAG
AACACCGGAGACTACTATGAAGATAGCTACGAGGACATCTCTGCTTATCT
GCTGTCCAAAAACAATGCCATCGAGCCCAGGAGCTTCTCTCAGAACCCTC
CAGTGCTGAAGCGCCACCAGCGGGAGATCACCAGAACCACCCTGCAGAGC
GATCAGGAAGAGATCGACTACGACGATACCATCTCCGTGGAAATGAAGAA
AGAGGACTTCGATATCTATGACGAAGATGAGAACCAGTCTCCCAGGTCCT
TCCAGAAGAAAACCAGACATTACTTTATCGCCGCTGTGGAGCGGCTGTGG
GACTATGGCATGTCCAGCTCTCCTCACGTGCTGAGAAATAGAGCTCAGTC
CGGAAGCGTCCCACAGTTCAAGAAAGTGGTCTTCCAGGAGTTTACCGACG
GAAGCTTTACCCAGCCACTGTACCGCGGCGAACTGAACGAGCACCTGGGG
CTGCTGGGACCCTATATCCGGGCTGAAGTGGAGGATAACATCATGGTCAC
CTTCAGGAATCAGGCCAGCAGACCCTACTCTTTTTATTCCAGCCTGATCT
CCTACGAAGAGGACCAGAGACAGGGAGCTGAACCAAGAAAAAACTTCGTG
AAGCCTAATGAGACCAAAACCTACTTTTGGAAGGTGCAGCACCATATGGC
CCCTACCAAAGACGAGTTCGATTGCAAGGCCTGGGCTTATTTTAGCGACG
TGGATCTGGAGAAGGACGTCCACTCCGGCCTGATCGGGCCACTGCTGGTG
TGTCATACCAACACCCTGAATCCAGCTCACGGAAGGCAGGTGACCGTCCA
GGAATTCGCCCTGTTCTTTACCATCTTTGATGAGACCAAGAGCTGGTACT
TCACCGAAAACATGGAGAGGAATTGCAGAGCCCCATGTAACATCCAGATG
GAAGACCCCACCTTCAAGGAGAACTACAGATTTCATGCTATCAATGGGTA
TATCATGGATACCCTGCCAGGACTGGTCATGGCTCAGGACCAGAGGATCA
GATGGTACCTGCTGAGCATGGGGTCTAACGAGAATATCCACTCCATCCAT
TTCAGCGGACACGTGTTTACCGTCCGCAAGAAAGAAGAGTACAAGATGGC
CCTGTACAACCTGTATCCCGGCGTGTTCGAAACCGTCGAGATGCTGCCTT
CCAAGGCTGGGATCTGGCGGGTGGAATGCCTGATCGGGGAGCACCTGCAT
GCCGGAATGTCTACCCTGTTCCTGGTGTACTCCAATAAGTGTCAGACCCC
CCTGGGGATGGCTAGCGGACATATCCGCGACTTCCAGATCACCGCTTCCG
GACAGTACGGACAGTGGGCTCCTAAGCTGGCTAGACTGCACTATTCTGGC
TCCATCAACGCTTGGTCTACCAAAGAGCCTTTCTCCTGGATCAAGGTGGA
CCTGCTGGCTCCAATGATCATCCATGGCATCAAAACCCAGGGGGCCAGGC
AGAAGTTCTCTTCCCTGTACATCAGCCAGTTTATCATCATGTATTCTCTG
GATGGGAAGAAATGGCAGACCTACAGAGGCAATTCCACCGGGACCCTGAT
GGTGTTCTTTGGCAACGTCGACAGCTCTGGGATCAAGCACAACATCTTCA
ATCCCCCTATCATCGCCCGCTACATCCGGCTGCACCCAACCCATTATTCC
ATCCGCAGCACCCTGCGGATGGAGCTGATGGGGTGCGATCTGAACAGCTG
TTCTATGCCCCTGGGAATGGAGTCTAAGGCCATCTCCGACGCTCAGATCA
CCGCCTCCAGCTACTTCACCAATATGTTTGCTACCTGGTCCCCAAGCAAG

-continued

```
GCTAGACTGCATCTGCAGGGAAGAAGCAACGCTTGGAGACCACAGGTGAA
CAATCCCAAGGAGTGGCTGCAGGTCGACTTCCAGAAAACCATGAAGGTGA
CCGGAGTCACCACCCAGGGCGTGAAAAGCCTGCTGACCTCTATGTACGTC
AAGGAGTTCCTGATCTCTTCCAGCCAGGACGGGCACCAGTGGACCCTGTT
CTTTCAGAACGGAAAGGTGAAAGTCTTCCAGGGCAATCAGGATTCCTTTA
CCCCTGTGGTCAACAGCCTGGACCCACCCCTGCTGACCAGGTACCTGAGA
ATCCACCCACAGTCCTGGGTGCATCAGATCGCTCTGAGGATGGAAGTCCT
GGGCTGCGAGGCCCAGGACCTGTATTGAGCGGCCGCAATAAAATATCTTT
ATTTTCATTACATCTGTGTGTTGGTTTTTTGTGTGCAATTGAGGAACCCC
TAGTGATGGAGTTGGCCACTCCCTCTCTGCGCGCTCGCTCGCTCACTGAG
GCCGGGCGACCAAAGGTCGCCCGACGCCCGGGCTTTGCCCGGGCGGCCTC
AGTGAGCGAGCGAGCGCGCAGCTGCCTGCAGG
```

Another exemplary AAV vector including a fVIII transgene driven by the HCB promoter is provided as SEQ ID NO: 130, which provides a prototypical design of an AAV cassette encoding a therapeutic transgene under control of the HCB promoter. Each element is separated by one or two restriction enzyme (RE) sites, which allow for easy substitution of these elements. In SEQ ID NO: 130, the order of elements is as follows:

(5'AAV2 ITR)-RE-(HCB Promoter)-RE-(MVM Intron)-RE-Kozak-(ET3 coding region)-RE-(poly adenylation signal)-RE-(3'AAV2 ITR)

AAV2-HCB-ET3-LCO-NCG-SpA

| Element | Start (bp) | End (bp) |
|---|---|---|
| 5' AAV2 ITR | 1 | 141 |
| AgeI (restriction site) | 142 | 147 |
| HCB promoter | 148 | 293 |
| SalI + PacI (restriction sites) | 294 | 307 |
| MVM intron | 308 | 399 |
| XhoI (restriction site) | 400 | 405 |
| Kozak consensus sequence | 406 | 410 |
| Liver optimized ET3 no CpGs | 411 | 4814 |
| NotI (restriction site) | 4815 | 4822 |
| Rabbit beta globin polyA signal | 4823 | 4871 |
| MunI (restriction site) | 4872 | 4877 |
| 3' AAV2 ITR | 4878 | 5018 |

The intron and restriction sites can optionally be removed from the cassette to provide a shortened recombinant AAV genome. Additionally, the transgene can be substituted as needed. Removing the intron and restriction sites elements would generate a vector of 4885 base pairs (ET3) or 4855 (HSQ).

Figure 19:
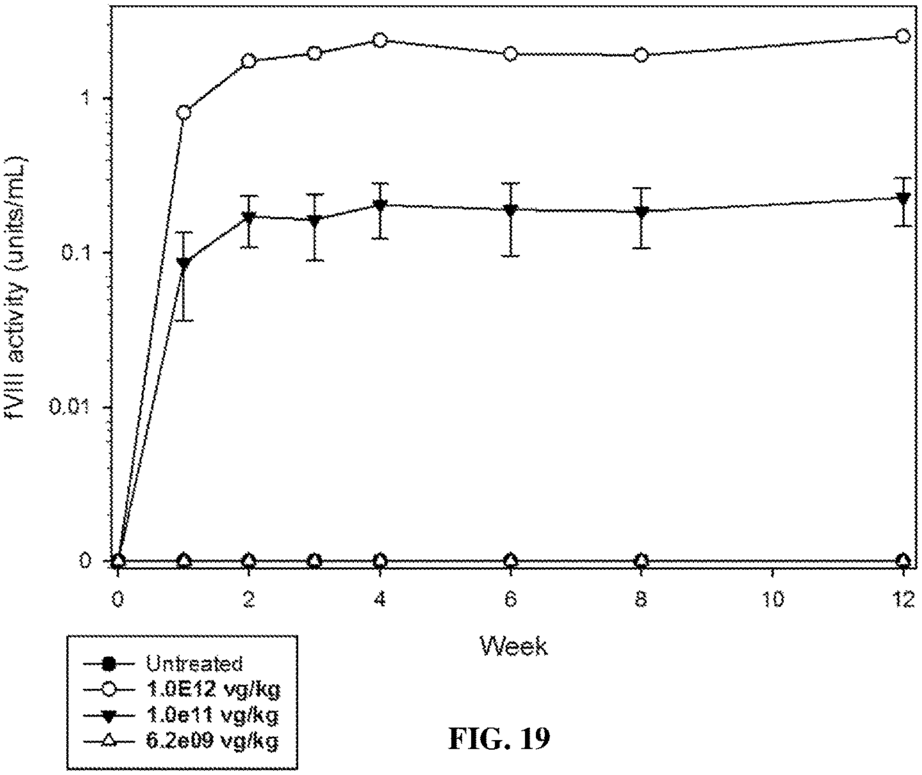
FIG. 19 is a graph showing that transduction of mice with the AAV2-HCB-ET3-LCO-NCG-SpA vector (SEQ ID NO: 130) encoding liver codon-optimized ET3 with deleted CpG motifs leads to a significant increase in fVIII activity in transduced mice.

AAV2-HCB-ET3-LCO-NCG-SpA virus particles were generated and used to transduce mice. fVIII activity in serum was assayed at various time point post-transduction (see FIG. 19). The in vivo gene therapy assay was performed substantially as described in Brown et al. ("Bioengineered Factor FVIII Enables Long-Term Correction of Murine Hemophilia A Following Liver-Directed Adeno-Associated Viral Vector Delivery," *Molecular Therapy—Methods and Clinical Development*. 1:14036, 2014).

```
SEQ ID NO: 130:
CCTGCAGGCAGCTGCGCGCTCGCTCGCTCACTGAGGCCGCCCGGGCAAAG
CCCGGGCGTCGGGCGACCTTTGGTCGCCCGGCCTCAGTGAGCGAGCGAGC
```

-continued

```
GCGCAGAGAGGGAGTGGCCAACTCCATCACTAGGGGTTCCTACCGGTGTT
AATCATTAAGTCGTTAATTTTTGTGGCCCTTGCGATGTTTGCTCTGGTTA
ATAATCTCAGGACAAACAGAGGTTAATAATTTTCCAGATCTCTCTGAGCA
ATAGTATAAAAGGCCAGCAGCAGCCTGACCACATCTCATCCTCGTCGACT
TAATTAAAAGAGGTAAGGGTTTAAGGGATGGTTGGTTGGTGGGGTATTAA
TGTTTAATTACCTGGAGCACCTGCCTGAAATCACTTTTTTTCAGGTTGGC
TCGAGCCACCATGCAGCTGGAACTGTCTACCTGTGTGTTTCTGTGTCTGC
TGCCTCTGGGGTTTTCTGCTATCAGGAGATACTATCTGGGAGCTGTGGAG
CTGTCCTGGGACTACAGGCAGTCTGAGCTGCTGAGAGAACTGCATGTGGA
TACCAGATTCCCAGCTACAGCTCCAGGAGCTCTGCCTCTGGGCCCATCTG
TGCTGTACAAGAAAACAGTCTTTGTGGAGTTTACAGACCAGCTGTTCTCT
GTGGCCAGGCCAAGACCACCTTGGATGGGACTGCTGGGACCAACCATCCA
GGCTGAGGTGTATGATACAGTGGTGGTGACCCTGAAAAACATGGCCTCCC
ATCCTGTGAGCCTGCATGCTGTGGGGGTGTCCTTCTGGAAGTCCTCTGAG
GGAGCTGAGTATGAAGACCATACCTCCCAGAGGGAGAAAGAAGATGATAA
GGTGCTGCCTGGCAAAAGCCAGACCTATGTCTGGCAGGTGCTGAAGGAGA
ATGGACCAACTGCTTCTGACCCACCATGCCTGACCTACTCTTATCTGTCC
CATGTGGATCTGGTGAAGGACCTGAATTCTGGACTGATTGGAGCTCTGCT
GGTGTGTAGAGAGGGAAGCCTGACCAGAGAAAGAACCCAGAACCTGCATG
AGTTTGTCCTGCTGTTTGCTGTGTTTGATGAAGGGAAGAGCTGGCACTCT
GCCAGGAATGACTCCTGGACCAGAGCTATGGATCCAGCTCCTGCTAGAGC
TCAGCCTGCTATGCACACAGTCAATGGCTATGTGAATAGGTCTCTGCCAG
GACTGATTGGCTGCCATAAGAAATCTGTCTATTGGCATGTGATTGGAATG
GGCACCAGCCCTGAGGTGCATTCTATCTTCCTGGAAGGCCACACCTTTCT
GGTCAGGCACCATAGACAGGCCTCTCTGGAGATCTCCCCTCTGACCTTCC
TGACAGCTCAGACCTTTCTGATGGACCTGGGGCAGTTCCTGCTGTTTTGC
CATATCTCTTCCCACCATCATGGAGGAATGGAGGCTCATGTCAGGGTGGA
ATCCTGTGCTGAGGAACCACAGCTGAGAAGAAAGGCTGATGAGGAAGAGG
ACTATGATGATAACCTGTATGACTCTGATATGGATGTGGTGAGGCTGGAT
GGGGATGATGTCAGCCCTTTCATCCAGATCAGGTCTGTGGCCAAGAAACA
TCCAAAGACCTGGGTCCACTACATTGCTGCTGAAGAGGAAGATTGGGACT
ATGCCCCCCTGGTGCTGGCTCCTGATGATAGATCCTACAAAAGCCAGTAT
CTGAACAATGGGCCCCAGAGGATTGGAAGGAAGTACAAGAAAGTGAGGTT
CATGGCCTATACAGATGAGACCTTTAAGACCAGAGAGGCTATCCAGCATG
AATCTGGGATCCTGGGACCTCTGCTGTATGGAGAAGTGGGGGATACCCTG
CTGATCATCTTCAAGAACCAGGCCTCCAGGCCATACAATATCTATCCCCA
TGGCATCACAGATGTGAGACCACTGTACAGCAGGAGACTGCCCAAGGGGG
TCAAACACCTGAAGGATTTCCCCATCCTGCCTGGAGAGATCTTTAAGTAT
AAATGGACAGTCACAGTGGAAGATGGGCCTACCAAGTCTGATCCAAGGTG
```

-continued

CCTGACCAGATACTATAGCTCTTTTGTGAACATGGAGAGAGACCTGGCTT

CTGGACTGATTGGACCCCTGCTGATCTGTTACAAAGAGTCTGTGGACCAG

AGGGGCAACCAGATCATGTCTGATAAGAGAAATGTCATCCTGTTCTCTGT

GTTTGATGAGAACAGGAGCTGGTACCTGACAGAGAACATCCAGAGGTTCC

TGCCAAATCCAGCTGGAGTGCAGCTGGAGGACCCAGAATTTCAGGCTTCC

AACATCATGCATAGCATCAATGGCTATGTGTTTGATAGCCTGCAGCTGTC

TGTCTGCCTGCATGAGGTGGCCTACTGGTATATCCTGTCCATTGGAGCTC

AGACAGACTTCCTGTCTGTGTTCTTTAGTGGGTACACCTTTAAGCATAAA

ATGGTGTATGAGGATACCCTGACCCTGTTCCCCTTTTCTGGGGAGACAGT

GTTCATGTCCATGGAAAACCCTGGCCTGTGGATCCTGGGGTGCCACAACT

CTGACTTCAGGAATAGAGGAATGACAGCCCTGCTGAAAGTGTCCAGCTGT

GATAAGAATACAGGGGATTACTATGAGGACTCTTATGAAGATATCTCTGC

TTATCTGCTGAGCAAGAACAATGCCATTGAGCCCAGGTCTTTTGCTCAGA

ACTCCAGACCTCCATCTGCTTCTGCTCCTAAGCCACCTGTGCTGAGAAGA

CATCAGAGGGACATCTCCCTGCCTACCTTCCAGCCAGAGGAAGATAAAAT

GGACTATGATGATATCTTCAGCACAGAGACCAAGGGGGAAGATTTTGACA

TCTATGGAGAGGATGAAAACCAGGATCCAAGATCCTTCCAGAAGAGAACC

AGACACTACTTTATTGCTGCTGTGGAGCAGCTGTGGGACTATGGGATGTC

TGAAAGCCCAAGGGCCCTGAGGAACAGAGCTCAGAATGGAGAGGTGCCCA

GATTCAAGAAAGTGGTGTTCAGAGAGTTTGCTGATGGCAGCTTTACCCAG

CCATCTTACAGGGGGGAGCTGAACAAGCATCTGGGGCTGCTGGGACCCTA

TATCAGAGCTGAGGTGGAAGATAACATCATGGTGACCTTCAAGAATCAGG

CTTCTAGGCCCTACTCCTTTTATTCTTCCCTGATCTCCTACCCTGATGAT

CAGGAGCAGGGAGCTGAACCTAGGCACAACTTTGTGCAGCCAAATGAGAC

CAGAACCTACTTTTGGAAGGTGCAGCATCACATGGCTCCCACAGAGGATG

AATTTGACTGCAAAGCTTGGGCCTATTTTTCTGATGTGGACCTGGAGAAG

GATGTGCATTCTGGCCTGATTGGGCCTCTGCTGATCTGTAGGGCCAACAC

CCTGAATGCTGCTCATGGAAGACAGGTCACAGTGCAGGAGTTTGCTCTGT

TCTTTACCATCTTTGATGAAACCAAGAGCTGGTACTTCACAGAGAATGTG

GAAAGGAATTGCAGAGCCCCCTGTCATCTGCAGATGGAGGACCCTACCCT

GAAGGAAAACTACAGGTTCCATGCCATCAATGGATATGTCATGGATACCC

TGCCTGGCCTGGTCATGGCTCAGAACCAGAGGATCAGATGGTACCTGCTG

TCTATGGGATCCAATGAGAATATCCATAGCATCCACTTCTCTGGCCATGT

CTTTTCTGTGAGGAAGAAAGAGGAATACAAAATGGCTGTGTACAATCTGT

ATCCTGGGGTCTTTGAGACAGTGGAAATGCTGCCAAGCAAAGTGGGAATC

TGGAGAATTGAGTGCCTGATTGGGGAACACCTGCAGGCTGGGATGAGCAC

CACCTTCCTGGTGTACTCTAAGAAATGTCAGACCCCACTGGGGATGGCCT

CTGGACATATCAGGGACTTCCAGATCACAGCTTCTGGACAGTATGGACAG

TGGGCTCCAAAGCTGGCTAGACTGCACTATTCTGGCTCCATCAATGCCTG

GTCTACCAAAGAGCCATTCTCCTGGATCAAGGTGGACCTGCTGGCCCCCA

TGATCATCCATGGAATCAAAACCCAGGGAGCTAGGCAGAAGTTCAGCTCT

-continued

CTGTACATCTCCCAGTTTATCATCATGTATAGCCTGGATGGGAAGAAATG

GCAGACCTACAGAGGCAATTCCACTGGGACCCTGATGGTCTTCTTTGGAA

ATGTGGATTCCTCTGGCATCAAGCACAACATCTTCAATCCACCCATCATT

GCCAGGTACATCAGGCTGCATCCTACCCACTATAGCATCAGGTCTACCCT

GAGAATGGAGCTGATGGGATGTGACCTGAACAGCTGTTCTATGCCACTGG

GCATGGAGTCCAAGGCTATCTCTGATGCCCAGATCACAGCTTCTTCCTAC

TTCACCAATATGTTTGCTACCTGGTCCCCAAGCAAGGCTAGACTGCACCT

GCAGGGAAGATCCAATGCTTGGAGACCCCAGGTGAACAATCCTAAGGAGT

GGCTGCAGGTGGACTTCCAGAAAACCATGAAGGTCACAGGGGTGACCACC

CAGGGAGTGAAATCTCTGCTGACCTCCATGTATGTCAAGGAGTTCCTGAT

CAGCTCTTCCCAGGATGGCCACCAGTGGACCCTGTTCTTTCAGAATGGCA

AGGTCAAAGTGTTCCAGGGGAATCAGGACTCTTTTACCCCAGTGGTGAAC

TCCCTGGATCCTCCACTGCTGACCAGGTACCTGAGAATCCATCCTCAGAG

CTGGGTGCACCAGATTGCTCTGAGAATGGAGGTCCTGGGATGTGAAGCTC

AGGACCTGTATTGAGCGGCCGCAATAAAATATCTTTATTTTCATTACATC

TGTGTGTTGGTTTTTTGTGTGCAATTGAGGAACCCCTAGTGATGGAGTTG

GCCACTCCCTCTCTGCGCGCTCGCTCGCTCACTGAGGCCGGGCGACCAAA

GGTCGCCCGACGCCCGGGCTTTGCCCGGGCGGCCTCAGTGAGCGAGCGAG

CGCGCAGCTGCCTGCAGG

Example 4

Treatment of Human Hemophilia a Using AAV-Based Gene Therapy

This example describes an exemplary method for the clinical use of AAV vectors encoding fVIII for the treatment of hemophilia A.

A patient diagnosed with hemophilia A is selected for treatment. The patient is administered a therapeutically effective amount of a recombinant AAV encoding the ET3 or HSQ fVIII variant, such as AAV-ET3 or AAV-HSQ under control of a HCB promoter as disclosed herein. The recombinant AAV can be administered intravenously. An appropriate therapeutic dose can be selected by a medical practitioner. In some cases, the therapeutically effective dose is in the range of $1\times10^{11}$ to $1\times10^{14}$ viral particles (vp)/kg, such as about $1\times10^{12}$ vp/kg. In most instances, the patient is administered a single dose. The health of the subject can be monitored over time to determine the effectiveness of the treatment.

It will be apparent that the precise details of the methods or compositions described may be varied or modified without departing from the spirit of the described embodiments. We claim all such modifications and variations that fall within the scope and spirit of the claims below.

We claim:

1. A recombinant nucleic acid molecule, comprising:
a liver-specific promoter comprising a first response element of no more than 160 nucleotides in length that comprises:
a HNF1a transcription factor (TF) binding site;
a HNF1-1 TF binding site;
a HNF4 TF binding site;
a HNF3a TF binding site;
a HNF1-2 TF binding site;
a HNF3-2 TF binding site;
a HP1 TF binding site
a TATA box; and
a Transcription Start Site.

2. The recombinant nucleic acid molecule of claim 1, wherein:
the HNF1a TF binding site comprises or consists of nucleotides 1-12 of SEQ ID NO: 4;
the HNF1-1 TF binding site comprises or consists of nucleotides 16-23 of SEQ ID NO: 4;
the HNF4 TF binding site comprises or consists of nucleotides 26-36 of SEQ ID NO: 4;
the HNF3a TF binding site comprises or consists of nucleotides 39-45 of SEQ ID NO: 4;
the HNF1-2 TF binding site comprises or consists of nucleotides 48-62 of SEQ ID NO: 4;
the HNF3-2 TF binding site comprises or consists of nucleotides 65-71 of SEQ ID NO: 4;
the HP1 TF binding site comprises or consists of nucleotides 75-87 of SEQ ID NO: 4;
the TATA box comprises or consists of nucleotides 108-114 of SEQ ID NO: 4; and
the Transcription Start Site (TSS) comprises or consists of nucleotides 116-146 of SEQ ID NO: 4.

3. The recombinant nucleic acid molecule of claim 1, wherein the first response element comprises, from 5' to 3', the HNF1a TF binding site, the HNF1-1 TF binding site, the HNF4 TF binding site, the HNF3a TF binding site, the HNF1-2 TF binding site, the HNF3-2 TF binding site, the HP1 TF binding site, the TATA box, and the Transcription Start Site (TSS).

4. The recombinant nucleic acid molecule of claim 1, wherein the first response element is no more than 150 nucleotides in length.

5. The recombinant nucleic acid molecule of claim 1, wherein the first response element is 146 nucleotides in length.

6. The recombinant nucleic acid molecule of claim 1, wherein the first response element comprises or consists of a nucleotide sequence at least 90% identical to SEQ ID NO: 4.

7. The recombinant nucleic acid molecule of claim 6, wherein the first response element comprises or consists of the nucleotide sequence set forth as SEQ ID NO: 4.

8. The recombinant nucleic acid molecule of claim 1, wherein the promoter consists of the first response element.

9. The recombinant nucleic acid molecule of claim 1, further comprising a second response element upstream of the first response element, the second response element comprising one of:
a HSh response element comprising or consisting of a nucleotide sequence at least 90% identical to SEQ ID NO: 111;
a 5'HS response element comprising or consisting of a nucleotide sequence at least 90% identical to nucleotides 6-32 of SEQ ID NO: 111; or
a 3'HS response element comprising or consisting of a nucleotide sequence at least 90% identical to nucleotides 44-68 of SEQ ID NO: 111.

10. The recombinant nucleic acid molecule of claim 9, wherein the
the HSh response element comprises or consists of the nucleotide sequence set forth as SEQ ID NO: 111;
the 5'HS response element comprises or consists of nucleotides 6-32 of SEQ ID NO: 111; or
the 3'HS response element comprises or consists of nucleotides 44-68 of SEQ ID NO: 111.

11. The recombinant nucleic acid molecule of claim 10, wherein the
the HSh response element consists of the nucleotide sequence set forth as SEQ ID NO: 111;
the 5'HS response element consists of nucleotides 6-32 of SEQ ID NO: 111; or
the 3'HS response element consists of nucleotides 44-68 of SEQ ID NO: 111.

12. The recombinant nucleic acid molecule of claim 9, wherein the recombinant promoter comprises or consists of a nucleotide sequence at least 90% identical to one of SEQ ID NO: 102 (HSh-HCB), SEQ ID NO: 104 (5'HSh-HCB), or SEQ ID NO: 103 (3'HSh-HCB).

13. The recombinant nucleic acid molecule of claim 12, wherein the recombinant promoter comprises or consists of the nucleotide sequence set forth as SEQ ID NO: 102 (HSh-HCB), SEQ ID NO: 104 (5'HSh-HCB), or SEQ ID NO: 103 (3'HSh-HCB).

14. A recombinant nucleic acid molecule comprising or consisting of the nucleotide sequence set forth as any one of SEQ ID NO: 5 (shortABP-HP1-God-TSS), SEQ ID NO: 7 (ABP-HP1-God-TSS), SEQ ID NO: 105 (HSh-SynO-TSS), SEQ ID NO: 106 (sHS-SynO-TSS), SEQ ID NO: 107 (Agro), SEQ ID NO: 108 (HS-SynO-TSS), or SEQ ID NO: 112 (HNF1-ShortABPExact-SynO-TSS-Int), or a nucleotide sequence at least 90% identical thereto.

15. A vector comprising the recombinant nucleic acid molecule of claim 1.

16. The vector of claim 15, wherein the vector is a viral vector.

17. The vector of claim 16, wherein the viral vector is an AAV vector.

18. The vector of claim 15, wherein the viral vector is a gamma-retroviral vector, a lentiviral vector, or an adenoviral vector.

19. The vector of claim 15, comprising a nucleic acid molecule encoding a clotting factor that is operably linked to the promoter.

20. The vector of claim 19, wherein the clotting factor is fVIII, or an ET3 or B domain deleted human (HSQ) fVIII variant.

21. The vector of claim 20, wherein the fVIII comprises the nucleic acid sequence set forth as SEQ ID NO: 2, SEQ ID NO: 11, SEQ ID NO: 12, SEQ ID NO: 125, or SEQ ID NO: 126, or a nucleic acid sequence at least 90% identical to SEQ ID NO: 2, SEQ ID NO: 11, SEQ ID NO: 12, SEQ ID NO: 125, or SEQ ID NO: 126.

22. The vector of claim 19, wherein the clotting factor is fIX.

23. The vector of claim 22, wherein the fIX comprises the nucleic acid sequence set forth as SEQ ID NO: 8, SEQ ID NO: 9, SEQ ID NO: 10, SEQ ID NO: 124, or SEQ ID NO: 127, or a nucleic acid sequence at least 90% identical SEQ ID NO: 8, SEQ ID NO: 9, SEQ ID NO: 10, SEQ ID NO: 124, or SEQ ID NO: 127.

24. A composition comprising the vector of claim 15 in a pharmaceutically acceptable carrier.

25. An isolated nucleic acid molecule, comprising:

a nucleic acid sequence encoding fVIII and comprising the nucleotide sequence set forth as one of SEQ ID NO: 2, SEQ ID NO: 11, SEQ ID NO: 12, SEQ ID NO: 125, or SEQ ID NO: 126, or a nucleotide sequence at least 90% identical to one of SEQ ID NO: 2, SEQ ID NO: 11, SEQ ID NO: 12 SEQ ID NO: 125, or SEQ ID NO: 126; or a nucleic acid sequence encoding fIX and comprising the nucleotide sequence set forth as one of SEQ ID NO: 8, SEQ ID NO: 9, SEQ ID NO: 10, SEQ ID NO: 124, or SEQ ID NO: 127, or a nucleotide sequence at least 90% identical to one of SEQ ID NO: 8, SEQ ID NO: 9, SEQ ID NO: 10, SEQ ID NO: 124, or SEQ ID NO: 127.

26. A method of inducing blood clotting in a subject in need thereof, comprising administering to the subject a therapeutically effective amount of the vector of claim 19.

27. A method of treating a subject with a clotting disorder, comprising selecting a subject with the clotting disorder and administering to the subject a therapeutically effective amount of the vector of claim 19.

28. The method of claim 27, wherein the clotting disorder is:

hemophilia A and the subject is administered a vector comprising a nucleic acid molecule encoding a protein with fVIII activity; or hemophilia B and the subject is administered a vector comprising a nucleic acid molecule encoding a protein with fIX activity.

* * * * *

SEQUENCE LISTING

<160> NUMBER OF SEQ ID NOS: 131

<210> SEQ ID NO 1
<211> LENGTH: 2351
<212> TYPE: PRT
<213> ORGANISM: homo sapiens

<400> SEQUENCE: 1

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365
```

-continued

```
Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
```

-continued

```
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro  Ala Leu Leu Thr Lys  Asp Asn Ala
        995                 1000                1005

Leu Phe  Lys Val Ser Ile Ser  Leu Leu Lys Thr Asn  Lys Thr Ser
    1010                1015                1020

Asn Asn  Ser Ala Thr Asn Arg  Lys Thr His Ile Asp  Gly Pro Ser
    1025                1030                1035

Leu Leu  Ile Glu Asn Ser Pro  Ser Val Trp Gln Asn  Ile Leu Glu
    1040                1045                1050

Ser Asp  Thr Glu Phe Lys Lys  Val Thr Pro Leu Ile  His Asp Arg
    1055                1060                1065

Met Leu  Met Asp Lys Asn Ala  Thr Ala Leu Arg Leu  Asn His Met
    1070                1075                1080

Ser Asn  Lys Thr Thr Ser Ser  Lys Asn Met Glu Met  Val Gln Gln
    1085                1090                1095

Lys Lys  Glu Gly Pro Ile Pro  Pro Asp Ala Gln Asn  Pro Asp Met
    1100                1105                1110

Ser Phe  Phe Lys Met Leu Phe  Leu Pro Glu Ser Ala  Arg Trp Ile
    1115                1120                1125

Gln Arg  Thr His Gly Lys Asn  Ser Leu Asn Ser Gly  Gln Gly Pro
    1130                1135                1140

Ser Pro  Lys Gln Leu Val Ser  Leu Gly Pro Glu Lys  Ser Val Glu
    1145                1150                1155

Gly Gln  Asn Phe Leu Ser Glu  Lys Asn Lys Val Val  Val Gly Lys
    1160                1165                1170

Gly Glu  Phe Thr Lys Asp Val  Gly Leu Lys Glu Met  Val Phe Pro
    1175                1180                1185

Ser Ser  Arg Asn Leu Phe Leu  Thr Asn Leu Asp Asn  Leu His Glu
    1190                1195                1200
```

```
Asn Asn  Thr His Asn Gln Glu  Lys Lys Ile Gln Glu  Glu Ile Glu
    1205                 1210                 1215

Lys Lys  Glu Thr Leu Ile Gln  Glu Asn Val Val Leu  Pro Gln Ile
    1220                 1225                 1230

His Thr  Val Thr Gly Thr Lys  Asn Phe Met Lys Asn  Leu Phe Leu
    1235                 1240                 1245

Leu Ser  Thr Arg Gln Asn Val  Glu Gly Ser Tyr Asp  Gly Ala Tyr
    1250                 1255                 1260

Ala Pro  Val Leu Gln Asp Phe  Arg Ser Leu Asn Asp  Ser Thr Asn
    1265                 1270                 1275

Arg Thr  Lys Lys His Thr Ala  His Phe Ser Lys Lys  Gly Glu Glu
    1280                 1285                 1290

Glu Asn  Leu Glu Gly Leu Gly  Asn Gln Thr Lys Gln  Ile Val Glu
    1295                 1300                 1305

Lys Tyr  Ala Cys Thr Thr Arg  Ile Ser Pro Asn Thr  Ser Gln Gln
    1310                 1315                 1320

Asn Phe  Val Thr Gln Arg Ser  Lys Arg Ala Leu Lys  Gln Phe Arg
    1325                 1330                 1335

Leu Pro  Leu Glu Glu Thr Glu  Leu Glu Lys Arg Ile  Ile Val Asp
    1340                 1345                 1350

Asp Thr  Ser Thr Gln Trp Ser  Lys Asn Met Lys His  Leu Thr Pro
    1355                 1360                 1365

Ser Thr  Leu Thr Gln Ile Asp  Tyr Asn Glu Lys Glu  Lys Gly Ala
    1370                 1375                 1380

Ile Thr  Gln Ser Pro Leu Ser  Asp Cys Leu Thr Arg  Ser His Ser
    1385                 1390                 1395

Ile Pro  Gln Ala Asn Arg Ser  Pro Leu Pro Ile Ala  Lys Val Ser
    1400                 1405                 1410

Ser Phe  Pro Ser Ile Arg Pro  Ile Tyr Leu Thr Arg  Val Leu Phe
    1415                 1420                 1425

Gln Asp  Asn Ser Ser His Leu  Pro Ala Ala Ser Tyr  Arg Lys Lys
    1430                 1435                 1440

Asp Ser  Gly Val Gln Glu Ser  Ser His Phe Leu Gln  Gly Ala Lys
    1445                 1450                 1455

Lys Asn  Asn Leu Ser Leu Ala  Ile Leu Thr Leu Glu  Met Thr Gly
    1460                 1465                 1470

Asp Gln  Arg Glu Val Gly Ser  Leu Gly Thr Ser Ala  Thr Asn Ser
    1475                 1480                 1485

Val Thr  Tyr Lys Lys Val Glu  Asn Thr Val Leu Pro  Lys Pro Asp
    1490                 1495                 1500

Leu Pro  Lys Thr Ser Gly Lys  Val Glu Leu Leu Pro  Lys Val His
    1505                 1510                 1515

Ile Tyr  Gln Lys Asp Leu Phe  Pro Thr Glu Thr Ser  Asn Gly Ser
    1520                 1525                 1530

Pro Gly  His Leu Asp Leu Val  Glu Gly Ser Leu Leu  Gln Gly Thr
    1535                 1540                 1545

Glu Gly  Ala Ile Lys Trp Asn  Glu Ala Asn Arg Pro  Gly Lys Val
    1550                 1555                 1560

Pro Phe  Leu Arg Val Ala Thr  Glu Ser Ser Ala Lys  Thr Pro Ser
    1565                 1570                 1575

Lys Leu  Leu Asp Pro Leu Ala  Trp Asp Asn His Tyr  Gly Thr Gln
    1580                 1585                 1590
```

```
Ile Pro  Lys Glu Glu Trp Lys  Ser Gln Glu Lys Ser  Pro Glu Lys
    1595                 1600                 1605

Thr Ala  Phe Lys Lys Lys Asp  Thr Ile Leu Ser Leu  Asn Ala Cys
    1610                 1615                 1620

Glu Ser  Asn His Ala Ile Ala  Ala Ile Asn Glu Gly  Gln Asn Lys
    1625                 1630                 1635

Pro Glu  Ile Glu Val Thr Trp  Ala Lys Gln Gly Arg  Thr Glu Arg
    1640                 1645                 1650

Leu Cys  Ser Gln Asn Pro Pro  Val Leu Lys Arg His  Gln Arg Glu
    1655                 1660                 1665

Ile Thr  Arg Thr Thr Leu Gln  Ser Asp Gln Glu Glu  Ile Asp Tyr
    1670                 1675                 1680

Asp Asp  Thr Ile Ser Val Glu  Met Lys Lys Glu Asp  Phe Asp Ile
    1685                 1690                 1695

Tyr Asp  Glu Asp Glu Asn Gln  Ser Pro Arg Ser Phe  Gln Lys Lys
    1700                 1705                 1710

Thr Arg  His Tyr Phe Ile Ala  Ala Val Glu Arg Leu  Trp Asp Tyr
    1715                 1720                 1725

Gly Met  Ser Ser Ser Pro His  Val Leu Arg Asn Arg  Ala Gln Ser
    1730                 1735                 1740

Gly Ser  Val Pro Gln Phe Lys  Lys Val Val Phe Gln  Glu Phe Thr
    1745                 1750                 1755

Asp Gly  Ser Phe Thr Gln Pro  Leu Tyr Arg Gly Glu  Leu Asn Glu
    1760                 1765                 1770

His Leu  Gly Leu Leu Gly Pro  Tyr Ile Arg Ala Glu  Val Glu Asp
    1775                 1780                 1785

Asn Ile  Met Val Thr Phe Arg  Asn Gln Ala Ser Arg  Pro Tyr Ser
    1790                 1795                 1800

Phe Tyr  Ser Ser Leu Ile Ser  Tyr Glu Glu Asp Gln  Arg Gln Gly
    1805                 1810                 1815

Ala Glu  Pro Arg Lys Asn Phe  Val Lys Pro Asn Glu  Thr Lys Thr
    1820                 1825                 1830

Tyr Phe  Trp Lys Val Gln His  His Met Ala Pro Thr  Lys Asp Glu
    1835                 1840                 1845

Phe Asp  Cys Lys Ala Trp Ala  Tyr Phe Ser Asp Val  Asp Leu Glu
    1850                 1855                 1860

Lys Asp  Val His Ser Gly Leu  Ile Gly Pro Leu Leu  Val Cys His
    1865                 1870                 1875

Thr Asn  Thr Leu Asn Pro Ala  His Gly Arg Gln Val  Thr Val Gln
    1880                 1885                 1890

Glu Phe  Ala Leu Phe Phe Thr  Ile Phe Asp Glu Thr  Lys Ser Trp
    1895                 1900                 1905

Tyr Phe  Thr Glu Asn Met Glu  Arg Asn Cys Arg Ala  Pro Cys Asn
    1910                 1915                 1920

Ile Gln  Met Glu Asp Pro Thr  Phe Lys Glu Asn Tyr  Arg Phe His
    1925                 1930                 1935

Ala Ile  Asn Gly Tyr Ile Met  Asp Thr Leu Pro Gly  Leu Val Met
    1940                 1945                 1950

Ala Gln  Asp Gln Arg Ile Arg  Trp Tyr Leu Leu Ser  Met Gly Ser
    1955                 1960                 1965

Asn Glu  Asn Ile His Ser Ile  His Phe Ser Gly His  Val Phe Thr
    1970                 1975                 1980

Val Arg  Lys Lys Glu Glu Tyr  Lys Met Ala Leu Tyr  Asn Leu Tyr
```

```
    1985                1990                1995

Pro Gly  Val Phe Glu Thr Val  Glu Met Leu Pro Ser  Lys Ala Gly
    2000                2005                2010

Ile Trp  Arg Val Glu Cys Leu  Ile Gly Glu His Leu  His Ala Gly
    2015                2020                2025

Met Ser  Thr Leu Phe Leu Val  Tyr Ser Asn Lys Cys  Gln Thr Pro
    2030                2035                2040

Leu Gly  Met Ala Ser Gly His  Ile Arg Asp Phe Gln  Ile Thr Ala
    2045                2050                2055

Ser Gly  Gln Tyr Gly Gln Trp  Ala Pro Lys Leu Ala  Arg Leu His
    2060                2065                2070

Tyr Ser  Gly Ser Ile Asn Ala  Trp Ser Thr Lys Glu  Pro Phe Ser
    2075                2080                2085

Trp Ile  Lys Val Asp Leu Leu  Ala Pro Met Ile Ile  His Gly Ile
    2090                2095                2100

Lys Thr  Gln Gly Ala Arg Gln  Lys Phe Ser Ser Leu  Tyr Ile Ser
    2105                2110                2115

Gln Phe  Ile Ile Met Tyr Ser  Leu Asp Gly Lys Lys  Trp Gln Thr
    2120                2125                2130

Tyr Arg  Gly Asn Ser Thr Gly  Thr Leu Met Val Phe  Phe Gly Asn
    2135                2140                2145

Val Asp  Ser Ser Gly Ile Lys  His Asn Ile Phe Asn  Pro Pro Ile
    2150                2155                2160

Ile Ala  Arg Tyr Ile Arg Leu  His Pro Thr His Tyr  Ser Ile Arg
    2165                2170                2175

Ser Thr  Leu Arg Met Glu Leu  Met Gly Cys Asp Leu  Asn Ser Cys
    2180                2185                2190

Ser Met  Pro Leu Gly Met Glu  Ser Lys Ala Ile Ser  Asp Ala Gln
    2195                2200                2205

Ile Thr  Ala Ser Ser Tyr Phe  Thr Asn Met Phe Ala  Thr Trp Ser
    2210                2215                2220

Pro Ser  Lys Ala Arg Leu His  Leu Gln Gly Arg Ser  Asn Ala Trp
    2225                2230                2235

Arg Pro  Gln Val Asn Asn Pro  Lys Glu Trp Leu Gln  Val Asp Phe
    2240                2245                2250

Gln Lys  Thr Met Lys Val Thr  Gly Val Thr Thr Gln  Gly Val Lys
    2255                2260                2265

Ser Leu  Leu Thr Ser Met Tyr  Val Lys Glu Phe Leu  Ile Ser Ser
    2270                2275                2280

Ser Gln  Asp Gly His Gln Trp  Thr Leu Phe Phe Gln  Asn Gly Lys
    2285                2290                2295

Val Lys  Val Phe Gln Gly Asn  Gln Asp Ser Phe Thr  Pro Val Val
    2300                2305                2310

Asn Ser  Leu Asp Pro Pro Leu  Leu Thr Arg Tyr Leu  Arg Ile His
    2315                2320                2325

Pro Gln  Ser Trp Val His Gln  Ile Ala Leu Arg Met  Glu Val Leu
    2330                2335                2340

Gly Cys  Glu Ala Gln Asp Leu  Tyr
    2345                2350
```

<210> SEQ ID NO 2
<211> LENGTH: 4374
<212> TYPE: DNA
<213> ORGANISM: Artificial Sequence -continued
<220> FEATURE:
<223> OTHER INFORMATION: recombinant fVIII

<400> SEQUENCE: 2

```
atgcagattg aactgtctac ctgtttcttt ctgtgcctgc tgaggttttg tttttctgct     60
accagaagat actacctggg agctgtggaa ctgagctggg attacatgca gtctgacctg    120
ggagagctgc ctgtggatgc tagattccca cctagagtcc ctaagtcctt ccccttcaac    180
acctctgtgg tctacaagaa aaccctgttt gtggagttta cagaccacct gttcaacatt    240
gctaagccta gaccaccatg gatgggactg ctgggaccaa ccatccaggc agaggtgtat    300
gacacagtgg tcatcaccct gaaaaacatg gcttctcacc ctgtgtccct gcatgctgtg    360
ggagtctcct actggaaggc ctctgaaggg gctgagtatg atgatcagac cagccagagg    420
gaaaaagagg atgataaggt gttccctgga gggtcccata cctatgtgtg gcaggtcctg    480
aaggagaatg gaccaatggc ttctgaccct ctgtgcctga cctactctta tctgtcccat    540
gtggacctgg tcaaggatct gaactctggc ctgattgggg ctctgctggt gtgtagggaa    600
gggtccctgg ccaaggagaa aacccagacc ctgcataagt tcatcctgct gtttgctgtg    660
tttgatgaag gaaaaagctg gcactctgag accaagaact ctctgatgca ggacagggat    720
gctgcttctg ccagagcttg gcccaagatg cacacagtga atggctatgt caataggagc    780
ctgcctggac tgattggctg ccacagaaag tctgtgtatt ggcatgtcat tggaatgggc    840
accacccctg aagtgcacag catcttcctg gaggggcata cctttctggt caggaaccac    900
aggcaggcta gcctggagat ctctccaatc accttcctga cagcccagac cctgctgatg    960
gacctgggac agttcctgct gttttgccac atctccagcc accagcatga tggcatggag   1020
gcttatgtga aagtggactc ctgtcctgag gaacctcagc tgaggatgaa gaacaatgag   1080
gaagctgaag actatgatga tgacctgaca gactctgaga tggatgtggt caggtttgat   1140
gatgataact ctccctcctt tatccagatc aggtctgtgg ccaagaaaca ccctaagacc   1200
tgggtccatt acattgctgc tgaggaagag gactgggatt atgctccact ggtgctggcc   1260
cctgatgata gatcctacaa aagccagtat ctgaacaatg gaccccagag gattggcaga   1320
aagtacaaga aagtgaggtt catggcttat acagatgaga cctttaagac cagagaagcc   1380
atccagcatg agtctgggat cctgggacct ctgctgtatg gggaagtggg ggacaccctg   1440
ctgatcatct tcaagaacca ggccagcagg ccttacaata tctatccaca tggcatcaca   1500
gatgtgagac ctctgtactc caggaggctg ccaaaggggg tgaaacacct gaaggacttc   1560
ccaatcctgc ctggggaaat ctttaagtat aaatggacag tcacagtgga ggatgggccc   1620
accaagtctg accctaggtg cctgaccaga tactattctt cctttgtgaa tatggagaga   1680
gacctggctt ctggactgat tggacccctg ctgatctgtt acaaagagtc tgtggatcag   1740
aggggcaacc agatcatgtc tgacaagagg aatgtgatcc tgttctctgt ctttgatgaa   1800
aacaggtctt ggtacctgac agagaacatc cagaggttcc tgcctaatcc agctggagtg   1860
cagctggaag atcctgagtt ccaggcctct aacatcatgc attccatcaa tggctatgtg   1920
tttgactccc tgcagctgtc tgtgtgcctg catgaggtgg cttactggta tatcctgagc   1980
attggagccc agacagattt cctgtctgtg ttcttttctg gctacacctt taagcataaa   2040
atggtgtatg aggacaccct gaccctgttc ccattttctg gagaaactgt gttcatgagc   2100
atggagaatc ctgggctgtg gatcctggga tgccacaact ctgatttcag gaatagaggg   2160
atgacagccc tgctgaaagt gagctcttgt gacaagaaca caggagacta ctatgaagat   2220
```

agctatgagg acatctctgc ttatctgctg tccaaaaaca atgccattga gcccaggagc 2280
ttctctcaga accctccagt gctgaagagg caccagaggg agatcaccag aaccaccctg 2340
cagtctgatc aggaagagat tgactatgat gataccatct ctgtggaaat gaagaaagag 2400
gactttgata tctatgatga agatgagaac cagtctccca ggtccttcca gaagaaaacc 2460
agacattact ttattgctgc tgtggagagg ctgtgggact atggcatgtc cagctctcct 2520
catgtgctga gaaatagagc tcagtctgga tctgtcccac agttcaagaa agtggtcttc 2580
caggagttta cagatggaag ctttacccag ccactgtaca ggggagaact gaatgagcac 2640
ctggggctgc tgggacccta tatcagggct gaagtggagg ataacatcat ggtcaccttc 2700
aggaatcagg ccagcagacc ctactctttt tattccagcc tgatctccta tgaagaggac 2760
cagagacagg gagctgaacc aagaaaaaac tttgtgaagc ctaatgagac caaaacctac 2820
ttttggaagg tgcagcacca tatggcccct accaaagatg agtttgattg caaggcctgg 2880
gcttattttt ctgatgtgga tctggagaag gatgtccact ctggcctgat tgggccactg 2940
ctggtgtgtc ataccaacac cctgaatcca gctcatggaa ggcaggtgac agtccaggaa 3000
tttgccctgt tctttaccat ctttgatgag accaagagct ggtacttcac agaaaacatg 3060
gagaggaatt gcagagcccc atgtaacatc cagatggaag accccacctt caaggagaac 3120
tacagatttc atgctatcaa tgggtatatc atggataccc tgccaggact ggtcatggct 3180
caggaccaga ggatcagatg gtacctgctg agcatggggt ctaatgagaa tatccactcc 3240
atccatttct ctggacatgt gtttacagta aggaagaaag aagagtacaa gatggccctg 3300
tacaacctgt atcctggggt gtttgaaaca gtggagatgc tgccttccaa ggctgggatc 3360
tggagggtgg aatgcctgat tggggagcac ctgcatgctg gaatgtctac cctgttcctg 3420
gtgtactcca ataagtgtca gacccccctg ggatggcttc ctggacatat cagggacttc 3480
cagatcacag cttctggaca gtatggacag tgggctccta agctggctag actgcactat 3540
tctggctcca tcaatgcttg gtctaccaaa gagcctttct cctggatcaa ggtggacctg 3600
ctggctccaa tgatcatcca tggcatcaaa acccaggggg ccaggcagaa gttctcttcc 3660
ctgtacatca gccagtttat catcatgtat tctctggatg ggaagaaatg gcagacctac 3720
agaggcaatt ccacagggac cctgatggtg ttctttggca atgtggacag ctctgggatc 3780
aagcacaaca tcttcaatcc ccctatcatt gccaggtaca tcagactgca cccaacccat 3840
tattccatca ggagcaccct gagaatggag ctgatggggt gtgatctgaa cagctgttct 3900
atgcccctgg gaatggagtc taaggccatc tctgatgctc agatcacagc ctccagctac 3960
ttcaccaata tgtttgctac ctggtcccca agcaaggcta gactgcatct gcagggaaga 4020
agcaatgctt ggagaccaca ggtgaacaat cccaaggagt ggctgcaggt ggacttccag 4080
aaaaccatga aggtgacagg agtcaccacc cagggagtga aaagcctgct gacctctatg 4140
tatgtcaagg agttcctgat ctcttccagc caggatgggc accagtggac cctgttcttt 4200
cagaatggaa aggtgaaagt cttccagggc aatcaggatt cctttacccc tgtggtcaac 4260
agcctggacc cacccctgct gaccaggtac ctgagaatcc acccacagtc ctgggtgcat 4320
cagattgctc tgaggatgga agtcctgggc tgtgaggccc aggacctgta ttga 4374

<210> SEQ ID NO 3
<211> LENGTH: 1457
<212> TYPE: PRT
<213> ORGANISM: Artificial Sequence
<220> FEATURE:
<223> OTHER INFORMATION: recombinant fVIII

<400> SEQUENCE: 3

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
```

```
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830
```

```
Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230
```

-continued

```
Gly Lys  Lys Trp Gln Thr Tyr  Arg Gly Asn Ser Thr  Gly Thr Leu
    1235                 1240                 1245

Met Val  Phe Phe Gly Asn Val  Asp Ser Ser Gly Ile  Lys His Asn
    1250                 1255                 1260

Ile Phe  Asn Pro Pro Ile Ile  Ala Arg Tyr Ile Arg  Leu His Pro
    1265                 1270                 1275

Thr His  Tyr Ser Ile Arg Ser  Thr Leu Arg Met Glu  Leu Met Gly
    1280                 1285                 1290

Cys Asp  Leu Asn Ser Cys Ser  Met Pro Leu Gly Met  Glu Ser Lys
    1295                 1300                 1305

Ala Ile  Ser Asp Ala Gln Ile  Thr Ala Ser Ser Tyr  Phe Thr Asn
    1310                 1315                 1320

Met Phe  Ala Thr Trp Ser Pro  Ser Lys Ala Arg Leu  His Leu Gln
    1325                 1330                 1335

Gly Arg  Ser Asn Ala Trp Arg  Pro Gln Val Asn Asn  Pro Lys Glu
    1340                 1345                 1350

Trp Leu  Gln Val Asp Phe Gln  Lys Thr Met Lys Val  Thr Gly Val
    1355                 1360                 1365

Thr Thr  Gln Gly Val Lys Ser  Leu Leu Thr Ser Met  Tyr Val Lys
    1370                 1375                 1380

Glu Phe  Leu Ile Ser Ser Ser  Gln Asp Gly His Gln  Trp Thr Leu
    1385                 1390                 1395

Phe Phe  Gln Asn Gly Lys Val  Lys Val Phe Gln Gly  Asn Gln Asp
    1400                 1405                 1410

Ser Phe  Thr Pro Val Val Asn  Ser Leu Asp Pro Pro  Leu Leu Thr
    1415                 1420                 1425

Arg Tyr  Leu Arg Ile His Pro  Gln Ser Trp Val His  Gln Ile Ala
    1430                 1435                 1440

Leu Arg  Met Glu Val Leu Gly  Cys Glu Ala Gln Asp  Leu Tyr
    1445                 1450                 1455
```

<210> SEQ ID NO 4
<211> LENGTH: 146
<212> TYPE: DNA
<213> ORGANISM: Artificial Sequence
<220> FEATURE:
<223> OTHER INFORMATION: recombinant promoter sequence

<400> SEQUENCE: 4

```
gttaatcatt aagtcgttaa tttttgtggc ccttgcgatg tttgctctgg ttaataatct     60

caggacaaac agaggttaat aattttccag atctctctga gcaatagtat aaaaggccag    120

cagcagcctg accacatctc atcctc                                         146
```

<210> SEQ ID NO 5
<211> LENGTH: 159
<212> TYPE: DNA
<213> ORGANISM: Artificial Sequence
<220> FEATURE:
<223> OTHER INFORMATION: recombinant promoter sequence

<400> SEQUENCE: 5

```
gttaattttt gtggcccttg cgatgtttgc tctggttaat aatctcagga caaacataca     60

ttttcagtca tatgtttgct cactgaaggt tactagttaa caggcatccc ttaaacagga    120

tataaaaggc cagcagcagc ctgaccacat ctcatcctc                           159
```

<210> SEQ ID NO 6

<211> LENGTH: 172
<212> TYPE: DNA
<213> ORGANISM: Artificial Sequence
<220> FEATURE:
<223> OTHER INFORMATION: recombinant promoter sequence

<400> SEQUENCE: 6

```
gttaatttt aaaaagcagt caaaagtcca agtggccctt gcgagcattt actctctctg     60

tttgctctgg ttaataatct caggagcaca aacagaggtt aataattttc agtcatatgt    120

ttgctcactg aaggttacta gttaacaggc atcccttaaa caggatataa aa            172
```

<210> SEQ ID NO 7
<211> LENGTH: 204
<212> TYPE: DNA
<213> ORGANISM: Artificial Sequence
<220> FEATURE:
<223> OTHER INFORMATION: recombinant promoter sequence

<400> SEQUENCE: 7

```
gttaatttt aaaaagcagt caaaagtcca agtggccctt gcgagcattt actctctctg     60

tttgctctgg ttaataatct caggagcaca aacagaggtt aataattttc agtcatatgt    120

ttgctcactg aaggttacta gttaacaggc atcccttaaa caggatataa aaggccagca    180

gcagcctgac cacatctcat cctc                                           204
```

<210> SEQ ID NO 8
<211> LENGTH: 1386
<212> TYPE: DNA
<213> ORGANISM: Artificial Sequence
<220> FEATURE:
<223> OTHER INFORMATION: recombinant fIX

<400> SEQUENCE: 8

```
atgcagaggg tgaacatgat catggctgag tctcctggac tgatcaccat ctgcctgctg     60

ggctatctgc tgtctgctga gtgtacagtg ttcctggacc atgaaaatgc taataaaatc    120

ctgaacaggc caaagaggta caattctggg aaactggagg aatttgtgca gggaaacctg    180

gagagggaat gcatggagga aaagtgtagc tttgaggaag ccagggaggt gtttgaaaat    240

acagagagga ccacagagtt ctggaaacag tatgtggatg gggatcagtg tgagtccaac    300

ccctgtctga atggagggtc ttgcaaggat gatatcaact cctatgagtg ctggtgtcct    360

tttggatttg aaggcaagaa ttgtgagctg gatgtgacct gtaacatcaa aaatgggagg    420

tgtgagcagt tctgtaagaa ctctgctgat aataaagtgg tctgcagctg tacagaaggc    480

tacaggctgg ctgagaacca gaagagctgt gaaccagctg tgcccttccc ttgtgggagg    540

gtgtctgtca gccagaccag caagctgacc agagctgagg ctgtgtttcc tgatgtggat    600

tatgtcaact ctacagaggc tgaaaccatc ctggacaaca tcacccagtc tacccagtcc    660

ttcaatgact ttaccagggt ggtgggaggg gaggatgcta agccaggaca gttcccctgg    720

caggtggtcc tgaatggcaa agtggatgct ttttgtgggg gctccattgt gaatgagaag    780

tggattgtca cagctgctca ctgtgtggaa actggggtca agatcacagt ggtggctgga    840

gagcacaaca ttgaggaaac tgaacataca gagcagaaaa ggaatgtgat cagaatcatc    900

ccccaccata actacaatgc tgctatcaac aagtataatc atgacattgc cctgctggaa    960

ctggatgagc ctctggtgct gaacagctat gtcaccccaa tctgcattgc tgacaaggag   1020

tataccaata tcttcctgaa atttgggtct ggatatgtgt ctgggtgggg aagggtcttc   1080

cacaagggaa ggtctgctct ggtgctgcag tatctgaggg tgcccctggt ggacagagct   1140
```

acctgcctga ggagcaccaa gttcaccatc tacaacaata tgttctgtgc tggatttcat 1200
gagggaggga gggactcctg tcagggagat tctggaggcc ctcatgtgac agaggtggaa 1260
ggcaccagct tcctgactgg catcatctct tggggggagg aatgtgctat gaaggggaaa 1320
tatggaatct ataccaaggt gtccagatat gtcaactgga tcaaggagaa aaccaagctg 1380
acctga 1386

<210> SEQ ID NO 9
<211> LENGTH: 1386
<212> TYPE: DNA
<213> ORGANISM: Artificial Sequence
<220> FEATURE:
<223> OTHER INFORMATION: recombinant fIX

<400> SEQUENCE: 9
atgcagaggg tgaacatgat catggctgag tctcctggac tgatcaccat ctgcctgctg 60
ggctatctgc tgtctgctga gtgtacagtg ttcctggacc atgaaaatgc taataaaatc 120
ctgaacaggc caaagaggta caattctggg aaactggagg aatttgtgca gggaaacctg 180
gagagggaat gcatggagga aaagtgtagc tttgaggaag ccagggaggt gtttgaaaat 240
acagagagga ccacagagtt ctggaaacag tatgtggatg gggatcagtg tgagtccaac 300
ccctgtctga atggagggtc ttgcaaggat gatatcaact cctatgagtg ctggtgtcct 360
tttggatttg aaggcaagaa ttgtgagctg gatgtgacct gtaacatcaa aaatgggagg 420
tgtgagcagt tctgtaagaa ctctgctgat aataaagtgg tctgcagctg tacagaaggc 480
tacaggctgg ctgagaacca gaagagctgt gaaccagctg tgcccttccc ttgtgggagg 540
gtgtctgtca gccagaccag caagctgacc agagctgagg ctgtgtttcc tgatgtggat 600
tatgtcaact ctacagaggc tgaaaccatc ctggacaaca tcacccagtc tacccagtcc 660
ttcaatgact ttaccagggt ggtgggaggg gaggatgcta agccaggaca gttcccctgg 720
caggtggtcc tgaatggcaa agtggatgct ttttgtgggg gctccattgt gaatgagaag 780
tggattgtca cagctgctca ctgtgtggaa actggggtca agatcacagt ggtggctgga 840
gagcacaaca ttgaggaaac tgaacataca gagcagaaaa ggaatgtgat cagaatcatc 900
ccccaccata actacaatgc tgctatcaac aagtataatc atgacattgc cctgctggaa 960
ctggatgagc ctctggtgct gaacagctat gtcaccccaa tctgcattgc tgacaaggag 1020
tataccaata tcttcctgaa atttgggtct ggatatgtgt ctgggtgggg aagggtcttc 1080
cacaagggaa ggtctgctct ggtgctgcag tatctgaggg tgcccctggt ggacagagct 1140
acctgcctgc tgagcaccaa gttcaccatc tacaacaata tgttctgtgc tggatttcat 1200
gagggaggga gggactcctg tcagggagat tctggaggcc ctcatgtgac agaggtggaa 1260
ggcaccagct tcctgactgg catcatctct tggggggagg aatgtgctat gaaggggaaa 1320
tatggaatct ataccaaggt gtccagatat gtcaactgga tcaaggagaa aaccaagctg 1380
acctga 1386

<210> SEQ ID NO 10
<211> LENGTH: 1386
<212> TYPE: DNA
<213> ORGANISM: Artificial Sequence
<220> FEATURE:
<223> OTHER INFORMATION: recombinant fIX

<400> SEQUENCE: 10

-continued atgcagaggg tgaacatgat catggctgag tctcctggac tgatcaccat ctgcctgctg 60
ggctatctgc tgtctgctga gtgtacagtg ttcctggacc atgaaaatgc taataaaatc 120
ctgaacaggc caaagaggta caattctggg aaactggagg aatttgtgca gggaaacctg 180
gagagggaat gcatggagga aaagtgtagc tttgaggaag ccagggaggt gtttgaaaat 240
acagagagga ccacagagtt ctggaaacag tatgtggatg gggatcagtg tgagtccaac 300
ccctgtctga atggagggtc ttgcaaggat gatatcaact cctatgagtg ctggtgtcct 360
tttggatttg aaggcaagaa ttgtgagctg gatgtgacct gtaacatcaa aaatgggagg 420
tgtgagcagt tctgtaagaa ctctgctgat aataaagtgg tctgcagctg tacagaaggc 480
tacaggctgg ctgagaacca gaagagctgt gaaccagctg tgcccttccc ttgtgggagg 540
gtgtctgtca gccagaccag caagctgacc agagctgaga cagtgtttcc tgatgtggat 600
tatgtcaact ctacagaggc tgaaaccatc ctggacaaca tcacccagtc tacccagtcc 660
ttcaatgact ttaccagggt ggtgggaggg gaggatgcta agccaggaca gttcccctgg 720
caggtggtcc tgaatggcaa agtggatgct ttttgtgggg gctccattgt gaatgagaag 780
tggattgtca cagctgctca ctgtgtggaa actggggtca agatcacagt ggtggctgga 840
gagcacaaca ttgaggaaac tgaacataca gagcagaaaa ggaatgtgat cagaatcatc 900
ccccaccata actacaatgc tgctatcaac aagtataatc atgacattgc cctgctggaa 960
ctggatgagc ctctggtgct gaacagctat gtcaccccaa tctgcattgc tgacaaggag 1020
tataccaata tcttcctgaa atttgggtct ggatatgtgt ctgggtgggg aagggtcttc 1080
cacaagggaa ggtctgctct ggtgctgcag tatctgaggg tgcccctggt ggacagagct 1140
acctgcctgc tgagcaccaa gttcaccatc tacaacaata tgttctgtgc tggatttcat 1200
gagggaggga gggactcctg tcagggagat tctggaggcc ctcatgtgac agaggtggaa 1260
ggcaccagct tcctgactgg catcatctct tgggggggagg aatgtgctat gaaggggaaa 1320
tatggaatct ataccaaggt gtccagatat gtcaactgga tcaaggagaa aaccaagctg 1380
acctga 1386

<210> SEQ ID NO 11
<211> LENGTH: 4404
<212> TYPE: DNA
<213> ORGANISM: Artificial Sequence
<220> FEATURE:
<223> OTHER INFORMATION: recombinant fVIII

<400> SEQUENCE: 11
atgcagctgg aactgtctac ctgtgtgttt ctgtgtctgc tgcctctggg gttttctgct 60
atcaggagat actatctggg agctgtggag ctgtcctggg actacaggca gtctgagctg 120
ctgagagaac tgcatgtgga taccagattc ccagctacag ctccaggagc tctgcctctg 180
ggcccatctg tgctgtacaa gaaaacagtc tttgtggagt ttacagacca gctgttctct 240
gtggccaggc caagaccacc ttggatggga ctgctgggac caaccatcca ggctgaggtg 300
tatgatacag tggtggtgac cctgaaaaac atggcctccc atcctgtgag cctgcatgct 360
gtgggggtgt ccttctggaa gtcctctgag ggagctgagt atgaagacca tacctcccag 420
agggagaaag aagatgataa ggtgctgcct ggcaaaagcc agacctatgt ctggcaggtg 480
ctgaaggaga atggaccaac tgcttctgac ccaccatgcc tgacctactc ttatctgtcc 540
catgtggatc tggtgaagga cctgaattct ggactgattg gagctctgct ggtgtgtaga 600
gagggaagcc tgaccagaga aagaacccag aacctgcatg agtttgtcct gctgtttgct 660

-continued

```
gtgtttgatg aagggaagag ctggcactct gccaggaatg actcctggac cagagctatg    720
gatccagctc ctgctagagc tcagcctgct atgcacacag tcaatggcta tgtgaatagg    780
tctctgccag gactgattgg ctgccataag aaatctgtct attggcatgt gattggaatg    840
ggcaccagcc ctgaggtgca ttctatcttc ctggaaggcc acacctttct ggtcaggcac    900
catagacagg cctctctgga gatctcccct ctgaccttcc tgacagctca gacctttctg    960
atggacctgg ggcagttcct gctgttttgc catatctctt cccaccatca tggaggaatg   1020
gaggctcatg tcagggtgga atcctgtgct gaggaaccac agctgagaag aaaggctgat   1080
gaggaagagg actatgatga taacctgtat gactctgata tggatgtggt gaggctggat   1140
ggggatgatg tcagcccttt catccagatc aggtctgtgg ccaagaaaca tccaaagacc   1200
tgggtccact acattgctgc tgaagaggaa gattgggact atgccccct ggtgctggct   1260
cctgatgata gatcctacaa aagccagtat ctgaacaatg ggccccagag gattggaagg   1320
aagtacaaga aagtgaggtt catggcctat acagatgaga cctttaagac cagagaggct   1380
atccagcatg aatctgggat cctgggacct ctgctgtatg gagaagtggg ggataccctg   1440
ctgatcatct tcaagaacca ggcctccagg ccatacaata tctatcccca tggcatcaca   1500
gatgtgagac cactgtacag caggagactg cccaaggggg tcaaacacct gaaggatttc   1560
cccatcctgc ctggagagat ctttaagtat aaatggacag tcacagtgga agatgggcct   1620
accaagtctg atccaaggtg cctgaccaga tactatagct cttttgtgaa catggagaga   1680
gacctggctt ctggactgat tggacccctg ctgatctgtt acaaagagtc tgtggaccag   1740
aggggcaacc agatcatgtc tgataagaga aatgtcatcc tgttctctgt gtttgatgag   1800
aacaggagct ggtacctgac agagaacatc cagaggttcc tgccaaatcc agctggagtg   1860
cagctggagg acccagaatt tcaggcttcc aacatcatgc atagcatcaa tggctatgtg   1920
tttgatagcc tgcagctgtc tgtctgcctg catgaggtgg cctactggta tatcctgtcc   1980
attggagctc agacagactt cctgtctgtg ttctttagtg ggtacacctt taagcataaa   2040
atggtgtatg aggataccct gaccctgttc cccttttctg ggagacagt gttcatgtcc   2100
atggaaaacc ctggcctgtg gatcctgggg tgccacaact ctgacttcag gaatagagga   2160
atgacagccc tgctgaaagt gtccagctgt gataagaata caggggatta ctatgaggac   2220
tcttatgaag atatctctgc ttatctgctg agcaagaaca atgccattga gcccaggtct   2280
tttgctcaga actccagacc tccatctgct tctgctccta agccacctgt gctgagaaga   2340
catcagaggg acatctccct gcctaccttc cagccagagg aagataaaat ggactatgat   2400
gatatcttca gcacagagac caagggggaa gattttgaca tctatggaga ggatgaaaac   2460
caggatccaa gatccttcca gaagagaacc agacactact ttattgctgc tgtggagcag   2520
ctgtgggact atgggatgtc tgaaagccca agggccctga ggaacagagc tcagaatgga   2580
gaggtgccca gattcaagaa agtggtgttc agagagtttg ctgatggcag ctttacccag   2640
ccatcttaca ggggggagct gaacaagcat ctggggctgc tgggacccta tatcagagct   2700
gaggtggaag ataacatcat ggtgaccttc aagaatcagg cttctaggcc ctactccttt   2760
tattcttccc tgatctccta ccctgatgat caggagcagg gagctgaacc taggcacaac   2820
tttgtgcagc caaatgagac cagaacctac ttttggaagg tgcagcatca catggctccc   2880
acagaggatg aatttgactg caaagcttgg gcctattttt ctgatgtgga cctggagaag   2940
gatgtgcatt ctggcctgat tgggcctctg ctgatctgta gggccaacac cctgaatgct   3000
```

```
gctcatggaa gacaggtcac agtgcaggag tttgctctgt tctttaccat ctttgatgaa   3060

accaagagct ggtacttcac agagaatgtg gaaaggaatt gcagagcccc ctgtcatctg   3120

cagatggagg accctaccct gaaggaaaac tacaggttcc atgccatcaa tggatatgtc   3180

atggataccc tgcctggcct ggtcatggct cagaaccaga ggatcagatg gtacctgctg   3240

tctatgggat ccaatgagaa tatccatagc atccacttct ctggccatgt cttttctgtg   3300

aggaagaaag aggaatacaa aatggctgtg tacaatctgt atcctggggt ctttgagaca   3360

gtggaaatgc tgccaagcaa agtgggaatc tggagaattg agtgcctgat tggggaacac   3420

ctgcaggctg ggatgagcac caccttcctg gtgtactcta agaaatgtca gaccccactg   3480

gggatggcct ctggacatat cagggacttc cagatcacag cttctggaca gtatggacag   3540

tgggctccaa agctggctag actgcactat tctggctcca tcaatgcctg gtctaccaaa   3600

gagccattct cctggatcaa ggtggacctg ctggccccca tgatcatcca tggaatcaaa   3660

acccagggag ctaggcagaa gttcagctct ctgtacatct cccagtttat catcatgtat   3720

agcctggatg ggaagaaatg gcagacctac agaggcaatt ccactgggac cctgatggtc   3780

ttctttggaa atgtggattc ctctggcatc aagcacaaca tcttcaatcc acccatcatt   3840

gccaggtaca tcaggctgca tcctacccac tatagcatca ggtctaccct gagaatggag   3900

ctgatgggat gtgacctgaa cagctgttct atgccactgg gcatggagtc caaggctatc   3960

tctgatgccc agatcacagc ttcttcctac ttcaccaata tgtttgctac ctggtcccca   4020

agcaaggcta gactgcacct gcagggaaga tccaatgctt ggagacccca ggtgaacaat   4080

cctaaggagt ggctgcaggt ggacttccag aaaaccatga aggtcacagg ggtgaccacc   4140

cagggagtga aatctctgct gacctccatg tatgtcaagg agttcctgat cagctcttcc   4200

caggatggcc accagtggac cctgttcttt cagaatggca aggtcaaagt gttccagggg   4260

aatcaggact cttttacccc agtggtgaac tccctggatc ctccactgct gaccaggtac   4320

ctgagaatcc atcctcagag ctgggtgcac cagattgctc tgagaatgga ggtcctggga   4380

tgtgaagctc aggacctgta ttga                                          4404
```

```
<210> SEQ ID NO 12
<211> LENGTH: 4404
<212> TYPE: DNA
<213> ORGANISM: Artificial Sequence
<220> FEATURE:
<223> OTHER INFORMATION: recombinant fVIII

<400> SEQUENCE: 12

atgcagctgg aactgtctac ctgtgtgttt ctgtgtctgc tgcctctggg gttttctgct     60

atccgccgct actatctggg agccgtggag ctgtcctggg actacaggca gagcgagctg    120

ctgagagaac tgcacgtgga taccagattc ccagctaccg ctccaggagc tctgcctctg    180

ggcccatccg tgctgtacaa gaaaaccgtc ttcgtggagt ttaccgacca gctgttcagc    240

gtggccaggc caagaccacc ttggatggga ctgctgggac caaccatcca ggctgaggtg    300

tacgataccg tggtcgtgac cctgaaaaac atggcctccc atcccgtgag cctgcacgct    360

gtcggggtgt ccttctggaa gtccagcgag ggagccgagt acgaagacca tacctcccag    420

cgcgagaaag aagacgataa ggtgctgcct ggcaaaagcc agacctatgt ctggcaggtg    480

ctgaaggaga acggaccaac cgctagcgac ccaccatgcc tgacctactc ttatctgtcc    540

cacgtcgatc tggtgaagga cctgaattcc ggactgatcg gagctctgct ggtgtgtaga    600

gagggaagcc tgaccagaga aagaacccag aacctgcatg agttcgtcct gctgttcgcc    660
```

-continued

```
gtgtttgacg aagggaagag ctggcactct gcccgcaatg actcctggac cagagctatg    720
gatccagctc ctgctagagc tcagcctgct atgcacaccg tcaacggcta cgtgaatcgg    780
tctctgccag gactgatcgg ctgccataag aaaagcgtct attggcacgt gatcggaatg    840
ggcaccagcc ccgaggtgca ttctatcttc ctggaaggcc acacctttct ggtcaggcac    900
catagacagg cctctctgga gatctcccct ctgaccttcc tgaccgctca gacctttctg    960
atggacctgg ggcagttcct gctgttttgc catatctctt cccaccatca cggaggaatg   1020
gaggctcacg tcagggtgga atcctgtgct gaggaaccac agctgagaag aaaggctgat   1080
gaggaagagg actacgacga taacctgtat gacagcgata tggacgtcgt gcgcctggac   1140
ggcgacgatg tcagcccttt catccagatc cggtctgtgg ccaagaaaca tccaaagacc   1200
tgggtccact acatcgccgc tgaagaggaa gattgggact atgcccccct ggtgctggct   1260
cctgacgata gatcctacaa aagccagtat ctgaacaatg ggccccagcg catcggacgg   1320
aagtacaaga aagtgaggtt catggcctat accgacgaga cctttaagac cagagaggct   1380
atccagcacg aatccgggat cctgggacct ctgctgtacg gcgaagtggg ggataccctg   1440
ctgatcatct tcaagaacca ggcctccagg ccatacaata tctatcccca tggcatcacc   1500
gacgtgagac cactgtacag caggagactg cccaaggggg tcaaacacct gaaggatttc   1560
cccatcctgc ctggagagat ctttaagtat aaatggaccg tcaccgtgga agacgggcct   1620
accaagtccg atccacgctg cctgacccgg tactatagct ctttcgtgaa catggagaga   1680
gacctggcta gcggactgat cggacccctg ctgatctgtt acaaagagag cgtggaccag   1740
aggggcaacc agatcatgtc tgataagaga aatgtcatcc tgttctccgt gtttgacgag   1800
aaccgcagct ggtacctgac cgagaacatc cagcggttcc tgccaaatcc agctggagtg   1860
cagctggagg acccagaatt tcaggcttcc aacatcatgc atagcatcaa tggctacgtg   1920
ttcgatagcc tgcagctgtc tgtctgcctg cacgaggtgg cctactggta tatcctgtcc   1980
atcggcgctc agaccgactt cctgtccgtg ttctttagcg ggtacacctt taagcataaa   2040
atggtgtatg aggataccct gaccctgttc cccttttctg gcgagaccgt gttcatgtcc   2100
atggaaaacc ctggcctgtg gatcctgggg tgccacaaca gcgacttcag gaatagagga   2160
atgaccgccc tgctgaaagt gtccagctgt gataagaata ccggcgatta ctatgaggac   2220
tcttacgaag atatctccgc ttatctgctg agcaagaaca atgccatcga gcccaggtct   2280
ttcgctcaga actccagacc tccaagcgct tctgctccta agccacctgt gctgagaaga   2340
catcagaggg acatctccct gcctaccttc cagccagagg aagataaaat ggactacgac   2400
gatatcttca gcaccgagac caagggggaa gattttgaca tctatggaga ggacgaaaac   2460
caggatccaa gatccttcca gaagagaacc agacactact ttatcgccgc tgtggagcag   2520
ctgtgggact atgggatgtc cgaaagccca cgggccctga ggaacagagc tcagaatgga   2580
gaggtgcccc gcttcaagaa agtcgtgttc cgggagtttg ccgacggcag ctttacccag   2640
ccatcttaca ggggggagct gaacaagcat ctggggctgc tgggacccta tatcagagcc   2700
gaggtcgaag ataacatcat ggtgaccttc aagaatcagg cttctcgccc ctactccttt   2760
tattcttccc tgatctccta ccctgacgat caggagcagg gcgccgaacc taggcacaac   2820
ttcgtgcagc caaatgagac cagaacctac ttttggaagg tgcagcatca catggctccc   2880
accgaggatg aattcgactg caaagcttgg gcctattttt ccgatgtcga cctggagaag   2940
gacgtgcata gcggcctgat cgggcctctg ctgatctgtc gcgccaacac cctgaatgct   3000
```

-continued

```
gctcacggaa gacaggtcac cgtgcaggag ttcgctctgt tctttaccat ctttgacgaa   3060

accaagagct ggtacttcac cgagaacgtg gaaaggaatt gcagagcccc ctgtcatctg   3120

cagatggagg accctaccct gaaggaaaac tacaggttcc acgccatcaa tggatatgtc   3180

atggataccc tgcccggcct ggtcatggct cagaaccagc gcatccggtg gtacctgctg   3240

tctatgggat ccaacgagaa tatccatagc atccacttct ctggccatgt cttttccgtg   3300

aggaagaaag aggaatacaa aatggccgtg tacaatctgt atcctggggt cttcgagacc   3360

gtggaaatgc tgccaagcaa agtgggaatc tggagaatcg agtgcctgat cggcgaacac   3420

ctgcaggccg ggatgagcac caccttcctg gtgtactcta agaaatgtca gaccccactg   3480

gggatggcct ccggacatat ccgcgacttc cagatcaccg ctagcggaca gtacggacag   3540

tgggctccaa agctggctag actgcactat tctggctcca tcaacgcctg gtctaccaaa   3600

gagccattct cctggatcaa ggtggacctg ctggccccca tgatcatcca cggaatcaaa   3660

acccagggcg ctaggcagaa gttcagctct ctgtacatct cccagtttat catcatgtat   3720

agcctggacg ggaagaaatg gcagacctac agaggcaatt ccaccgggac cctgatggtc   3780

ttctttggaa acgtggattc cagcggcatc aagcacaaca tcttcaatcc acccatcatc   3840

gcccgctaca tccggctgca tcctacccac tatagcatca ggtctaccct gagaatggag   3900

ctgatgggat gcgacctgaa cagctgttct atgccactgg gcatggagtc caaggctatc   3960

agcgatgccc agatcaccgc ttcttcctac ttcaccaata tgtttgctac ctggtcccca   4020

agcaaggcta gactgcacct gcagggaaga tccaacgctt ggagacccca ggtgaacaat   4080

cctaaggagt ggctgcaggt cgacttccag aaaaccatga aggtcaccgg ggtgaccacc   4140

cagggagtga aatctctgct gacctccatg tacgtcaagg agttcctgat cagctcttcc   4200

caggacggcc accagtggac cctgttcttt cagaacggca aggtcaaagt gttccagggg   4260

aatcaggact cttttacccc cgtcgtgaac tccctggatc ctccactgct gaccaggtac   4320

ctgagaatcc atcctcagag ctgggtgcac cagatcgctc tgagaatgga ggtcctggga   4380

tgcgaagctc aggacctgta ttga                                          4404
```

<210> SEQ ID NO 13
<211> LENGTH: 391
<212> TYPE: PRT
<213> ORGANISM: Artificial Sequence
<220> FEATURE:
<223> OTHER INFORMATION: recombinant promoter sequence

<400> SEQUENCE: 13

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110
```

-continued

```
His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg
385                 390
```

<210> SEQ ID NO 14
<211> LENGTH: 391
<212> TYPE: PRT
<213> ORGANISM: Artificial Sequence
<220> FEATURE:
<223> OTHER INFORMATION: recombinant promoter sequence

<400> SEQUENCE: 14

```
Met Gln Leu Glu Leu Ser Thr Cys Val Phe Leu Cys Leu Leu Pro Leu
1               5                   10                  15

Gly Phe Ser Ala Ile Arg Arg Tyr Tyr Leu Gly Ala Val Glu Leu Ser
            20                  25                  30

Trp Asp Tyr Arg Gln Ser Glu Leu Leu Arg Glu Leu His Val Asp Thr
        35                  40                  45

Arg Phe Pro Ala Thr Ala Pro Gly Ala Leu Pro Leu Gly Pro Ser Val
    50                  55                  60

Leu Tyr Lys Lys Thr Val Phe Val Glu Phe Thr Asp Gln Leu Phe Ser
65                  70                  75                  80
```

```
Val Ala Arg Pro Arg Pro Pro Trp Met Gly Leu Leu Gly Pro Thr Ile
                85                  90                  95

Gln Ala Glu Val Tyr Asp Thr Val Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala
    290                 295                 300

Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
            340                 345                 350

Pro Gln Leu Arg Arg Lys Ala Asp Glu Glu Glu Asp Tyr Asp Asp Asn
        355                 360                 365

Leu Tyr Asp Ser Asp Met Asp Val Val Arg Leu Asp Gly Asp Asp Val
    370                 375                 380

Ser Pro Phe Ile Gln Ile Arg
385                 390


<210> SEQ ID NO 15
<211> LENGTH: 371
<212> TYPE: PRT
<213> ORGANISM: Artificial Sequence
<220> FEATURE:
<223> OTHER INFORMATION: recombinant promoter sequence

<400> SEQUENCE: 15

Glu Ile Thr Arg Thr Thr Leu Gln Ser Asp Gln Glu Glu Ile Asp Tyr
1               5                   10                  15

Asp Asp Thr Ile Ser Val Glu Met Lys Lys Glu Asp Phe Asp Ile Tyr
            20                  25                  30

Asp Glu Asp Glu Asn Gln Ser Pro Arg Ser Phe Gln Lys Lys Thr Arg
        35                  40                  45
```

-continued

```
His Tyr Phe Ile Ala Ala Val Glu Arg Leu Trp Asp Tyr Gly Met Ser
    50                  55                  60

Ser Ser Pro His Val Leu Arg Asn Arg Ala Gln Ser Gly Ser Val Pro
65                  70                  75                  80

Gln Phe Lys Lys Val Val Phe Gln Glu Phe Thr Asp Gly Ser Phe Thr
                85                  90                  95

Gln Pro Leu Tyr Arg Gly Glu Leu Asn Glu His Leu Gly Leu Leu Gly
            100                 105                 110

Pro Tyr Ile Arg Ala Glu Val Glu Asp Asn Ile Met Val Thr Phe Arg
        115                 120                 125

Asn Gln Ala Ser Arg Pro Tyr Ser Phe Tyr Ser Ser Leu Ile Ser Tyr
    130                 135                 140

Glu Glu Asp Gln Arg Gln Gly Ala Glu Pro Arg Lys Asn Phe Val Lys
145                 150                 155                 160

Pro Asn Glu Thr Lys Thr Tyr Phe Trp Lys Val Gln His His Met Ala
                165                 170                 175

Pro Thr Lys Asp Glu Phe Asp Cys Lys Ala Trp Ala Tyr Phe Ser Asp
            180                 185                 190

Val Asp Leu Glu Lys Asp Val His Ser Gly Leu Ile Gly Pro Leu Leu
        195                 200                 205

Val Cys His Thr Asn Thr Leu Asn Pro Ala His Gly Arg Gln Val Thr
    210                 215                 220

Val Gln Glu Phe Ala Leu Phe Phe Thr Ile Phe Asp Glu Thr Lys Ser
225                 230                 235                 240

Trp Tyr Phe Thr Glu Asn Met Glu Arg Asn Cys Arg Ala Pro Cys Asn
                245                 250                 255

Ile Gln Met Glu Asp Pro Thr Phe Lys Glu Asn Tyr Arg Phe His Ala
            260                 265                 270

Ile Asn Gly Tyr Ile Met Asp Thr Leu Pro Gly Leu Val Met Ala Gln
        275                 280                 285

Asp Gln Arg Ile Arg Trp Tyr Leu Leu Ser Met Gly Ser Asn Glu Asn
    290                 295                 300

Ile His Ser Ile His Phe Ser Gly His Val Phe Thr Val Arg Lys Lys
305                 310                 315                 320

Glu Glu Tyr Lys Met Ala Leu Tyr Asn Leu Tyr Pro Gly Val Phe Glu
                325                 330                 335

Thr Val Glu Met Leu Pro Ser Lys Ala Gly Ile Trp Arg Val Glu Cys
            340                 345                 350

Leu Ile Gly Glu His Leu His Ala Gly Met Ser Thr Leu Phe Leu Val
        355                 360                 365

Tyr Ser Asn
    370
```

<210> SEQ ID NO 16
<211> LENGTH: 371
<212> TYPE: PRT
<213> ORGANISM: Artificial Sequence
<220> FEATURE:
<223> OTHER INFORMATION: recombinant promoter sequence

<400> SEQUENCE: 16

```
Asp Ile Ser Leu Pro Thr Phe Gln Pro Glu Glu Asp Lys Met Asp Tyr
1               5                   10                  15

Asp Asp Ile Phe Ser Thr Glu Thr Lys Gly Glu Asp Phe Asp Ile Tyr
            20                  25                  30
```

-continued

```
Gly Glu Asp Glu Asn Gln Asp Pro Arg Ser Phe Gln Lys Arg Thr Arg
        35                  40                  45

His Tyr Phe Ile Ala Ala Val Glu Gln Leu Trp Asp Tyr Gly Met Ser
    50                  55                  60

Glu Ser Pro Arg Ala Leu Arg Asn Arg Ala Gln Asn Gly Glu Val Pro
65                  70                  75                  80

Arg Phe Lys Lys Val Val Phe Arg Glu Phe Ala Asp Gly Ser Phe Thr
                85                  90                  95

Gln Pro Ser Tyr Arg Gly Glu Leu Asn Lys His Leu Gly Leu Leu Gly
            100                 105                 110

Pro Tyr Ile Arg Ala Glu Val Glu Asp Asn Ile Met Val Thr Phe Lys
        115                 120                 125

Asn Gln Ala Ser Arg Pro Tyr Ser Phe Tyr Ser Ser Leu Ile Ser Tyr
    130                 135                 140

Pro Asp Asp Gln Glu Gln Gly Ala Glu Pro Arg His Asn Phe Val Gln
145                 150                 155                 160

Pro Asn Glu Thr Arg Thr Tyr Phe Trp Lys Val Gln His His Met Ala
                165                 170                 175

Pro Thr Glu Asp Glu Phe Asp Cys Lys Ala Trp Ala Tyr Phe Ser Asp
            180                 185                 190

Val Asp Leu Glu Lys Asp Val His Ser Gly Leu Ile Gly Pro Leu Leu
        195                 200                 205

Ile Cys Arg Ala Asn Thr Leu Asn Ala Ala His Gly Arg Gln Val Thr
    210                 215                 220

Val Gln Glu Phe Ala Leu Phe Phe Thr Ile Phe Asp Glu Thr Lys Ser
225                 230                 235                 240

Trp Tyr Phe Thr Glu Asn Val Glu Arg Asn Cys Arg Ala Pro Cys His
                245                 250                 255

Leu Gln Met Glu Asp Pro Thr Leu Lys Glu Asn Tyr Arg Phe His Ala
            260                 265                 270

Ile Asn Gly Tyr Val Met Asp Thr Leu Pro Gly Leu Val Met Ala Gln
        275                 280                 285

Asn Gln Arg Ile Arg Trp Tyr Leu Leu Ser Met Gly Ser Asn Glu Asn
    290                 295                 300

Ile His Ser Ile His Phe Ser Gly His Val Phe Ser Val Arg Lys Lys
305                 310                 315                 320

Glu Glu Tyr Lys Met Ala Val Tyr Asn Leu Tyr Pro Gly Val Phe Glu
                325                 330                 335

Thr Val Glu Met Leu Pro Ser Lys Val Gly Ile Trp Arg Ile Glu Cys
            340                 345                 350

Leu Ile Gly Glu His Leu Gln Ala Gly Met Ser Thr Thr Phe Leu Val
        355                 360                 365

Tyr Ser Lys
    370


<210> SEQ ID NO 17
<211> LENGTH: 461
<212> TYPE: PRT
<213> ORGANISM: Artificial Sequence
<220> FEATURE:
<223> OTHER INFORMATION: recombinant fIX

<400> SEQUENCE: 17

Met Gln Arg Val Asn Met Ile Met Ala Glu Ser Pro Gly Leu Ile Thr
1               5                   10                  15
```

```
Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
```

```
        435                 440                 445

Arg Tyr Val Asn Trp Ile Lys Glu Lys Thr Lys Leu Thr
    450                 455                 460


<210> SEQ ID NO 18
<211> LENGTH: 461
<212> TYPE: PRT
<213> ORGANISM: Artificial Sequence
<220> FEATURE:
<223> OTHER INFORMATION: recombinant fIX

<400> SEQUENCE: 18

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
```

340 345 350

Val Ser Gly Trp Gly Arg Val Phe His Lys Gly Arg Ser Ala Leu Val
355 360 365

Leu Gln Tyr Leu Arg Val Pro Leu Val Asp Arg Ala Thr Cys Leu Leu
370 375 380

Ser Thr Lys Phe Thr Ile Tyr Asn Asn Met Phe Cys Ala Gly Phe His
385 390 395 400

Glu Gly Gly Arg Asp Ser Cys Gln Gly Asp Ser Gly Gly Pro His Val
405 410 415

Thr Glu Val Glu Gly Thr Ser Phe Leu Thr Gly Ile Ile Ser Trp Gly
420 425 430

Glu Glu Cys Ala Met Lys Gly Lys Tyr Gly Ile Tyr Thr Lys Val Ser
435 440 445

Arg Tyr Val Asn Trp Ile Lys Glu Lys Thr Lys Leu Thr
450 455 460

<210> SEQ ID NO 19
<211> LENGTH: 461
<212> TYPE: PRT
<213> ORGANISM: Artificial Sequence
<220> FEATURE:
<223> OTHER INFORMATION: recombinant fIX

<400> SEQUENCE: 19

Met Gln Arg Val Asn Met Ile Met Ala Glu Ser Pro Gly Leu Ile Thr
1 5 10 15

Ile Cys Leu Leu Gly Tyr Leu Leu Ser Ala Glu Cys Thr Val Phe Leu
20 25 30

Asp His Glu Asn Ala Asn Lys Ile Leu Asn Arg Pro Lys Arg Tyr Asn
35 40 45

Ser Gly Lys Leu Glu Glu Phe Val Gln Gly Asn Leu Glu Arg Glu Cys
50 55 60

Met Glu Glu Lys Cys Ser Phe Glu Glu Ala Arg Glu Val Phe Glu Asn
65 70 75 80

Thr Glu Arg Thr Thr Glu Phe Trp Lys Gln Tyr Val Asp Gly Asp Gln
85 90 95

Cys Glu Ser Asn Pro Cys Leu Asn Gly Gly Ser Cys Lys Asp Asp Ile
100 105 110

Asn Ser Tyr Glu Cys Trp Cys Pro Phe Gly Phe Glu Gly Lys Asn Cys
115 120 125

Glu Leu Asp Val Thr Cys Asn Ile Lys Asn Gly Arg Cys Glu Gln Phe
130 135 140

Cys Lys Asn Ser Ala Asp Asn Lys Val Val Cys Ser Cys Thr Glu Gly
145 150 155 160

Tyr Arg Leu Ala Glu Asn Gln Lys Ser Cys Glu Pro Ala Val Pro Phe
165 170 175

Pro Cys Gly Arg Val Ser Val Ser Gln Thr Ser Lys Leu Thr Arg Ala
180 185 190

Glu Thr Val Phe Pro Asp Val Asp Tyr Val Asn Ser Thr Glu Ala Glu
195 200 205

Thr Ile Leu Asp Asn Ile Thr Gln Ser Thr Gln Ser Phe Asn Asp Phe
210 215 220

Thr Arg Val Val Gly Gly Glu Asp Ala Lys Pro Gly Gln Phe Pro Trp
225 230 235 240

Gln Val Val Leu Asn Gly Lys Val Asp Ala Phe Cys Gly Gly Ser Ile

```
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Leu
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460


<210> SEQ ID NO 20
<211> LENGTH: 39
<212> TYPE: DNA
<213> ORGANISM: Artificial Sequence
<220> FEATURE:
<223> OTHER INFORMATION: recombinant promoter sequence

<400> SEQUENCE: 20

tataaaaggc cagcagcagc ctgaccacat ctcatcctc                          39


<210> SEQ ID NO 21
<211> LENGTH: 38
<212> TYPE: DNA
<213> ORGANISM: Artificial Sequence
<220> FEATURE:
<223> OTHER INFORMATION: recombinant promoter sequence

<400> SEQUENCE: 21

gttaattttt gtggcccttg cgatgtttgc tctggtta                           38


<210> SEQ ID NO 22
<211> LENGTH: 14
<212> TYPE: PRT
<213> ORGANISM: Artificial Sequence
<220> FEATURE:
<223> OTHER INFORMATION: recombinant peptide linker

<400> SEQUENCE: 22

Ser Phe Ser Gln Asn Pro Pro Val Leu Lys Arg His Gln Arg
1               5                   10
```

<210> SEQ ID NO 23
<211> LENGTH: 24
<212> TYPE: PRT
<213> ORGANISM: Artificial Sequence
<220> FEATURE:
<223> OTHER INFORMATION: recombinant peptide linker

<400> SEQUENCE: 23

Ser Phe Ala Gln Asn Ser Arg Pro Pro Ser Ala Ser Ala Pro Lys Pro
1 5 10 15

Pro Val Leu Arg Arg His Gln Arg
20

<210> SEQ ID NO 24
<211> LENGTH: 4
<212> TYPE: PRT
<213> ORGANISM: Artificial Sequence
<220> FEATURE:
<223> OTHER INFORMATION: recombinant promoter sequence

<400> SEQUENCE: 24

Arg His Gln Arg
1

<210> SEQ ID NO 25
<211> LENGTH: 6
<212> TYPE: DNA
<213> ORGANISM: Artificial Sequence
<220> FEATURE:
<223> OTHER INFORMATION: recombinant promoter sequence

<400> SEQUENCE: 25 gttaat 6

<210> SEQ ID NO 26
<211> LENGTH: 5
<212> TYPE: DNA
<213> ORGANISM: Artificial Sequence
<220> FEATURE:
<223> OTHER INFORMATION: recombinant promoter sequence

<400> SEQUENCE: 26 tataa 5

<210> SEQ ID NO 27
<211> LENGTH: 5
<212> TYPE: DNA
<213> ORGANISM: Artificial Sequence
<220> FEATURE:
<223> OTHER INFORMATION: recombinant promoter sequence

<400> SEQUENCE: 27 gttaa 5

<210> SEQ ID NO 28
<211> LENGTH: 4
<212> TYPE: DNA
<213> ORGANISM: Artificial Sequence
<220> FEATURE:
<223> OTHER INFORMATION: recombinant promoter sequence

<400> SEQUENCE: 28 gtta 4

<210> SEQ ID NO 29
<211> LENGTH: 3

<212> TYPE: DNA
<213> ORGANISM: Artificial Sequence
<220> FEATURE:
<223> OTHER INFORMATION: recombinant promoter sequence

<400> SEQUENCE: 29 gtt 3

<210> SEQ ID NO 30
<211> LENGTH: 5
<212> TYPE: DNA
<213> ORGANISM: Artificial Sequence
<220> FEATURE:
<223> OTHER INFORMATION: recombinant promoter sequence

<400> SEQUENCE: 30 ttaat 5

<210> SEQ ID NO 31
<211> LENGTH: 4
<212> TYPE: DNA
<213> ORGANISM: Artificial Sequence
<220> FEATURE:
<223> OTHER INFORMATION: recombinant promoter sequence

<400> SEQUENCE: 31 ttaa 4

<210> SEQ ID NO 32
<211> LENGTH: 3
<212> TYPE: DNA
<213> ORGANISM: Artificial Sequence
<220> FEATURE:
<223> OTHER INFORMATION: recombinant promoter sequence

<400> SEQUENCE: 32 tta 3

<210> SEQ ID NO 33
<211> LENGTH: 3
<212> TYPE: DNA
<213> ORGANISM: Artificial Sequence
<220> FEATURE:
<223> OTHER INFORMATION: recombinant promoter sequence

<400> SEQUENCE: 33 aat 3

<210> SEQ ID NO 34
<211> LENGTH: 56
<212> TYPE: DNA
<213> ORGANISM: Artificial Sequence
<220> FEATURE:
<223> OTHER INFORMATION: recombinant promoter sequence

<400> SEQUENCE: 34
gttaattttt gtggcccttg cgatgtttgc tctggttaat aatctcagga caaaca 56

<210> SEQ ID NO 35
<211> LENGTH: 55
<212> TYPE: DNA
<213> ORGANISM: Artificial Sequence
<220> FEATURE:
<223> OTHER INFORMATION: recombinant promoter sequence

<400> SEQUENCE: 35
ttaatttttg tggcccttgc gatgtttgct ctggttaata atctcaggac aaaca 55

<210> SEQ ID NO 36
<211> LENGTH: 54
<212> TYPE: DNA
<213> ORGANISM: Artificial Sequence
<220> FEATURE:
<223> OTHER INFORMATION: recombinant promoter sequence

<400> SEQUENCE: 36
taatttttgt ggcccttgcg atgtttgctc tggttaataa tctcaggaca aaca 54

<210> SEQ ID NO 37
<211> LENGTH: 53
<212> TYPE: DNA
<213> ORGANISM: Artificial Sequence
<220> FEATURE:
<223> OTHER INFORMATION: recombinant promoter sequence

<400> SEQUENCE: 37
aatttttgtg gcccttgcga tgtttgctct ggttaataat ctcaggacaa aca 53

<210> SEQ ID NO 38
<211> LENGTH: 52
<212> TYPE: DNA
<213> ORGANISM: Artificial Sequence
<220> FEATURE:
<223> OTHER INFORMATION: recombinant promoter sequence

<400> SEQUENCE: 38
atttttgtgg cccttgcgat gtttgctctg gttaataatc tcaggacaaa ca 52

<210> SEQ ID NO 39
<211> LENGTH: 51
<212> TYPE: DNA
<213> ORGANISM: Artificial Sequence
<220> FEATURE:
<223> OTHER INFORMATION: recombinant promoter sequence

<400> SEQUENCE: 39
tttttgtggc ccttgcgatg tttgctctgg ttaataatct caggacaaac a 51

<210> SEQ ID NO 40
<211> LENGTH: 50
<212> TYPE: DNA
<213> ORGANISM: Artificial Sequence
<220> FEATURE:
<223> OTHER INFORMATION: recombinant promoter sequence

<400> SEQUENCE: 40
ttttgtggcc cttgcgatgt ttgctctggt taataatctc aggacaaaca 50

<210> SEQ ID NO 41
<211> LENGTH: 49
<212> TYPE: DNA
<213> ORGANISM: Artificial Sequence
<220> FEATURE:
<223> OTHER INFORMATION: recombinant promoter sequence

<400> SEQUENCE: 41
tttgtggccc ttgcgatgtt tgctctggtt aataatctca ggacaaaca 49

<210> SEQ ID NO 42
<211> LENGTH: 48
<212> TYPE: DNA
<213> ORGANISM: Artificial Sequence
<220> FEATURE:
<223> OTHER INFORMATION: recombinant promoter sequence

<400> SEQUENCE: 42
ttgtggccct tgcgatgttt gctctggtta ataatctcag gacaaaca 48

<210> SEQ ID NO 43
<211> LENGTH: 18
<212> TYPE: DNA
<213> ORGANISM: Artificial Sequence
<220> FEATURE:
<223> OTHER INFORMATION: recombinant promoter sequence

<400> SEQUENCE: 43
ataatctcag gacaaaca 18

<210> SEQ ID NO 44
<211> LENGTH: 47
<212> TYPE: DNA
<213> ORGANISM: Artificial Sequence
<220> FEATURE:
<223> OTHER INFORMATION: recombinant promoter sequence

<400> SEQUENCE: 44
tgtggccctt gcgatgtttg ctctggttaa taatctcagg acaaaca 47

<210> SEQ ID NO 45
<211> LENGTH: 46
<212> TYPE: DNA
<213> ORGANISM: Artificial Sequence
<220> FEATURE:
<223> OTHER INFORMATION: recombinant promoter sequence

<400> SEQUENCE: 45
gtggcccttg cgatgtttgc tctggttaat aatctcagga caaaca 46

<210> SEQ ID NO 46
<211> LENGTH: 45
<212> TYPE: DNA
<213> ORGANISM: Artificial Sequence
<220> FEATURE:
<223> OTHER INFORMATION: recombinant promoter sequence

<400> SEQUENCE: 46
tggcccttgc gatgtttgct ctggttaata atctcaggac aaaca 45

<210> SEQ ID NO 47
<211> LENGTH: 43
<212> TYPE: DNA
<213> ORGANISM: Artificial Sequence
<220> FEATURE:
<223> OTHER INFORMATION: recombinant promoter sequence

<400> SEQUENCE: 47
gcccttgcga tgtttgctct ggttaataat ctcaggacaa aca 43

<210> SEQ ID NO 48
<211> LENGTH: 42
<212> TYPE: DNA
<213> ORGANISM: Artificial Sequence
<220> FEATURE:
<223> OTHER INFORMATION: recombinant promoter sequence

<400> SEQUENCE: 48
cccttgcgat gtttgctctg gttaataatc tcaggacaaa ca 42

<210> SEQ ID NO 49
<211> LENGTH: 41
<212> TYPE: DNA
<213> ORGANISM: Artificial Sequence
<220> FEATURE:
<223> OTHER INFORMATION: recombinant promoter sequence

<400> SEQUENCE: 49
ccttgcgatg tttgctctgg ttaataatct caggacaaac a 41

<210> SEQ ID NO 50
<211> LENGTH: 40
<212> TYPE: DNA
<213> ORGANISM: Artificial Sequence
<220> FEATURE:
<223> OTHER INFORMATION: recombinant promoter sequence

<400> SEQUENCE: 50
cttgcgatgt ttgctctggt taataatctc aggacaaaca 40

<210> SEQ ID NO 51
<211> LENGTH: 55
<212> TYPE: DNA
<213> ORGANISM: Artificial Sequence
<220> FEATURE:
<223> OTHER INFORMATION: recombinant promoter sequence

<400> SEQUENCE: 51
gttaattttt gtggcccttg cgatgtttgc tctggttaat aatctcagga caaac 55

<210> SEQ ID NO 52
<211> LENGTH: 54
<212> TYPE: DNA
<213> ORGANISM: Artificial Sequence
<220> FEATURE:
<223> OTHER INFORMATION: recombinant promoter sequence

<400> SEQUENCE: 52
gttaattttt gtggcccttg cgatgtttgc tctggttaat aatctcagga caaa 54

<210> SEQ ID NO 53
<211> LENGTH: 53
<212> TYPE: DNA
<213> ORGANISM: Artificial Sequence
<220> FEATURE:
<223> OTHER INFORMATION: recombinant promoter sequence

<400> SEQUENCE: 53
gttaattttt gtggcccttg cgatgtttgc tctggttaat aatctcagga caa 53

<210> SEQ ID NO 54
<211> LENGTH: 53
<212> TYPE: DNA
<213> ORGANISM: Artificial Sequence
<220> FEATURE:
<223> OTHER INFORMATION: recombinant promoter sequence

<400> SEQUENCE: 54
gttaattttt gtggcccttg cgatgtttgc tctggttaat aatctcagga caa 53

<210> SEQ ID NO 55
<211> LENGTH: 52
<212> TYPE: DNA
<213> ORGANISM: Artificial Sequence
<220> FEATURE:
<223> OTHER INFORMATION: recombinant promoter sequence -continued

<400> SEQUENCE: 55
gttaattttt gtggcccttg cgatgtttgc tctggttaat aatctcagga ca    52

<210> SEQ ID NO 56
<211> LENGTH: 51
<212> TYPE: DNA
<213> ORGANISM: Artificial Sequence
<220> FEATURE:
<223> OTHER INFORMATION: recombinant promoter sequence

<400> SEQUENCE: 56
gttaattttt gtggcccttg cgatgtttgc tctggttaat aatctcagga c    51

<210> SEQ ID NO 57
<211> LENGTH: 50
<212> TYPE: DNA
<213> ORGANISM: Artificial Sequence
<220> FEATURE:
<223> OTHER INFORMATION: recombinant promoter sequence

<400> SEQUENCE: 57
gttaattttt gtggcccttg cgatgtttgc tctggttaat aatctcagga    50

<210> SEQ ID NO 58
<211> LENGTH: 49
<212> TYPE: DNA
<213> ORGANISM: Artificial Sequence
<220> FEATURE:
<223> OTHER INFORMATION: recombinant promoter sequence

<400> SEQUENCE: 58
gttaattttt gtggcccttg cgatgtttgc tctggttaat aatctcagg    49

<210> SEQ ID NO 59
<211> LENGTH: 48
<212> TYPE: DNA
<213> ORGANISM: Artificial Sequence
<220> FEATURE:
<223> OTHER INFORMATION: recombinant promoter sequence

<400> SEQUENCE: 59
gttaattttt gtggcccttg cgatgtttgc tctggttaat aatctcag    48

<210> SEQ ID NO 60
<211> LENGTH: 47
<212> TYPE: DNA
<213> ORGANISM: Artificial Sequence
<220> FEATURE:
<223> OTHER INFORMATION: recombinant promoter sequence

<400> SEQUENCE: 60
gttaattttt gtggcccttg cgatgtttgc tctggttaat aatctca    47

<210> SEQ ID NO 61
<211> LENGTH: 46
<212> TYPE: DNA
<213> ORGANISM: Artificial Sequence
<220> FEATURE:
<223> OTHER INFORMATION: recombinant promoter sequence

<400> SEQUENCE: 61
gttaattttt gtggcccttg cgatgtttgc tctggttaat aatctc    46

<210> SEQ ID NO 62

<211> LENGTH: 45
<212> TYPE: DNA
<213> ORGANISM: Artificial Sequence
<220> FEATURE:
<223> OTHER INFORMATION: recombinant promoter sequence

<400> SEQUENCE: 62
gttaattttt gtggcccttg cgatgtttgc tctggttaat aatct 45

<210> SEQ ID NO 63
<211> LENGTH: 44
<212> TYPE: DNA
<213> ORGANISM: Artificial Sequence
<220> FEATURE:
<223> OTHER INFORMATION: recombinant promoter sequence

<400> SEQUENCE: 63
gttaattttt gtggcccttg cgatgtttgc tctggttaat aatc 44

<210> SEQ ID NO 64
<211> LENGTH: 43
<212> TYPE: DNA
<213> ORGANISM: Artificial Sequence
<220> FEATURE:
<223> OTHER INFORMATION: recombinant promoter sequence

<400> SEQUENCE: 64
gttaattttt gtggcccttg cgatgtttgc tctggttaat aat 43

<210> SEQ ID NO 65
<211> LENGTH: 42
<212> TYPE: DNA
<213> ORGANISM: Artificial Sequence
<220> FEATURE:
<223> OTHER INFORMATION: recombinant promoter sequence

<400> SEQUENCE: 65
gttaattttt gtggcccttg cgatgtttgc tctggttaat aa 42

<210> SEQ ID NO 66
<211> LENGTH: 55
<212> TYPE: DNA
<213> ORGANISM: Artificial Sequence
<220> FEATURE:
<223> OTHER INFORMATION: recombinant promoter sequence

<400> SEQUENCE: 66
gttaattttt gtggcccttg cgatgtttgc tctggttaat aatctcagga caaac 55

<210> SEQ ID NO 67
<211> LENGTH: 53
<212> TYPE: DNA
<213> ORGANISM: Artificial Sequence
<220> FEATURE:
<223> OTHER INFORMATION: recombinant promoter sequence

<400> SEQUENCE: 67
ttaatttttg tggcccttgc gatgtttgct ctggttaata atctcaggac aaa 53

<210> SEQ ID NO 68
<211> LENGTH: 51
<212> TYPE: DNA
<213> ORGANISM: Artificial Sequence
<220> FEATURE:
<223> OTHER INFORMATION: recombinant promoter sequence

<400> SEQUENCE: 68
taatttttgt ggcccttgcg atgtttgctc tggttaataa tctcaggaca a 51

<210> SEQ ID NO 69
<211> LENGTH: 49
<212> TYPE: DNA
<213> ORGANISM: Artificial Sequence
<220> FEATURE:
<223> OTHER INFORMATION: recombinant promoter sequence

<400> SEQUENCE: 69
aatttttgtg gcccttgcga tgtttgctct ggttaataat ctcaggaca 49

<210> SEQ ID NO 70
<211> LENGTH: 47
<212> TYPE: DNA
<213> ORGANISM: Artificial Sequence
<220> FEATURE:
<223> OTHER INFORMATION: recombinant promoter sequence

<400> SEQUENCE: 70
atttttgtgg cccttgcgat gtttgctctg gttaataatc tcaggac 47

<210> SEQ ID NO 71
<211> LENGTH: 45
<212> TYPE: DNA
<213> ORGANISM: Artificial Sequence
<220> FEATURE:
<223> OTHER INFORMATION: recombinant promoter sequence

<400> SEQUENCE: 71
tttttgtggc ccttgcgatg tttgctctgg ttaataatct cagga 45

<210> SEQ ID NO 72
<211> LENGTH: 43
<212> TYPE: DNA
<213> ORGANISM: Artificial Sequence
<220> FEATURE:
<223> OTHER INFORMATION: recombinant promoter sequence

<400> SEQUENCE: 72
ttttgtggcc cttgcgatgt ttgctctggt taataatctc agg 43

<210> SEQ ID NO 73
<211> LENGTH: 41
<212> TYPE: DNA
<213> ORGANISM: Artificial Sequence
<220> FEATURE:
<223> OTHER INFORMATION: recombinant promoter sequence

<400> SEQUENCE: 73
tttgtggccc ttgcgatgtt tgctctggtt aataatctca g 41

<210> SEQ ID NO 74
<211> LENGTH: 39
<212> TYPE: DNA
<213> ORGANISM: Artificial Sequence
<220> FEATURE:
<223> OTHER INFORMATION: recombinant promoter sequence

<400> SEQUENCE: 74
ttgtggccct tgcgatgttt gctctggtta ataatctca 39

<210> SEQ ID NO 75
<211> LENGTH: 37
<212> TYPE: DNA

<213> ORGANISM: Artificial Sequence
<220> FEATURE:
<223> OTHER INFORMATION: recombinant promoter sequence

<400> SEQUENCE: 75
tgtggccctt gcgatgtttg ctctggttaa taatctc 37

<210> SEQ ID NO 76
<211> LENGTH: 35
<212> TYPE: DNA
<213> ORGANISM: Artificial Sequence
<220> FEATURE:
<223> OTHER INFORMATION: recombinant promoter sequence

<400> SEQUENCE: 76
gtggcccttg cgatgtttgc tctggttaat aatct 35

<210> SEQ ID NO 77
<211> LENGTH: 33
<212> TYPE: DNA
<213> ORGANISM: Artificial Sequence
<220> FEATURE:
<223> OTHER INFORMATION: recombinant promoter sequence

<400> SEQUENCE: 77
tggcccttgc gatgtttgct ctggttaata atc 33

<210> SEQ ID NO 78
<211> LENGTH: 30
<212> TYPE: DNA
<213> ORGANISM: Artificial Sequence
<220> FEATURE:
<223> OTHER INFORMATION: recombinant promoter sequence

<400> SEQUENCE: 78
gcccttgcga tgtttgctct ggttaataat 30

<210> SEQ ID NO 79
<211> LENGTH: 28
<212> TYPE: DNA
<213> ORGANISM: Artificial Sequence
<220> FEATURE:
<223> OTHER INFORMATION: recombinant promoter sequence

<400> SEQUENCE: 79
cccttgcgat gtttgctctg gttaataa 28

<210> SEQ ID NO 80
<211> LENGTH: 26
<212> TYPE: DNA
<213> ORGANISM: Artificial Sequence
<220> FEATURE:
<223> OTHER INFORMATION: recombinant promoter sequence

<400> SEQUENCE: 80
ccttgcgatg tttgctctgg ttaata 26

<210> SEQ ID NO 81
<211> LENGTH: 24
<212> TYPE: DNA
<213> ORGANISM: Artificial Sequence
<220> FEATURE:
<223> OTHER INFORMATION: recombinant promoter sequence

<400> SEQUENCE: 81
cttgcgatgt ttgctctggt taat 24

<210> SEQ ID NO 82
<211> LENGTH: 54
<212> TYPE: DNA
<213> ORGANISM: Artificial Sequence
<220> FEATURE:
<223> OTHER INFORMATION: recombinant promoter sequence

<400> SEQUENCE: 82
ttaatttttg tggcccttgc gatgtttgct ctggttaata atctcaggac aaac 54

<210> SEQ ID NO 83
<211> LENGTH: 52
<212> TYPE: DNA
<213> ORGANISM: Artificial Sequence
<220> FEATURE:
<223> OTHER INFORMATION: recombinant promoter sequence

<400> SEQUENCE: 83
taatttttgt ggcccttgcg atgtttgctc tggttaataa tctcaggaca aa 52

<210> SEQ ID NO 84
<211> LENGTH: 50
<212> TYPE: DNA
<213> ORGANISM: Artificial Sequence
<220> FEATURE:
<223> OTHER INFORMATION: recombinant promoter sequence

<400> SEQUENCE: 84
aatttttgtg gcccttgcga tgtttgctct ggttaataat ctcaggacaa 50

<210> SEQ ID NO 85
<211> LENGTH: 49
<212> TYPE: DNA
<213> ORGANISM: Artificial Sequence
<220> FEATURE:
<223> OTHER INFORMATION: recombinant promoter sequence

<400> SEQUENCE: 85
atttttgtgg cccttgcgat gtttgctctg gttaataatc tcaggacaa 49

<210> SEQ ID NO 86
<211> LENGTH: 47
<212> TYPE: DNA
<213> ORGANISM: Artificial Sequence
<220> FEATURE:
<223> OTHER INFORMATION: recombinant promoter sequence

<400> SEQUENCE: 86
tttttgtggc ccttgcgatg tttgctctgg ttaataatct caggaca 47

<210> SEQ ID NO 87
<211> LENGTH: 45
<212> TYPE: DNA
<213> ORGANISM: Artificial Sequence
<220> FEATURE:
<223> OTHER INFORMATION: recombinant promoter sequence

<400> SEQUENCE: 87
ttttgtggcc cttgcgatgt ttgctctggt taataatctc aggac 45

<210> SEQ ID NO 88
<211> LENGTH: 43
<212> TYPE: DNA
<213> ORGANISM: Artificial Sequence
<220> FEATURE:

<223> OTHER INFORMATION: recombinant promoter sequence

<400> SEQUENCE: 88
tttgtggccc ttgcgatgtt tgctctggtt aataatctca gga 43

<210> SEQ ID NO 89
<211> LENGTH: 41
<212> TYPE: DNA
<213> ORGANISM: Artificial Sequence
<220> FEATURE:
<223> OTHER INFORMATION: recombinant promoter sequence

<400> SEQUENCE: 89
ttgtggccct tgcgatgttt gctctggtta ataatctcag g 41

<210> SEQ ID NO 90
<211> LENGTH: 39
<212> TYPE: DNA
<213> ORGANISM: Artificial Sequence
<220> FEATURE:
<223> OTHER INFORMATION: recombinant promoter sequence

<400> SEQUENCE: 90
tgtggccctt gcgatgtttg ctctggttaa taatctcag 39

<210> SEQ ID NO 91
<211> LENGTH: 36
<212> TYPE: DNA
<213> ORGANISM: Artificial Sequence
<220> FEATURE:
<223> OTHER INFORMATION: recombinant promoter sequence

<400> SEQUENCE: 91
tggcccttgc gatgtttgct ctggttaata atctca 36

<210> SEQ ID NO 92
<211> LENGTH: 34
<212> TYPE: DNA
<213> ORGANISM: Artificial Sequence
<220> FEATURE:
<223> OTHER INFORMATION: recombinant promoter sequence

<400> SEQUENCE: 92
ggcccttgcg atgtttgctc tggttaataa tctc 34

<210> SEQ ID NO 93
<211> LENGTH: 32
<212> TYPE: DNA
<213> ORGANISM: Artificial Sequence
<220> FEATURE:
<223> OTHER INFORMATION: recombinant promoter sequence

<400> SEQUENCE: 93
gcccttgcga tgtttgctct ggttaataat ct 32

<210> SEQ ID NO 94
<211> LENGTH: 30
<212> TYPE: DNA
<213> ORGANISM: Artificial Sequence
<220> FEATURE:
<223> OTHER INFORMATION: recombinant promoter sequence

<400> SEQUENCE: 94
cccttgcgat gtttgctctg gttaataatc 30

<210> SEQ ID NO 95
<211> LENGTH: 28
<212> TYPE: DNA
<213> ORGANISM: Artificial Sequence
<220> FEATURE:
<223> OTHER INFORMATION: recombinant promoter sequence

<400> SEQUENCE: 95
ccttgcgatg tttgctctgg ttaataat 28

<210> SEQ ID NO 96
<211> LENGTH: 26
<212> TYPE: DNA
<213> ORGANISM: Artificial Sequence
<220> FEATURE:
<223> OTHER INFORMATION: recombinant promoter sequence

<400> SEQUENCE: 96
cttgcgatgt ttgctctggt taataa 26

<210> SEQ ID NO 97
<211> LENGTH: 17
<212> TYPE: DNA
<213> ORGANISM: Artificial Sequence
<220> FEATURE:
<223> OTHER INFORMATION: recombinant promoter sequence

<400> SEQUENCE: 97
cggaggagca aacaggg 17

<210> SEQ ID NO 98
<211> LENGTH: 28
<212> TYPE: DNA
<213> ORGANISM: Artificial Sequence
<220> FEATURE:
<223> OTHER INFORMATION: recombinant promoter sequence

<400> SEQUENCE: 98
cggaggagca aacaggggct aagtccac 28

<210> SEQ ID NO 99
<211> LENGTH: 27
<212> TYPE: DNA
<213> ORGANISM: Artificial Sequence
<220> FEATURE:
<223> OTHER INFORMATION: recombinant promoter sequence

<400> SEQUENCE: 99
ggctgctggt gaatattaac caaggtc 27

<210> SEQ ID NO 100
<211> LENGTH: 71
<212> TYPE: DNA
<213> ORGANISM: Artificial Sequence
<220> FEATURE:
<223> OTHER INFORMATION: recombinant promoter sequence

<400> SEQUENCE: 100
ggggaggctg ctggtgaata ttaaccaagg tcaccccagt tatcggagga gcaaacaggg 60
gctaagtcca c 71

<210> SEQ ID NO 101
<211> LENGTH: 71
<212> TYPE: DNA
<213> ORGANISM: Artificial Sequence
<220> FEATURE:

<223> OTHER INFORMATION: recombinant promoter sequence

<400> SEQUENCE: 101
ggggaggctg ctggtgaata ttaaccaagg tcaccccagt tatcggagga gcaaacaggg 60
actaagtcca c 71

<210> SEQ ID NO 102
<211> LENGTH: 220
<212> TYPE: DNA
<213> ORGANISM: Artificial Sequence
<220> FEATURE:
<223> OTHER INFORMATION: recombinant promoter sequence

<400> SEQUENCE: 102
ggggaggctg ctggtgaata ttaaccaagg tcaccccagt tatcggagga gcaaacaggg 60
gctaagtcca ctaggttaat cattaagtcg ttaatttttg tggcccttgc gatgtttgct 120
ctggttaata atctcaggac aaacagaggt taataatttt ccagatctct ctgagcaata 180
gtataaaagg ccagcagcag cctgaccaca tctcatcctc 220

<210> SEQ ID NO 103
<211> LENGTH: 171
<212> TYPE: DNA
<213> ORGANISM: Artificial Sequence
<220> FEATURE:
<223> OTHER INFORMATION: recombinant promoter sequence

<400> SEQUENCE: 103
cggaggagca aacaggggct aagtcgttaa tcattaagtc gttaattttt gtggcccttg 60
cgatgtttgc tctggttaat aatctcagga caaacagagg ttaataattt tccagatctc 120
tctgagcaat agtataaaag gccagcagca gcctgaccac atctcatcct c 171

<210> SEQ ID NO 104
<211> LENGTH: 173
<212> TYPE: DNA
<213> ORGANISM: Artificial Sequence
<220> FEATURE:
<223> OTHER INFORMATION: recombinant promoter sequence

<400> SEQUENCE: 104
ggctgctggt gaatattaac caaggtcgtt aatcattaag tcgttaattt ttgtggccct 60
tgcgatgttt gctctggtta ataatctcag gacaaacaga ggttaataat tttccagatc 120
tctctgagca atagtataaa aggccagcag cagcctgacc acatctcatc ctc 173

<210> SEQ ID NO 105
<211> LENGTH: 146
<212> TYPE: DNA
<213> ORGANISM: Artificial Sequence
<220> FEATURE:
<223> OTHER INFORMATION: recombinant promoter sequence

<400> SEQUENCE: 105
ggggaggctg ctggtgaata ttaaccaagg tcaccccagt tatcggagga gcaaacaggg 60
gctaagtcca cgaggttaat aattttccag atctctctga gcaatagtat aaaaggccag 120
cagcagcctg accacatctc atcctc 146

<210> SEQ ID NO 106
<211> LENGTH: 129
<212> TYPE: DNA
<213> ORGANISM: Artificial Sequence
<220> FEATURE:
<223> OTHER INFORMATION: recombinant promoter sequence

<400> SEQUENCE: 106
ggctgctggt gaatattaac caaggtcatc ggaggagcaa acagggacta agtcgaggtt 60
aataattttc cagatctctc tgagcaatag tataaaaggc cagcagcagc ctgaccacat 120
ctcatcctc 129

<210> SEQ ID NO 107
<211> LENGTH: 142
<212> TYPE: DNA
<213> ORGANISM: Artificial Sequence
<220> FEATURE:
<223> OTHER INFORMATION: recombinant promoter sequence

<400> SEQUENCE: 107
ggctgctggt gaatattaac caaggtcccc ttgctggtta ataatctcag ttaatttgtt 60
tgcacaaaca cggaggagca aacaggggag gttaataatt ttctataaaa ggccagcagc 120
agcctgacca catctcatcc tc 142

<210> SEQ ID NO 108
<211> LENGTH: 146
<212> TYPE: DNA
<213> ORGANISM: Artificial Sequence
<220> FEATURE:
<223> OTHER INFORMATION: recombinant promoter sequence

<400> SEQUENCE: 108
ggggaggctg ctggtgaata ttaaccaagg tcaccccagt tatcggagga gcaaacaggg 60
actaagtcca cgaggttaat aattttccag atctctctga gcaatagtat aaaaggccag 120
cagcagcctg accacatctc atcctc 146

<210> SEQ ID NO 109
<211> LENGTH: 8
<212> TYPE: DNA
<213> ORGANISM: Artificial Sequence
<220> FEATURE:
<223> OTHER INFORMATION: recombinant promoter sequence

<400> SEQUENCE: 109 tcatcctc 8

<210> SEQ ID NO 110
<211> LENGTH: 24
<212> TYPE: DNA
<213> ORGANISM: Artificial Sequence
<220> FEATURE:
<223> OTHER INFORMATION: recombinant promoter sequence

<400> SEQUENCE: 110
ggccagcagc agcctgacca catc 24

<210> SEQ ID NO 111
<211> LENGTH: 71
<212> TYPE: DNA
<213> ORGANISM: Artificial Sequence
<220> FEATURE:
<223> OTHER INFORMATION: recombinant promoter sequence

<400> SEQUENCE: 111
ggggaggctg ctggtgaata ttaaccaagg tcaccccagt tatcggagga gcaaacaggg 60
gctaagtcca c 71

<210> SEQ ID NO 112
<211> LENGTH: 255
<212> TYPE: DNA
<213> ORGANISM: Artificial Sequence
<220> FEATURE:
<223> OTHER INFORMATION: recombinant promoter sequence

<400> SEQUENCE: 112
gttaatcatt aagtcgttaa tcattaactt aggtcaaagg tcagacaatg ttgactctcg 60
ttaatgatta accggaattg ttgacttgag gttaataatt ttccagatct ctctgagcaa 120
tagtataaaa ggccagcagc agcctgacca catctcatcc tcctctaagg taaatataaa 180
atttttaagt gtataatgtg ttaaactact gattctaatt gtttgtgtat tttagattcc 240
aacctatgga actga 255

<210> SEQ ID NO 113
<211> LENGTH: 94
<212> TYPE: DNA
<213> ORGANISM: Artificial Sequence
<220> FEATURE:
<223> OTHER INFORMATION: recombinant promoter sequence

<400> SEQUENCE: 113
gttaattttt aaaaagcagt caaaagtcca agtggccctt gcgagcattt actctctctg 60
tttgctctgg ttaataatct caggagcaca aaca 94

<210> SEQ ID NO 114
<211> LENGTH: 43
<212> TYPE: DNA
<213> ORGANISM: Artificial Sequence
<220> FEATURE:
<223> OTHER INFORMATION: recombinant promoter sequence

<400> SEQUENCE: 114
gaggttaata attttccaga tctctctgag caatagtata aaa 43

<210> SEQ ID NO 115
<211> LENGTH: 55
<212> TYPE: DNA
<213> ORGANISM: Artificial Sequence
<220> FEATURE:
<223> OTHER INFORMATION: recombinant promoter sequence

<400> SEQUENCE: 115
agtcatatgt ttgctcactg aaggttacta gttaacaggc atcccttaaa cagga 55

<210> SEQ ID NO 116
<211> LENGTH: 108
<212> TYPE: DNA
<213> ORGANISM: Artificial Sequence
<220> FEATURE:
<223> OTHER INFORMATION: recombinant promoter sequence

<400> SEQUENCE: 116
gttaatcatt aacttaaaaa gcagtcaaaa gtccaaaggt caaaggtcag agcatttact 60
ctctccaatg ttgactctcg ttaatgatta aggagcaatt gttgactt 108

<210> SEQ ID NO 117
<211> LENGTH: 72
<212> TYPE: DNA
<213> ORGANISM: Artificial Sequence
<220> FEATURE:
<223> OTHER INFORMATION: recombinant promoter sequence

<400> SEQUENCE: 117
gttaatcatt aacttaggtc aaaggtcaga caatgttgac tctcgttaat gattaaccgg 60
aattgttgac tt 72

<210> SEQ ID NO 118
<211> LENGTH: 151
<212> TYPE: DNA
<213> ORGANISM: Artificial Sequence
<220> FEATURE:
<223> OTHER INFORMATION: recombinant promoter sequence

<400> SEQUENCE: 118
gttaatcatt aacttaaaaa gcagtcaaaa gtccaaaggt caaaggtcag agcatttact 60
ctctccaatg ttgactctcg ttaatgatta aggagcaatt gttgacttga ggttaataat 120
tttccagatc tctctgagca atagtataaa a 151

<210> SEQ ID NO 119
<211> LENGTH: 115
<212> TYPE: DNA
<213> ORGANISM: Artificial Sequence
<220> FEATURE:
<223> OTHER INFORMATION: recombinant promoter sequence

<400> SEQUENCE: 119
gttaatcatt aacttaggtc aaaggtcaga caatgttgac tctcgttaat gattaaccgg 60
aattgttgac ttgaggttaa taattttcca gatctctctg agcaatagta taaaa 115

<210> SEQ ID NO 120
<211> LENGTH: 152
<212> TYPE: DNA
<213> ORGANISM: Artificial Sequence
<220> FEATURE:
<223> OTHER INFORMATION: recombinant promoter sequence

<400> SEQUENCE: 120
gttaatcatt aagtcgttaa tttttaaaaa gcagtcaaaa gtccaagtgg cccttgcgag 60
catttactct ctctgtttgc tctggttaat aatctcagga gcacaaacag aggttaataa 120
ttttccagat ctctctgagc aatagtataa aa 152

<210> SEQ ID NO 121
<211> LENGTH: 150
<212> TYPE: DNA
<213> ORGANISM: Artificial Sequence
<220> FEATURE:
<223> OTHER INFORMATION: recombinant promoter sequence

<400> SEQUENCE: 121
tgggcggagt gtcgttaatt tttaaaaagc agtcaaaagt ccaagtggcc cttgcgagca 60
tttactctct ctgtttgctc tggttaataa tctcaggagc acaaacagag gttaataatt 120
ttccagatct ctctgagcaa tagtataaaa 150

<210> SEQ ID NO 122
<211> LENGTH: 43
<212> TYPE: DNA
<213> ORGANISM: Artificial Sequence
<220> FEATURE:
<223> OTHER INFORMATION: recombinant promoter sequence

<400> SEQUENCE: 122
cccttgctgg ttaataatct cagttaattt gtttgcacaa aca 43

<210> SEQ ID NO 123
<211> LENGTH: 1467
<212> TYPE: PRT
<213> ORGANISM: Artificial Sequence
<220> FEATURE:
<223> OTHER INFORMATION: recombinant fVIII

<400> SEQUENCE: 123

Met Gln Leu Glu Leu Ser Thr Cys Val Phe Leu Cys Leu Leu Pro Leu
1 5 10 15

Gly Phe Ser Ala Ile Arg Arg Tyr Tyr Leu Gly Ala Val Glu Leu Ser
20 25 30

Trp Asp Tyr Arg Gln Ser Glu Leu Leu Arg Glu Leu His Val Asp Thr
35 40 45

Arg Phe Pro Ala Thr Ala Pro Gly Ala Leu Pro Leu Gly Pro Ser Val
50 55 60

Leu Tyr Lys Lys Thr Val Phe Val Glu Phe Thr Asp Gln Leu Phe Ser
65 70 75 80

Val Ala Arg Pro Arg Pro Pro Trp Met Gly Leu Leu Gly Pro Thr Ile
85 90 95

Gln Ala Glu Val Tyr Asp Thr Val Val Val Thr Leu Lys Asn Met Ala
100 105 110

Ser His Pro Val Ser Leu His Ala Val Gly Val Ser Phe Trp Lys Ser
115 120 125

Ser Glu Gly Ala Glu Tyr Glu Asp His Thr Ser Gln Arg Glu Lys Glu
130 135 140

Asp Asp Lys Val Leu Pro Gly Lys Ser Gln Thr Tyr Val Trp Gln Val
145 150 155 160

Leu Lys Glu Asn Gly Pro Thr Ala Ser Asp Pro Pro Cys Leu Thr Tyr
165 170 175

Ser Tyr Leu Ser His Val Asp Leu Val Lys Asp Leu Asn Ser Gly Leu
180 185 190

Ile Gly Ala Leu Leu Val Cys Arg Glu Gly Ser Leu Thr Arg Glu Arg
195 200 205

Thr Gln Asn Leu His Glu Phe Val Leu Leu Phe Ala Val Phe Asp Glu
210 215 220

Gly Lys Ser Trp His Ser Ala Arg Asn Asp Ser Trp Thr Arg Ala Met
225 230 235 240

Asp Pro Ala Pro Ala Arg Ala Gln Pro Ala Met His Thr Val Asn Gly
245 250 255

Tyr Val Asn Arg Ser Leu Pro Gly Leu Ile Gly Cys His Lys Lys Ser
260 265 270

Val Tyr Trp His Val Ile Gly Met Gly Thr Ser Pro Glu Val His Ser
275 280 285

Ile Phe Leu Glu Gly His Thr Phe Leu Val Arg His His Arg Gln Ala
290 295 300

Ser Leu Glu Ile Ser Pro Leu Thr Phe Leu Thr Ala Gln Thr Phe Leu
305 310 315 320

Met Asp Leu Gly Gln Phe Leu Leu Phe Cys His Ile Ser Ser His His
325 330 335

His Gly Gly Met Glu Ala His Val Arg Val Glu Ser Cys Ala Glu Glu
340 345 350

```
Pro Gln Leu Arg Arg Lys Ala Asp Glu Glu Glu Asp Tyr Asp Asp Asn
        355                 360                 365

Leu Tyr Asp Ser Asp Met Asp Val Val Arg Leu Asp Gly Asp Asp Val
    370                 375                 380

Ser Pro Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ala Gln Asn Ser Arg Pro Pro
        755                 760                 765
```

-continued

```
Ser Ala Ser Ala Pro Lys Pro Pro Val Leu Arg Arg His Gln Arg Asp
    770                 775                 780

Ile Ser Leu Pro Thr Phe Gln Pro Glu Glu Asp Lys Met Asp Tyr Asp
785                 790                 795                 800

Asp Ile Phe Ser Thr Glu Thr Lys Gly Glu Asp Phe Asp Ile Tyr Gly
                805                 810                 815

Glu Asp Glu Asn Gln Asp Pro Arg Ser Phe Gln Lys Arg Thr Arg His
            820                 825                 830

Tyr Phe Ile Ala Ala Val Glu Gln Leu Trp Asp Tyr Gly Met Ser Glu
        835                 840                 845

Ser Pro Arg Ala Leu Arg Asn Arg Ala Gln Asn Gly Glu Val Pro Arg
    850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
                885                 890                 895

Tyr Ile Arg Ala Glu Val Glu Asp Asn Ile Met Val Thr Phe Lys Asn
            900                 905                 910

Gln Ala Ser Arg Pro Tyr Ser Phe Tyr Ser Ser Leu Ile Ser Tyr Pro
        915                 920                 925

Asp Asp Gln Glu Gln Gly Ala Glu Pro Arg His Asn Phe Val Gln Pro
    930                 935                 940

Asn Glu Thr Arg Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
                965                 970                 975

Asp Leu Glu Lys Asp Val His Ser Gly Leu Ile Gly Pro Leu Leu Ile
            980                 985                 990

Cys Arg Ala Asn Thr Leu Asn Ala  Ala His Gly Arg Gln  Val Thr Val
        995                 1000                 1005

Gln Glu  Phe Ala Leu Phe Phe  Thr Ile Phe Asp Glu  Thr Lys Ser
    1010                 1015                 1020

Trp Tyr  Phe Thr Glu Asn Val  Glu Arg Asn Cys Arg  Ala Pro Cys
    1025                 1030                 1035

His Leu  Gln Met Glu Asp Pro  Thr Leu Lys Glu Asn  Tyr Arg Phe
    1040                 1045                 1050

His Ala  Ile Asn Gly Tyr Val  Met Asp Thr Leu Pro  Gly Leu Val
    1055                 1060                 1065

Met Ala  Gln Asn Gln Arg Ile  Arg Trp Tyr Leu Leu  Ser Met Gly
    1070                 1075                 1080

Ser Asn  Glu Asn Ile His Ser  Ile His Phe Ser Gly  His Val Phe
    1085                 1090                 1095

Ser Val  Arg Lys Lys Glu Glu  Tyr Lys Met Ala Val  Tyr Asn Leu
    1100                 1105                 1110

Tyr Pro  Gly Val Phe Glu Thr  Val Glu Met Leu Pro  Ser Lys Val
    1115                 1120                 1125

Gly Ile  Trp Arg Ile Glu Cys  Leu Ile Gly Glu His  Leu Gln Ala
    1130                 1135                 1140

Gly Met  Ser Thr Thr Phe Leu  Val Tyr Ser Lys Lys  Cys Gln Thr
    1145                 1150                 1155

Pro Leu  Gly Met Ala Ser Gly  His Ile Arg Asp Phe  Gln Ile Thr
    1160                 1165                 1170

Ala Ser  Gly Gln Tyr Gly Gln  Trp Ala Pro Lys Leu  Ala Arg Leu
```

```
    1175                1180                1185

His Tyr  Ser Gly Ser Ile Asn  Ala Trp Ser Thr Lys  Glu Pro Phe
    1190                1195                1200

Ser Trp  Ile Lys Val Asp Leu  Leu Ala Pro Met Ile  Ile His Gly
    1205                1210                1215

Ile Lys  Thr Gln Gly Ala Arg  Gln Lys Phe Ser Ser  Leu Tyr Ile
    1220                1225                1230

Ser Gln  Phe Ile Ile Met Tyr  Ser Leu Asp Gly Lys  Lys Trp Gln
    1235                1240                1245

Thr Tyr  Arg Gly Asn Ser Thr  Gly Thr Leu Met Val  Phe Phe Gly
    1250                1255                1260

Asn Val  Asp Ser Ser Gly Ile  Lys His Asn Ile Phe  Asn Pro Pro
    1265                1270                1275

Ile Ile  Ala Arg Tyr Ile Arg  Leu His Pro Thr His  Tyr Ser Ile
    1280                1285                1290

Arg Ser  Thr Leu Arg Met Glu  Leu Met Gly Cys Asp  Leu Asn Ser
    1295                1300                1305

Cys Ser  Met Pro Leu Gly Met  Glu Ser Lys Ala Ile  Ser Asp Ala
    1310                1315                1320

Gln Ile  Thr Ala Ser Ser Tyr  Phe Thr Asn Met Phe  Ala Thr Trp
    1325                1330                1335

Ser Pro  Ser Lys Ala Arg Leu  His Leu Gln Gly Arg  Ser Asn Ala
    1340                1345                1350

Trp Arg  Pro Gln Val Asn Asn  Pro Lys Glu Trp Leu  Gln Val Asp
    1355                1360                1365

Phe Gln  Lys Thr Met Lys Val  Thr Gly Val Thr Thr  Gln Gly Val
    1370                1375                1380

Lys Ser  Leu Leu Thr Ser Met  Tyr Val Lys Glu Phe  Leu Ile Ser
    1385                1390                1395

Ser Ser  Gln Asp Gly His Gln  Trp Thr Leu Phe Phe  Gln Asn Gly
    1400                1405                1410

Lys Val  Lys Val Phe Gln Gly  Asn Gln Asp Ser Phe  Thr Pro Val
    1415                1420                1425

Val Asn  Ser Leu Asp Pro Pro  Leu Leu Thr Arg Tyr  Leu Arg Ile
    1430                1435                1440

His Pro  Gln Ser Trp Val His  Gln Ile Ala Leu Arg  Met Glu Val
    1445                1450                1455

Leu Gly  Cys Glu Ala Gln Asp  Leu Tyr
    1460                1465
```

<210> SEQ ID NO 124
<211> LENGTH: 1386
<212> TYPE: DNA
<213> ORGANISM: Artificial Sequence
<220> FEATURE:
<223> OTHER INFORMATION: recombinant promoter sequence

<400> SEQUENCE: 124

```
atgcagaggg tcaatatgat catggctgaa tctcctgggc tgatcaccat ttgcctgctg     60

ggatacctgc tgtctgctga gtgtacagtg ttcctggacc atgagaatgc caataagatc    120

ctgaacaggc ccaaaagata caattctgga aagctggagg aatttgtgca gggcaacctg    180

gagagggaat gcatggagga aaagtgtagc tttgaggaag ctagggaggt gtttgaaaac    240

acagagagga ccacagaatt ctggaagcag tatgtggatg gagatcagtg tgagtccaac    300
```

```
ccctgtctga atggagggtc ttgcaaagat gatatcaact cctatgagtg ctggtgtcct    360

tttggatttg aaggcaaaaa ttgtgagctg gatgtgacct gtaacatcaa gaatggcagg    420

tgtgagcagt tctgtaaaaa ctctgctgat aataaggtgg tctgcagctg tacagaaggc    480

tataggctgg ctgagaacca gaagagctgt gaaccagctg tgcccttccc ttgtgggagg    540

gtgtctgtca gccagacctc taagctgacc agagctgaga ctgtgttccc agatgtggat    600

tatgtcaact ccacagaggc tgaaaccatc ctggacaaca tcacccagtc tacccagtcc    660

ttcaatgact ttaccagagt ggtgggagga gaggatgcca aaccaggcca gttcccctgg    720

caggtggtcc tgaatgggaa ggtggatgct ttttgtgggg gatccattgt gaatgagaaa    780

tggattgtca cagctgctca ctgtgtggag acaggggtca agatcactgt ggtggctgga    840

gagcacaaca ttgaggaaac agaacatact gagcagaaga ggaatgtgat cagaatcatc    900

cctcaccata actacaatgc tgctatcaac aaatataatc atgacattgc cctgctggaa    960

ctggatgagc ctctggtgct gaacagctat gtcaccccaa tctgcattgc tgacaaagag   1020

tataccaata tcttcctgaa gtttggatct ggatatgtgt ctggatgggg aagggtcttc   1080

cacaagggca ggtctgccct ggtgctgcag tatctgaggg tgcctctggt ggacagagct   1140

acctgcctgc tgtctaccaa gttcaccatc tacaacaata tgttctgtgc tggatttcat   1200

gagggaggca gggactcctg tcagggggat tctggaggcc cacatgtgac agaggtggaa   1260

ggcaccagct tcctgactgg catcatctct tgggggggagg aatgtgctat gaaggggaaa   1320

tatggaatct acaccaaagt gagcaggtat gtgaactgga tcaaagagaa gaccaaactg   1380

acctga                                                              1386
```

<210> SEQ ID NO 125
<211> LENGTH: 4404
<212> TYPE: DNA
<213> ORGANISM: Artificial Sequence
<220> FEATURE:
<223> OTHER INFORMATION: recombinant promoter sequence

<400> SEQUENCE: 125

```
atgcagctgg agctctcaac ctgtgtgttc ctctgcctgc tccccctggg attttcagct     60

atcaggagat actatctggg agcagtggaa ctgtcctggg actacaggca gtcagagctg    120

ctcagagaac tgcatgtgga tactaggttc cctgcaacag ctcctggagc actgccactg    180

ggaccttcag tgctgtacaa gaaaactgtc tttgtggagt ttacagacca gctgttcagt    240

gtggccaggc ccaggccccc ctggatgggg ctgctgggac ccaccatcca ggctgaagtg    300

tatgatactg tggtggtgac cctgaaaaac atggcctctc atccagtcag cctgcatgct    360

gtgggagtga gcttctggaa gagcagtgag ggagctgagt atgaagacca tacctcacag    420

agggagaaag aagatgataa ggtgctgcca ggaaaaagcc agacctatgt gtggcaggtg    480

ctgaaggaga atggccctac agcttcagat cctccctgcc tcacatactc ttatctgagc    540

catgtggatc tggtgaagga cctcaatagt ggcctgattg gggcactgct ggtgtgcaga    600

gaggggtccc tcacaaggga aagaactcag aacctgcatg agtttgtcct gctctttgct    660

gtgtttgatg agggaaagtc ctggcactca gcaaggaatg acagctggac cagggctatg    720

gacccagcac cagccagagc tcagccagct atgcacactg tcaatggcta tgtgaatagg    780

tccctgcctg gactcattgg ctgccataag aaatcagtct attggcatgt gattggaatg    840

ggcaccagcc cagaggtgca ttccatcttc ctggaaggcc acacatttct ggtcaggcac    900

catagacagg ccagcctgga gatcagccca ctgactttcc tcacagcaca gacatttctg    960
```

atggacctgg ggcagttcct gctcttttgc catatctcaa gtcaccatca tggagggatg 1020
gaggctcatg tcagggtgga aagctgtgca gaggaacctc agctgaggag gaaggcagat 1080
gaggaagagg actatgatga taacctgtat gactcagata tggatgtggt gaggctggat 1140
ggagatgatg tcagcccatt catccagatc aggtcagtgg ctaagaaaca ccctaagacc 1200
tgggtccact acattgcagc tgaagaggaa gattgggact atgcacccct ggtgctggcc 1260
ccagatgata gaagttacaa atctcagtat ctgaacaatg ggccccagag gattggaagg 1320
aagtacaaga aagtgaggtt catggcttat actgatgaga cctttaagac aagagaggca 1380
atccagcatg aaagtggcat cctgggacca ctgctctatg gagaagtggg ggataccctg 1440
ctcatcatct tcaagaacca ggcctcaagg ccttacaata tctatcccca tggcatcaca 1500
gatgtgaggc ctctctacag caggagactg cccaagggag tcaaacacct caaggatttc 1560
cccatcctgc caggggaaat cttcaagtat aaatggacag tcactgtgga agatgggcca 1620
actaagtcag atcctaggtg cctgaccagg tactattcta gctttgtgaa catggagagg 1680
gacctggctt caggactgat tggacctctg ctcatctgct acaaagaatc agtggaccag 1740
aggggcaacc agatcatgag tgataagaga aatgtcatcc tgttctcagt gtttgatgag 1800
aataggagtt ggtatctgac agaaaacatc cagaggttcc tgcctaatcc tgcaggagtg 1860
cagctggagg acccagaatt tcaggcttca aacatcatgc atagtatcaa tggctatgtg 1920
tttgatagtc tgcagctctc tgtctgcctg catgaggtgg cctactggta tatcctcagc 1980
attggagctc agactgactt cctgagtgtg ttcttttcag gctacacatt caagcataag 2040
atggtctatg aagataccct gacactcttc cccttttctg ggagactgt gtttatgagc 2100 atggaaaacc caggcctgtg gattctgggg tgccacaaca gtgacttcag gaatagaggg 2160
atgactgctc tgctcaaagt gtcctcatgt gataagaata ctggagatta ctatgaggac 2220
tcttatgaag atatcagtgc atatctgctc tccaaaaaca atgccattga gcccaggtca 2280
tttgctcaga acagtagacc accttctgca agtgcaccaa agcctccagt gctgaggaga 2340
caccagaggg acatcagcct gccaaccttc cagcctgagg aagataaaat ggactatgat 2400
gatatcttct ccactgagac caagggggaa gattttgaca tctatggaga ggatgaaaac 2460
caggacccca ggtccttcca gaagaggacc agacactact ttattgcagc tgtggagcag 2520
ctgtgggact atggcatgtc tgaatcacct agagctctga ggaacagagc acagaatggg 2580
gaggtgccca ggttcaagaa agtggtgttc agagaatttg cagatggctc ttttacccag 2640
cctagctaca ggggggagct caacaagcat ctggggctgc tgggacccta tatcagagca 2700
gaggtggaag ataacatcat ggtgacattc aagaatcagg cctcaagacc ctacagtttt 2760
tatagttctc tgatcagcta cccagatgat caggagcagg ggctgaaccc aaggcacaac 2820
tttgtgcagc ctaatgagac aagaacttac ttttggaagg tccagcatca catggctccc 2880
acagaggatg agtttgactg caaggcctgg gcatattttt ctgatgtgga cctggagaag 2940
gatgtgcata gtggcctcat tgggccactg ctcatctgca gggcaaacac actgaatgct 3000
gcacatggca ggcaggtcac tgtgcaggag tttgccctgt tctttacaat ctttgatgaa 3060
actaagtcct ggtacttcac agagaatgtg gaaaggaatt gcagagcccc ctgccatctc 3120
cagatggagg acccaactct gaaggaaaac tacaggttcc atgctatcaa tggatatgtc 3180
atggatacac tgccaggcct ggtgatggca cagaaccaga ggatcaggtg gtatctgctc 3240
agcatggggt ccaatgagaa tatccattct atccacttct caggacatgt cttttcagtg 3300

-continued aggaagaaag aggaatataa aatggctgtg tacaatctgt atccaggggt ctttgagaca 3360
gtggaaatgc tgcctagcaa agtggggatc tggagaattg agtgcctcat tggagaacac 3420
ctgcaggcag ggatgtccac cacatttctg gtgtactcaa agaaatgcca gactcccctg 3480
gggatggcaa gtggacatat cagggacttc cagatcactg catcaggaca gtatggacag 3540
tgggcaccaa agctggctag gctccactat agtggctcta tcaatgcttg gagtaccaaa 3600
gagcctttct cttggatcaa ggtggatctg ctggccccca tgatcatcca tggaatcaaa 3660
acacagggag ctagacagaa gttcagctcc ctgtacatca gtcagtttat catcatgtat 3720
tctctggatg ggaagaaatg gcagacctac aggggcaata gcactgggac actgatggtc 3780
ttctttggaa atgtggattc aagtggcatc aagcacaaca tcttcaatcc tcccatcatt 3840
gccaggtaca tcagactgca tcccacacac tattcaatca ggagtactct cagaatggag 3900
ctgatggggt gtgacctcaa cagctgctcc atgccactgg gaatggaatc caaggcaatc 3960
tcagatgccc agatcactgc ttctagctac ttcaccaata tgtttgcaac atggtcaccc 4020
agtaaagcaa ggctgcacct ccagggaagg tccaatgctt ggagacccca ggtgaacaat 4080
ccaaaggagt ggctgcaggt ggactttcag aaaaccatga aggtcacagg ggtgactacc 4140
cagggagtga aaagtctgct cacctctatg tatgtcaagg agttcctgat ctcctcaagt 4200
caggatggcc accagtggac actgttcttt cagaatggca aggtcaaagt gttccagggg 4260
aatcaggaca gctttacacc agtggtgaac agcctggacc cccctctgct cactagatat 4320
ctgagaatcc atccacagag ctgggtgcac cagattgcac tcagaatgga ggtcctgggc 4380
tgtgaagccc aggacctgta ttga 4404

<210> SEQ ID NO 126
<211> LENGTH: 4374
<212> TYPE: DNA
<213> ORGANISM: Artificial Sequence
<220> FEATURE:
<223> OTHER INFORMATION: recombinant promoter sequence

<400> SEQUENCE: 126
atgcagattg agctcagcac ctgcttcttt ctgtgcctgc tcaggttctg cttttcagcc 60
acaaggagat actatctggg agctgtggaa ctgtcatggg attacatgca gagtgacctg 120
ggagagctcc ctgtggatgc taggttcccc ccaagggtcc caaagtcttt cccttttaat 180
accagtgtgg tctataagaa aacactcttt gtggaattta ctgatcacct gttcaacatt 240
gcaaagccaa ggcctccctg gatgggactg ctgggaccta ccatccaggc tgaggtgtat 300
gacactgtgg tcatcacact gaaaaacatg gcatctcacc ctgtcagcct gcatgcagtg 360
ggagtcagct actggaaggc ttcagaaggg gcagagtatg atgatcagac aagccagaga 420
gaaaaagagg atgataaggt gttcccagga gggagccata cttatgtgtg gcaggtcctg 480
aaggagaatg gcccaatggc cagtgaccca ctgtgcctca cctactcata tctgagtcat 540
gtggacctgg tcaaggatct caactcaggc ctgattgggg cactgctggt gtgcagggaa 600
ggctcactgg ccaaggagaa aacccagaca ctgcataagt tcatcctgct ctttgctgtg 660
tttgatgaag ggaaatcttg gcacagtgag accaagaaca gtctgatgca ggacagggat 720
gctgcttctg ccagagcttg gcccaagatg cacacagtga atggatatgt caataggtcc 780
ctgccaggac tcattggctg ccacagaaag tcagtgtatt ggcatgtcat tggaatgggc 840
accacaccag aagtgcacag catcttcctg gaggggcata cctttctggt caggaaccac 900
aggcaggcca gcctggagat cagcccaatc accttcctga cagcccagac tctgctcatg 960

-continued

```
gatctggggc agttcctgct cttttgccac atcagctccc accagcatga tggaatggag   1020
gcatatgtga aagtggactc ctgcccagag gaaccacagc tgaggatgaa gaacaatgag   1080
gaagctgaag actatgatga tgacctgaca gactcagaga tggatgtggt caggtttgat   1140
gatgataaca gcccctcctt tatccagatc agaagtgtgg ccaagaaaca cccaaagaca   1200
tgggtccatt acattgcagc tgaggaagag gactgggatt atgcacctct ggtgctggcc   1260
ccagatgata gatcctacaa atcacagtat ctgaacaatg gaccccagag gattggcaga   1320
aagtacaaga aagtgaggtt catggcctat actgatgaaa catttaagac tagagaagct   1380
atccagcatg agtcaggcat cctgggacca ctgctctatg gagaagtggg ggacaccctg   1440
ctcatcatct tcaagaacca ggcttccagg ccatacaata tctatcctca tggcatcaca   1500
gatgtgagac cactctactc aaggagactg cctaagggag tcaaacacct caaggacttc   1560
cctatcctgc caggggaaat ctttaagtat aaatggactg tgacagtgga ggatgggccc   1620
actaagagtg acccaaggtg cctgaccaga tactattcaa gttttgtgaa tatggaaagg   1680
gatctggcat caggactgat tggacctctg ctcatctgct acaaagagag tgtggatcag   1740
aggggcaacc agatcatgtc agacaagagg aatgtgatcc tgttcagtgt ctttgatgaa   1800
aacaggtctt ggtatctgac agagaacatc cagagattcc tgccaaatcc tgcaggggtg   1860
cagctggaag atccagagtt tcaggcctca aacatcatgc atagtatcaa tggatatgtg   1920
tttgacagtc tgcagctctc tgtgtgcctg catgaagtgg cctactggta tatcctgtcc   1980
attggagctc agacagattt cctgagtgtg ttcttttcag gctacacttt taagcataaa   2040
atggtctatg aggacacact gactctcttc ccttttagtg ggaaacagt gtttatgagc   2100
atggagaatc cagggctgtg gattctggga tgccacaaca gtgatttcag gaatagaggc   2160
atgactgctc tgctcaaagt gtctagctgt gacaagaaca caggggacta ctatgaagat   2220
tcttatgagg acatcagtgc ttatctgctc tccaaaaaca atgcaattga acccagatca   2280
ttcagtcaga atccacctgt gctgaagagg caccagagag agatcactag gactaccctg   2340
cagtcagatc aggaagagat tgactatgat gataccatct cagtggaaat gaagaaagag   2400
gactttgata tctatgatga agatgagaac cagagtccaa ggtctttcca gaagaaaacc   2460
agacattact ttattgctgc agtggagagg ctgtgggatt atggaatgtc ctcaagtcca   2520
catgtgctga ggaatagggc acagtctggc agtgtccctc agttcaagaa agtggtcttc   2580
caggagttta cagatggcag cttcactcag cctctgtaca ggggagaact caatgagcac   2640
ctggggctgc tgggacccta tatcagagct gaagtggagg ataacatcat ggtcaccttc   2700
aggaatcagg cttcaagacc ctacagtttt tattctagcc tgatcagcta tgaagaggac   2760
cagaggcagg gagctgaacc taggaaaaac tttgtgaagc caaatgagac caaaacatac   2820
ttttggaagg tccagcacca catggcacca accaaagatg agtttgattg caaggcatgg   2880
gcctattttt cagatgtgga tctggagaag gatgtccaca gtggcctcat tgggcctctg   2940
ctggtgtgcc atactaacac cctgaatcca gctcatggca ggcaggtgac agtccaggag   3000
tttgcactgt tctttaccat ctttgatgag acaaagtcct ggtacttcac tgaaaacatg   3060
gagaggaatt gcagagctcc ttgcaacatc cagatggaag accccacctt caaggagaac   3120
tacagatttc atgcaatcaa tgggtatatc atggatacac tgccaggact ggtgatggcc   3180
caggaccaga ggatcagatg gtatctgctc agcatggggt ccaatgagaa tatccactct   3240
atccatttca gtggacatgt gtttacagtc agaaagaaag aagagtataa aatggccctg   3300
```

tacaacctct atccaggagt gtttgaaaca gtggagatgc tgccaagcaa ggctgggatc 3360
tggagggtgg aatgcctcat tggggagcac ctgcatgcag gaatgtcaac cctgtttctg 3420
gtctacagta ataagtgcca gacacctctg ggaatggcaa gtggacatat cagggatttc 3480
cagatcactg ctagtggaca gtatggacag tgggcaccaa agctggctag actccactat 3540
tcaggctcaa tcaatgcttg gtccaccaaa gagccattct catggatcaa ggtggacctg 3600
ctggctccta tgatcatcca tggcatcaaa acacaggggg caaggcagaa gttctcctca 3660
ctgtacatct ctcagtttat catcatgtat agcctggatg gcaagaaatg gcagacctac 3720
aggggcaata gcacagggac tctgatggtg ttctttggca atgtggacag cagtgggatc 3780
aagcacaaca tcttcaatcc cccaatcatt gcaaggtaca tcagactgca ccccacccat 3840
tattcaatca ggagtacact caggatggaa ctgatggggt gtgatctcaa cagttgctct 3900
atgccactgg gaatggagtc caaggcaatc tcagatgccc agatcactgc tagctcctac 3960
ttcactaata tgtttgctac ctggagcccc tccaaagcaa ggctgcacct ccagggaagg 4020
agcaatgcat ggaggcctca ggtgaacaat cccaaggaat ggctgcaggt ggatttccag 4080
aaaactatga aggtgactgg agtcacaact cagggagtga aaagtctgct cacttctatg 4140
tatgtcaagg agttcctgat ctcaagttct caggatggcc accagtggac cctgttcttt 4200
cagaatggaa aggtgaaagt cttccagggc aatcaggatt cctttacacc agtggtcaac 4260
tcactggacc ctcccctgct cactagatat ctgagaatcc accctcagag ctgggtgcat 4320
cagattgctc tcagaatgga agtcctgggc tgtgaggcac aggacctgta ttga 4374

<210> SEQ ID NO 127
<211> LENGTH: 1386
<212> TYPE: DNA
<213> ORGANISM: Artificial Sequence
<220> FEATURE:
<223> OTHER INFORMATION: recombinant promoter sequence

<400> SEQUENCE: 127
atgcagaggg tgaatatgat tatggctgag tcccctgggc tgattaccat ttgcctgctg 60
ggatacctgc tgtctgctga gtgtacagtg ttcctggacc atgagaatgc aaataagatc 120
ctgaacaggc ccaaaagata taatagtgga aagctggagg aatttgtgca gggcaacctg 180
gagagagaat gcatggagga aaagtgtagc tttgaggaag ccagggaggt gtttgaaaat 240
acagagagaa ccacagaatt ctggaagcag tatgtggatg gagatcagtg tgagagcaac 300
ccctgtctga atggagggag ttgcaaagat gatatcaact catatgaatg ctggtgtcct 360
tttggatttg aaggcaaaaa ttgtgagctg gatgtgacct gtaacattaa gaatgggagg 420
tgtgagcagt tttgtaaaaa ctctgctgat aataaggtgg tctgcagttg tacagaaggg 480
tatagactgg ctgagaacca gaagtcctgt gaaccagctg tgcccttccc ttgtggaagg 540
gtgtctgtct cccagacttc aaaactgacc agagctgaga ctgtgtttcc tgatgtggat 600
tatgtcaaca gcacagaggc tgaaactatc ctggacaaca ttactcagtc tacccagagt 660
ttcaatgact ttaccagagt ggtgggagga gaggatgcta aaccaggcca gttcccctgg 720
caggtggtcc tgaatgggaa ggtggatgca ttttgtgggg gatctattgt gaatgagaaa 780
tggattgtca cagctgctca ctgtgtggaa actggggtca agatcacagt ggtggctgga 840
gagcacaaca ttgaggaaac agaacatact gagcagaaga ggaatgtgat cagaatcatt 900
cctcaccata actacaatgc agccatcaac aaatataatc atgacattgc cctgctggaa 960
ctggatgagc ctctggtgct gaacagctat gtcacaccaa tctgcattgc tgacaaggag 1020

```
tacactaaca tcttcctgaa gtttgggtca ggatatgtgt ctggatgggg aagagtcttc   1080

cacaagggca ggtctgcact ggtgctgcag tatctgagag tgcctctggt ggatagggcc   1140

acttgtctgc tgtctaccaa gttcaccatc tacaacaata tgttctgtgc tggatttcat   1200

gagggaggga gagactcctg tcagggagat tctggaggcc cacatgtgac agaggtggaa   1260

ggcaccagct tcctgacagg catcatttcc tggggggagg aatgtgcaat gaaggggaaa   1320

tatggaatct acaccaaagt gagcaggtat gtgaactgga tcaaggaaaa gaccaaactg   1380

acatga                                                              1386
```

<210> SEQ ID NO 128
<211> LENGTH: 252
<212> TYPE: DNA
<213> ORGANISM: Artificial Sequence
<220> FEATURE:
<223> OTHER INFORMATION: recombinant promoter sequence

<400> SEQUENCE: 128

```
tgtttgctgc ttgcaatgtt tgcccatttt agggtggaca caggacgctg tggtttctga     60

gccagggggc gactcagatc ccagccagtg gacttagccc ctgtttgctc ctccgataac    120

tggggtgacc ttggttaata ttcaccagca gcctcccccg ttgcccctct ggatccactg    180

cttaaatacg gacgaggaca gggccctgtc tcctcagctt caggcaccac cactgacctg    240

ggacagtgaa tc                                                        252
```

<210> SEQ ID NO 129
<211> LENGTH: 4882
<212> TYPE: DNA
<213> ORGANISM: Artificial Sequence
<220> FEATURE:
<223> OTHER INFORMATION: recombinant AAV sequence

<400> SEQUENCE: 129

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc taccggtgtt aatcattaag tcgttaattt ttgtggccct    180

tgcgatgttt gctctggtta ataatctcag gacaaacaga ggttaataat tttccagatc    240

tctctgagca atagtataaa aggccagcag cagcctgacc acatctcatc ctcgtcgagc    300

caccatgcag atcgaactgt ctacctgttt ctttctgtgc ctgctgcggt tttgtttttc    360

cgctaccaga agatactacc tgggagccgt cgaactgagc tgggattaca tgcagtctga    420

cctgggagag ctgcccgtgg acgctagatt cccacctaga gtccctaagt ccttcccctt    480

caacaccagc gtggtctaca agaaaaccct gttcgtggag tttaccgacc acctgttcaa    540

catcgctaag cctagaccac catggatggg actgctggga ccaaccatcc aggccgaggt    600

gtacgacacc gtggtcatca ccctgaaaaa catggcttct caccccgtgt ccctgcatgc    660

tgtgggcgtc tcctactgga aggccagcga aggggctgag tatgacgatc agaccagcca    720

gcgggaaaaa gaggacgata aggtgttccc tggcgggtcc catacctacg tgtggcaggt    780

cctgaaggag aatggaccaa tggcttccga ccctctgtgc ctgacctact cttatctgtc    840

ccacgtggac ctggtcaagg atctgaacag cggcctgatc ggggctctgc tggtgtgtcg    900

cgaagggtcc ctggccaagg agaaaaccca gaccctgcat aagttcatcc tgctgttcgc    960

cgtgtttgac gaaggaaaaa gctggcactc tgagaccaag aactctctga tgcaggacag   1020
```

-continued

```
ggatgccgct tccgccagag cttggcccaa gatgcacacc gtgaacggct acgtcaatag   1080
gagcctgcct ggactgatcg gctgccacag aaagtccgtg tattggcatg tcatcggaat   1140
gggcaccacc cctgaagtgc acagcatctt cctggagggg catacctttc tggtccgcaa   1200
ccaccggcag gctagcctgg agatctctcc aatcaccttc ctgaccgccc agaccctgct   1260
gatggacctg ggacagttcc tgctgttttg ccacatctcc agccaccagc atgatggcat   1320
ggaggcttac gtgaaagtcg actcctgtcc cgaggaacct cagctgagga tgaagaacaa   1380
tgaggaagcc gaagactatg acgatgacct gaccgacagc gagatggatg tggtccgctt   1440
cgatgacgat aactctccct cctttatcca gatccggtcc gtggccaaga aacaccctaa   1500
gacctgggtc cattacatcg ccgctgagga agaggactgg gattatgctc cactggtgct   1560
ggcccccgac gatagatcct acaaaagcca gtatctgaac aatggacccc agaggatcgg   1620
cagaaagtac aagaaagtga ggttcatggc ttataccgat gagaccttta agaccagaga   1680
agccatccag cacgagtccg ggatcctggg acctctgctg tacggcgaag tgggggacac   1740
cctgctgatc atcttcaaga accaggccag caggccttac aatatctatc cacatggcat   1800
caccgatgtg agacctctgt actcccgccg gctgccaaag ggcgtgaaac acctgaagga   1860
cttcccaatc ctgcccgggg aaatctttaa gtataaatgg accgtcaccg tcgaggatgg   1920
gcccaccaag agcgacccta ggtgcctgac cagatactat tcttccttcg tgaatatgga   1980
gagagacctg gcttccggac tgatcggacc cctgctgatc tgttacaaag agagcgtgga   2040
tcagcgcggc aaccagatca tgtctgacaa gcggaatgtg atcctgttca gcgtctttga   2100
cgaaaaccgc tcttggtacc tgaccgagaa catccagcgg ttcctgccta atccagctgg   2160
agtgcagctg gaagatcccg agttccaggc ctctaacatc atgcattcca tcaatggcta   2220
cgtgttcgac tccctgcagc tgagcgtgtg cctgcacgag gtcgcttact ggtatatcct   2280
gagcatcgga gcccagaccg atttcctgtc tgtgttcttt tccggctaca cctttaagca   2340
taaaatggtg tatgaggaca ccctgaccct gttcccattt tccggcgaaa ccgtgttcat   2400
gagcatggag aatcccgggc tgtggatcct gggatgccac aactccgatt tcaggaatag   2460
agggatgacc gccctgctga aagtgagctc ttgtgacaag aacaccggag actactatga   2520
agatagctac gaggacatct ctgcttatct gctgtccaaa aacaatgcca tcgagcccag   2580
gagcttctct cagaaccctc cagtgctgaa gcgccaccag cgggagatca ccagaaccac   2640
cctgcagagc gatcaggaag agatcgacta cgacgatacc atctccgtgg aaatgaagaa   2700
agaggacttc gatatctatg acgaagatga gaaccagtct cccaggtcct tccagaagaa   2760
aaccagacat tactttatcg ccgctgtgga gcggctgtgg gactatggca tgtccagctc   2820
tcctcacgtg ctgagaaata gagctcagtc cggaagcgtc ccacagttca agaaagtggt   2880
cttccaggag tttaccgacg gaagctttac ccagccactg taccgcggcg aactgaacga   2940
gcacctgggg ctgctgggac cctatatccg ggctgaagtg gaggataaca tcatggtcac   3000
cttcaggaat caggccagca gaccctactc tttttattcc agcctgatct cctacgaaga   3060
ggaccagaga cagggagctg aaccaagaaa aaacttcgtg aagcctaatg agaccaaaac   3120
ctacttttgg aaggtgcagc accatatggc cctaccaaa gacgagttcg attgcaaggc   3180
ctgggcttat tttagcgacg tggatctgga gaaggacgtc cactccggcc tgatcgggcc   3240
actgctggtg tgtcatacca acaccctgaa tccagctcac ggaaggcagg tgaccgtcca   3300
ggaattcgcc ctgttcttta ccatctttga tgagaccaag agctggtact tcaccgaaaa   3360
catggagagg aattgcagag ccccatgtaa catccagatg gaagacccca ccttcaagga   3420
```

gaactacaga tttcatgcta tcaatgggta tatcatggat accctgccag gactggtcat 3480
ggctcaggac cagaggatca gatggtacct gctgagcatg ggtctaacg agaatatcca 3540 ctccatccat ttcagcggac acgtgtttac cgtccgcaag aaagaagagt acaagatggc 3600
cctgtacaac ctgtatcccg gcgtgttcga aaccgtcgag atgctgcctt ccaaggctgg 3660
gatctggcgg gtggaatgcc tgatcgggga gcacctgcat gccggaatgt ctaccctgtt 3720
cctggtgtac tccaataagt gtcagacccc cctggggatg gctagcggac atatccgcga 3780
cttccagatc accgcttccg gacagtacgg acagtgggct cctaagctgg ctagactgca 3840
ctattctggc tccatcaacg cttggtctac caaagagcct ttctcctgga tcaaggtgga 3900
cctgctggct ccaatgatca tccatggcat caaaacccag ggggccaggc agaagttctc 3960
ttccctgtac atcagccagt ttatcatcat gtattctctg gatgggaaga aatggcagac 4020
ctacagaggc aattccaccg ggaccctgat ggtgttcttt ggcaacgtcg acagctctgg 4080
gatcaagcac aacatcttca atcccccctat catcgcccgc tacatccggc tgcacccaac 4140
ccattattcc atccgcagca ccctgcggat ggagctgatg ggtgcgatc tgaacagctg 4200 ttctatgccc ctgggaatgg agtctaaggc catctccgac gctcagatca ccgcctccag 4260
ctacttcacc aatatgtttg ctacctggtc cccaagcaag gctagactgc atctgcaggg 4320
aagaagcaac gcttggagac cacaggtgaa caatcccaag gagtggctgc aggtcgactt 4380
ccagaaaacc atgaaggtga ccggagtcac cacccagggc gtgaaaagcc tgctgacctc 4440
tatgtacgtc aaggagttcc tgatctcttc cagccaggac gggcaccagt ggaccctgtt 4500
ctttcagaac ggaaaggtga aagtcttcca gggcaatcag gattccttta cccctgtggt 4560
caacagcctg gacccacccc tgctgaccag gtacctgaga atccacccac agtcctgggt 4620
gcatcagatc gctctgagga tggaagtcct gggctgcgag gcccaggacc tgtattgagc 4680
ggccgcaata aaatatcttt attttcatta catctgtgtg ttggtttttt gtgtgcaatt 4740
gaggaacccc tagtgatgga gttggccact ccctctctgc gcgctcgctc gctcactgag 4800
gccgggcgac caaaggtcgc ccgacgcccg ggctttgccc gggcggcctc agtgagcgag 4860
cgagcgcgca gctgcctgca gg 4882

<210> SEQ ID NO 130
<211> LENGTH: 5018
<212> TYPE: DNA
<213> ORGANISM: Artificial Sequence
<220> FEATURE:
<223> OTHER INFORMATION: recombinant AAV sequence

<400> SEQUENCE: 130
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc taccggtgtt aatcattaag tcgttaattt ttgtggccct 180
tgcgatgttt gctctggtta ataatctcag gacaaacaga ggttaataat tttccagatc 240
tctctgagca atagtataaa aggccagcag cagcctgacc acatctcatc ctcgtcgact 300
taattaaaag aggtaagggt ttaagggatg gttggttggt ggggtattaa tgtttaatta 360
cctggagcac ctgcctgaaa tcactttttt tcaggttggc tcgagccacc atgcagctgg 420
aactgtctac ctgtgtgttt ctgtgtctgc tgcctctggg gttttctgct atcaggagat 480
actatctggg agctgtggag ctgtcctggg actacaggca gtctgagctg ctgagagaac 540

-continued

```
tgcatgtgga taccagattc ccagctacag ctccaggagc tctgcctctg ggcccatctg    600
tgctgtacaa gaaaacagtc tttgtggagt ttacagacca gctgttctct gtggccaggc    660
caagaccacc ttggatggga ctgctgggac caaccatcca ggctgaggtg tatgatacag    720
tggtggtgac cctgaaaaac atggcctccc atcctgtgag cctgcatgct gtgggggtgt    780
ccttctggaa gtcctctgag ggagctgagt atgaagacca tacctcccag agggagaaag    840
aagatgataa ggtgctgcct ggcaaaagcc agacctatgt ctggcaggtg ctgaaggaga    900
atggaccaac tgcttctgac ccaccatgcc tgacctactc ttatctgtcc catgtggatc    960
tggtgaagga cctgaattct ggactgattg gagctctgct ggtgtgtaga gagggaagcc   1020
tgaccagaga aagaacccag aacctgcatg agtttgtcct gctgtttgct gtgtttgatg   1080
aagggaagag ctggcactct gccaggaatg actcctggac cagagctatg gatccagctc   1140
ctgctagagc tcagcctgct atgcacacag tcaatggcta tgtgaatagg tctctgccag   1200
gactgattgg ctgccataag aaatctgtct attggcatgt gattggaatg ggcaccagcc   1260
ctgaggtgca ttctatcttc ctggaaggcc acacctttct ggtcaggcac catagacagg   1320
cctctctgga gatctcccct ctgaccttcc tgacagctca gacctttctg atggacctgg   1380
ggcagttcct gctgttttgc catatctctt cccaccatca tggaggaatg gaggctcatg   1440
tcagggtgga atcctgtgct gaggaaccac agctgagaag aaaggctgat gaggaagagg   1500
actatgatga taacctgtat gactctgata tggatgtggt gaggctggat ggggatgatg   1560
tcagcccttt catccagatc aggtctgtgg ccaagaaaca tccaaagacc tgggtccact   1620
acattgctgc tgaagaggaa gattgggact atgccccccct ggtgctggct cctgatgata   1680
gatcctacaa aagccagtat ctgaacaatg ggccccagag gattggaagg aagtacaaga   1740
aagtgaggtt catggcctat acagatgaga cctttaagac cagagaggct atccagcatg   1800
aatctgggat cctgggacct ctgctgtatg gagaagtggg ggataccctg ctgatcatct   1860
tcaagaacca ggcctccagg ccatacaata tctatcccca tggcatcaca gatgtgagac   1920
cactgtacag caggagactg cccaaggggg tcaaacacct gaaggatttc cccatcctgc   1980
ctggagagat ctttaagtat aaatggacag tcacagtgga agatgggcct accaagtctg   2040
atccaaggtg cctgaccaga tactatagct cttttgtgaa catggagaga gacctggctt   2100
ctggactgat tggacccctg ctgatctgtt acaaagagtc tgtggaccag aggggcaacc   2160
agatcatgtc tgataagaga aatgtcatcc tgttctctgt gtttgatgag aacaggagct   2220
ggtacctgac agagaacatc cagaggttcc tgccaaatcc agctggagtg cagctggagg   2280
acccagaatt tcaggcttcc aacatcatgc atagcatcaa tggctatgtg tttgatagcc   2340
tgcagctgtc tgtctgcctg catgaggtgg cctactggta tatcctgtcc attggagctc   2400
agacagactt cctgtctgtg ttctttagtg ggtacacctt taagcataaa atggtgtatg   2460
aggataccct gaccctgttc cccttttctg ggagacagt gttcatgtcc atggaaaacc   2520
ctggcctgtg gatcctgggg tgccacaact ctgacttcag gaatagagga atgacagccc   2580
tgctgaaagt gtccagctgt gataagaata caggggatta ctatgaggac tcttatgaag   2640
atatctctgc ttatctgctg agcaagaaca atgccattga gcccaggtct tttgctcaga   2700
actccagacc tccatctgct tctgctccta agccacctgt gctgagaaga catcagaggg   2760
acatctccct gcctaccttc cagccagagg aagataaaat ggactatgat gatatcttca   2820
gcacagagac caagggggaa gattttgaca tctatggaga ggatgaaaac caggatccaa   2880
gatccttcca gaagagaacc agacactact ttattgctgc tgtggagcag ctgtgggact   2940
```

atgggatgtc tgaaagccca agggccctga ggaacagagc tcagaatgga gaggtgccca 3000
gattcaagaa agtggtgttc agagagtttg ctgatggcag ctttacccag ccatcttaca 3060 gggggagct gaacaagcat ctggggctgc tgggacccta tatcagagct gaggtggaag 3120
ataacatcat ggtgaccttc aagaatcagg cttctaggcc ctactccttt tattcttccc 3180
tgatctccta ccctgatgat caggagcagg gagctgaacc taggcacaac tttgtgcagc 3240
caaatgagac cagaacctac ttttggaagg tgcagcatca catggctccc acagaggatg 3300
aatttgactg caaagcttgg gcctattttt ctgatgtgga cctggagaag gatgtgcatt 3360
ctggcctgat tgggcctctg ctgatctgta gggccaacac cctgaatgct gctcatggaa 3420
gacaggtcac agtgcaggag tttgctctgt tctttaccat ctttgatgaa accaagagct 3480
ggtacttcac agagaatgtg gaaaggaatt gcagagcccc ctgtcatctg cagatggagg 3540
accctaccct gaaggaaaac tacaggttcc atgccatcaa tggatatgtc atggataccc 3600
tgcctggcct ggtcatggct cagaaccaga ggatcagatg gtacctgctg tctatgggat 3660
ccaatgagaa tatccatagc atccacttct ctggccatgt cttttctgtg aggaagaaag 3720
aggaatacaa aatggctgtg tacaatctgt atcctggggt ctttgagaca gtggaaatgc 3780
tgccaagcaa agtgggaatc tggagaattg agtgcctgat tggggaacac ctgcaggctg 3840
ggatgagcac caccttcctg gtgtactcta agaaatgtca gaccccactg ggatggcct 3900 ctggacatat cagggacttc cagatcacag cttctggaca gtatggacag tgggctccaa 3960
agctggctag actgcactat tctggctcca tcaatgcctg gtctaccaaa gagccattct 4020
cctggatcaa ggtggacctg ctggccccca tgatcatcca tggaatcaaa acccagggag 4080
ctaggcagaa gttcagctct ctgtacatct cccagtttat catcatgtat agcctggatg 4140
ggaagaaatg gcagacctac agaggcaatt ccactgggac cctgatggtc ttctttggaa 4200
atgtggattc ctctggcatc aagcacaaca tcttcaatcc acccatcatt gccaggtaca 4260
tcaggctgca tcctacccac tatagcatca ggtctaccct gagaatggag ctgatgggat 4320
gtgacctgaa cagctgttct atgccactgg gcatggagtc caaggctatc tctgatgccc 4380
agatcacagc ttcttcctac ttcaccaata tgtttgctac ctggtcccca agcaaggcta 4440
gactgcacct gcagggaaga tccaatgctt ggagacccca ggtgaacaat cctaaggagt 4500
ggctgcaggt ggacttccag aaaaccatga aggtcacagg ggtgaccacc cagggagtga 4560
aatctctgct gacctccatg tatgtcaagg agttcctgat cagctcttcc caggatggcc 4620
accagtggac cctgttcttt cagaatggca aggtcaaagt gttccagggg aatcaggact 4680
cttttacccc agtggtgaac tccctggatc ctccactgct gaccaggtac ctgagaatcc 4740
atcctcagag ctgggtgcac cagattgctc tgagaatgga ggtcctggga tgtgaagctc 4800
aggacctgta ttgagcggcc gcaataaaat atctttattt tcattacatc tgtgtgttgg 4860
ttttttgtgt gcaattgagg aacccctagt gatggagttg gccactccct ctctgcgcgc 4920
tcgctcgctc actgaggccg ggcgaccaaa ggtcgcccga cgcccgggct ttgcccgggc 4980
ggcctcagtg agcgagcgag cgcgcagctg cctgcagg 5018

<210> SEQ ID NO 131
<211> LENGTH: 137
<212> TYPE: DNA
<213> ORGANISM: Artificial Sequence
<220> FEATURE:
<223> OTHER INFORMATION: recombinant promoter sequence

```
<400> SEQUENCE: 131

gttaattttt aaaaagcagt caaaagtcca agtggccctt gcgagcattt actctctctg      60

tttgctctgg ttaataatct caggagcaca aacagaggtt aataattttc cagatctctc    120

tgagcaatag tataaaa                                                    137
```